(12) United States Patent
Song et al.

(10) Patent No.: US 12,041,847 B2
(45) Date of Patent: *Jul. 16, 2024

(54) COMPOUND FOR ORGANIC ELECTRIC ELEMENT, ORGANIC ELECTRIC ELEMENT USING THE SAME, AND ELECTRONIC DEVICE THEREOF

(71) Applicant: DUK SAN NEOLUX CO., LTD., Cheonan-si (KR)

(72) Inventors: Hyun Ju Song, Cheonan-si (KR); Ho Young Jung, Cheonan-si (KR); Mi Young Chae, Yongin-si (KR); Jae Taek Kwon, Cheonan-si (KR); Moo Jin Park, Cheonan-si (KR); Sun Hee Lee, Hwaseong-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 99 days.

This patent is subject to a terminal disclaimer.

(21) Appl. No.: 17/212,776

(22) Filed: Mar. 25, 2021

(65) Prior Publication Data

US 2021/0226127 A1 Jul. 22, 2021

Related U.S. Application Data

(63) Continuation of application No. 16/344,684, filed as application No. PCT/KR2019/000678 on Jan. 17, 2019.

(30) Foreign Application Priority Data

Feb. 2, 2018 (KR) .................. 10-2018-0013219

(51) Int. Cl.
*H01L 51/00* (2006.01)
*C07D 209/86* (2006.01)
(Continued)

(52) U.S. Cl.
CPC ......... *H10K 85/633* (2023.02); *C07D 209/86* (2013.01); *C07D 333/76* (2013.01);
(Continued)

(58) Field of Classification Search
None
See application file for complete search history.

(56) References Cited

U.S. PATENT DOCUMENTS

2006/0113905 A1\* 6/2006 Nakamura .......... H01L 27/3244
313/511
2015/0349268 A1 12/2015 Zeng et al.
2016/0172593 A1\* 6/2016 Takada ................ C07D 333/76
257/40

FOREIGN PATENT DOCUMENTS

CN 105658620 A 6/2016
CN 106164061 A 11/2016
(Continued)

OTHER PUBLICATIONS

Machine English translation of Cha et al. (KR-10-2017-0088650). Sep. 26, 2022.\*

*Primary Examiner* — Jay Yang
*Assistant Examiner* — J. L. Yang
(74) *Attorney, Agent, or Firm* — Vorys, Sater, Seymour and Pease LLP; Mih Suhn Koh

(57) ABSTRACT

Provided is a compound capable of improving luminous efficiency, stability and lifetime of an organic electronic device, an organic electric element using the same, and an electronic device comprising the element.

4 Claims, 1 Drawing Sheet

(51) Int. Cl.
| | |
|---|---|
| C07D 333/76 | (2006.01) |
| C07D 403/10 | (2006.01) |
| C07D 403/14 | (2006.01) |
| C07D 405/14 | (2006.01) |
| C07D 409/14 | (2006.01) |
| C09K 11/06 | (2006.01) |
| H01L 51/50 | (2006.01) |
| H10K 50/18 | (2023.01) |
| H10K 85/60 | (2023.01) |
| H10K 50/11 | (2023.01) |
| H10K 50/15 | (2023.01) |
| H10K 50/85 | (2023.01) |
| H10K 71/00 | (2023.01) |
| H10K 71/16 | (2023.01) |
| H10K 101/00 | (2023.01) |
| H10K 101/10 | (2023.01) |
| H10K 101/40 | (2023.01) |
| H10K 102/00 | (2023.01) |

(52) U.S. Cl.
CPC ......... *C07D 403/10* (2013.01); *C07D 403/14* (2013.01); *C07D 405/14* (2013.01); *C07D 409/14* (2013.01); *C09K 11/06* (2013.01); *H10K 50/18* (2023.02); *H10K 85/626* (2023.02); *H10K 85/636* (2023.02); *H10K 85/654* (2023.02); *H10K 85/6572* (2023.02); *H10K 85/6574* (2023.02); *H10K 85/6576* (2023.02); *C09K 2211/1018* (2013.01); *H10K 50/11* (2023.02); *H10K 50/15* (2023.02); *H10K 50/85* (2023.02); *H10K 71/00* (2023.02); *H10K 71/164* (2023.02); *H10K 2101/10* (2023.02); *H10K 2101/40* (2023.02); *H10K 2101/90* (2023.02); *H10K 2102/351* (2023.02)

(56) References Cited

FOREIGN PATENT DOCUMENTS

| | | | |
|---|---|---|---|
| CN | 106661445 A | | 5/2017 |
| CN | 106905222 A | | 6/2017 |
| KR | 10-2014-0010133 A | | 1/2014 |
| KR | 10-2016-0006633 A | | 1/2016 |
| KR | 10-1614738 B1 | | 4/2016 |
| KR | 10-2017-0088650 | * | 8/2017 |
| KR | 10-2017-0088650 A | | 8/2017 |
| KR | 10-2017-0116843 A | | 10/2017 |
| KR | 10-2017-0134132 A | | 12/2017 |
| WO | 2010/126270 A1 | | 11/2010 |
| WO | 2017/010626 A1 | | 1/2017 |
| WO | 2017/043757 A1 | | 3/2017 |

* cited by examiner

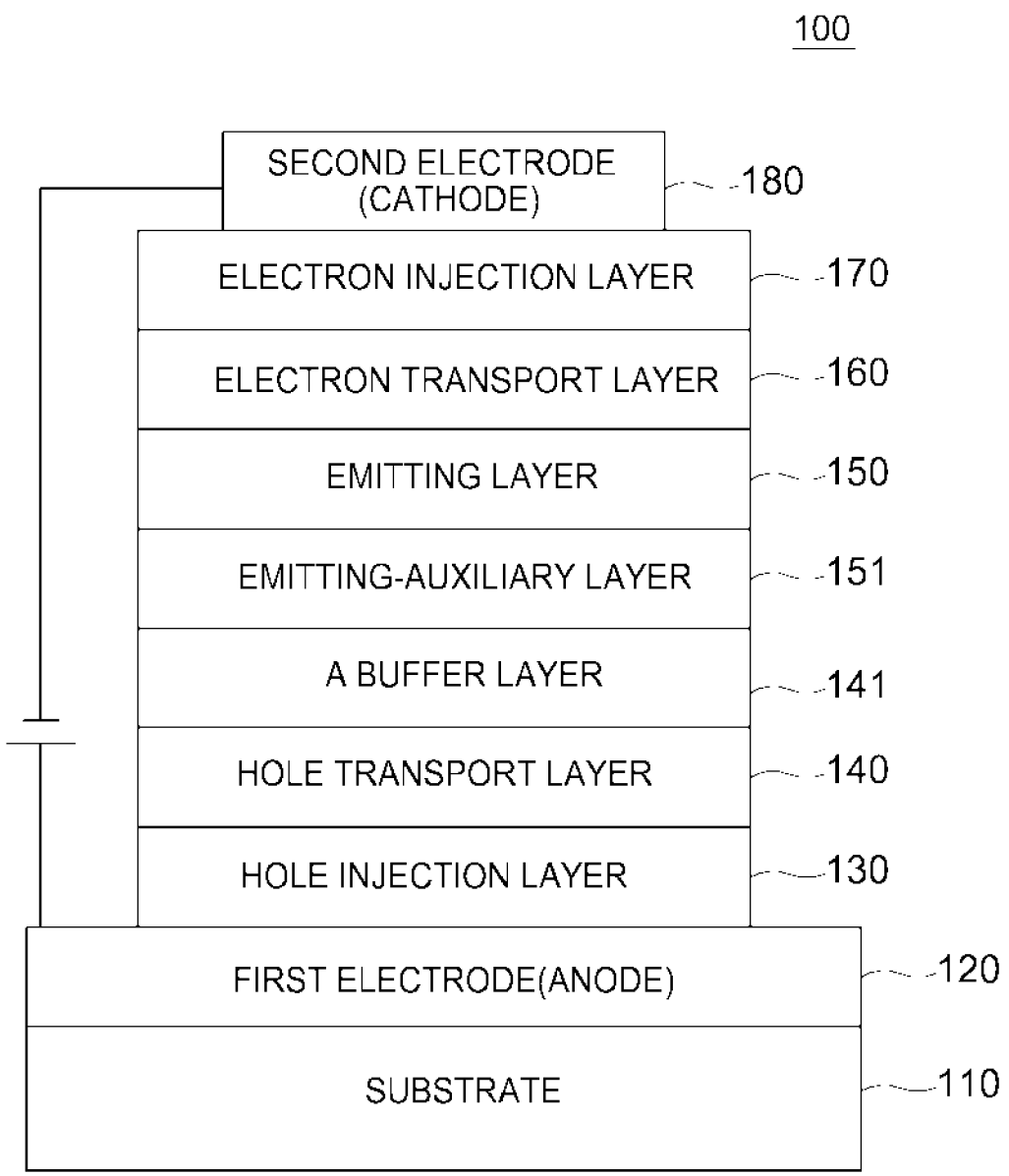

COMPOUND FOR ORGANIC ELECTRIC ELEMENT, ORGANIC ELECTRIC ELEMENT USING THE SAME, AND ELECTRONIC DEVICE THEREOF

BACKGROUND

Technical Field

The present invention relates to compound for organic electric element, organic electric element using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

And the light emitting material may be classified into a polymer type and a low molecular type depending on the molecular weight, and into a fluorescent material derived from the singlet excited state of electrons and a phosphorescent material derived from the triplet excited state of electrons depending on the light emitting mechanism. Further, the light emitting material can be classified into blue, green, and red light emitting materials and yellow and orange light emitting materials necessary for realizing better natural color depending on the luminescent color.

Meanwhile, when only one material is used as a light emitting material, there arises a problem that the maximum light emission wavelength shifts to a long wavelength due to intermolecular interaction, the color purity drops, or the efficiency of the device decreases due to the light emission attenuation effect, therefore a host/dopant system can be used as a light emitting material in order to increase luminous efficiency through increase of color purity and energy transfer. When the small amount of dopant having a smaller energy band gap than the host forming the emitting layer is mixed on the emitting layer, the excitons generated in the emitting layer are transported to the dopant to emit light with high efficiency. At this time, since the wavelength of the host is shifted to the wavelength band of the dopant, light of a desired wavelength can be obtained depending on the type of the dopant used.

Currently, the portable display market is growing in size as a large-area display, which requires more power than the power consumption required by existing portable displays. Therefore, power consumption is a very important factor for portable displays, which have a limited power source, such as a battery, and efficiency and lifetime issues must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase. However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time. Therefore, it is necessary to develop a light emitting material having a high thermal stability and achieving a charge balance in the emitting layer efficiently.

That is, in order to sufficiently exhibit the excellent characteristics of the organic electric element, a material for forming an organic material layer in an element such as a hole injection material, a hole transport material, a light emitting material, an electron transport material, an electron injection material, an emitting-auxiliary layer material, and the like should be supported by stable and efficient materials. However, such a stable and efficient organic material layer material for an organic electric element has not been sufficiently developed yet. Therefore, development of new materials is continuously required, and especially development of host materials for the emitting layer is urgently required.

Otherwise, in the case of a polycyclic compound including a heteroatom, the difference in properties according to the material structure is so large that it is applied to various layers as OLED material. In particular, it has characteristics of different band gaps (HOMO, LUMO), electrical characteristics, chemical properties, and physical properties depending on the number of rings, fused positions and the type and arrangement of heteroatoms, therefore application development for various OLED layers using the same has been progressed. Recently, development of OLED material for heteroatom type, number and position of pentacyclic compounds has been actively developed.

As a precedent reference, U.S. Pat. No. 8,334,058 B2 is referred to.

DETAILED DESCRIPTION OF THE INVENTION

Summary

Using the characteristics of the polycyclic compound, the present invention provides a compound capable of maximizing the effect of improving luminous efficiency and long life, while maintaining or slightly reducing the driving voltage of the device, and an organic electric element using the same and an electronic device thereof.

Technical Solution

The present invention provides compounds represented by Formula (1) and Formula (18), organic electric elements comprising the same and electronic devices thereof.

Formula (18)

-continued

Formula (1)

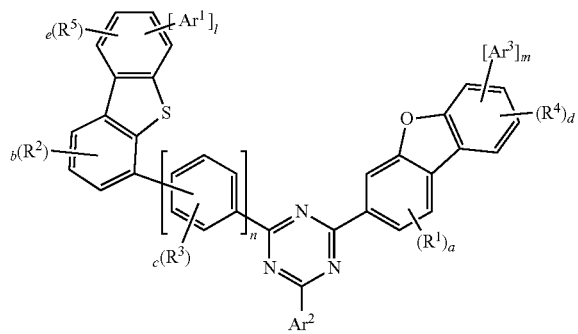

Effects of the Invention

By using the compound according to the present invention, it is possible to achieve a high luminous efficiency, a low driving voltage, and a high heat resistance of the element, and can greatly improve the color purity and lifetime of the element.

BRIEF DESCRIPTION OF THE DRAWINGS

The FIGURE illustrates an example of an organic electric element according to the present invention.
100: organic electric element, 110: substrate
120: the first electrode(anode), 130: the hole injection layer
140: the hole transport layer, 141: a buffer layer
150: the emitting layer, 151: the emitting auxiliary layer
160: the electron transport layer, 170: the electron injection layer
180: the second electrode(cathode)

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "heteroalkyl", as used herein, means alkyl substituted one or more of carbon atoms consisting of an alkyl with heteroatom.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxyl group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl including one or more of heteroatoms.

Unless otherwise stated, the term "heteroaryl group" or "heteroarylene group", as used herein, means a C2 to C60 aryl including one or more of heteroatoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including SO₂ instead of carbon consisting of cycle. For example, "heterocyclic group" includes compound below.

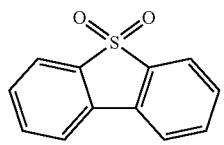 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

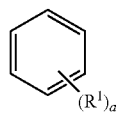

Wherein, when a is an integer of zero, it means the substituent $R^1$ is absent. That is, when a is 0, it means that all the carbons forming the benzene ring are bonded to hydrogen. In this case, the sign of the hydrogen bonded to the carbon may be omitted and the formula or compound may be described. When a is an integer of 1, the sole substituent $R^1$ is linked to any one of the carbon constituting the benzene ring, when a is an integer of 2 or 3, they are respectively bonded as follows, in which $R^1$ may be the same as or different from each other, and when a is an integer of 4 to 6, and it is bonded to the carbon of the benzene ring in a similar manner, whereas the indication of hydrogen bonded to the carbon forming the benzene ring is omitted.

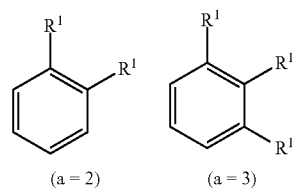

Hereinafter, a compound according to an aspect of the present invention and an organic electric element comprising the same will be described.

According to a specific example of the present invention, there is provided a compound represented by Formula (1).

Formula (1)

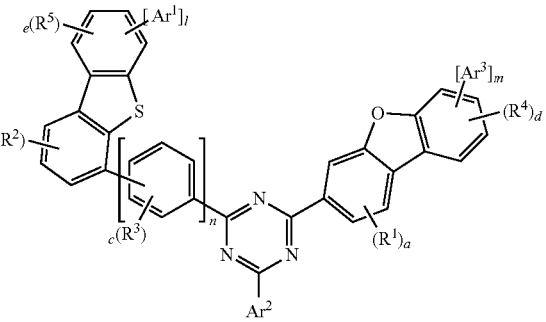

{In Formula (1),
1) $Ar^1$, $Ar^2$ and $Ar^3$ are each independently a $C_6$-$C_{60}$ aryl group;
2) l+e is an integer of 0 to 4, d+m is an integer of 0 to 4, a and b are an integer of 0 to 3, n is an integer of 1 to 3, c is an integer of 0 to 4,
3) $R^1$, $R^2$, $R^3$, $R^4$ and $R^5$ are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$);
wherein, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic group;
and the $R_a$ and $R_b$ are each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group including at least one heteroatom of O, N, S, Si, or P; or a plurality of $R^1$, a plurality of $R^2$, a plurality of $R^3$, a plurality of $R^4$, and a plurality of $R^5$ may be bonded to each other to form an aromatic ring or and heteroaromatic ring, wherein, the aryl group, fluorenyl group, arylene group, heterocyclic group, fluorenylene group, fused ring group, alkyl group, alkenyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may be bonded to each other to form a ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof and comprises a saturated or unsaturated ring.}

In a specific aspect of the invention, the compound represented by Formula (1) comprises a compound represented by any of Formulas (2) to (7) below.

<Formula (2)>

<Formula (3)>

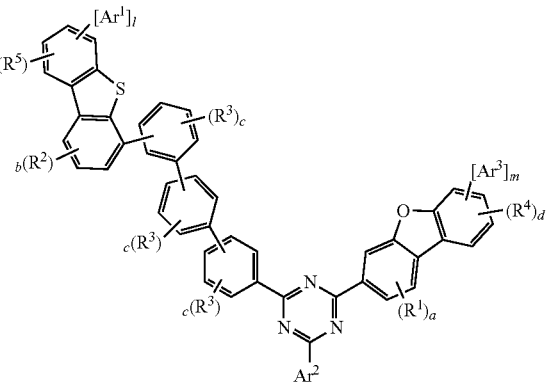

<Formula (4)>

<Formula (5)>

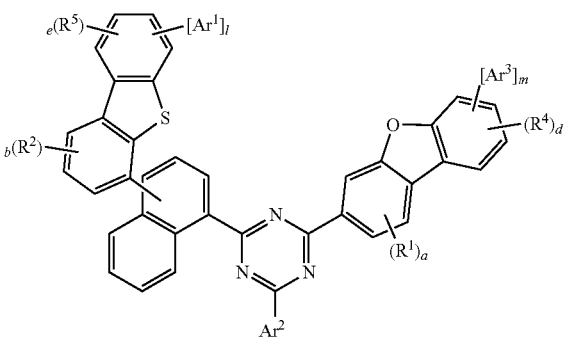

<Formula (6)>

<Formula (7)>

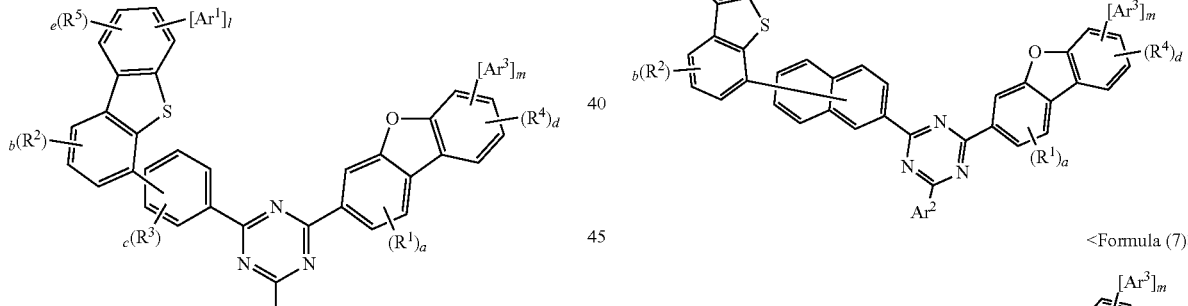

{In Formulas (2) to (7), $Ar^1$, $Ar^2$, $Ar^3$, l, m, n, a, b, c, d, e, $R^1$, $R^2$, $R^3$, $R^4$ and $R^5$ are the same as defined above.}

Preferably, at least one of $Ar^1$, $Ar^2$, and $R^3$ in Formula (1) comprises a $C_6$~$C_{24}$ aryl group, more preferably, $Ar^1$ or $Ar^3$ in Formula (1) comprises a $C_6$~$C_{24}$ aryl group.

Also, $R^3$ in Formula (1) is a $C_6$~$C_{24}$ aryl group.

Also, Formula (1) comprises a compound represented by any of the following Formulas (8) to (10)

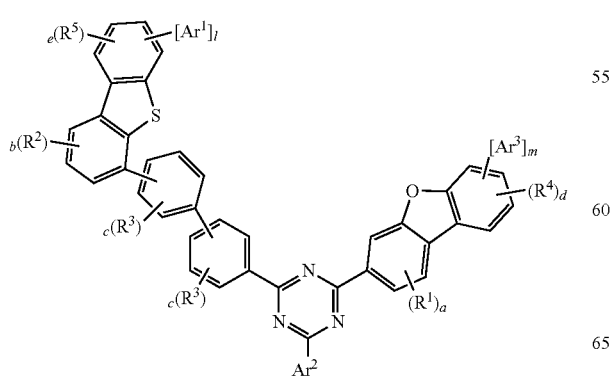

<Formula (8)>

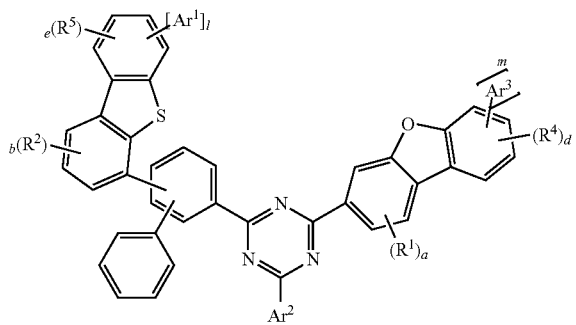

<Formula (9)>

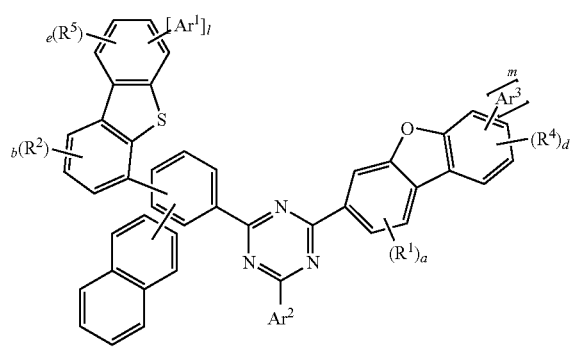

<Formula (10)>

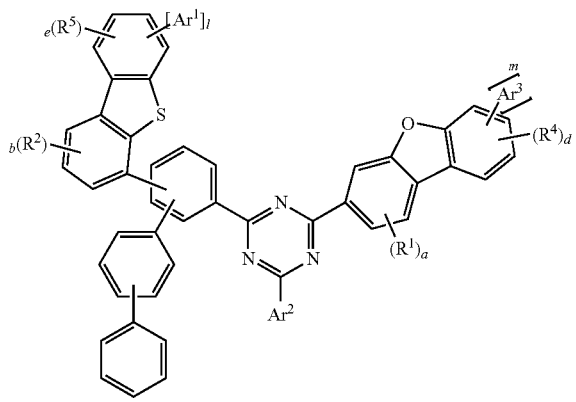

{In Formulas (8) to (10),
Ar$^1$, Ar$^2$, Ar$^3$, l, m, n, a, b, c, d, e, R$^1$, R$^2$, R$^3$, R$^4$ and R$^5$ are the same as defined above.}

Also, the compound represented by Formula (1) comprises compounds represented by Formula (11)

<Formula (11)>

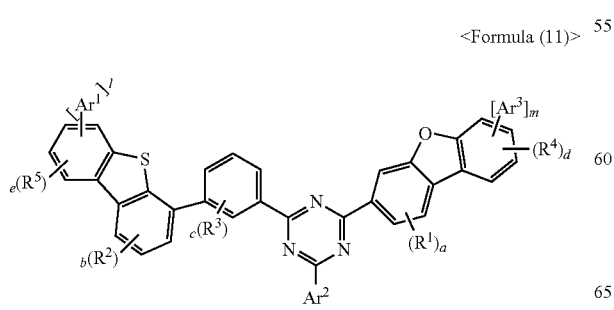

{In Formula (11),
Ar$^1$, Ar$^2$, Ar$^3$, l, m, n, a, b, c, d, e, R$^1$, R$^2$, R$^3$, R$^4$ and R$^5$ are the same as defined above.}

Specifically, in the present invention, the compound represented by Formula (1) includes the following compounds P-1 to P-160.

P-1

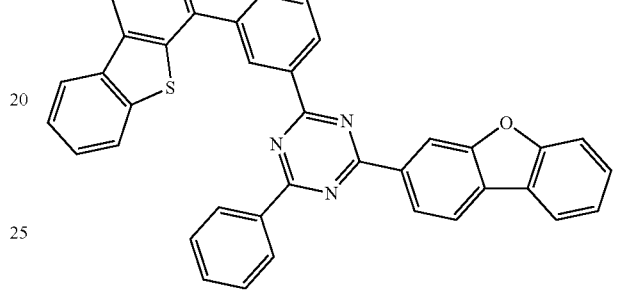

P-2

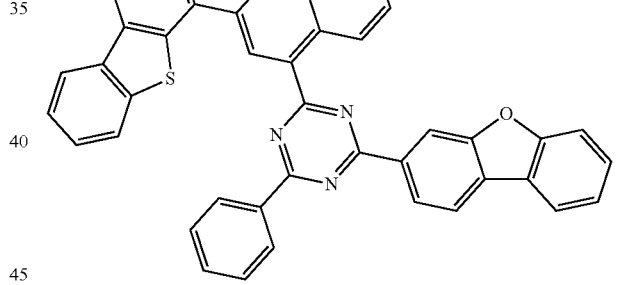

P-3

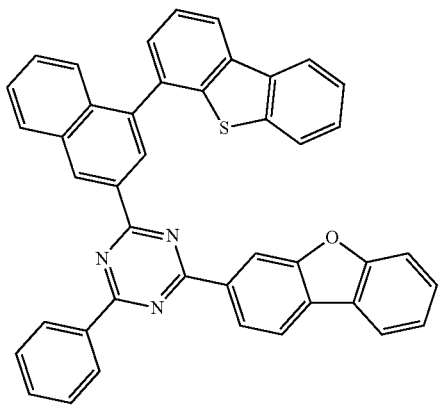

P-4
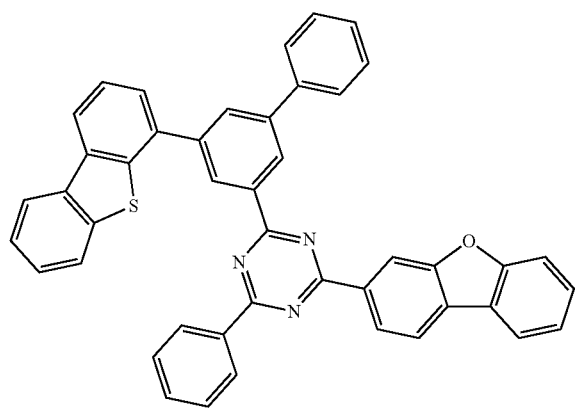
P-5
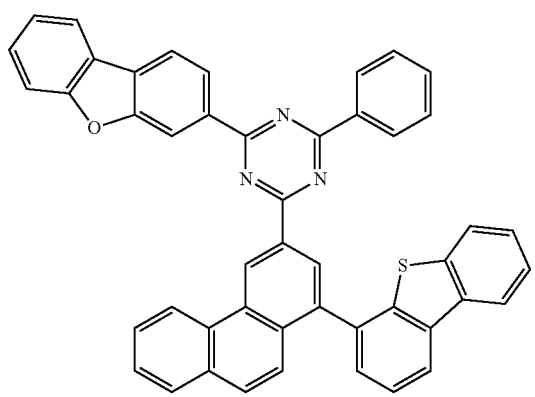
P-6
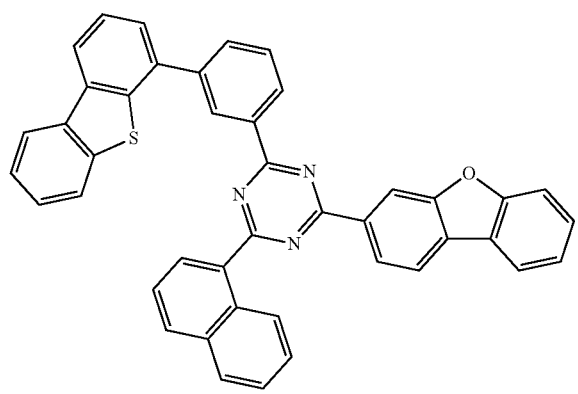
P-7
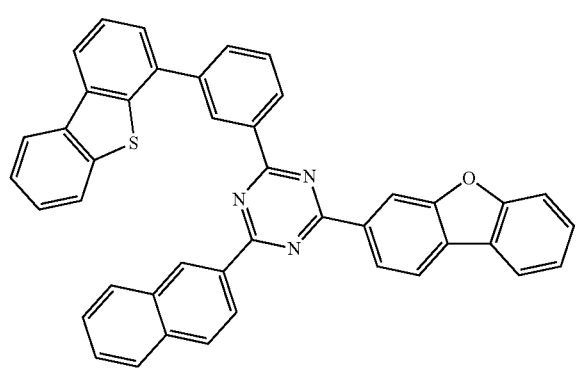
P-8
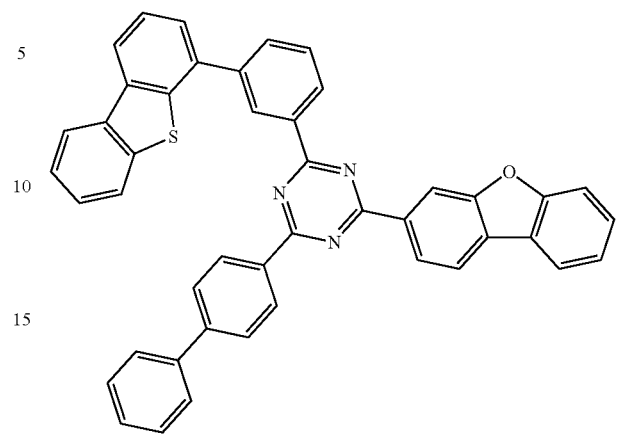
P-9
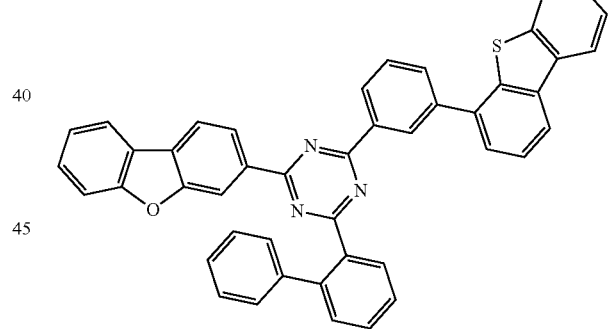
P-10
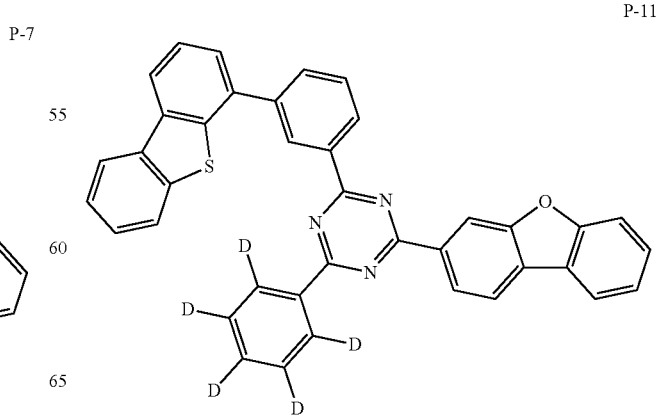
P-11

P-12
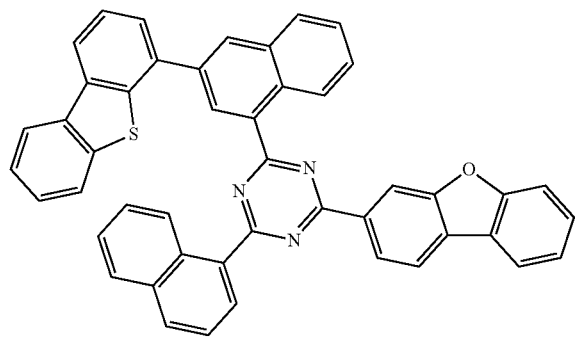
P-13
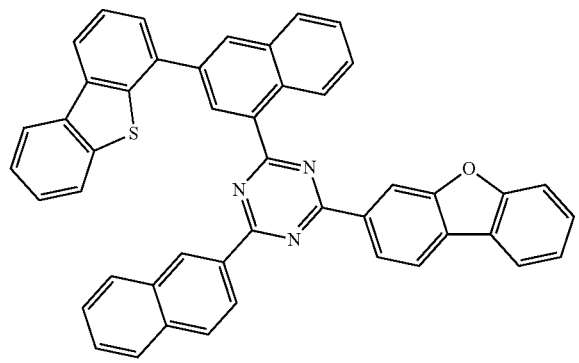
P-14
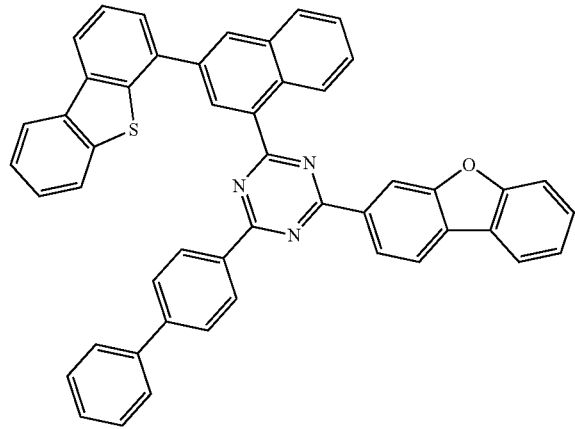
P-15
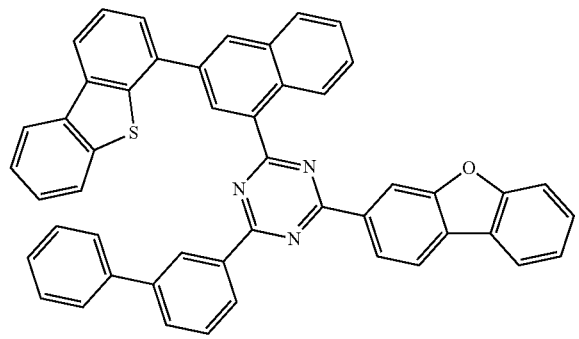
P-16
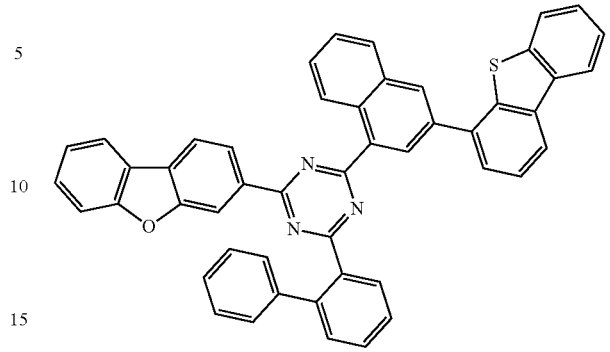
P-17
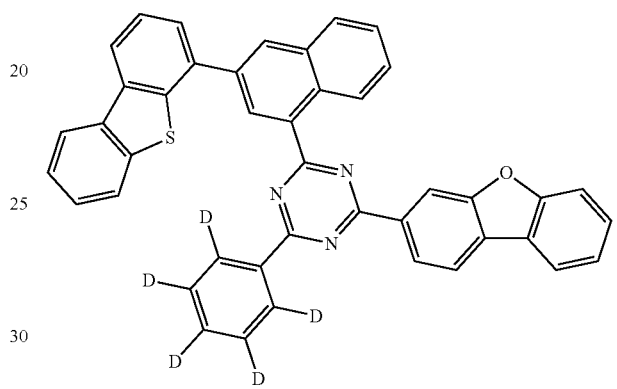
P-18
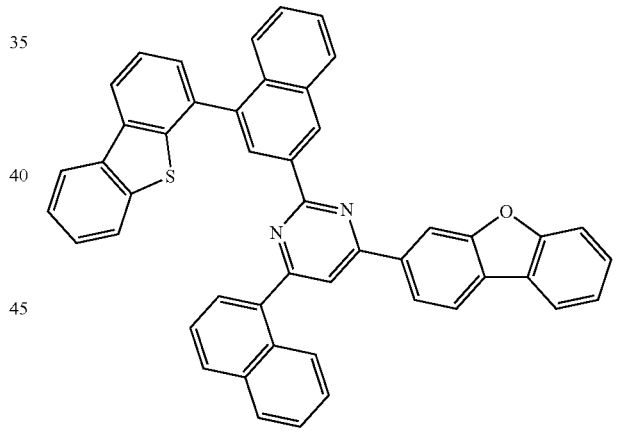
P-19
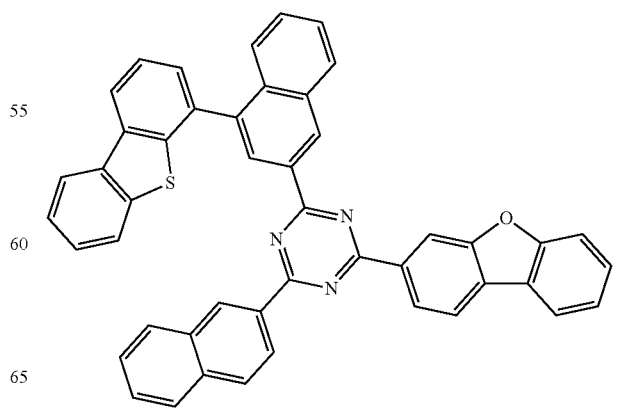

-continued
P-20
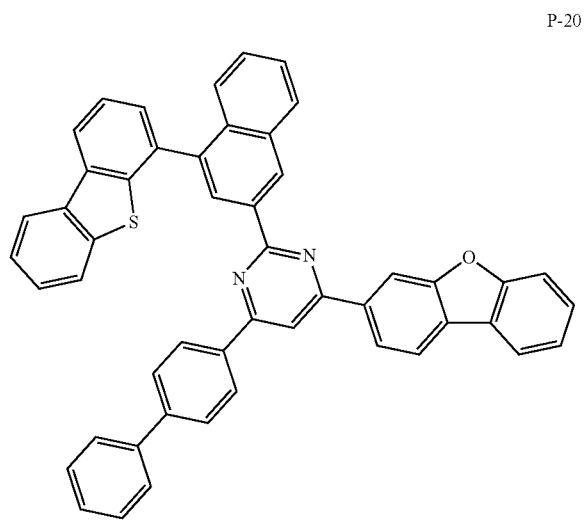
P-21
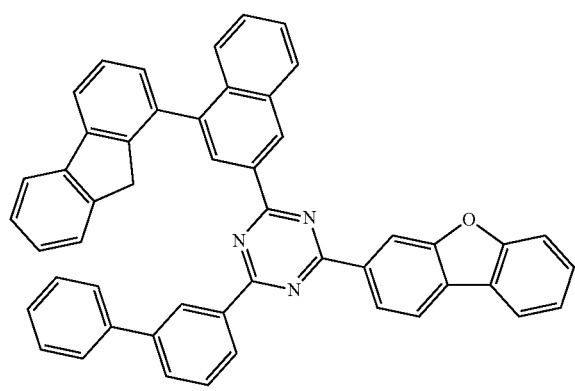
P-22
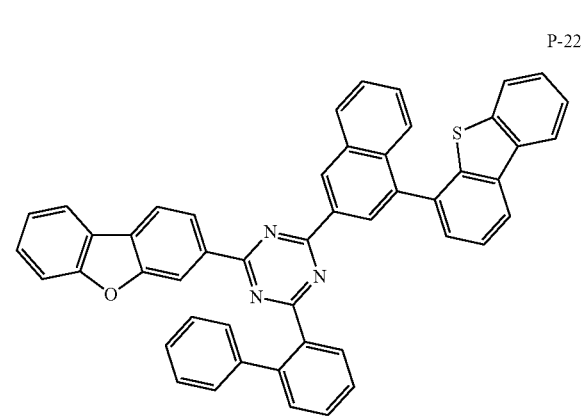
-continued
P-23
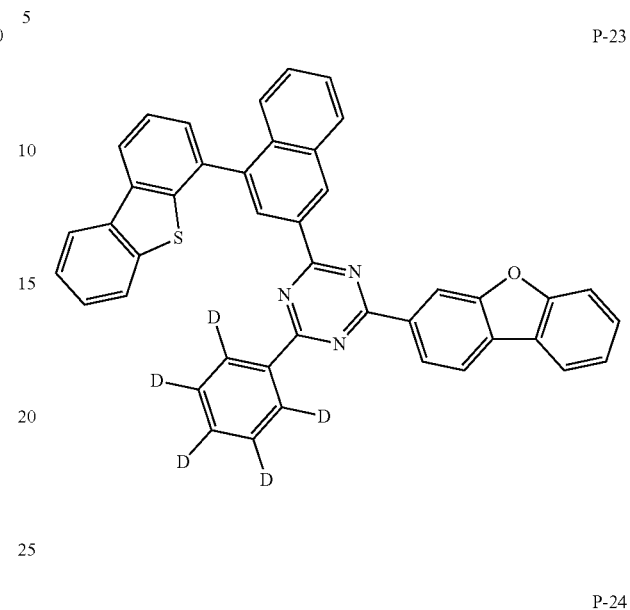
P-24
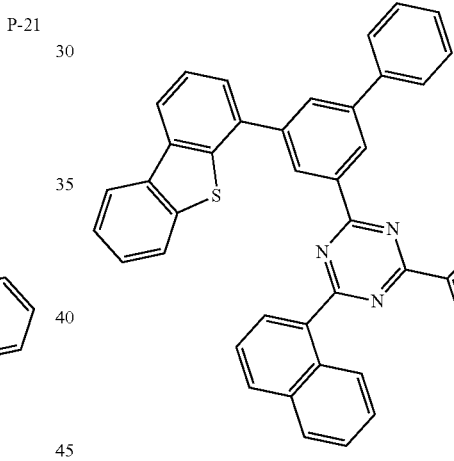
P-25
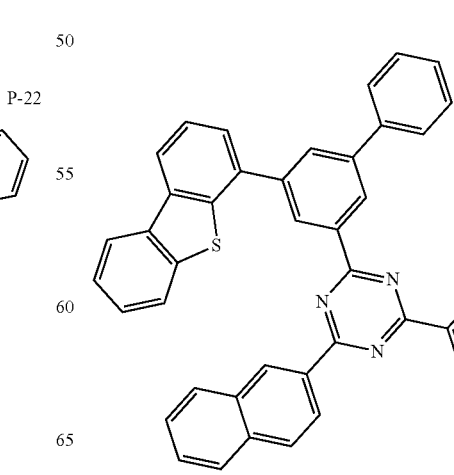

P-26
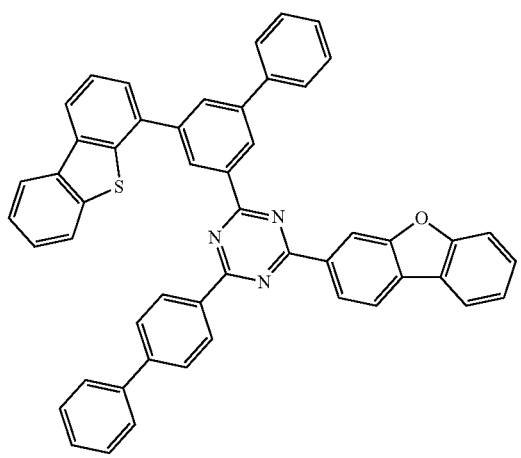
P-27
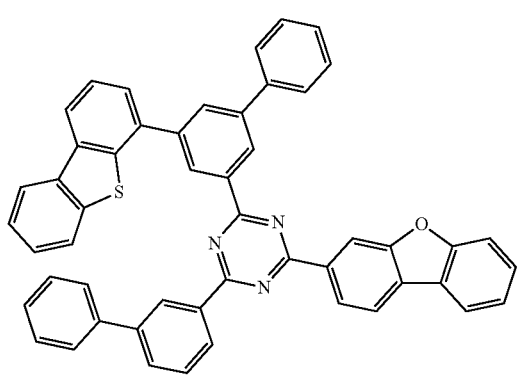
P-28
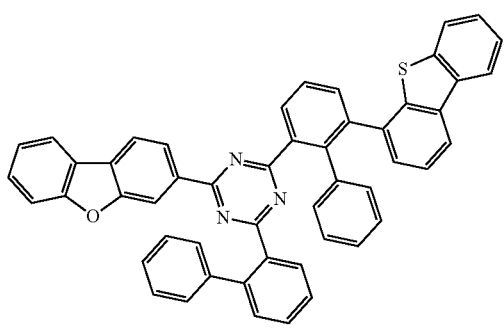
P-29
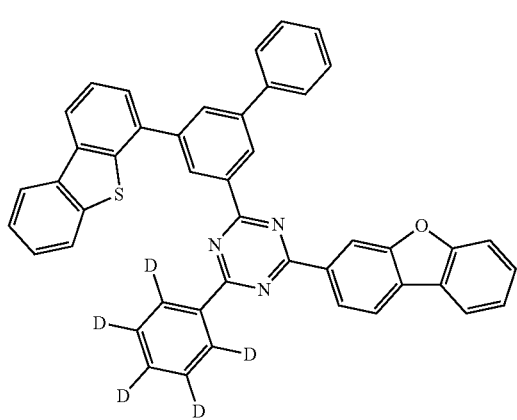
P-30
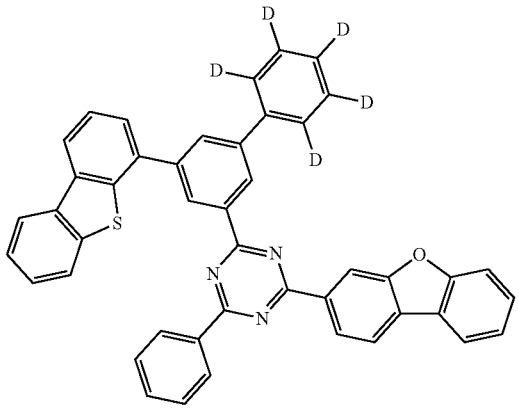
P-31
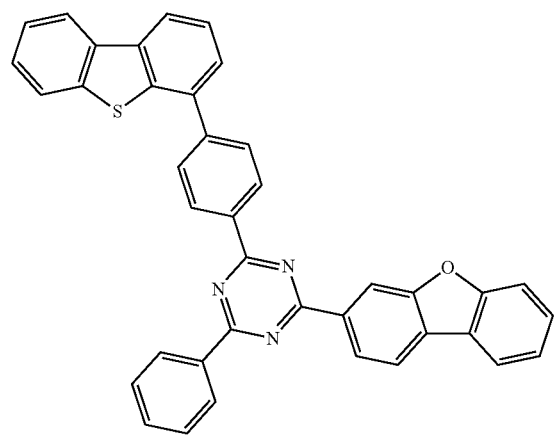
P-32
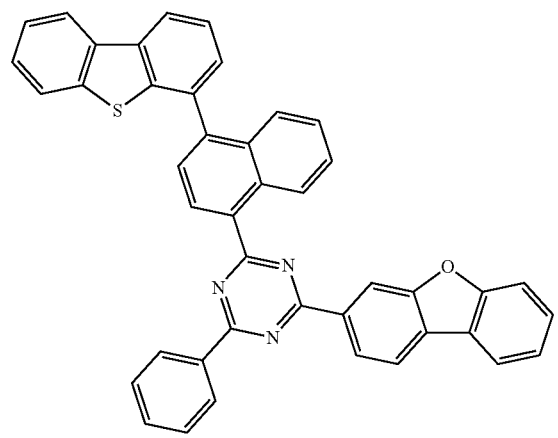

P-33
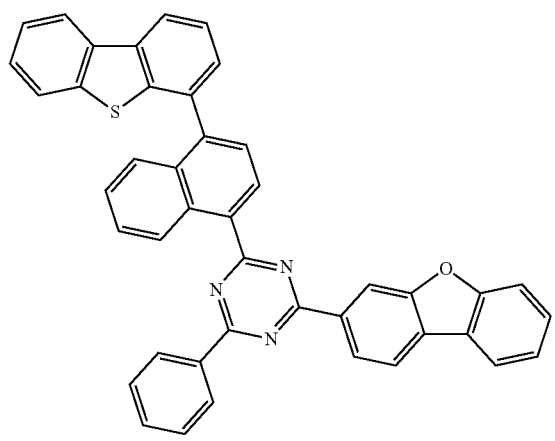
P-34
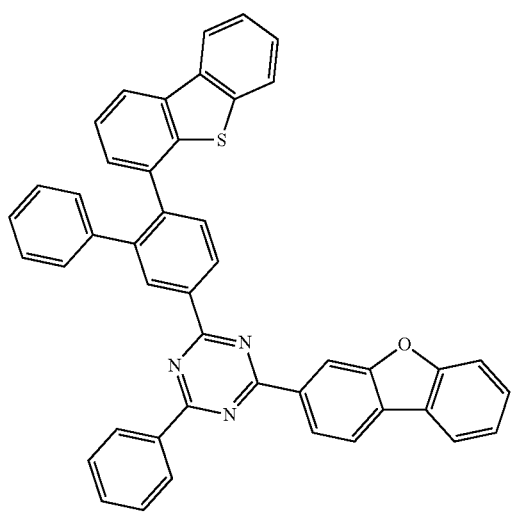
P-35
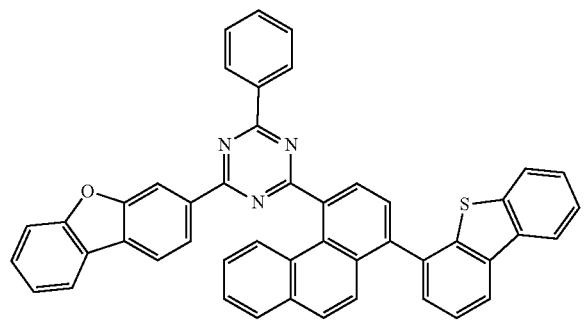
P-36
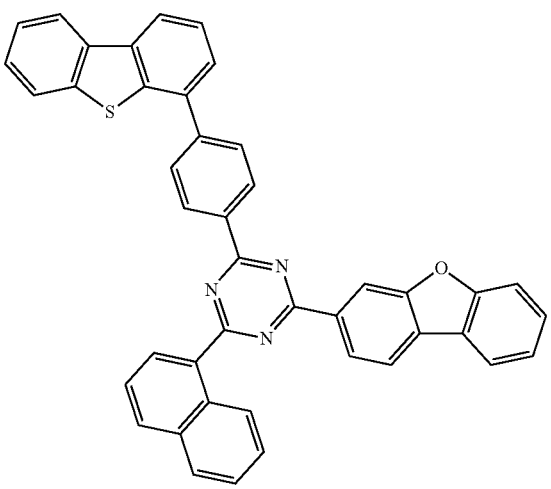
P-37
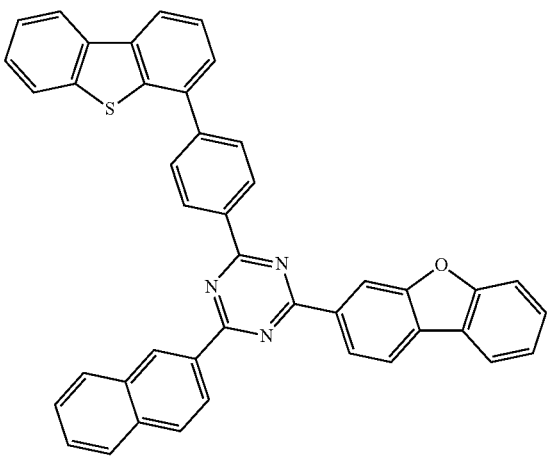
P-38
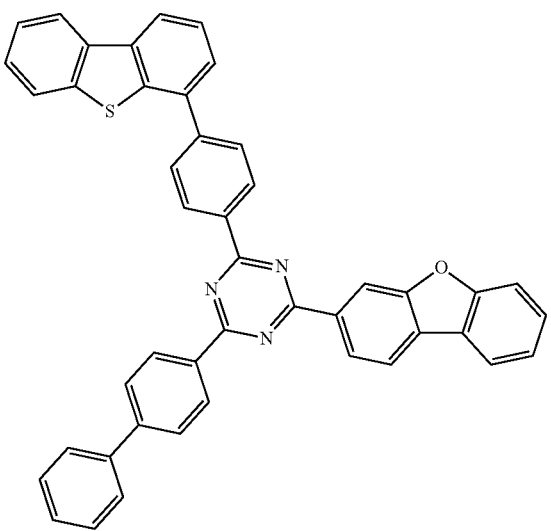

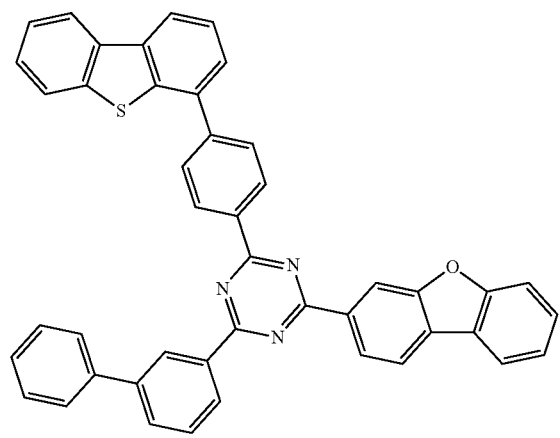
P-39
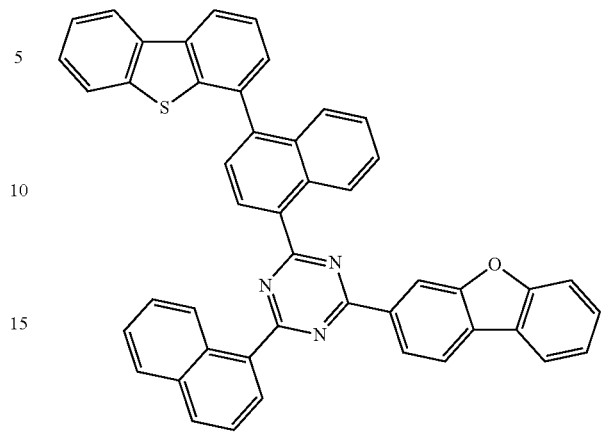
P-42
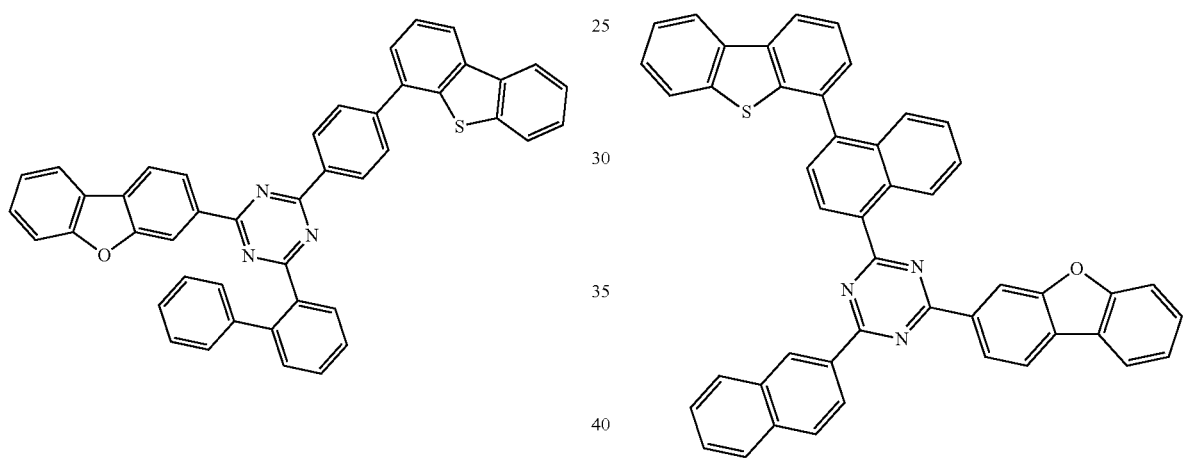
P-40
P-43
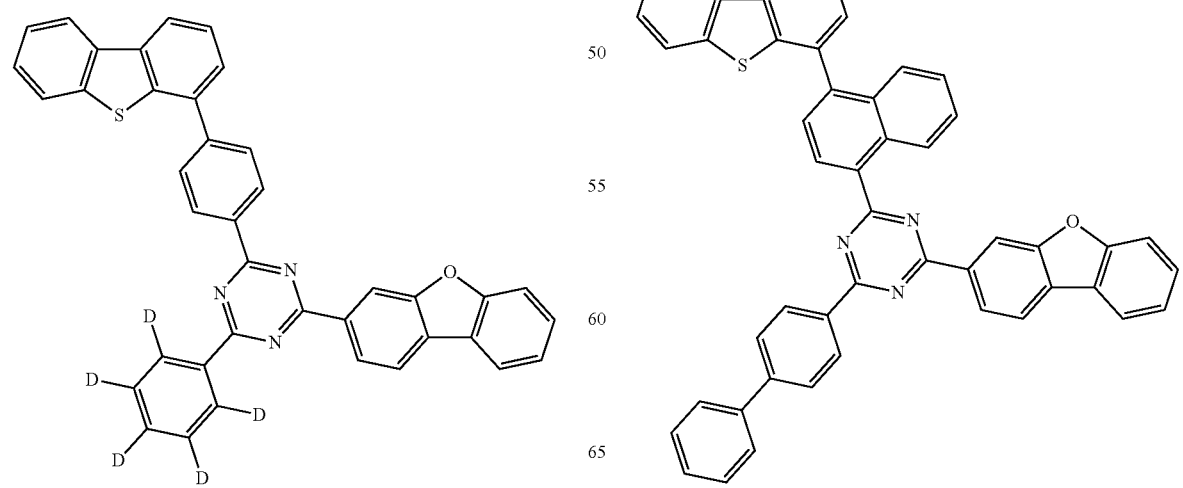
P-41
P-44

P-45
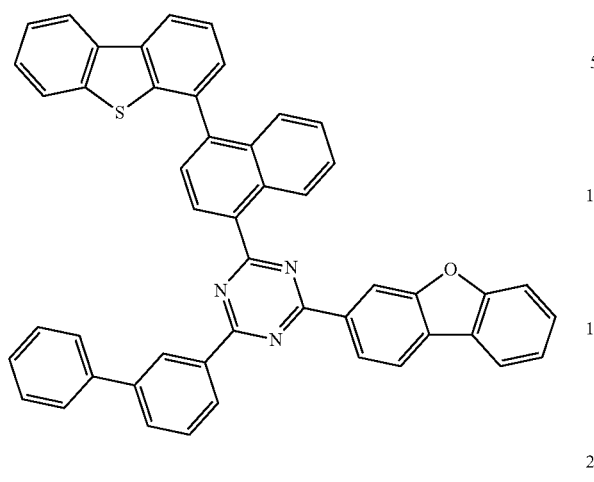
P-46
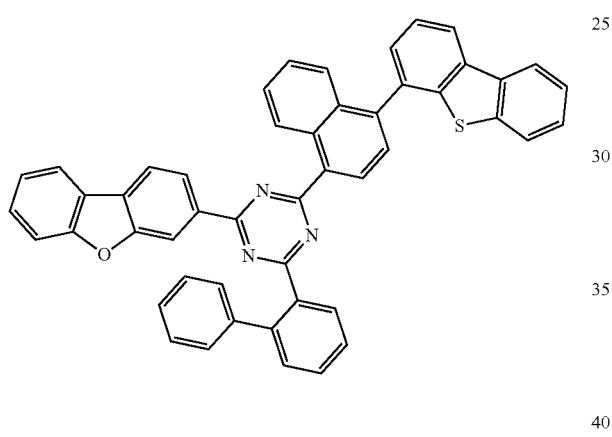
P-47
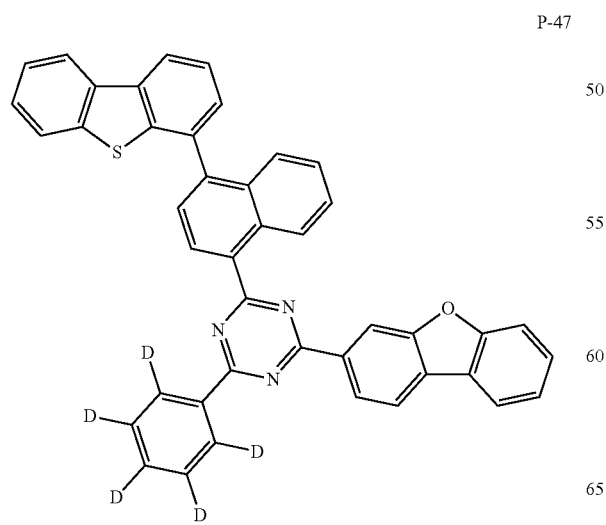
P-48
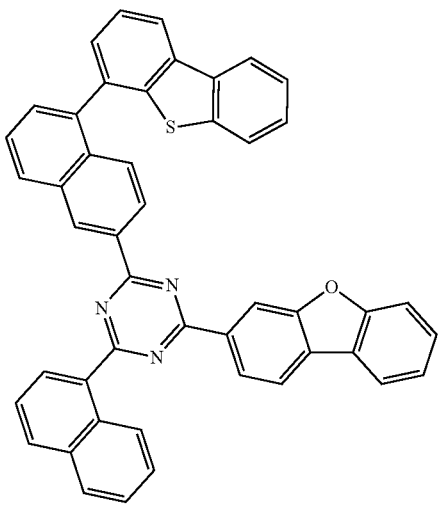
P-49
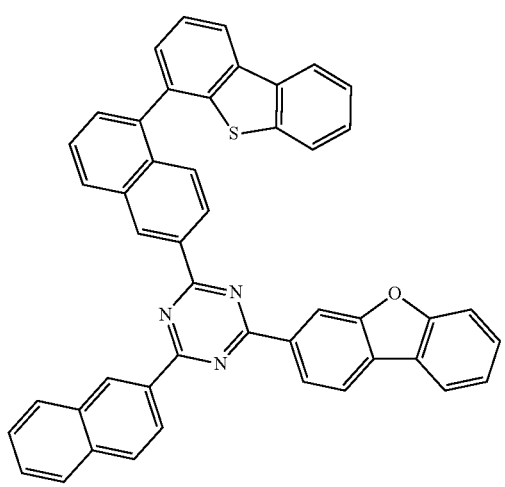
P-50
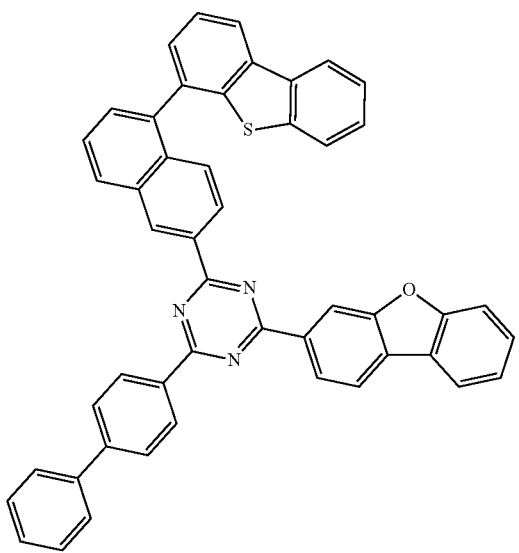

P-51
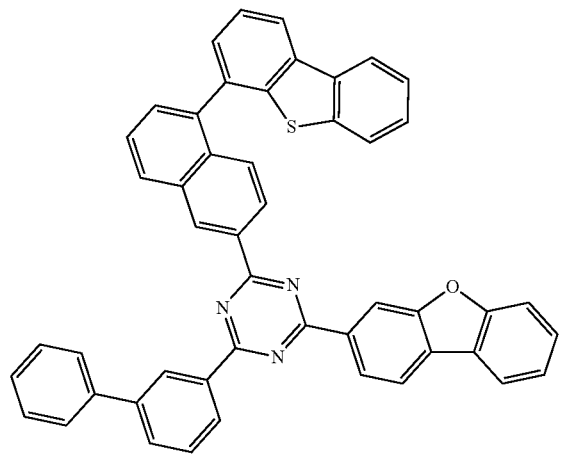
P-52
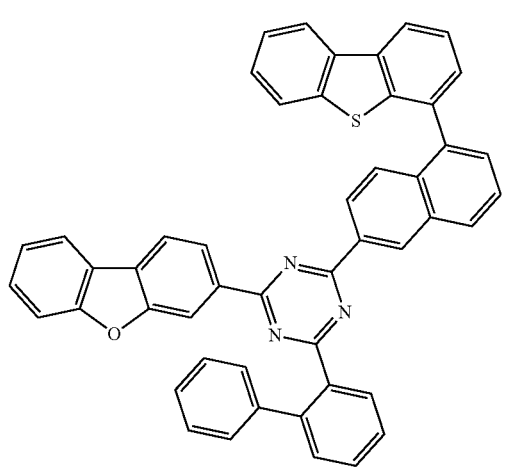
P-53
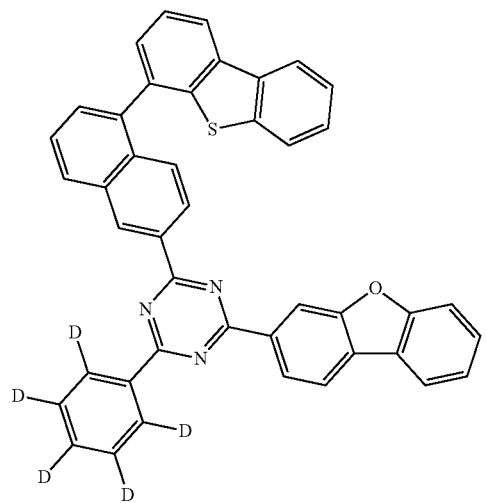
P-54
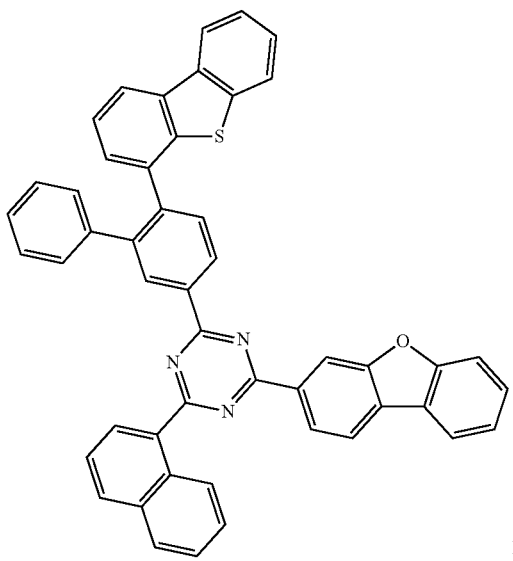
P-55
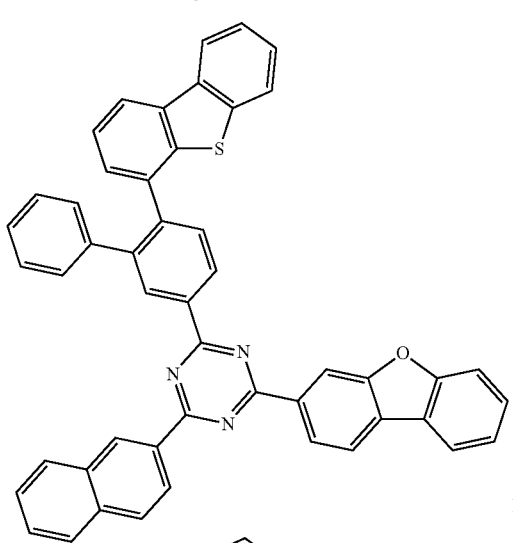
P-56
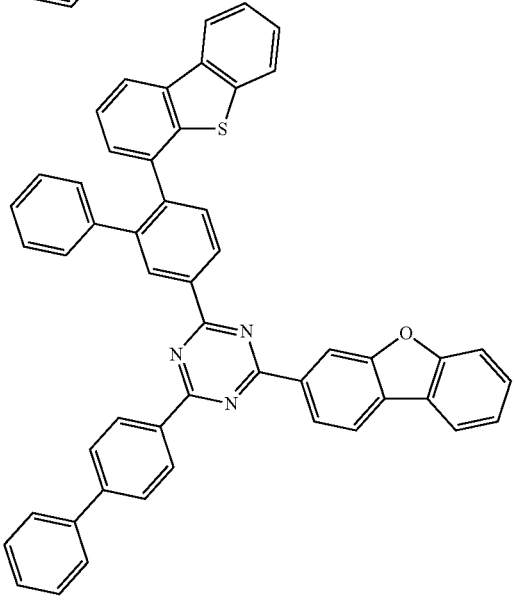

P-57
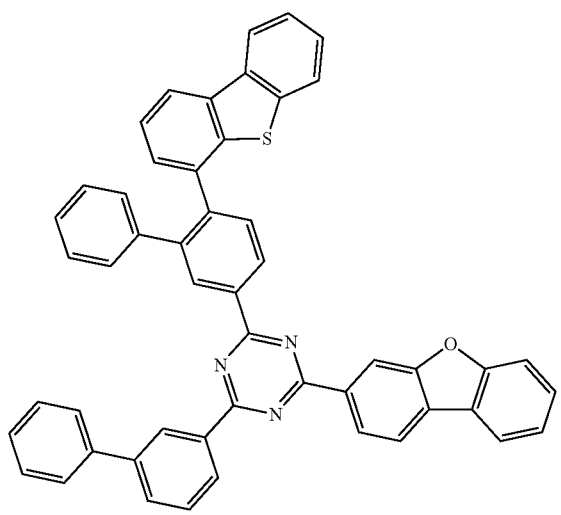
P-58
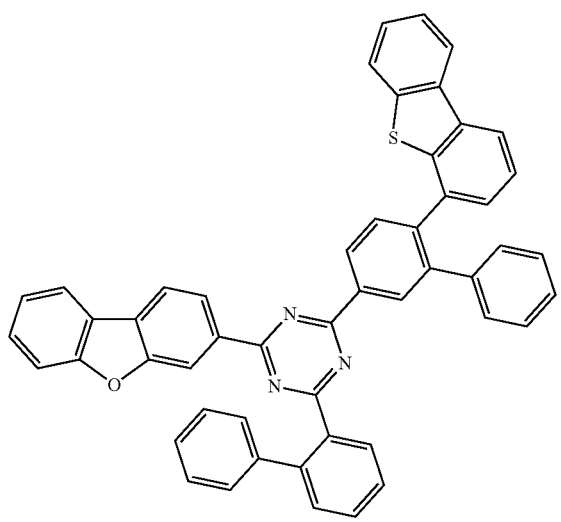
P-59
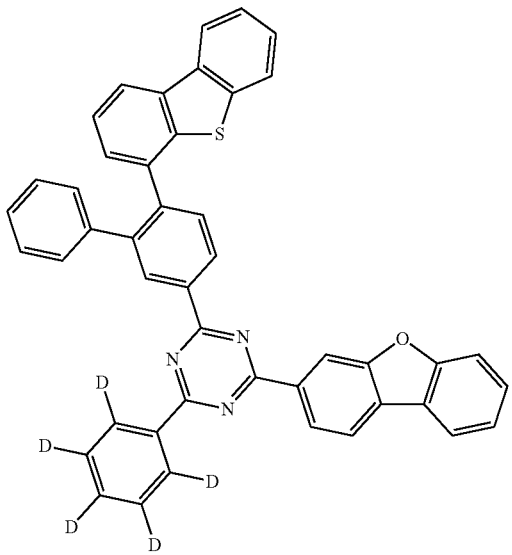
P-60
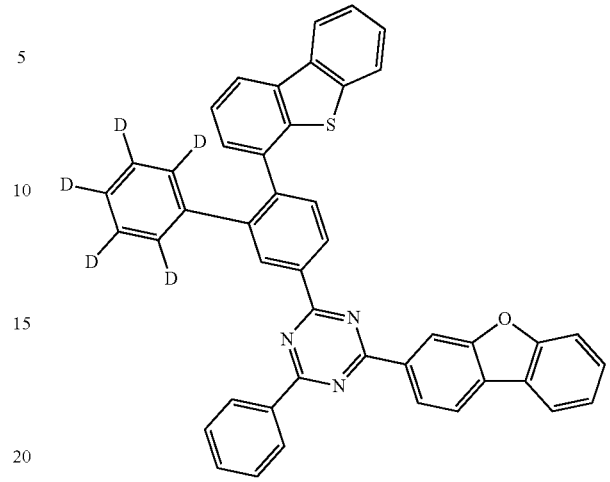
P-61
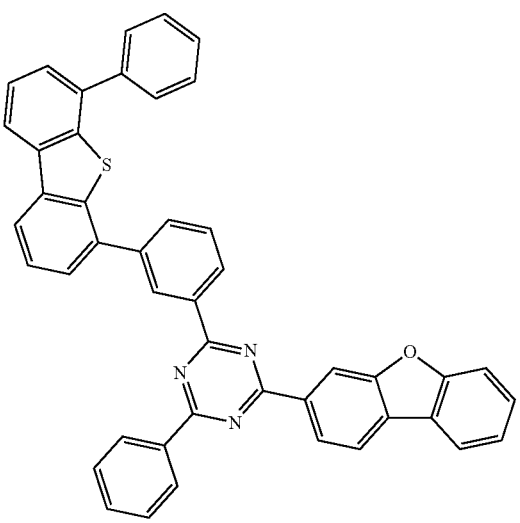
P-62
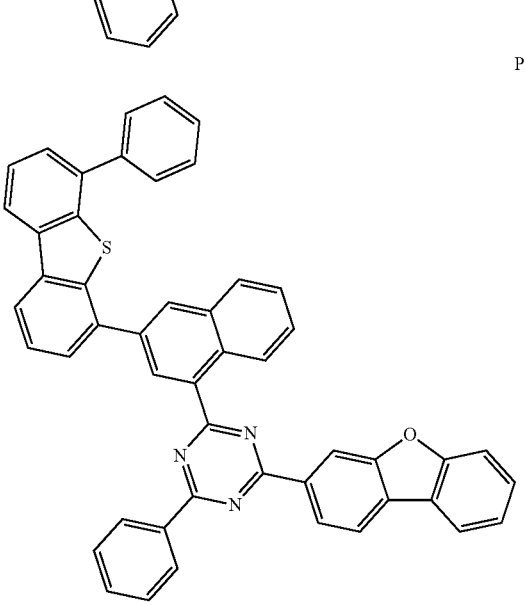

P-63
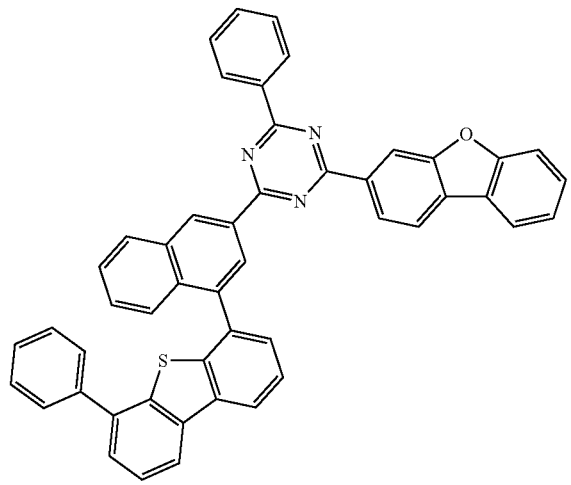
P-64
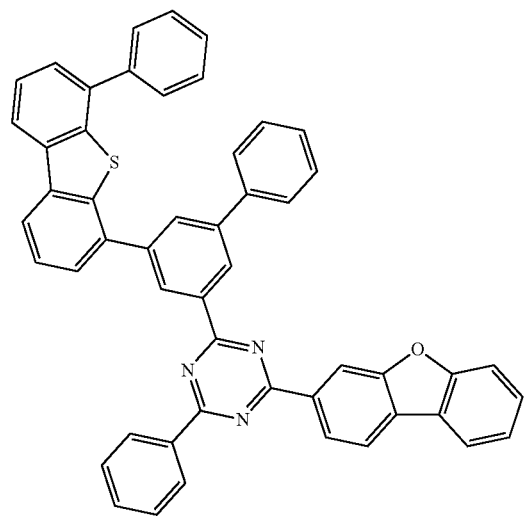
P-65
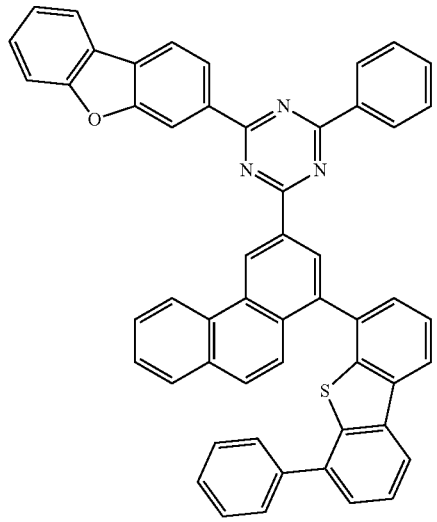
P-66
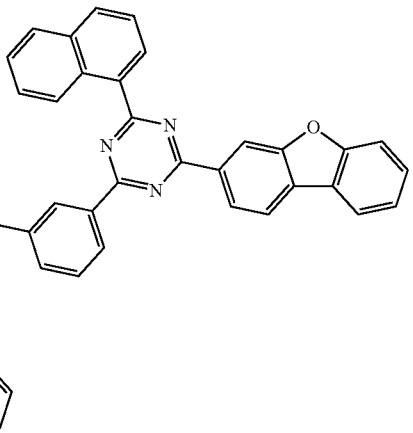
P-67
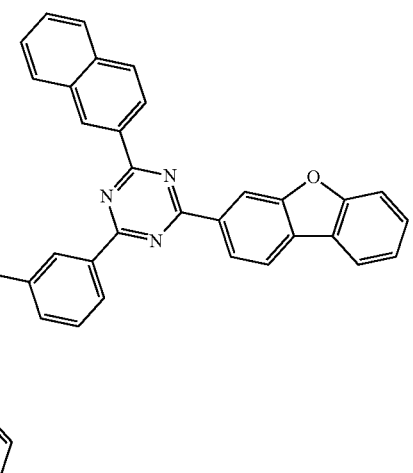
P-68
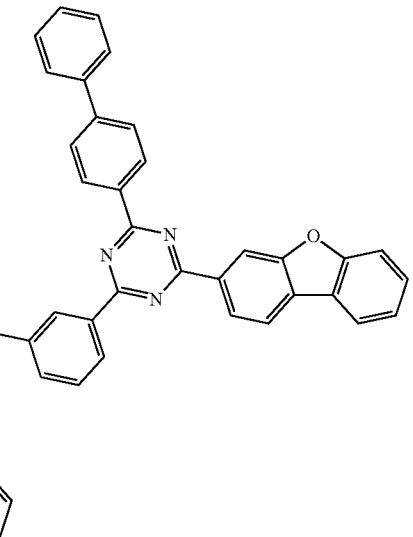

P-69
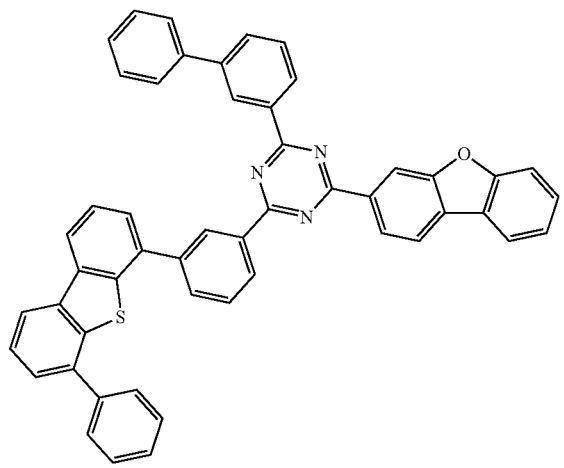
P-70
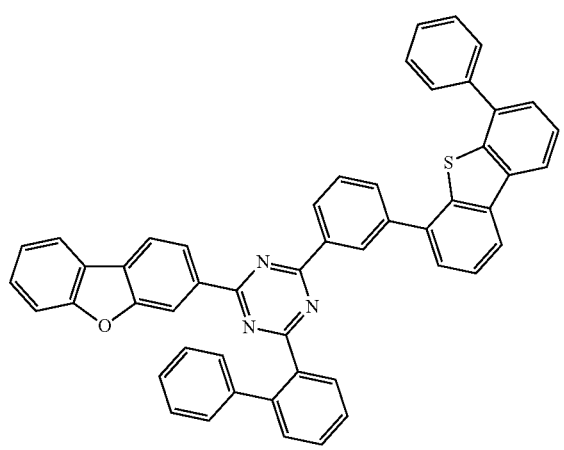
P-71
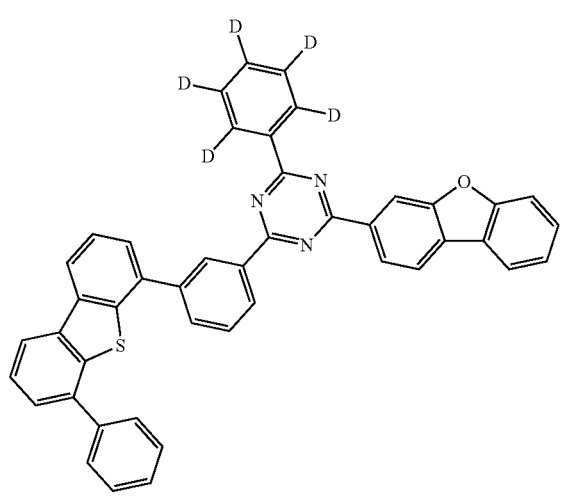
P-72
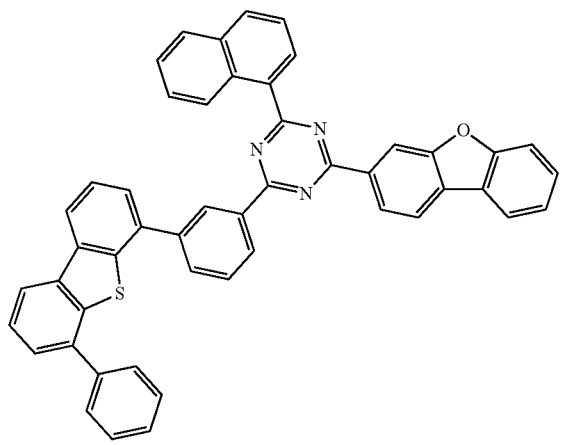
P-73
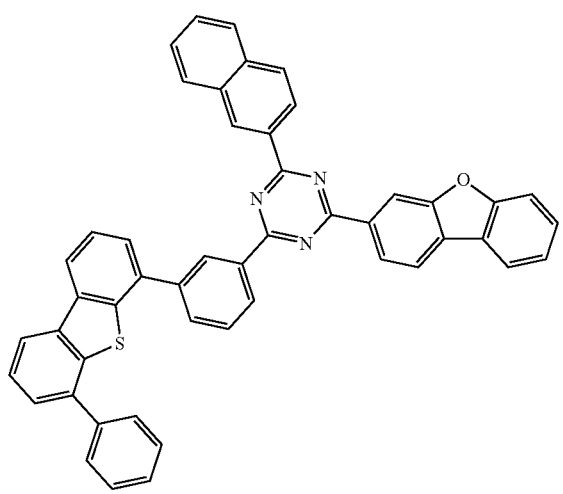
P-74
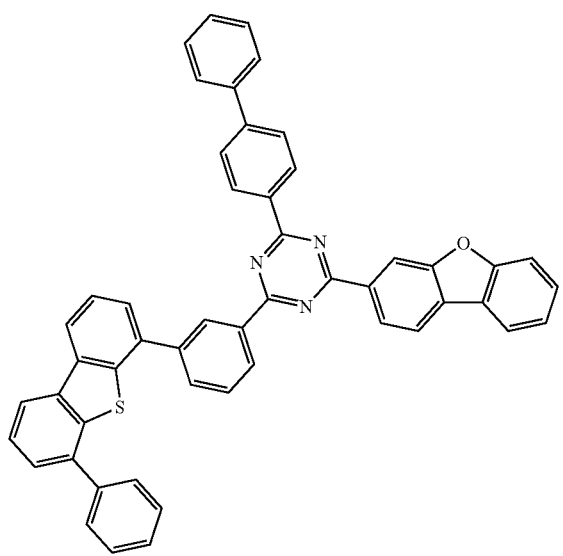

P-75
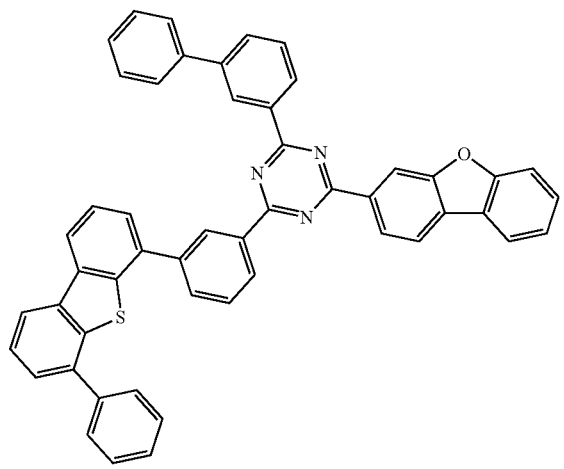
P-76
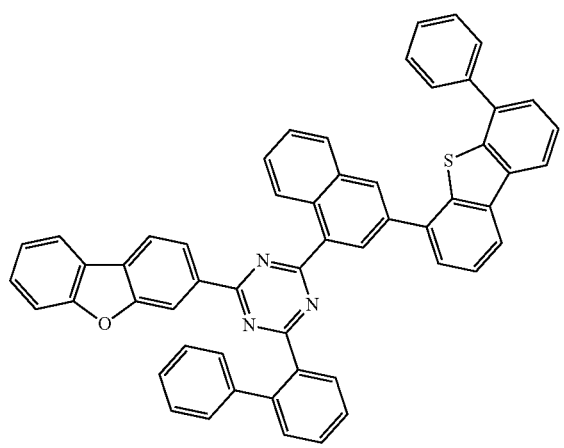
P-77
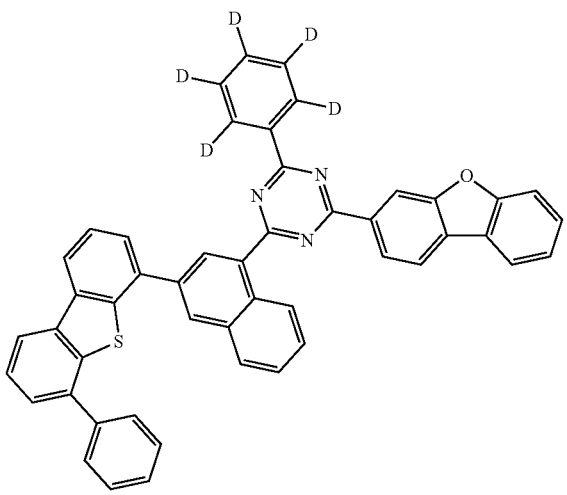
P-78
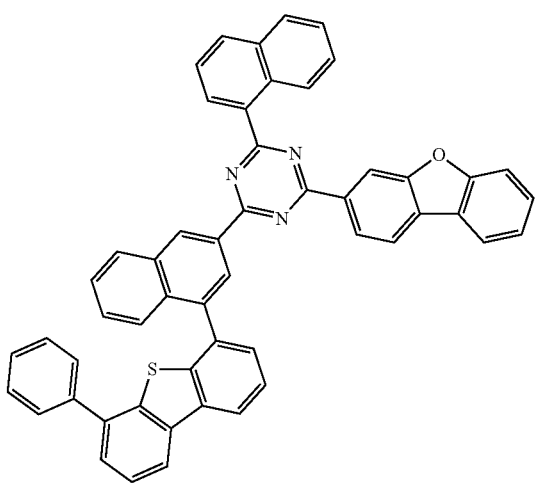
P-79
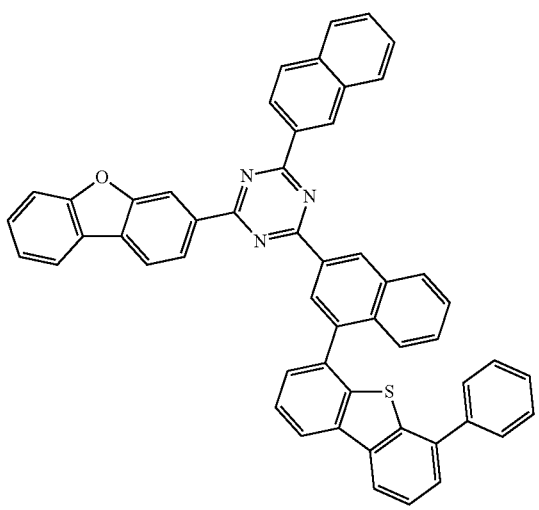
P-80
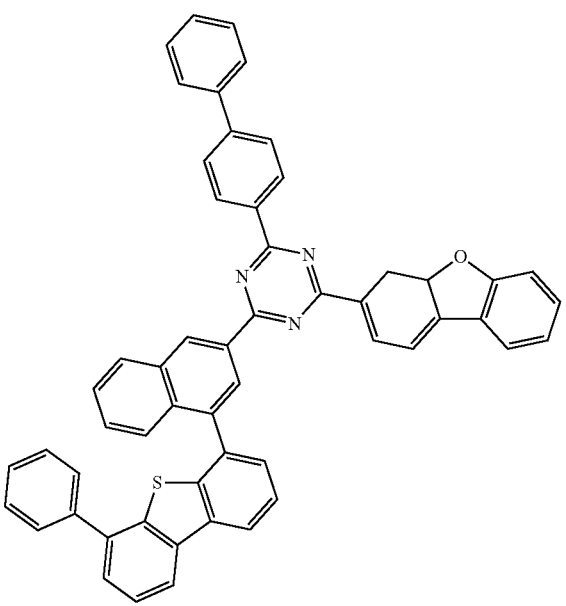

P-81
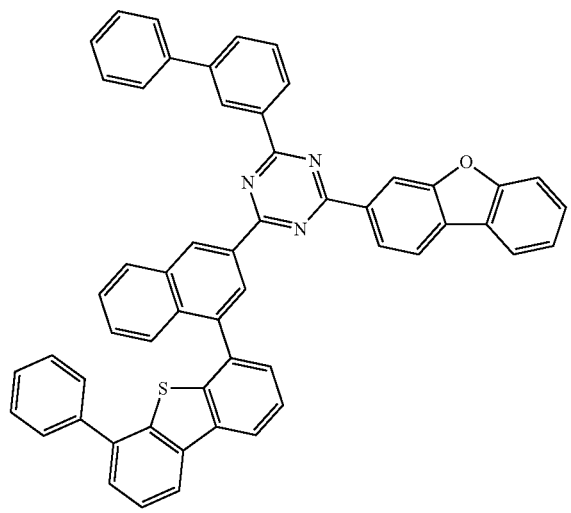
P-82
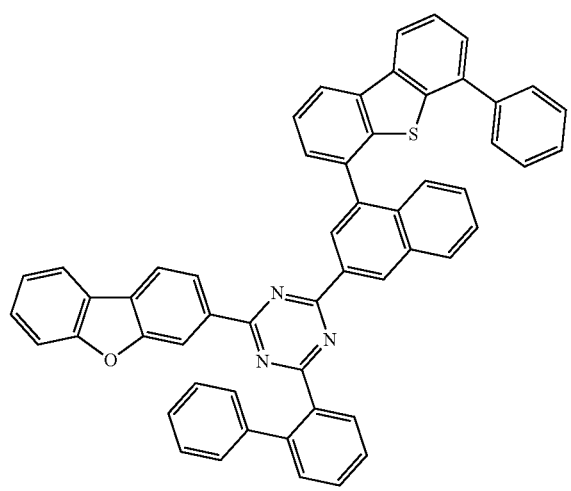
P-83
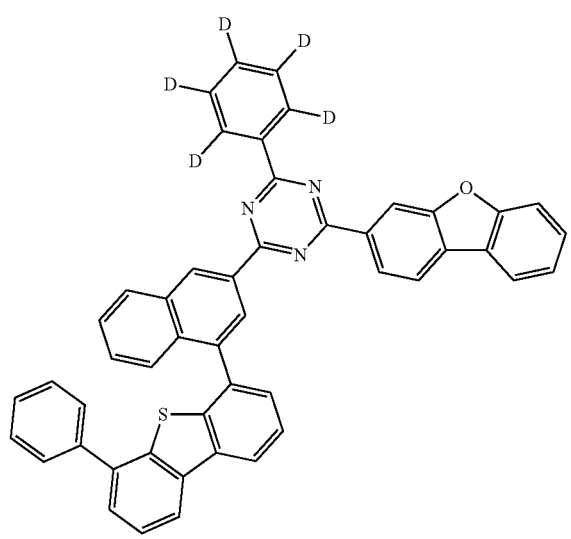
P-84
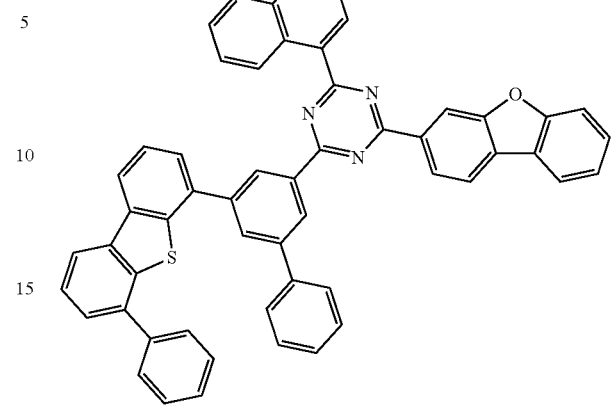
P-85
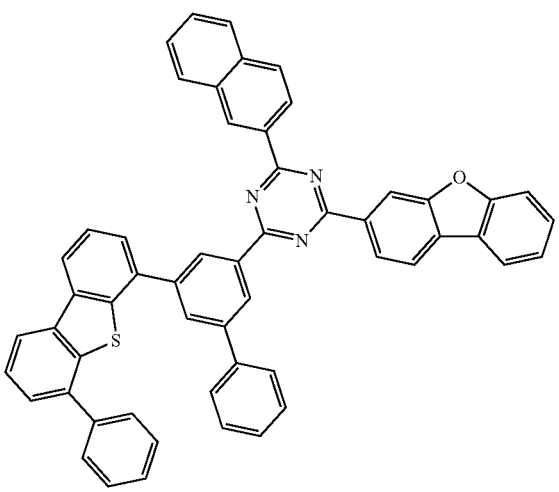
P-86
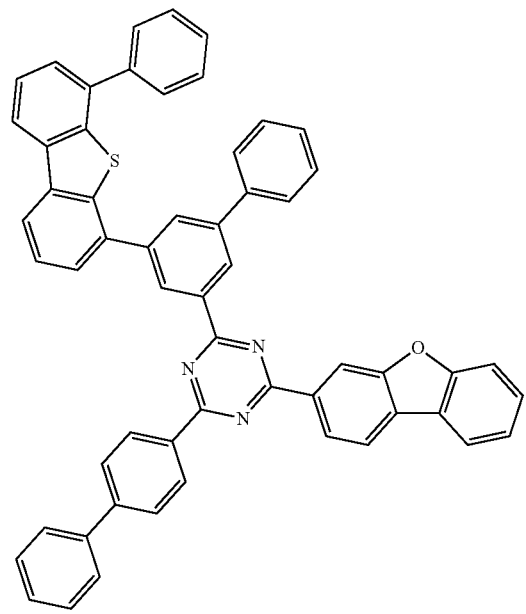

P-87
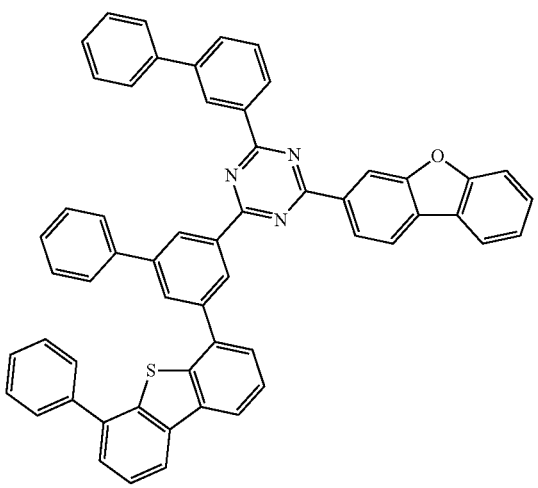
P-88
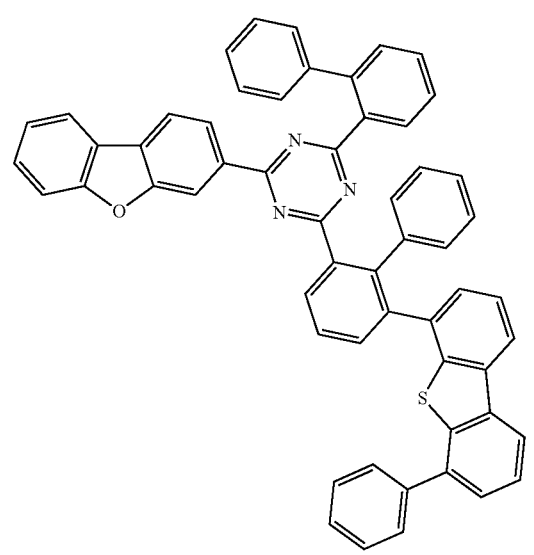
P-89
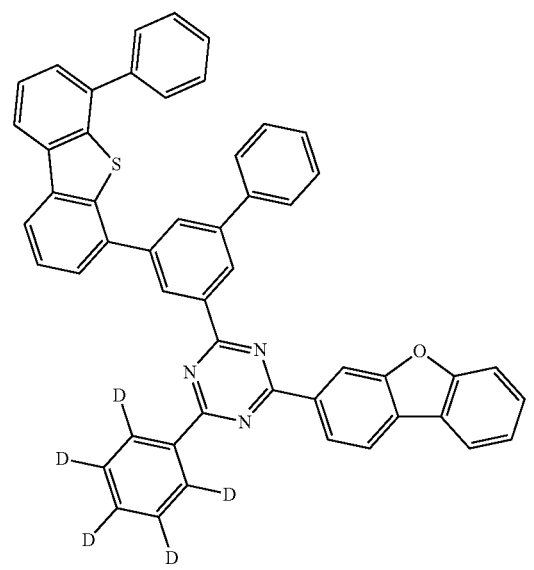
P-90
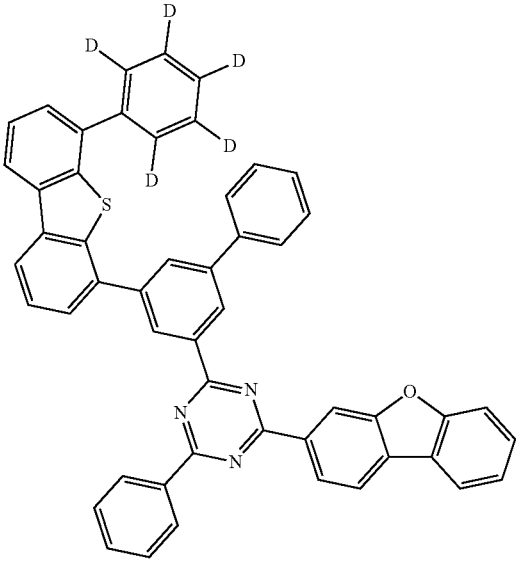
P-91
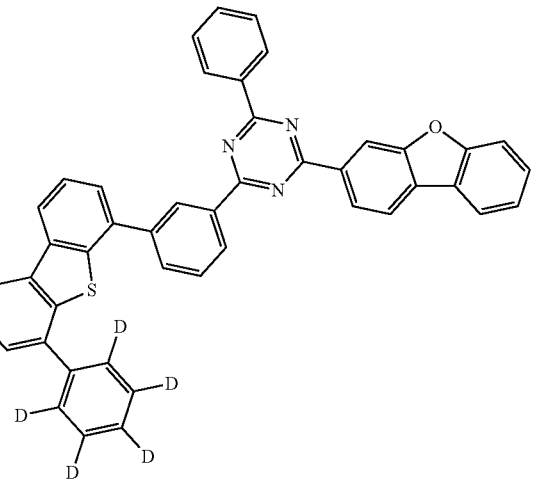
P-92
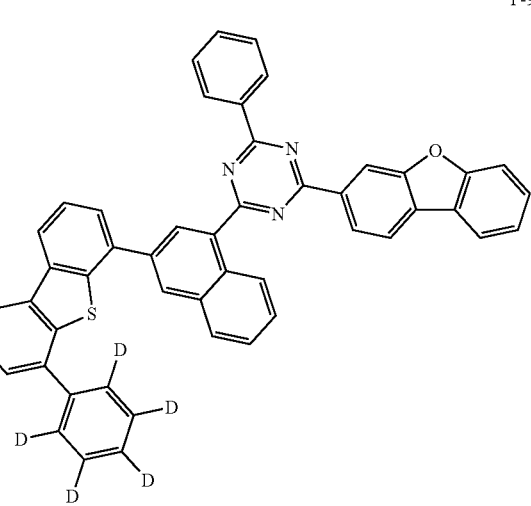

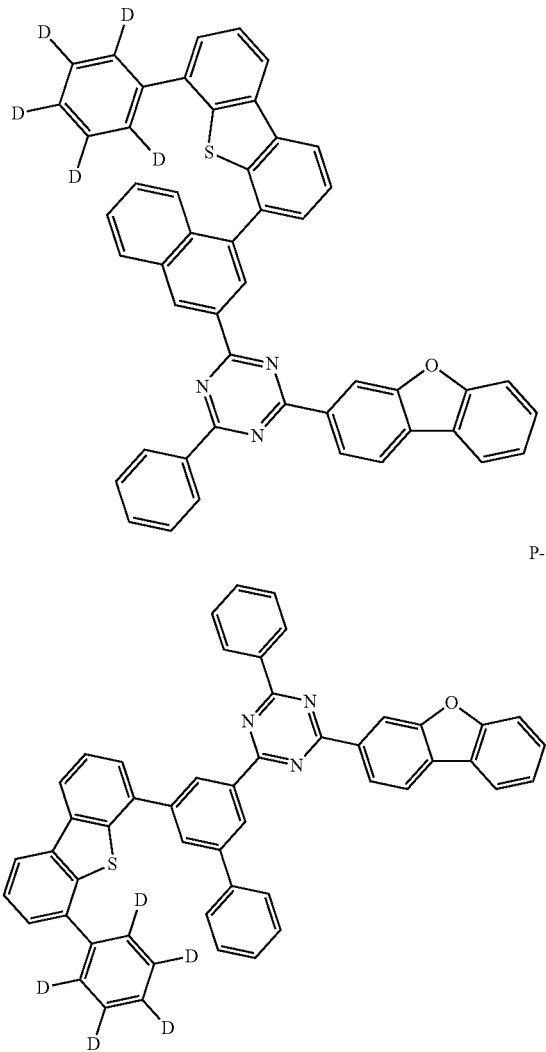

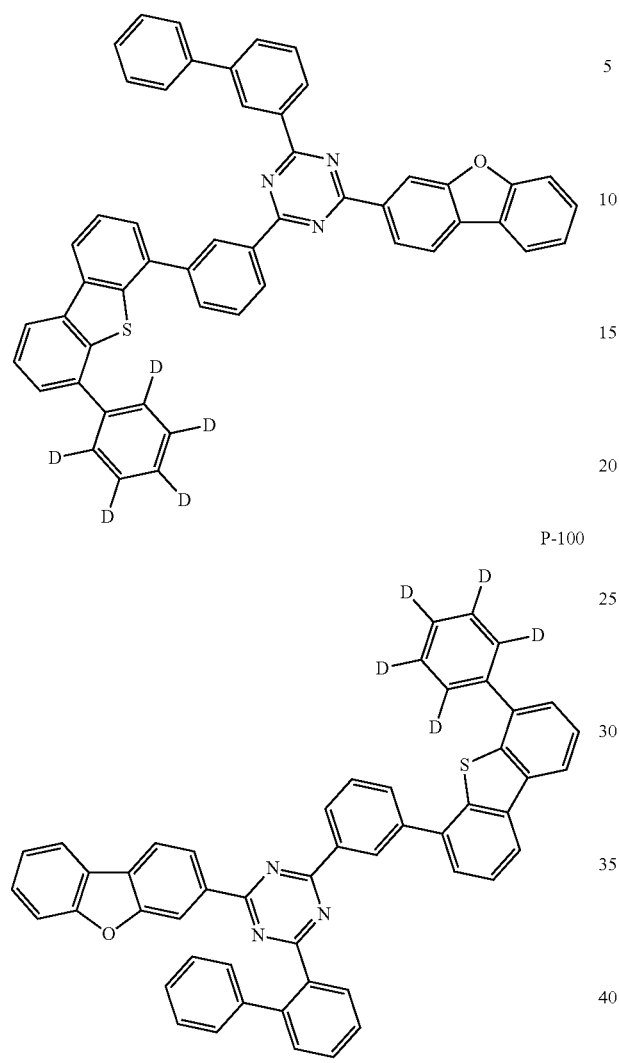

P-104
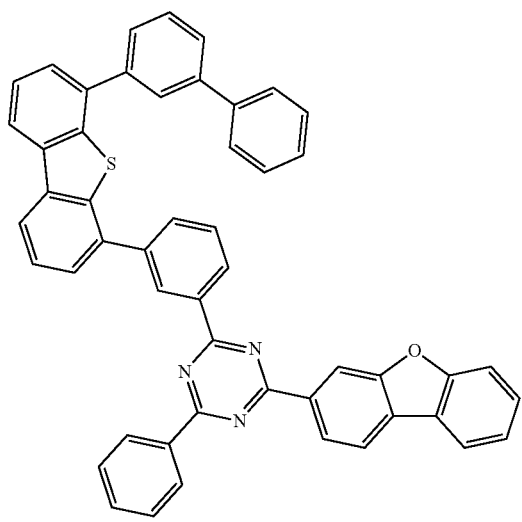
P-105
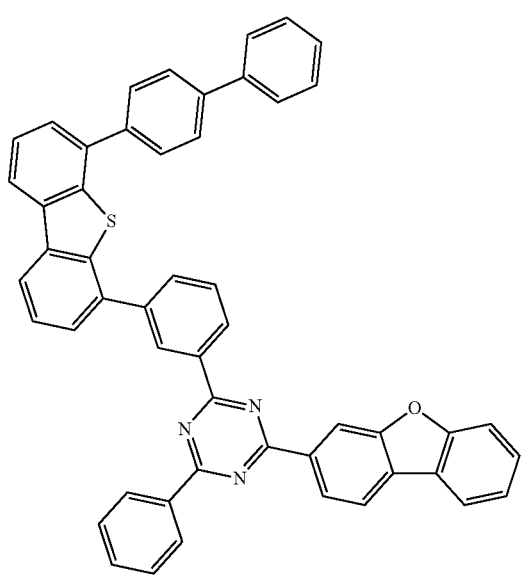
P-106
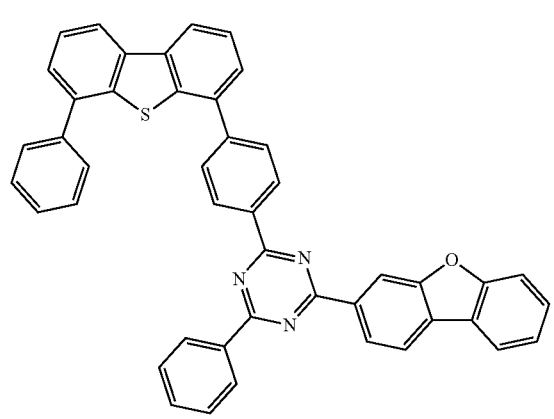
P-107
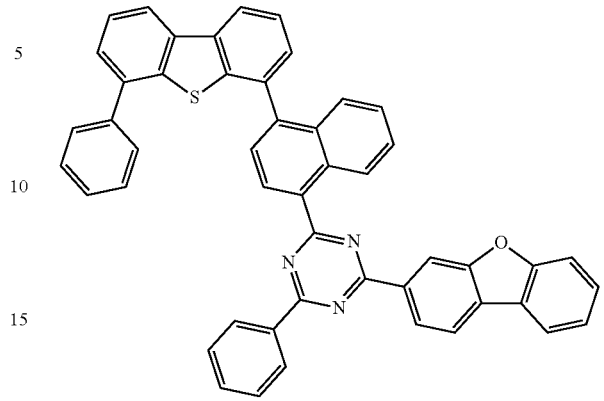
P-108
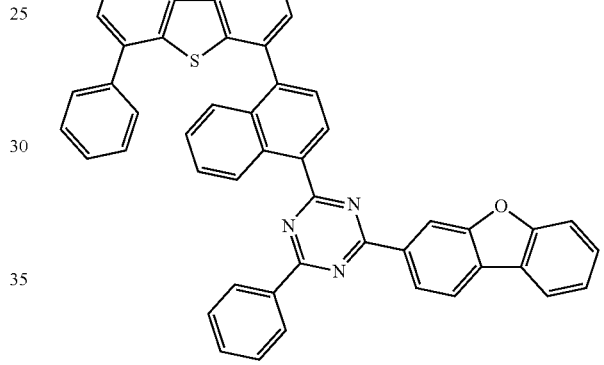
P-109
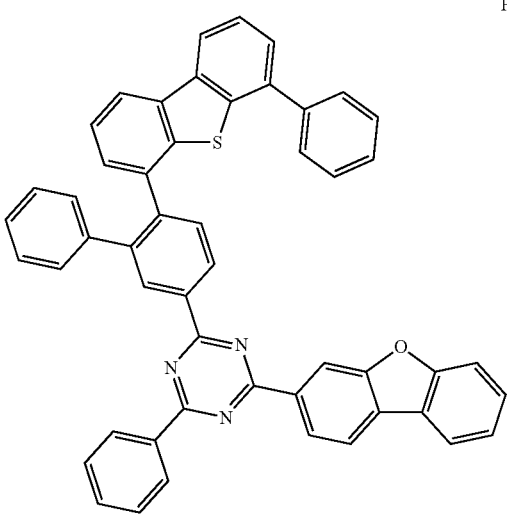

P-110
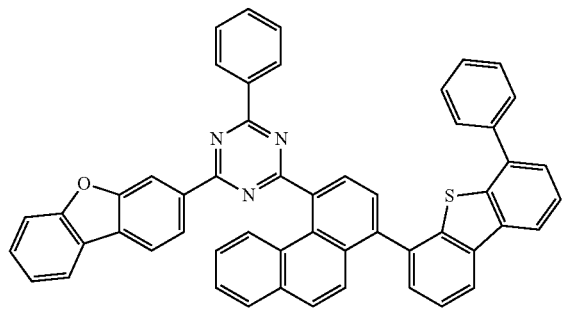
P-111
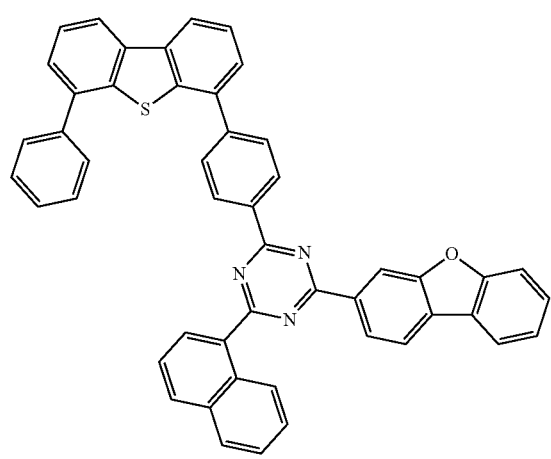
P-112
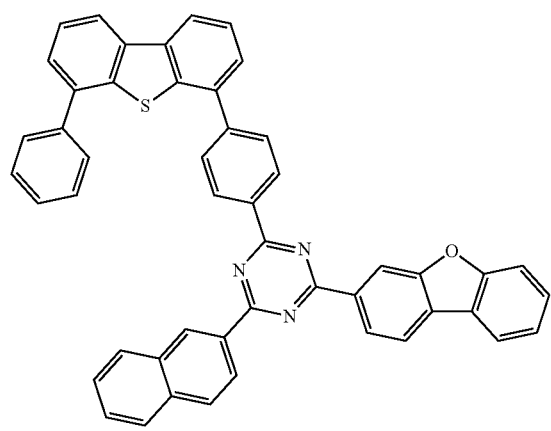
P-113
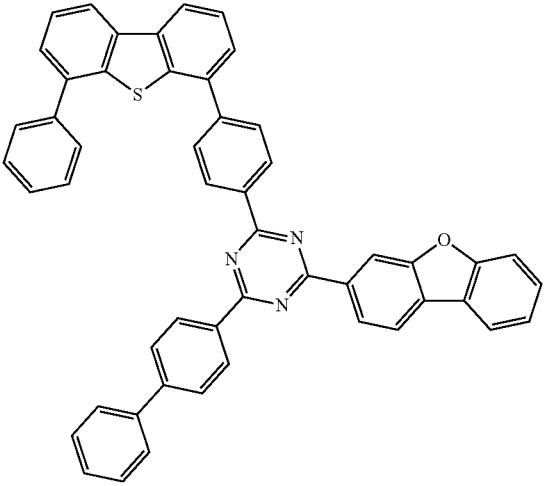
P-114
P-115
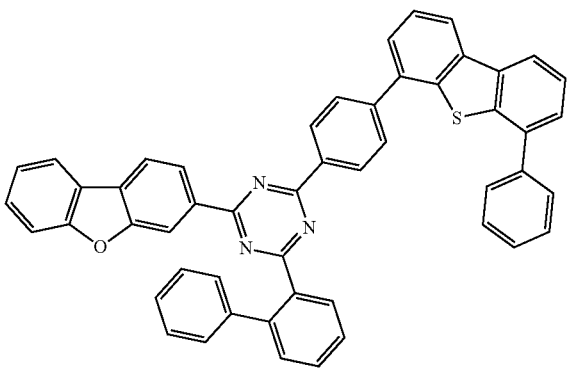

P-116
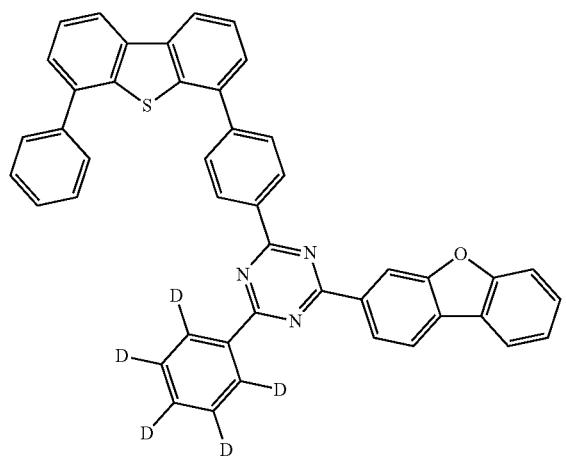
P-119
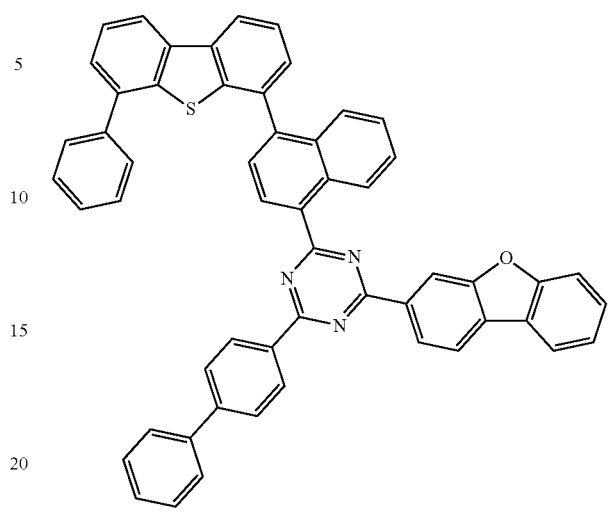
P-117
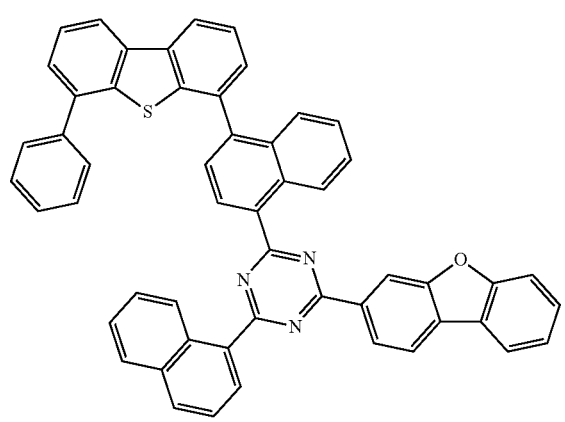
P-120
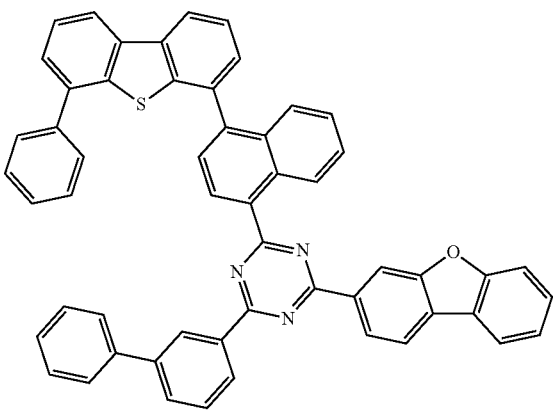
P-118
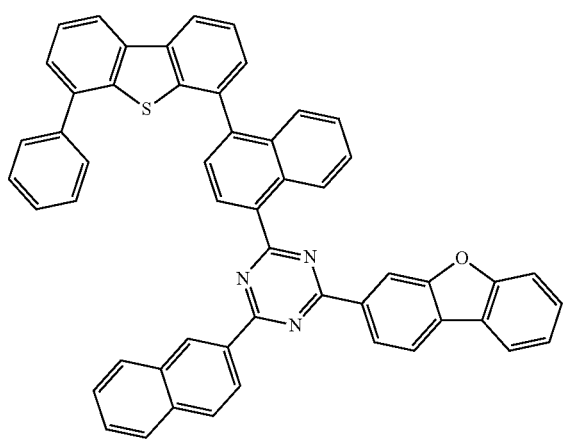
P-121
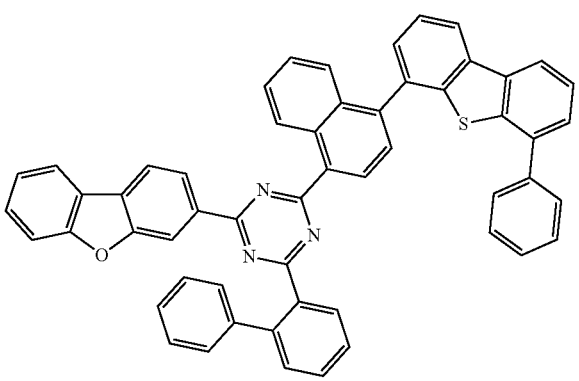

P-122
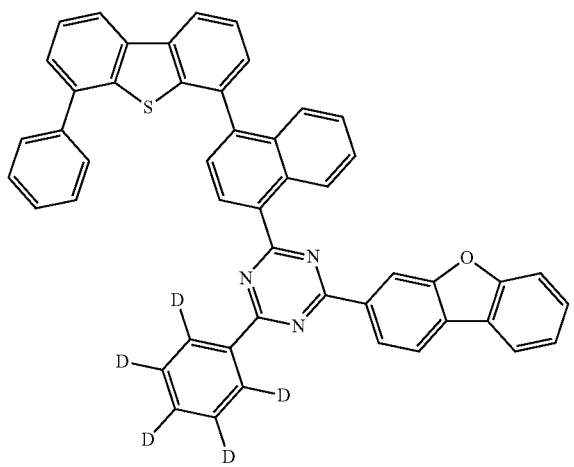
P-125
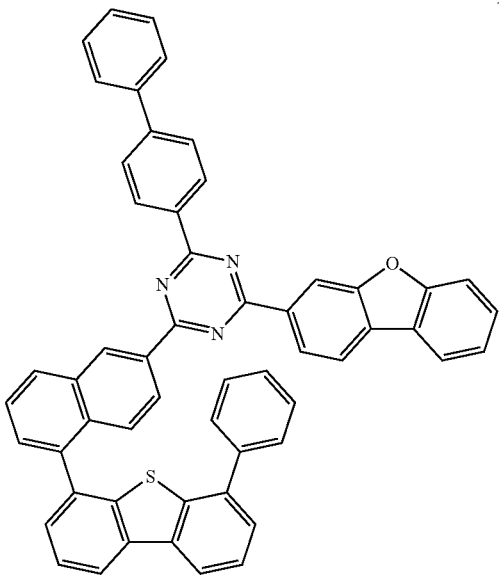
P-123
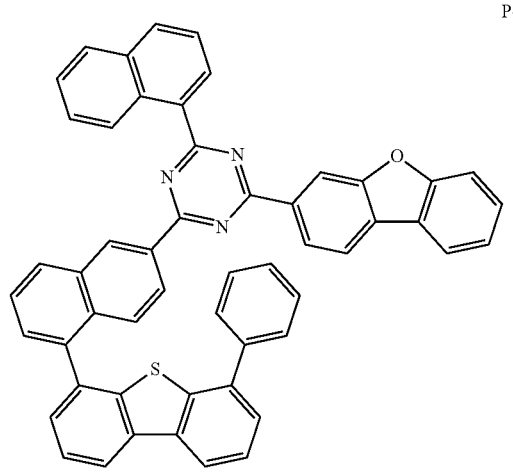
P-126
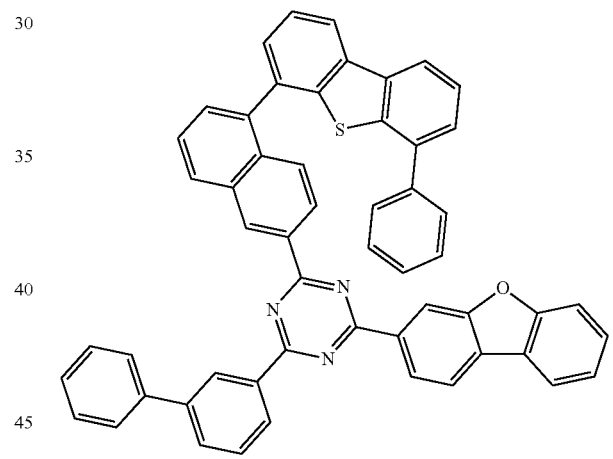
P-124
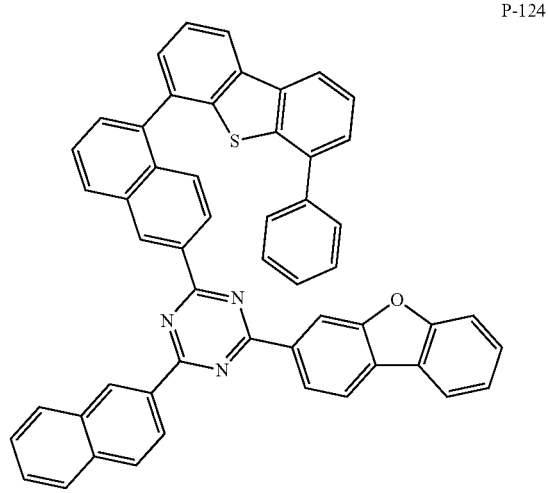
P-127
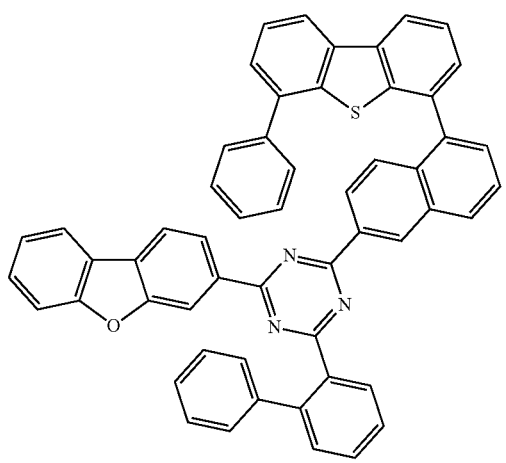

P-128
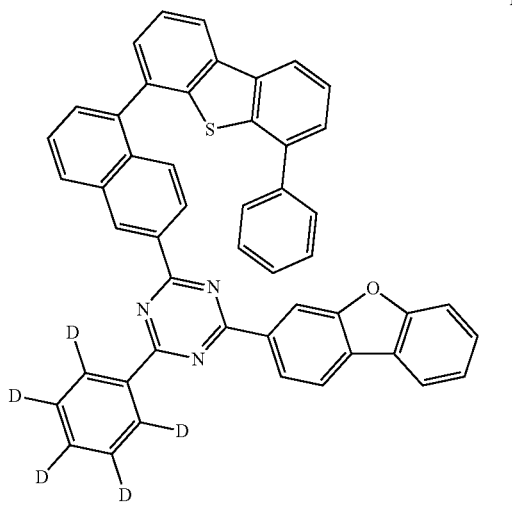
P-129
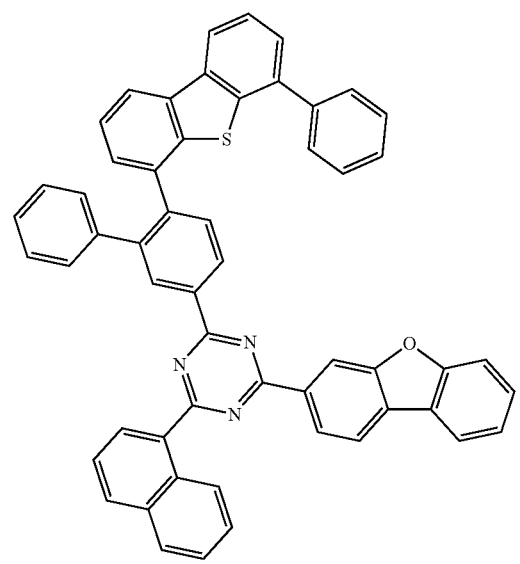
P-130
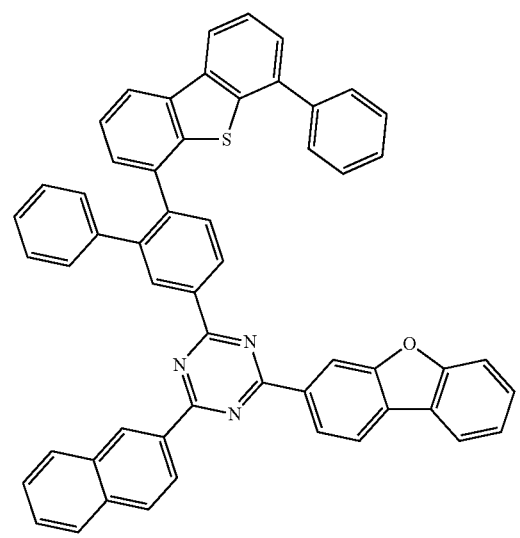
P-131
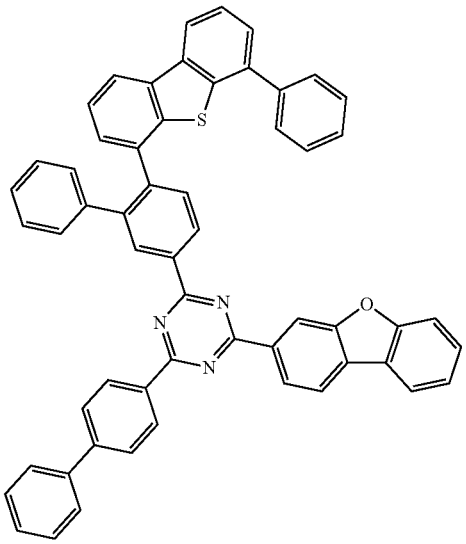
P-132
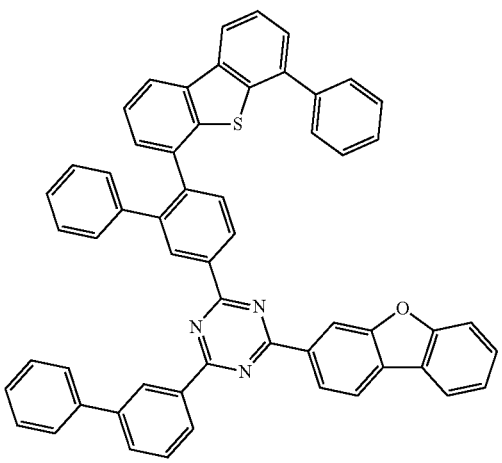
P-133
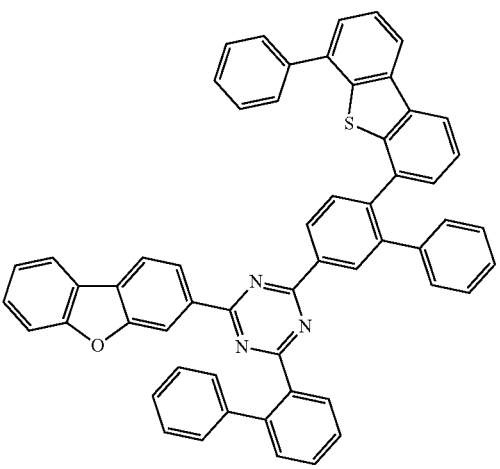

P-134
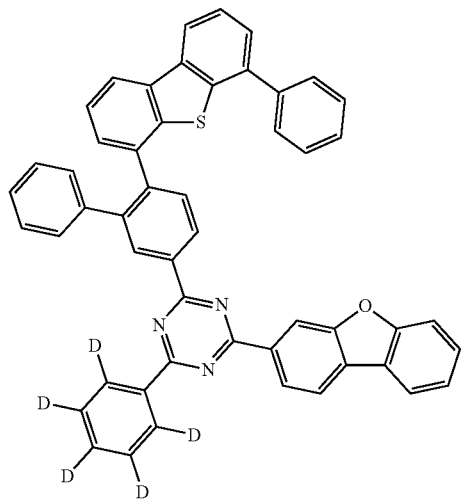
P-135
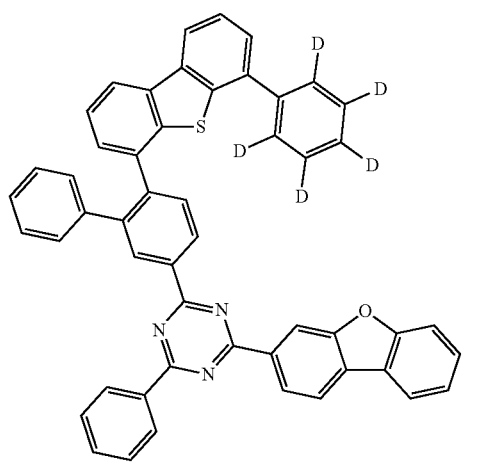
P-136
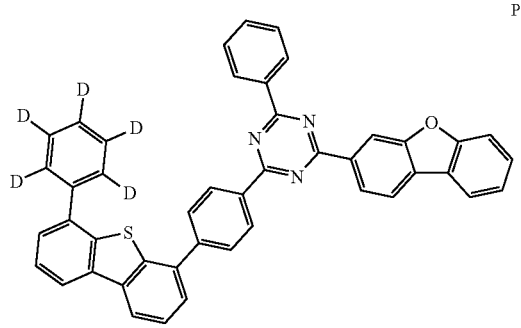
P-137
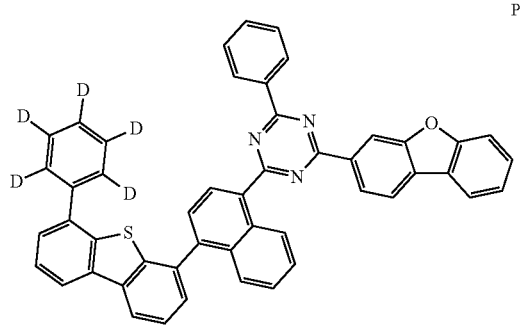
P-138
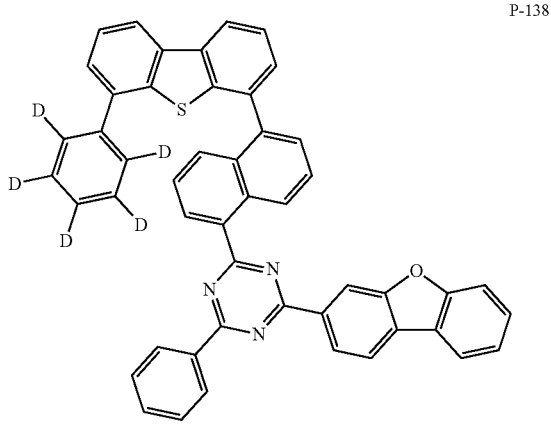
P-139
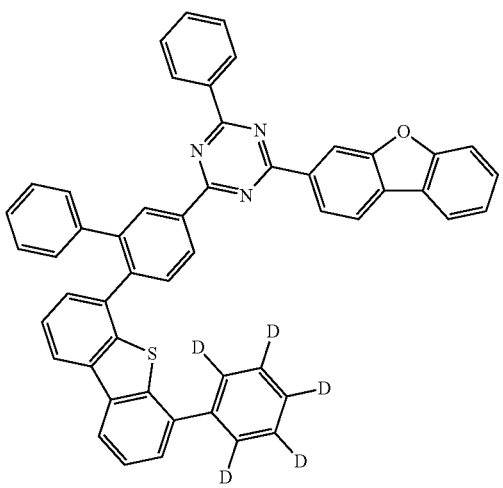
P-140
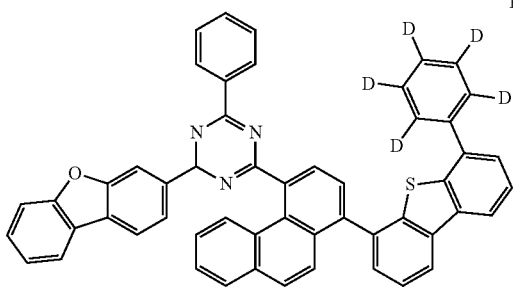
P-141
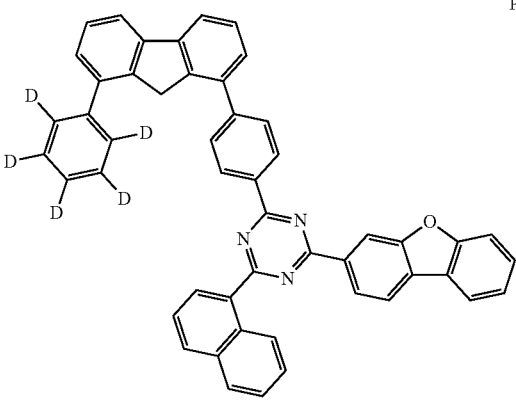

P-142
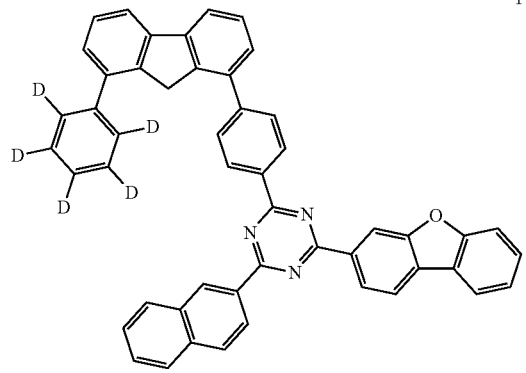
P-143
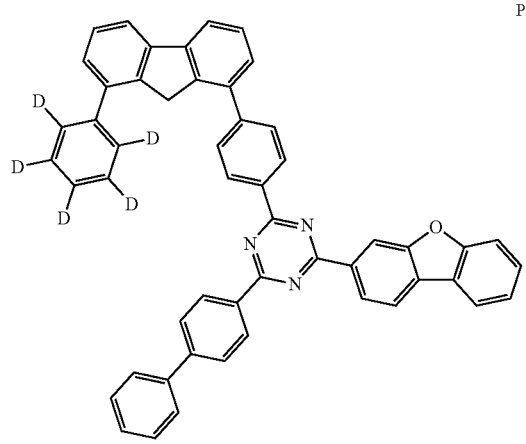
P-144
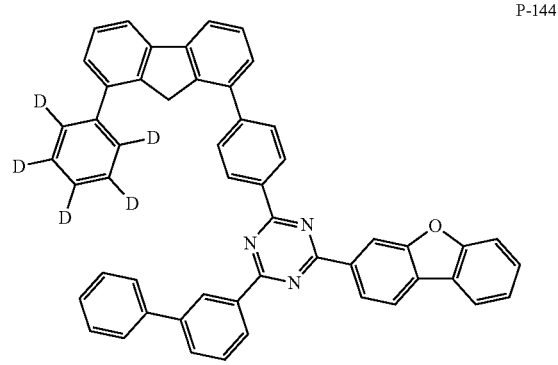
P-145
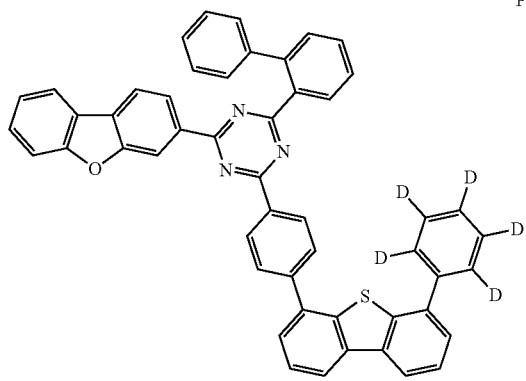
P-146
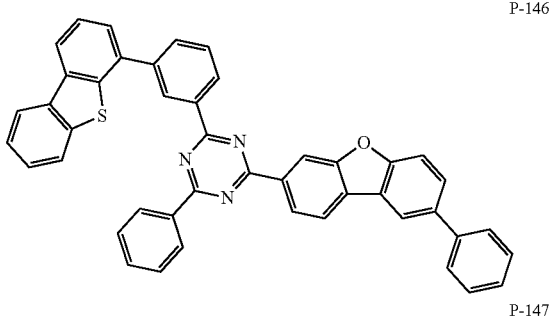
P-147
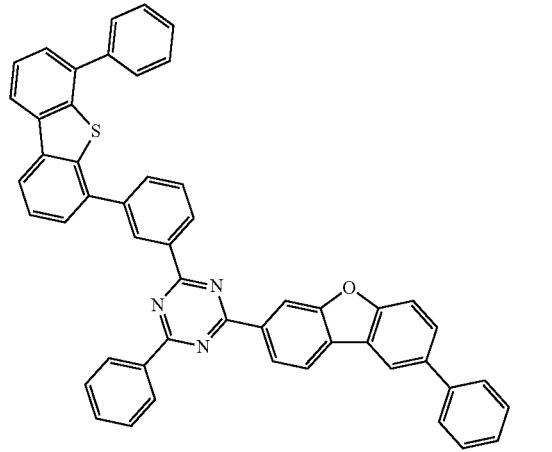
P-148
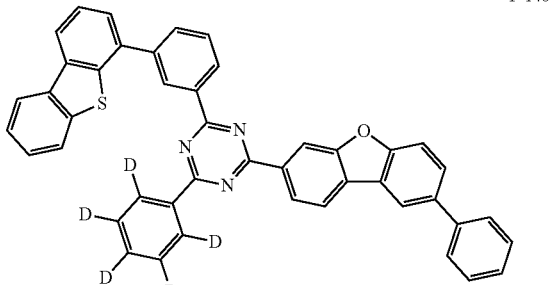
P-149
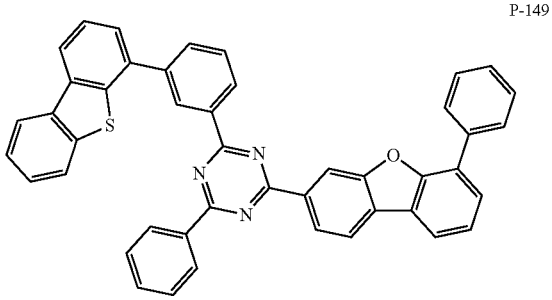
P-150
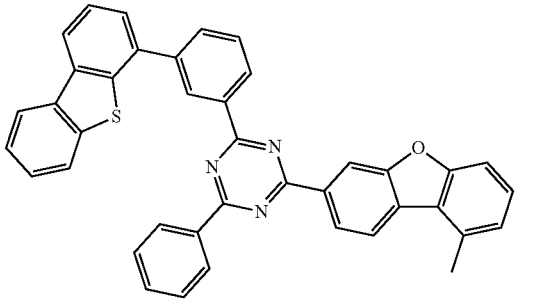

P-151
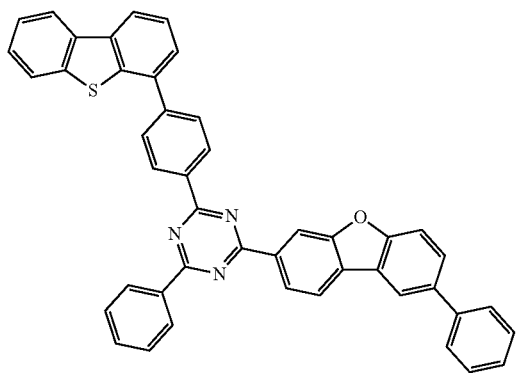
P-152
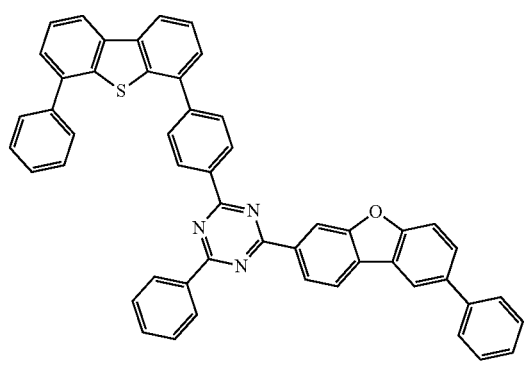
P-153
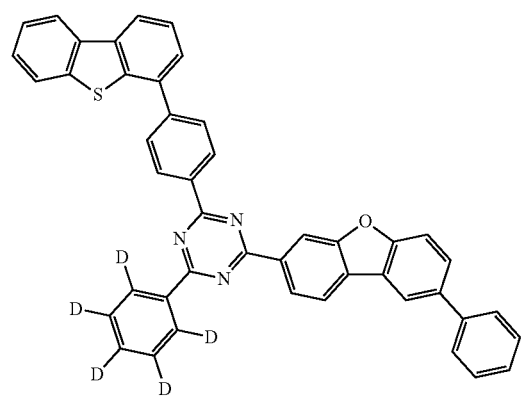
P-154
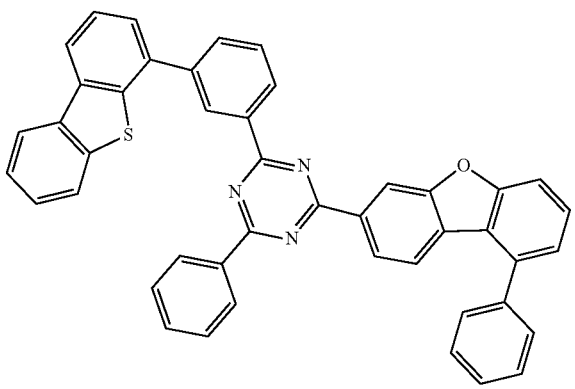
P-155
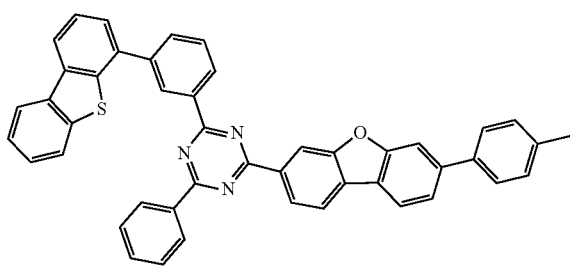
P-156
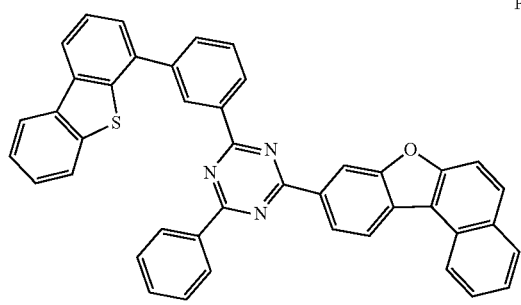
P-157
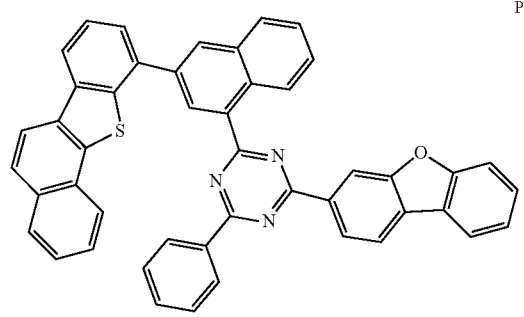
P-158
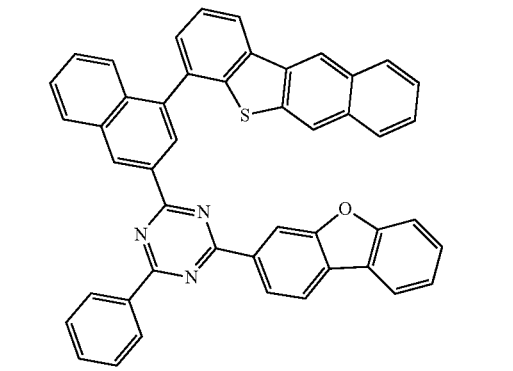
P-159
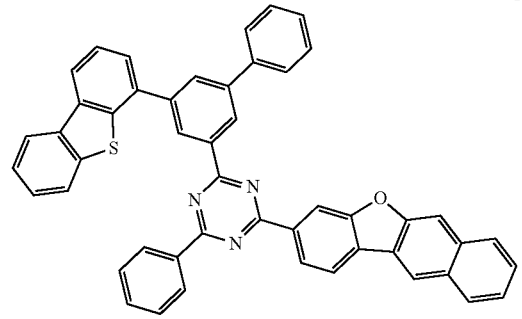

-continued

P-160

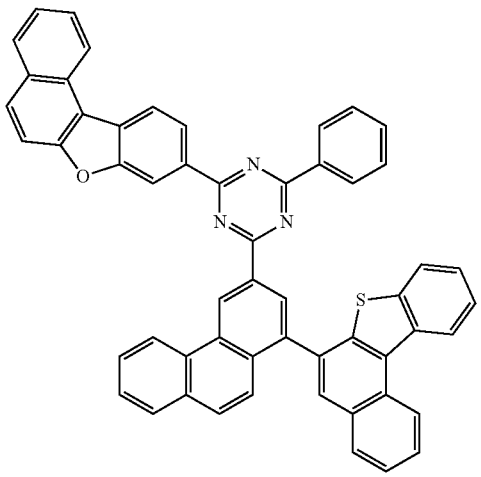

In another aspect, the present invention provides an organic electric element comprising a first electrode; a second electrode; and an organic material layer disposed between the first electrode and the second electrode and including a compound included in Formula (1).

Wherein the organic material layer comprises at least one of a hole injection layer, a hole transport layer, an emitting auxiliary layer, an emitting layer, an electron transport auxiliary layer, an electron transport layer and an electron injection layer, wherein at least one of the hole injection layer, the hole transport layer, the emitting auxiliary layer, the emitting layer, the electron transport auxiliary layer, the electron transport layer and the electron injection layer comprises one compound or 2 or more compounds of Formula (1). Preferably, the compound is included in the emitting layer.

More specifically, the present invention provides an organic electronic element further comprising a compound represented by Formula (12) in the emitting layer.

<Formula (12)>

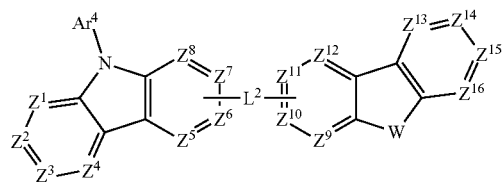

{In Formula (12),
1) $Z^1, Z^2, Z^3, Z^4, Z^5, Z^6, Z^7, Z^8, Z^9, Z^{10}, Z^{11}, Z^{12}, Z^{13}, Z^{14}, Z^{15}$ and $Z^{16}$ are each independently CR or N,
wherein R is hydrogen; a $C_6$-$C_{60}$ aryl group; a $C_3$-$C_{60}$ heterocyclic group including at least one heteroatom of O, N, S, Si, or P; a $C_1$-$C_{50}$ alkyl group; a $C_6$-$C_{60}$ arylamine group; a fluorene group; and is possible to form a ring by combining with neighboring groups,
2) $L^2$ is selected from the group consisting of a single bond; a $C_6$-$C_{60}$ arylene group; a $C_3$-$C_{60}$ heteroarylene group; and a divalent aliphatic hydrocarbon group;
3) W is $NAr^5$, O, S or CR'R";

R' and R" are each independently selected from the group of a $C_1$-$C_{50}$ alkyl group; a $C_6$-$C_{60}$ aryl group; a $C_3$-$C_{60}$ heterocyclic group including at least one heteroatom of O, N, S, Si, or P; and R' and R" may be bonded to each other to form a spiro.

4) $Ar^4$ and $Ar^5$ are each independently selected from the group consisting of a $C_6$-$C_{60}$ aryl group; a $C_3$-$C_{60}$ heterocyclic group including at least one heteroatom of O, N, S, Si, or P; a $C_1$-$C_{50}$ alkyl group; a $C_6$-$C_{60}$ arylamine group; a fluorene group}

Formula (12) comprises a compound represented by any of the following Formulas (13) to (16).

Formula (13)

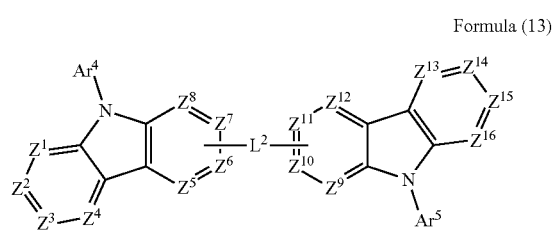

Formula (14)

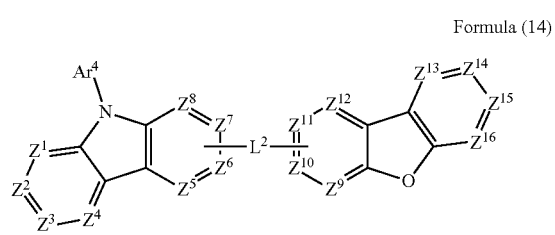

Formula (15)

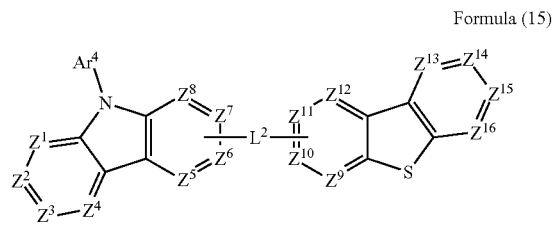

Formula (16)

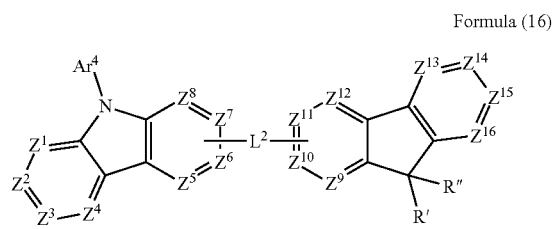

{In Formulas (13) to (16),
$Ar^4, Ar^6, Z^2, Z^2, Z^3, Z^4, Z^5, Z^6, Z^7, Z^8, Z^9, Z^{10}, Z^{11}, Z^{12}, Z^{13}, Z^{14}, Z^{15}, Z^{16}, L^2, R', R''$ are the same as defined above.}

Preferably, both $Ar^4$ and $Ar^5$ of Formula (12) comprise a compound represented by a $C_6$-$C_{30}$ aryl group.

Also, the compound represented by Formula (12) comprises a compound represented by Formula(17)

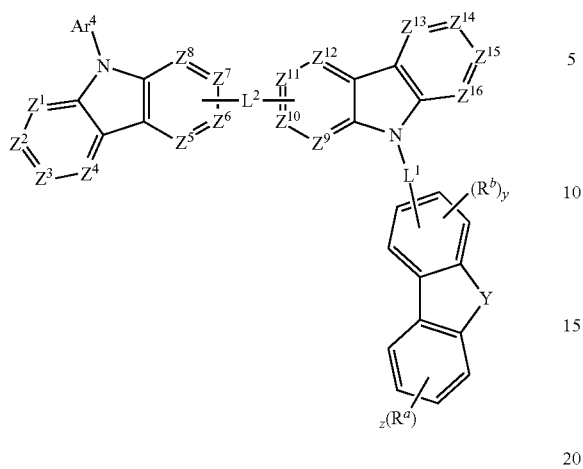

Formula(17)

{In Formula(17),

Ar$^4$, Ar$^5$, Z$^1$, Z$^2$, Z$^3$, Z$^4$, Z$^5$, Z$^6$, Z$^7$, Z$^8$, Z$^9$, Z$^{10}$, Z$^{11}$, Z$^{12}$, Z$^{13}$, Z$^{14}$, Z$^{15}$, Z$^{16}$, and L$^2$ are the same as defined above.

1) L$^1$ is selected from the group of a single bond; a C$_6$-C$_{60}$ arylene group; a C$_3$-C$_{60}$ heteroarylene group; and a divalent aliphatic hydrocarbon group;

2) Y is O, S or NAr$^5$,

3) R$^a$ and R$^b$ are each independently selected from the group consisting of hydrogen; deuterium; halogen; a C$_6$-C$_{60}$ aryl group; a fluorenyl group; a C$_2$-C$_{60}$ heterocyclic group including at least one heteroatom of O, N, S, Si or P; a fused ring group of a C$_3$-C$_{60}$ aliphatic ring and a C$_6$-C$_{60}$ aromatic ring; a C$_1$-C$_{50}$ alkyl group; a C$_2$-C$_{20}$ alkenyl group; a C$_2$-C$_{20}$ alkynyl group; a C$_1$-C$_{30}$ alkoxyl group; a C$_6$-C$_{30}$ aryloxy group; and -L'-N(R$_a$)(R$_b$); or a plurality of R$_a$ and a plurality of R$_b$ may be bonded to each other to form an aromatic ring or and heteroaromatic ring, 4) y is an integer of 0 to 3, and z is an integer of 0 to 4}

Specifically, the compound represented by Formula (12) comprises the following compounds 4-1 to 4-52

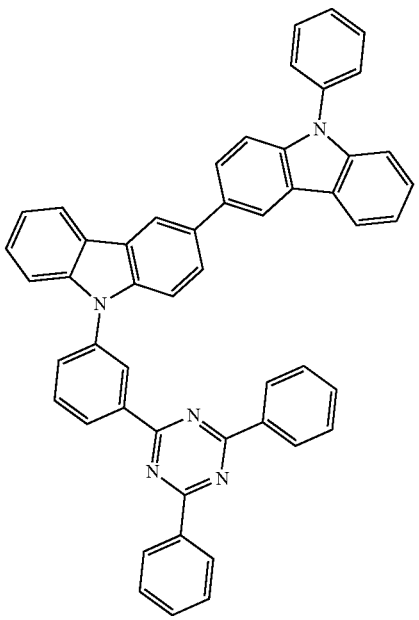

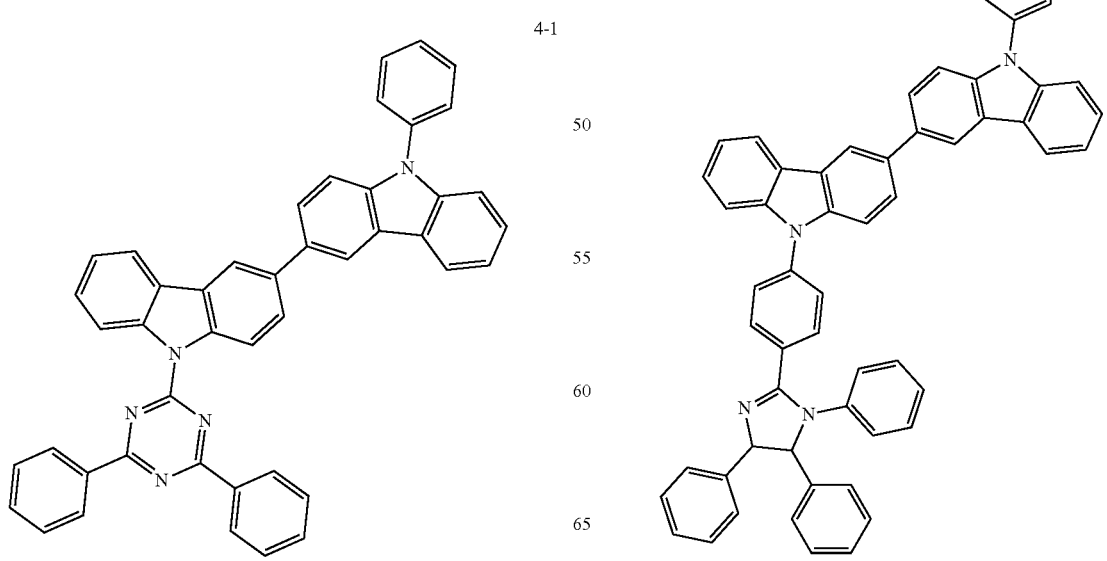

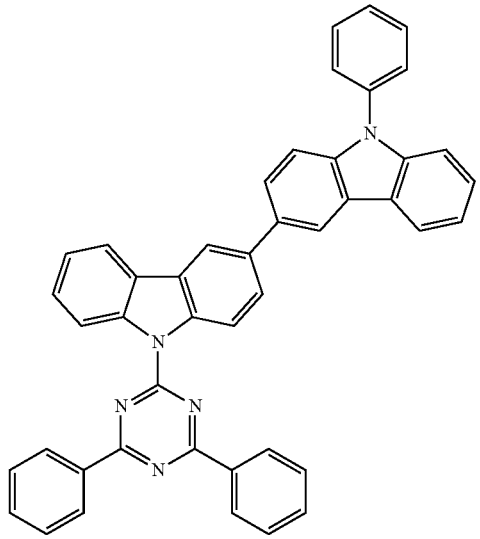
4-4
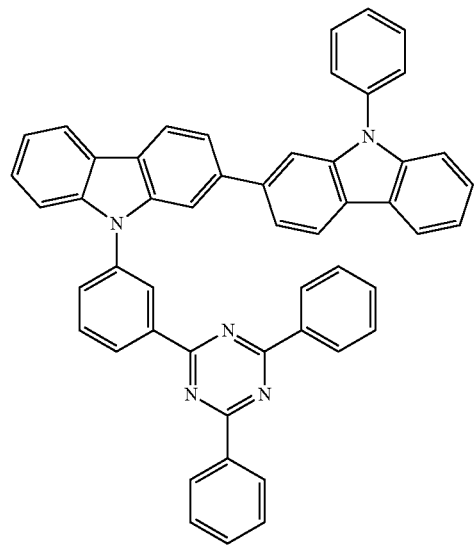
4-5
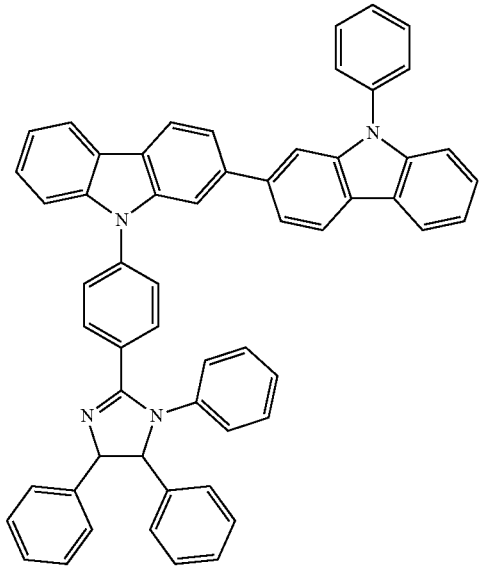
4-6
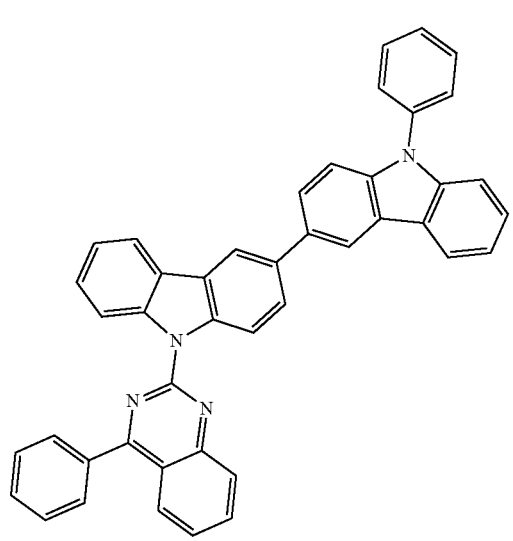
4-7
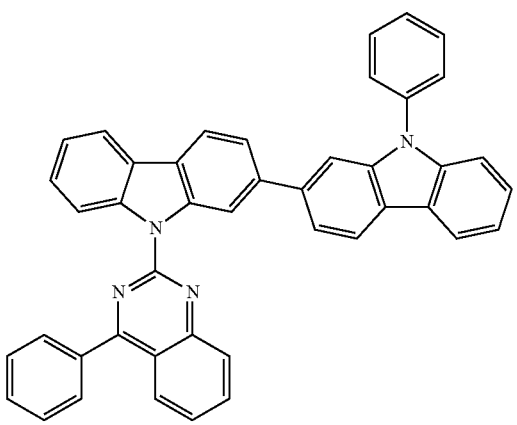
4-8
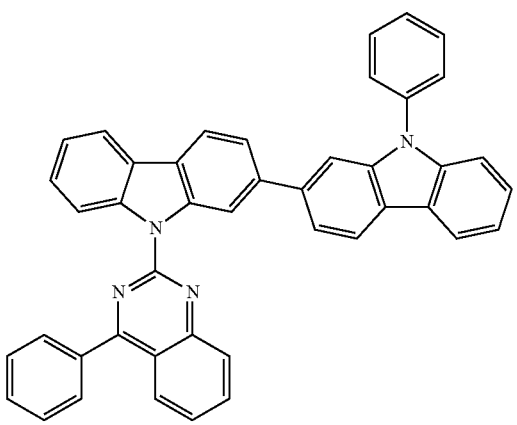
4-9

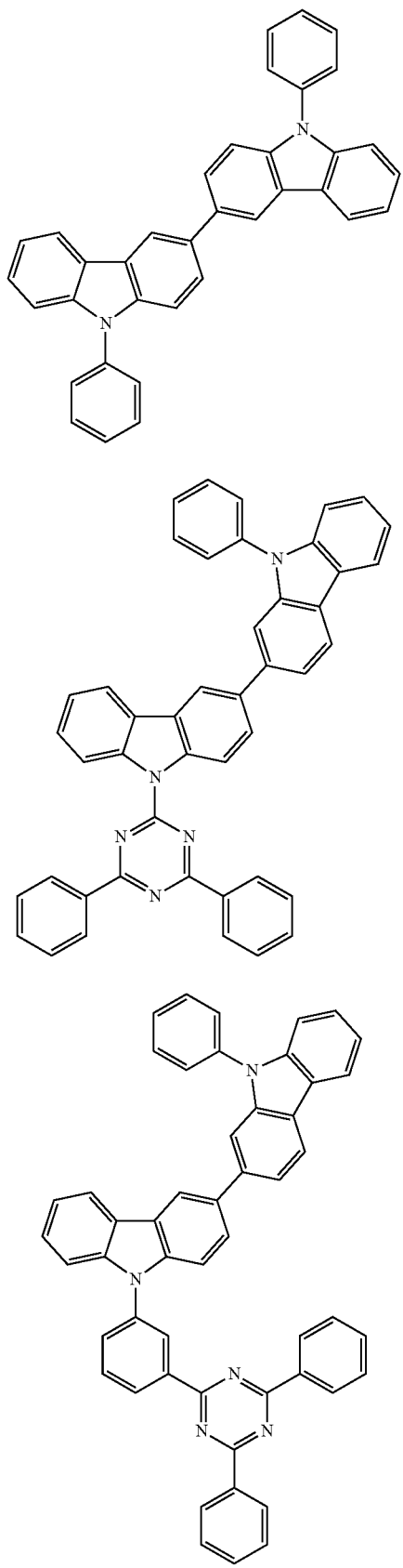
4-10
4-11
4-12
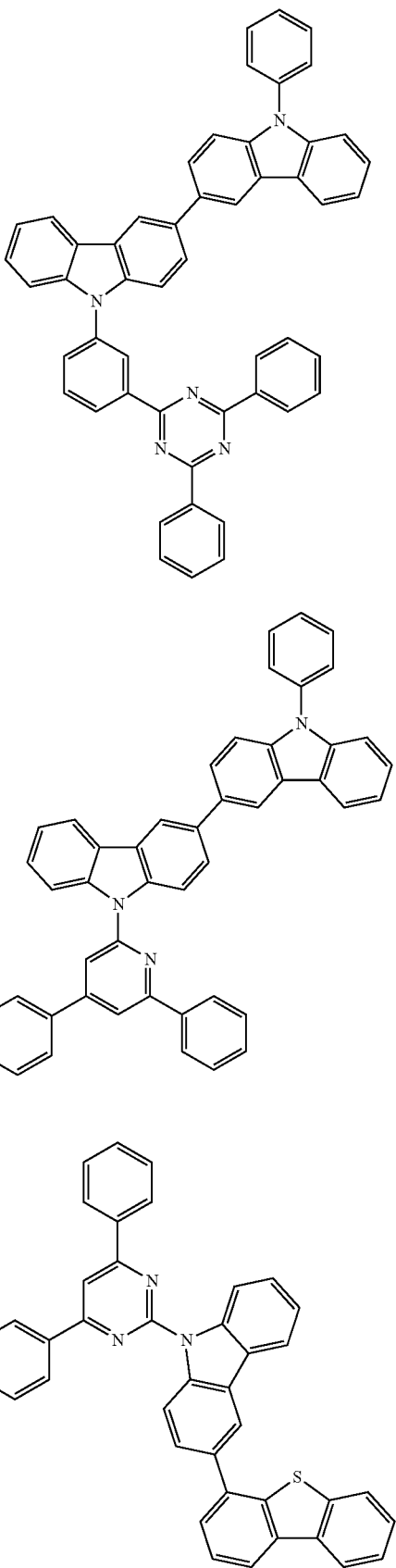
4-13
4-14
4-15

4-16
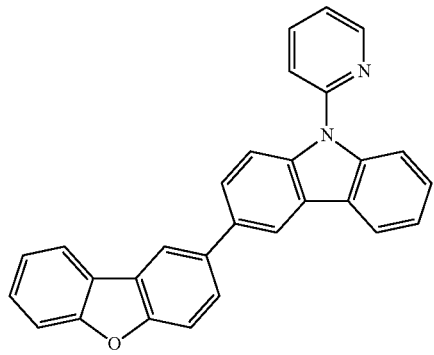
4-17
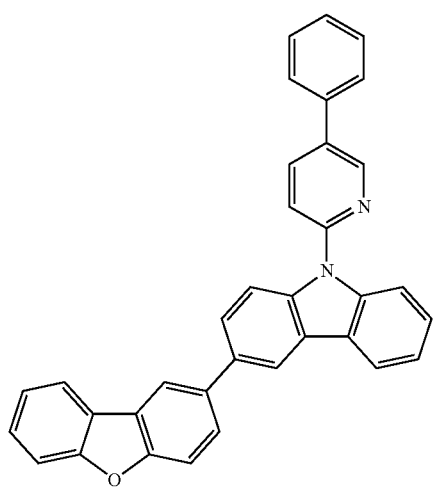
4-18
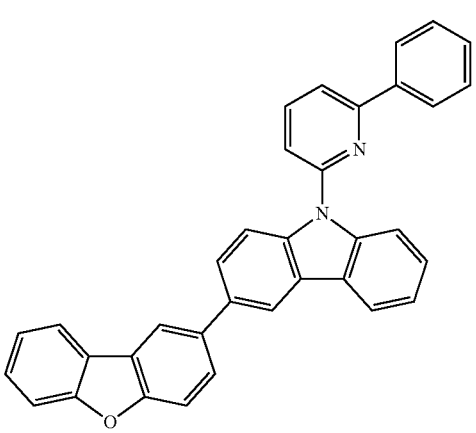
4-19
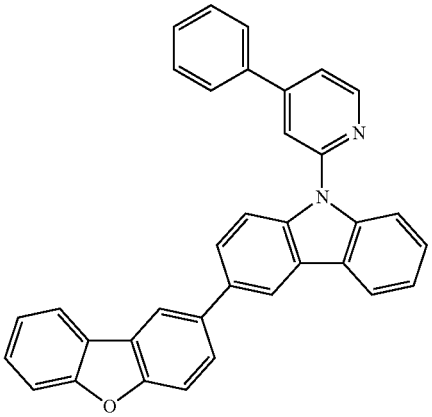
4-20
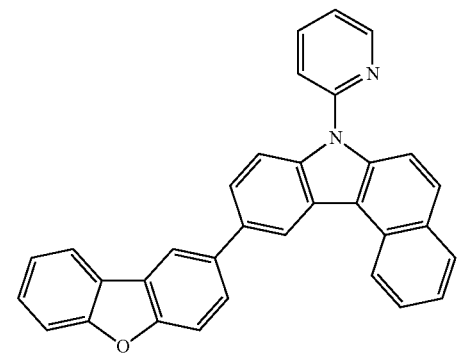
4-21
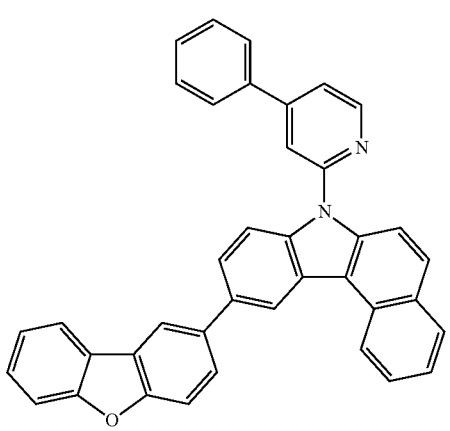
4-22

4-23
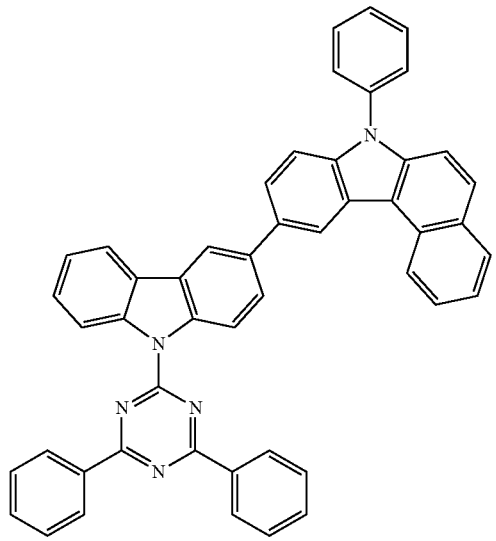
4-24
4-25
4-26
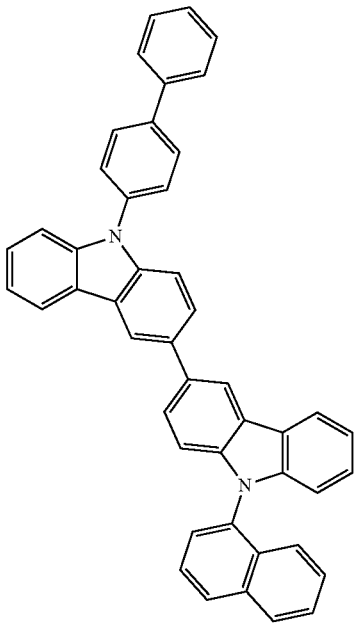
4-27
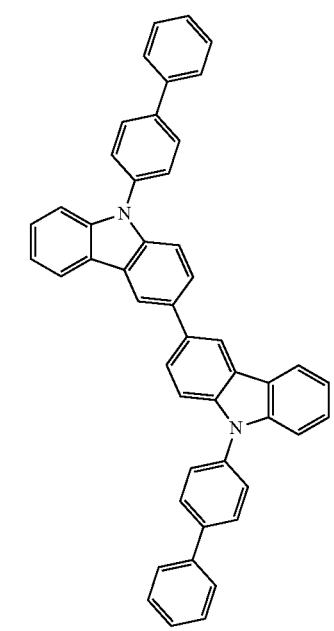

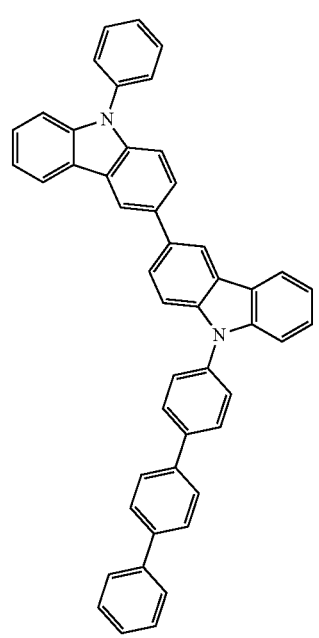
4-28
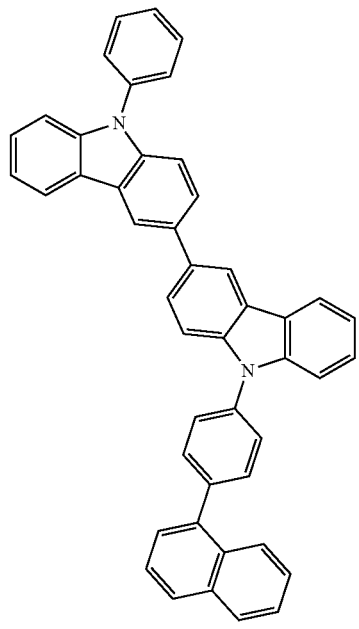
4-30
4-29
4-31
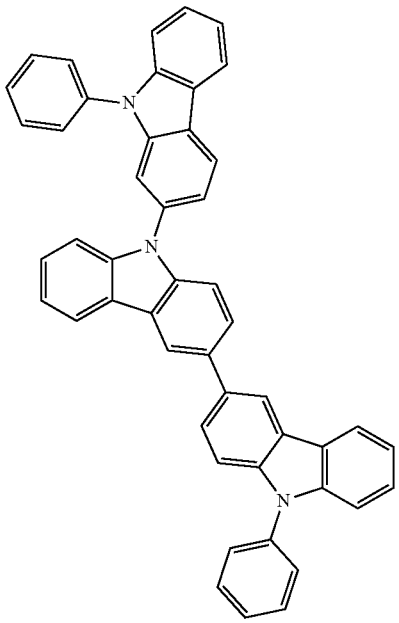

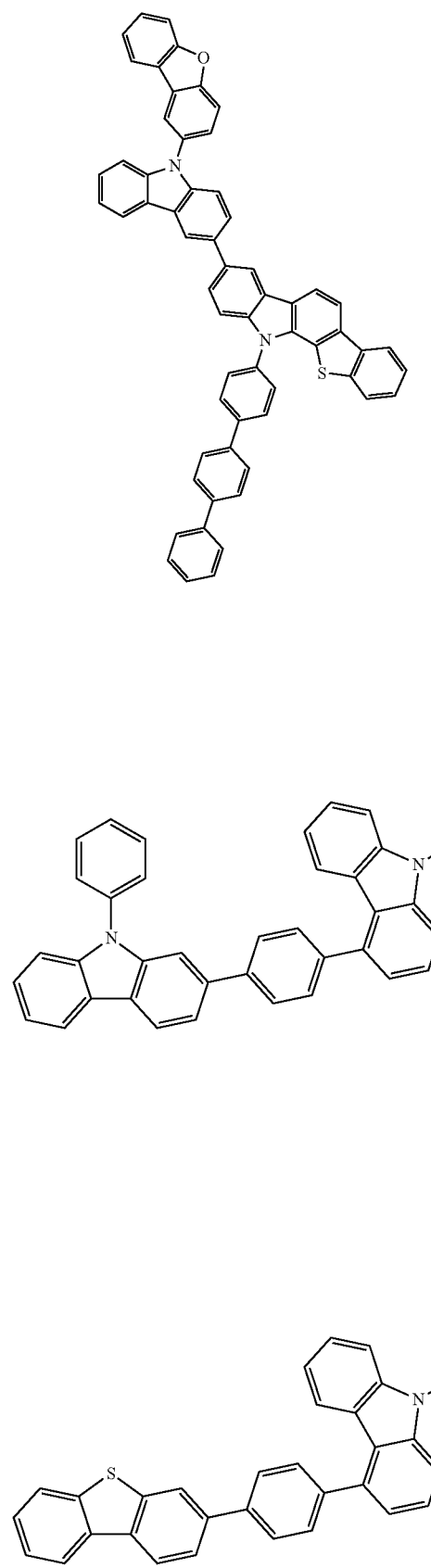
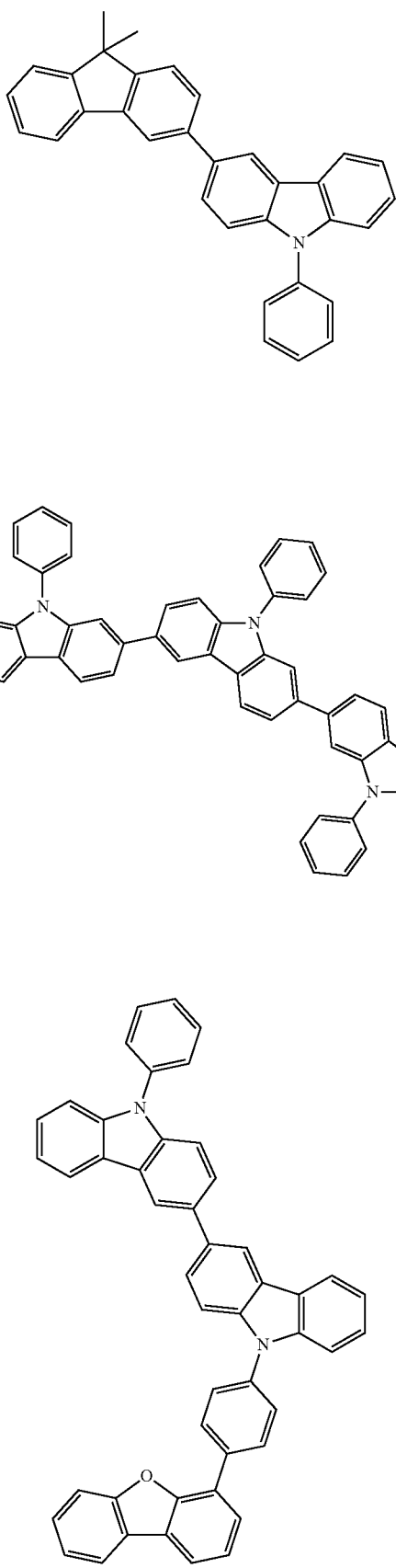

4-38
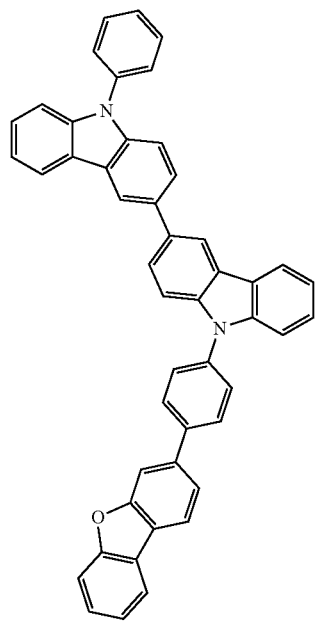
4-39
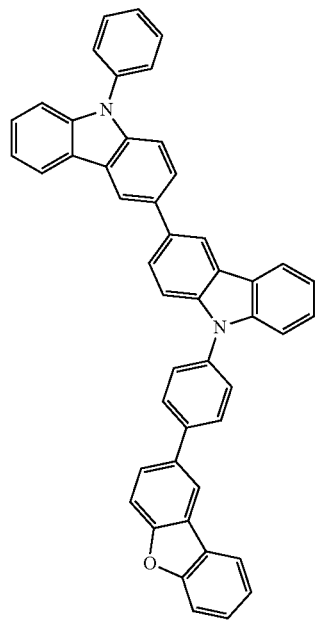
4-40
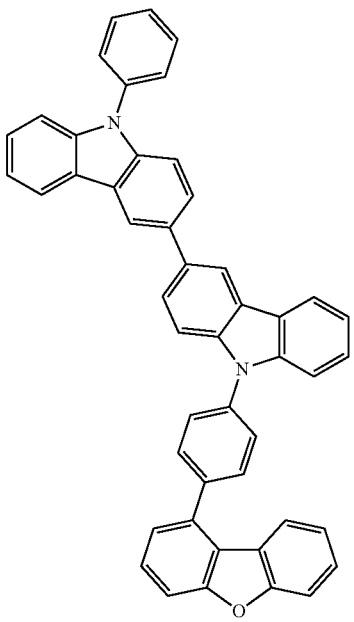
4-41
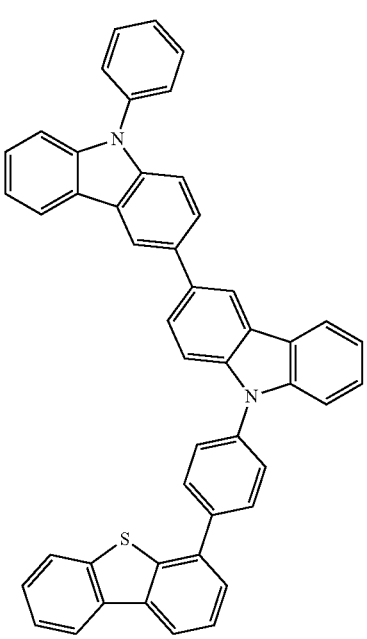

4-42
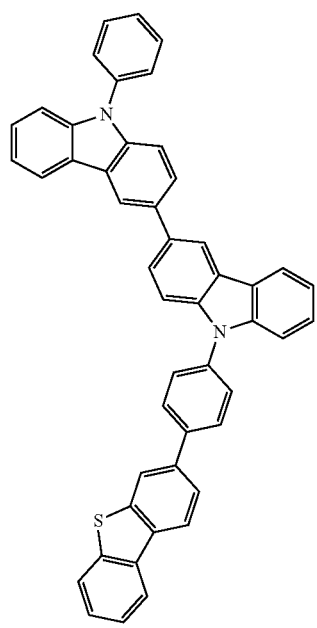
4-43
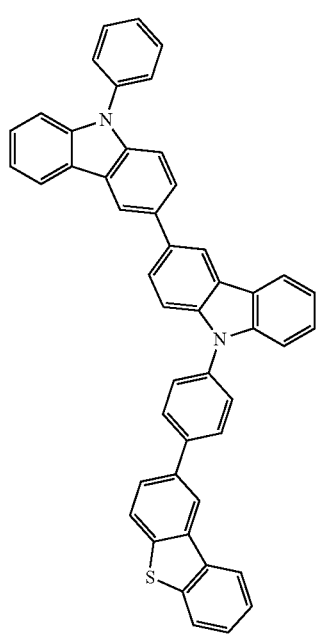
4-44
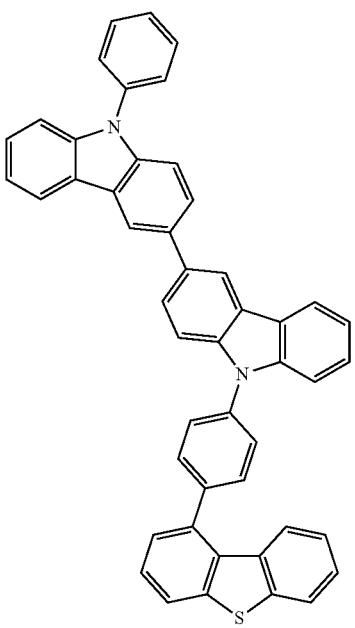
4-45
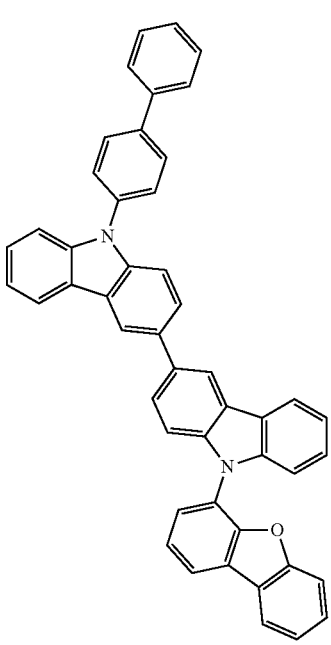

4-46
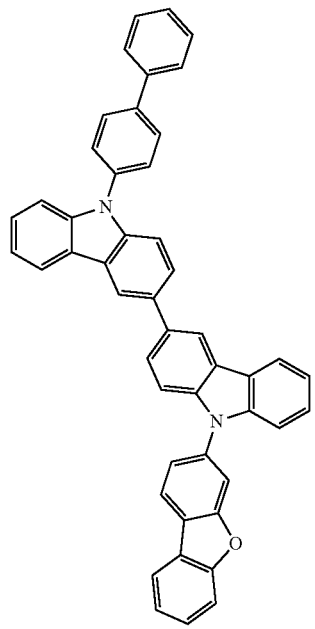
4-47
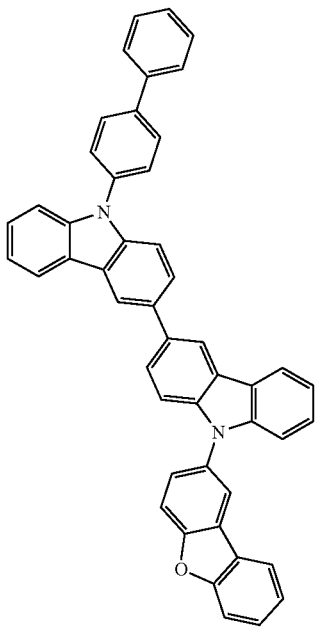
4-48
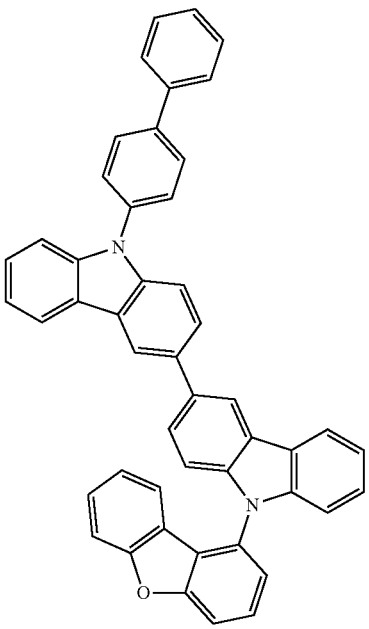
4-49
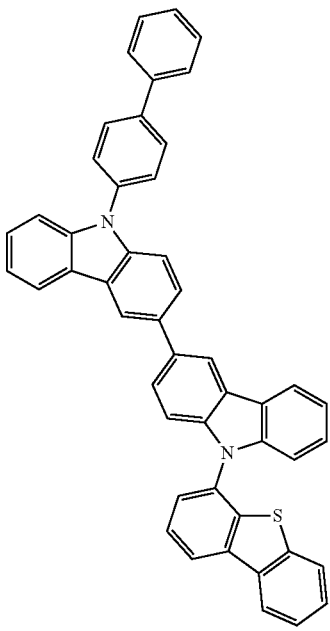

4-50

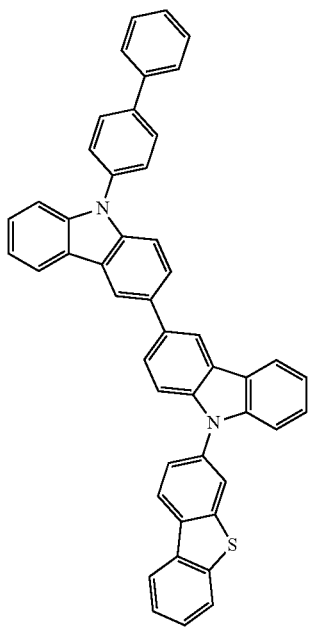

4-51

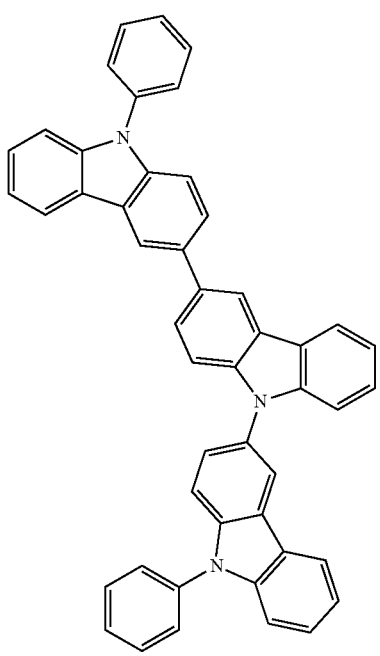

4-52

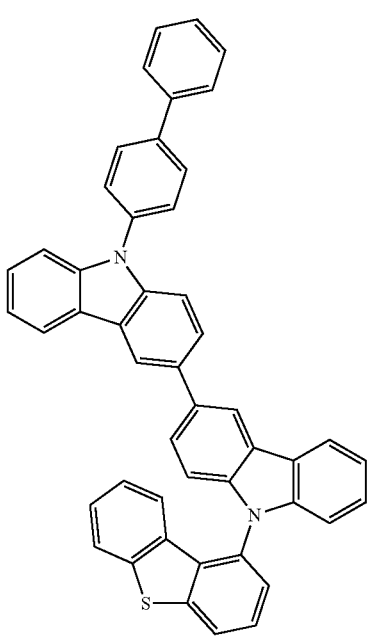

As another example, the present invention provides an organic electronic element comprising an anode; a cathode; an organic material layer formed between the anode and the cathode; wherein the organic material layer includes an emitting layer, an hole transport layer formed between the anode and the emitting layer; an emitting auxiliary layer formed between the emitting layer and the hole transport layer; wherein the hole transport layer or the emitting auxiliary layer comprises a compound represented by Formula(18), and the emitting layer comprises a compound represented by Formula(1).

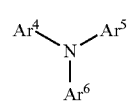

Formula(18)

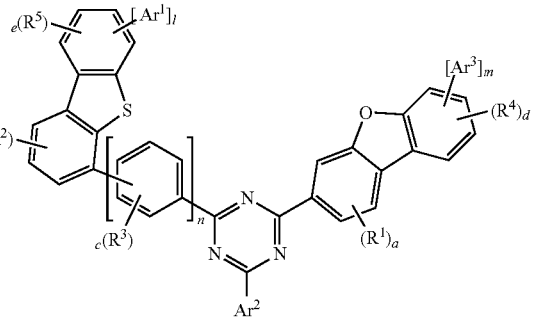

Formula(1)

{In Formula(1) and Formula(18),
1) $Ar^1$, $Ar^2$, $Ar^3$, l, m, n, a, b, c, d, e, $R^1$, $R^2$, $R^3$, $R^4$ and $R^5$ are the same as defined above.}
2) $Ar^4$ and $Ar^5$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$);
wherein, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic group;
and the $R_a$ and $R_b$ are each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group including at least one heteroatom of O, N, S, Si, or P;
or $Ar^4$ and $Ar^5$ may be bonded to each other to form a ring.
3) $Ar^6$ is selected from the group consisting of a $C_6$-$C_{60}$ aryl group; a fluorenyl group; a $C_2$-$C_{60}$ heterocyclic group including at least one heteroatom of O, N, S, Si, or P; or is at least one of the following Formulas (1-a), (1-b), (1-c)

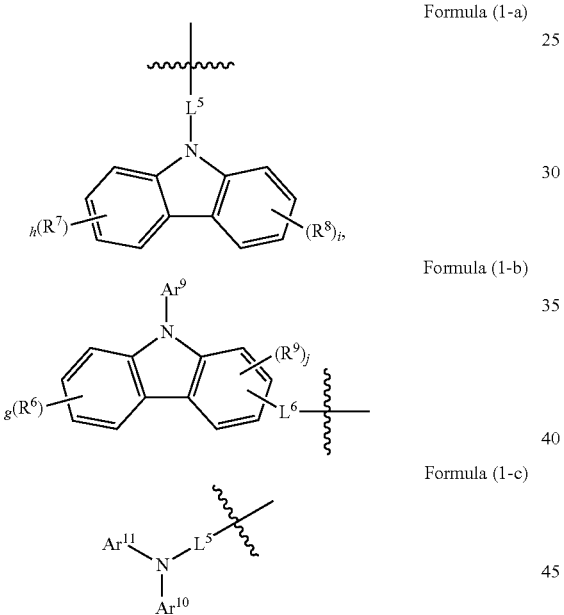

Formula (1-a)

Formula (1-b)

Formula (1-c)

4) $Ar^9$, $Ar^{10}$ and $Ar^{11}$ are each independently selected from the group consisting of a $C_6$-$C_{60}$ aryl group; a fluorenyl group; a $C_2$-$C_{60}$ heterocyclic group including at least one heteroatom of O, N, S, Si, or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$);
5) h, i and g are an integer of 0 to 4; j is an integer of 0 to 3; $R^6$, $R^7$, $R^8$ and $R^9$ are the same or different from each other, and are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$);

wherein in case g, h, i, j are 2 or more, $R^6$, $R^7$, $R^8$ and $R^9$ are each in plural being the same or different, and may be bonded to each other to form a ring,
6) $L^6$ is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic group including at least one heteroatom of O, N, S, Si or P;
7) $L^5$ is selected from the group consisting of a $C_6$-$C_{60}$ arylene group; a fluorenylene group; a fused ring group of a $C_3$-$C_{60}$ aliphatic ring and a $C_0$-$C_{60}$ aromatic ring; and a $C_2$-$C_{60}$ heterocyclic group including at least one heteroatom of O, N, S, Si or P}

The present invention also provides an organic electronic element including at least one compound represented by Formula (12) in the emitting layer.

Also, the hole transport layer comprises a compound represented by Formula(19) or Formula(20), and the emitting auxiliary layer comprises a compound represented by Formula(21) or Formula(22)

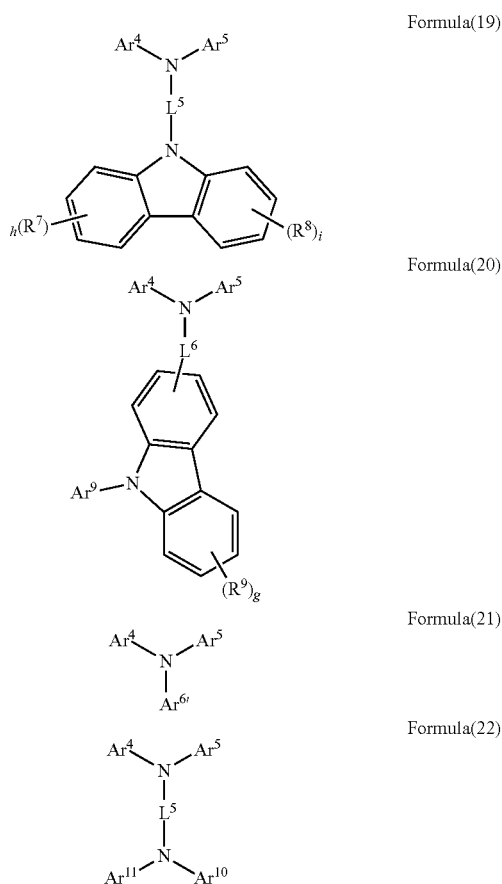

Formula(19)

Formula(20)

Formula(21)

Formula(22)

{In Formulas (19) to (22),
1) $Ar^6$ is selected from the group consisting of a $C_6$-$C_{60}$ aryl group; a fluorenyl group; a $C_2$-$C_{60}$ heterocyclic group including at least one heteroatom of O, N, S, Si or P;
2) $Ar^4$, $Ar^5$, $Ar^9$, $Ar^{10}$, $Ar^{11}$, h, i, g, $L^5$, $L^6$, $R^6$, $R^7$, $R^8$ and $R^9$ are the same as defined above.}

Specifically, the compound represented by Formula (18) comprises the following compounds 13-1 to 13-79 and compounds 2-1 to 2-76.

85                                               86
13-1
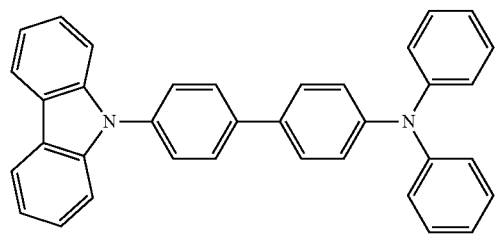
13-2
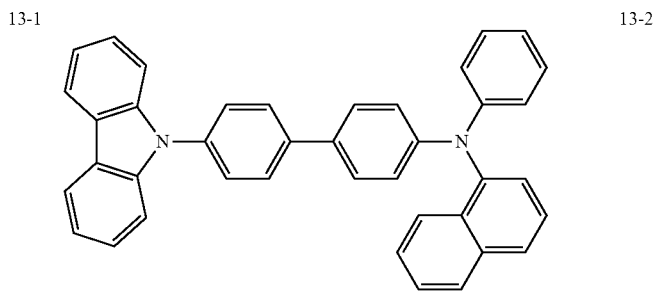
13-3
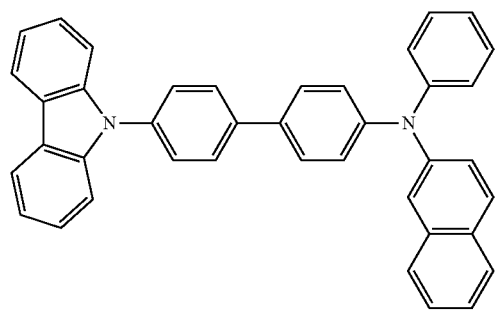
13-4
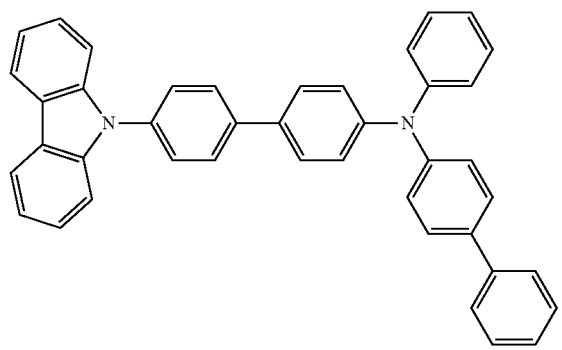
13-5
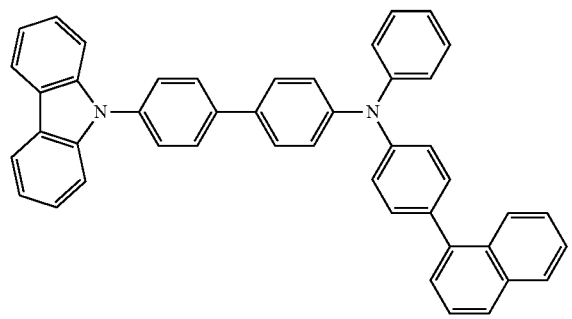
13-6
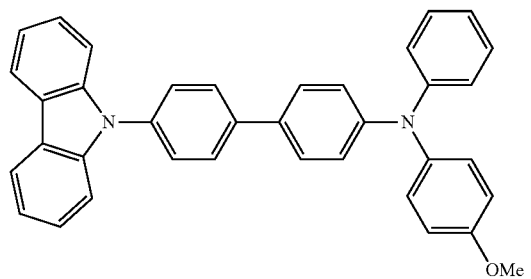
13-7
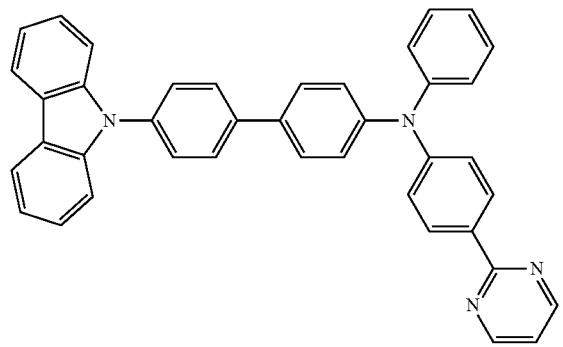
13-8
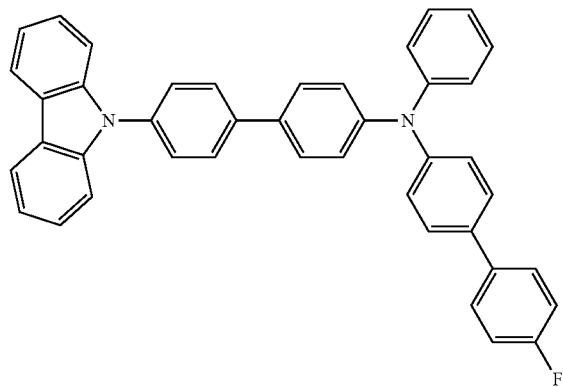

-continued
13-9
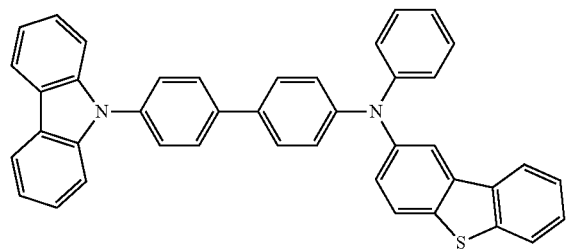
13-10
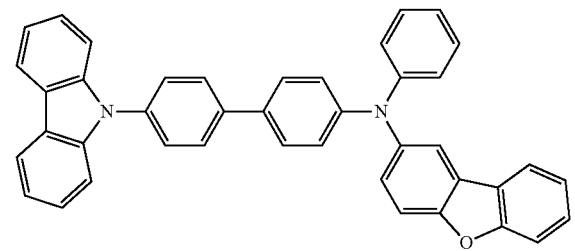
13-11
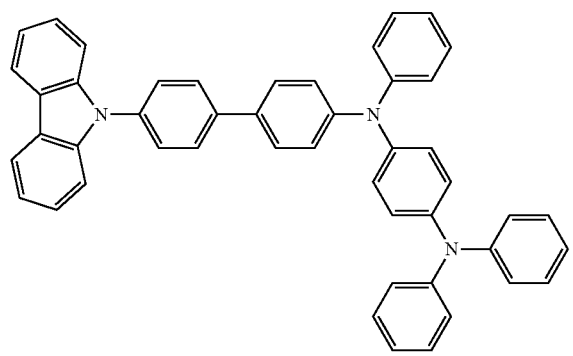
13-12
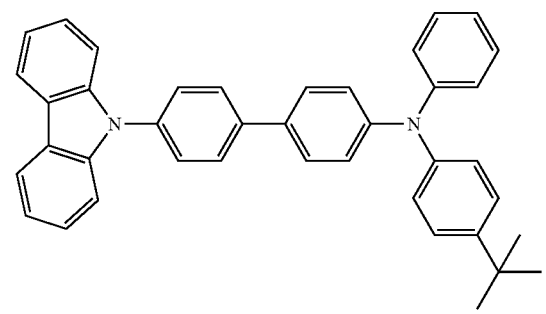
13-13
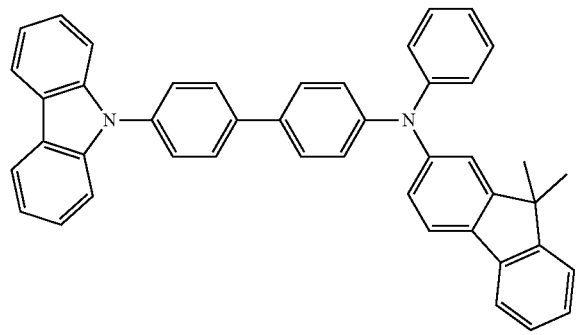
13-14
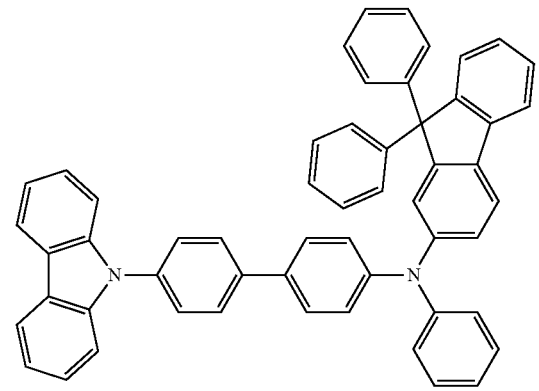
13-15
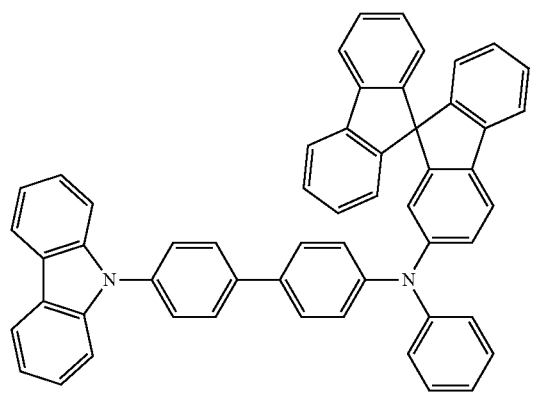
13-16
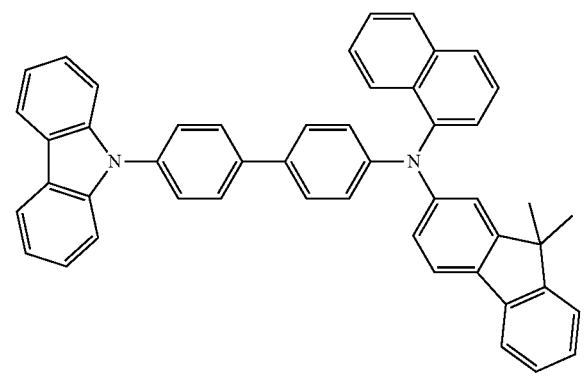

-continued
13-17
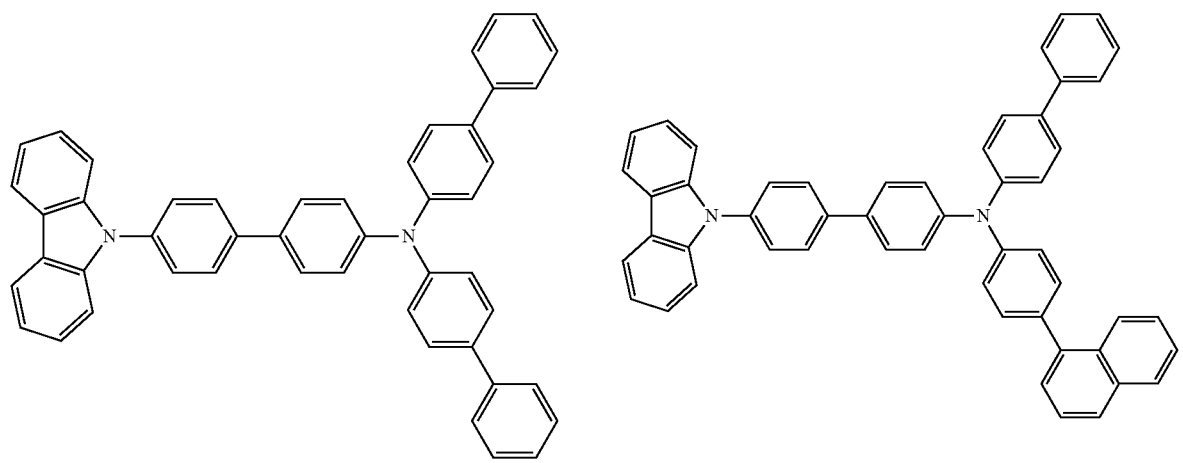
13-18
13-19
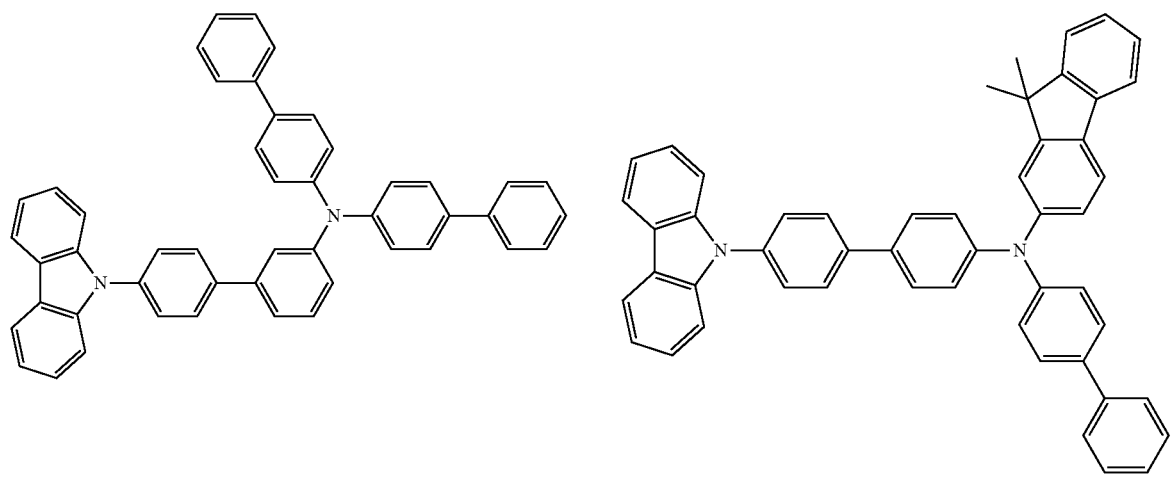
13-20
13-21
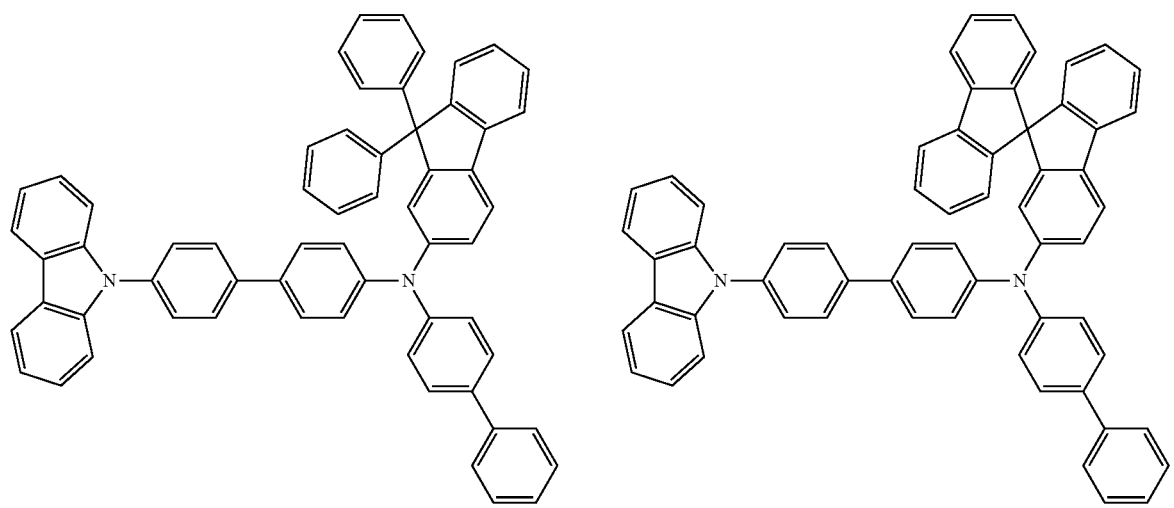
13-22

13-23
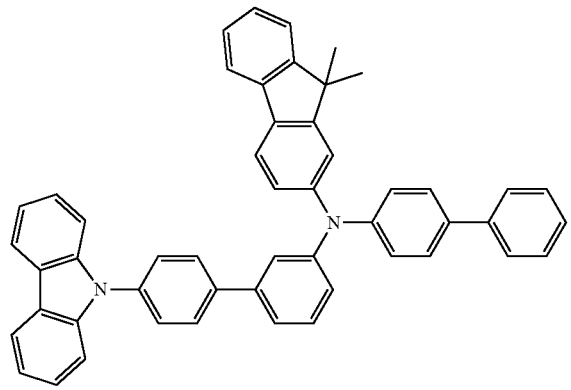
13-24
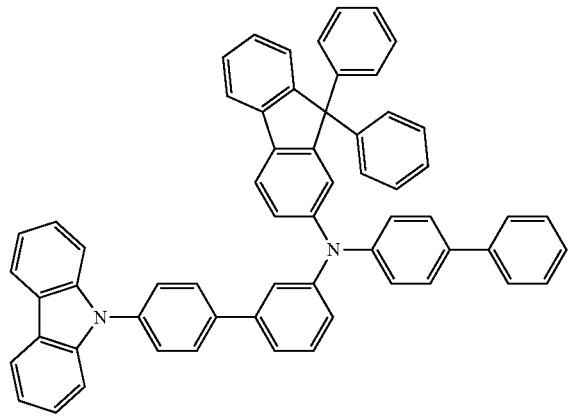
13-25
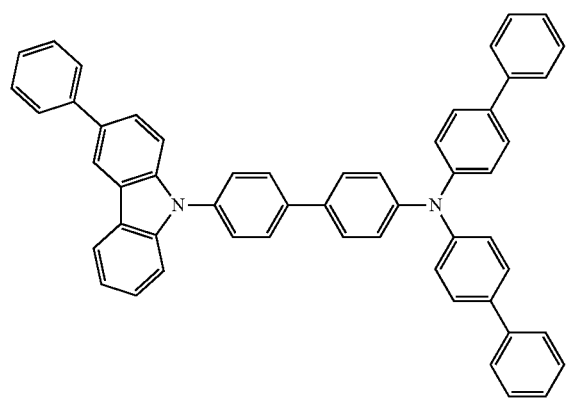
13-26
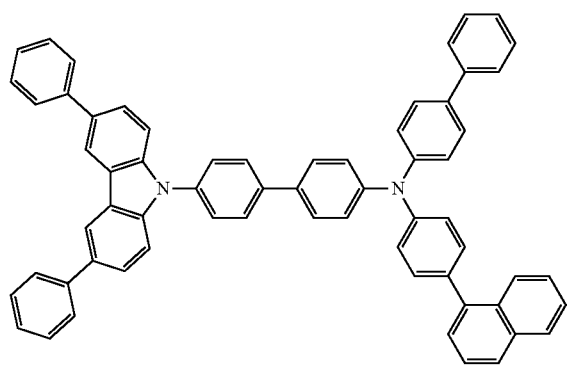
13-27
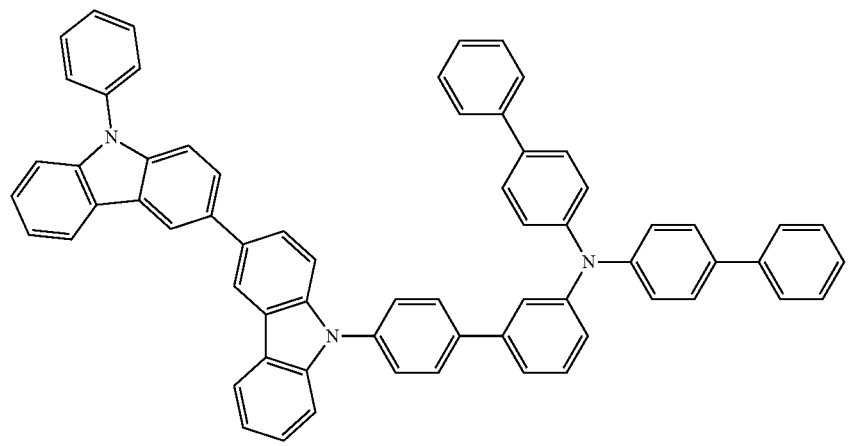

13-28
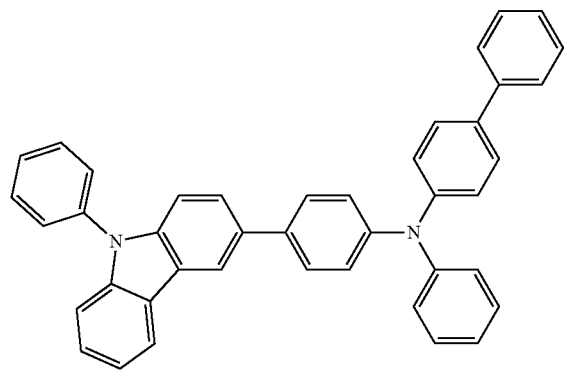
13-29
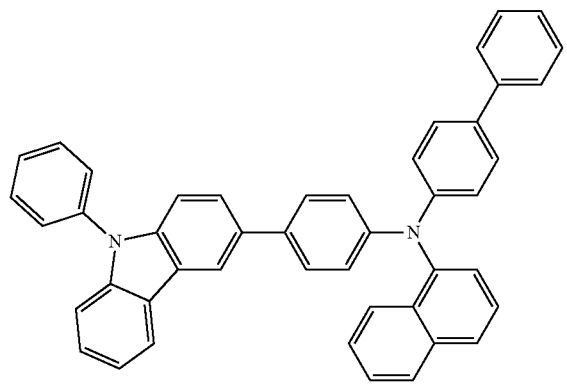
13-30
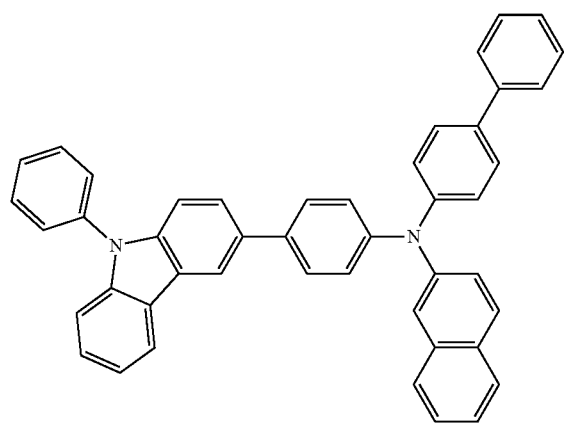
13-31
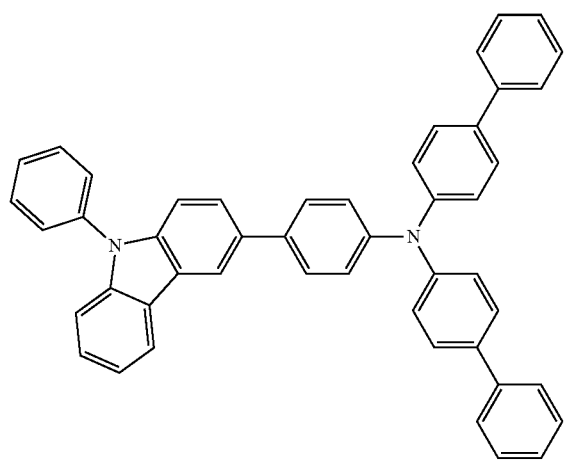
13-32
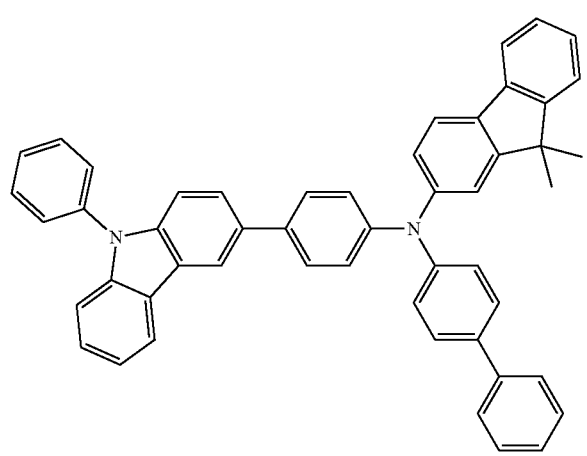
13-33
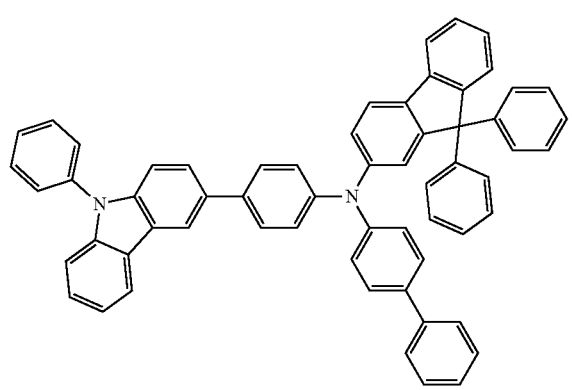

-continued
13-34
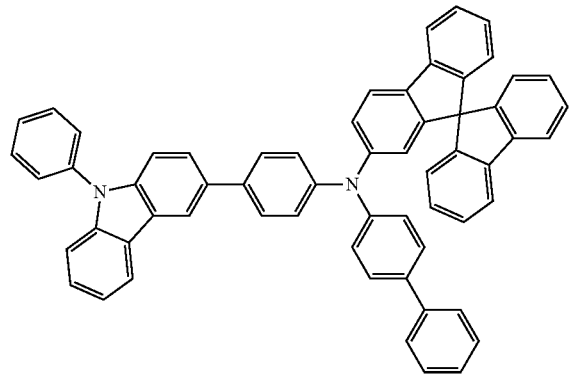
13-35
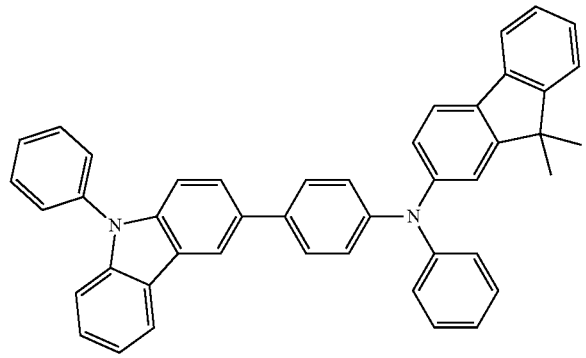
13-36
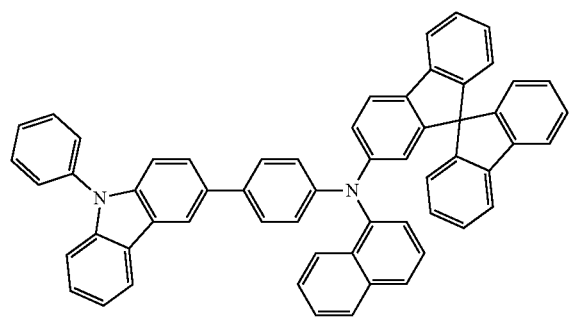
13-37
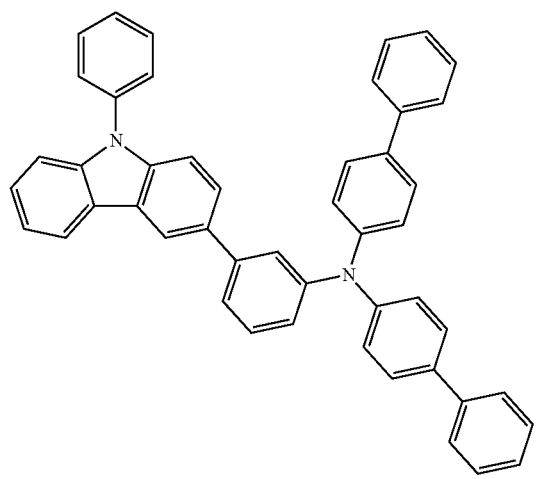
13-38
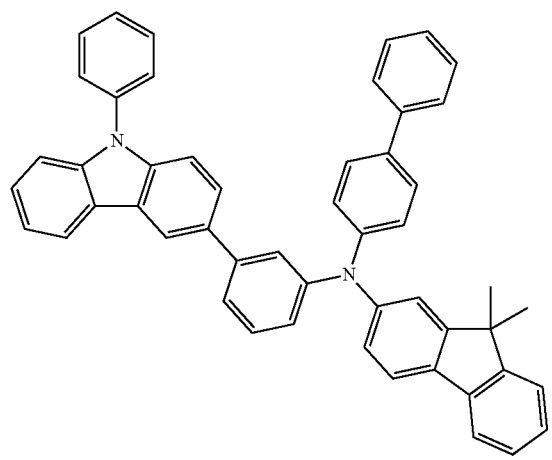
13-39
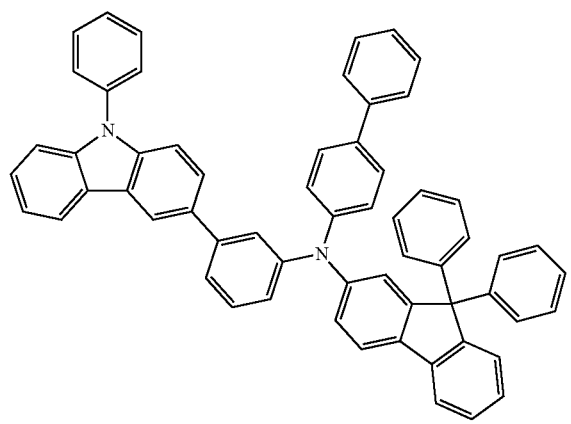

-continued
13-40
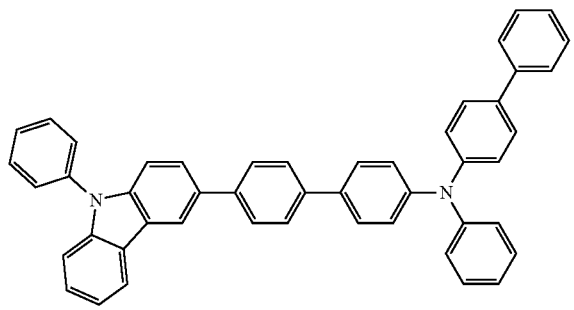
13-41
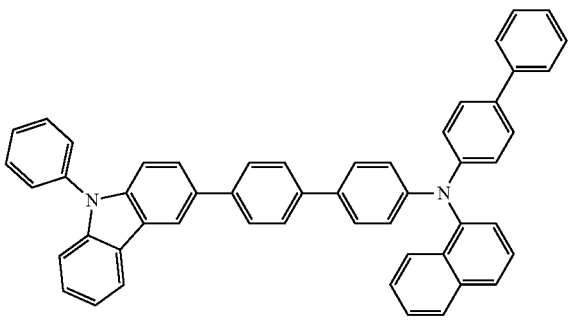
13-42
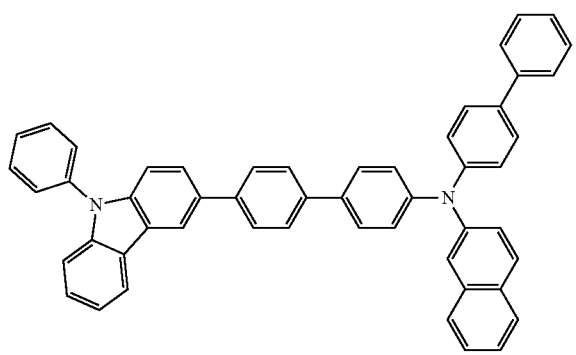
13-43
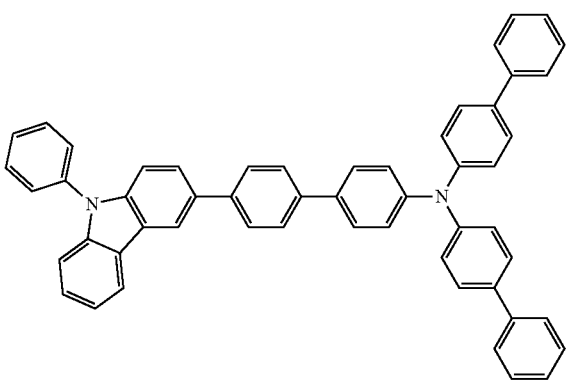
13-44
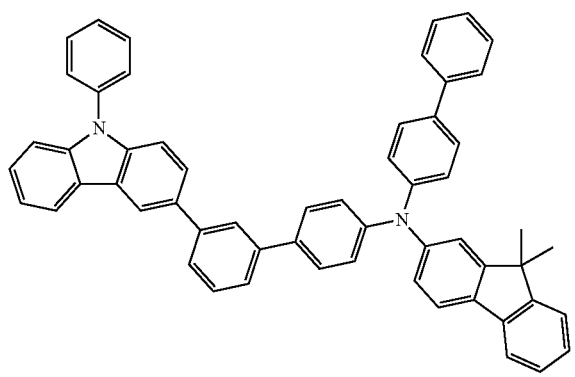
13-45
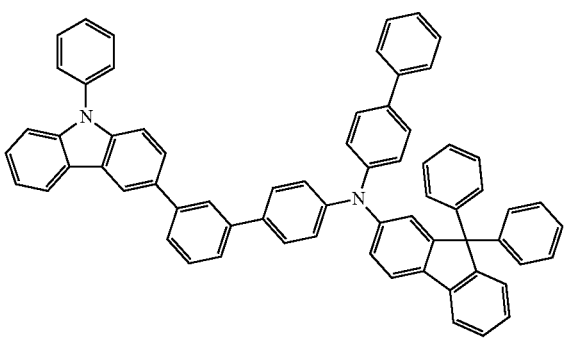
13-46
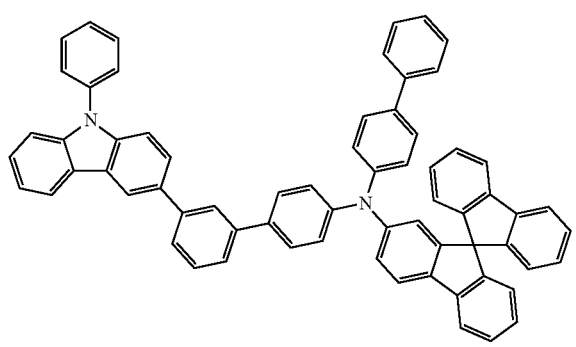
13-47
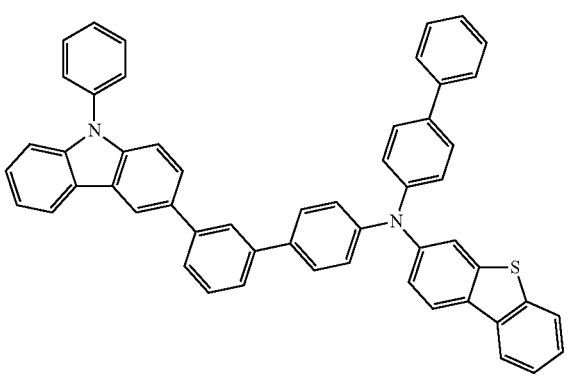

-continued
13-48 13-49
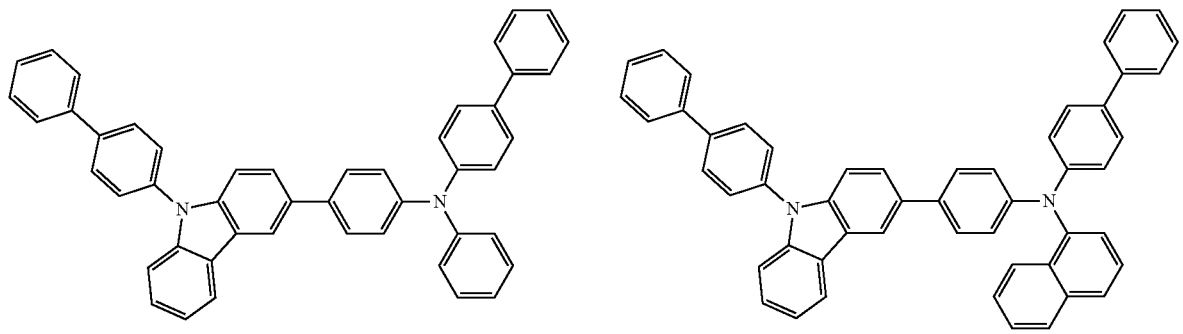
13-50 13-51
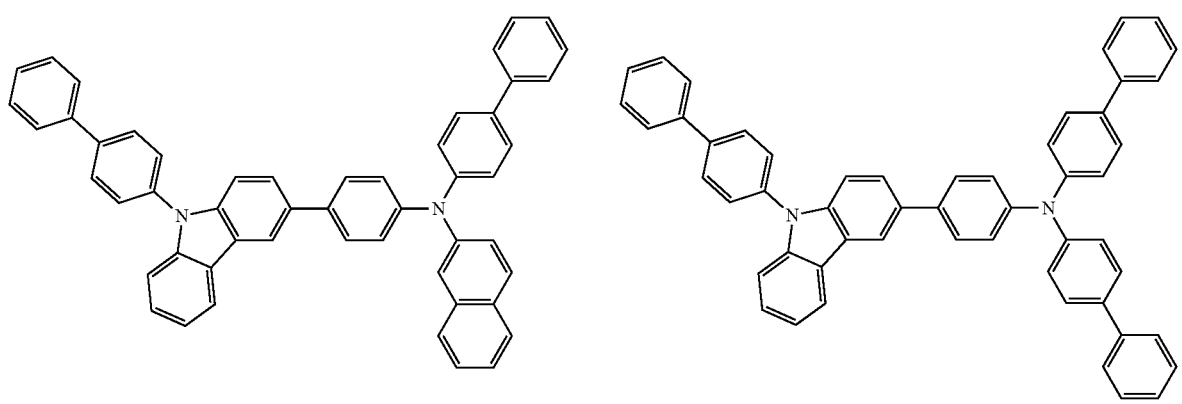
13-52 13-53
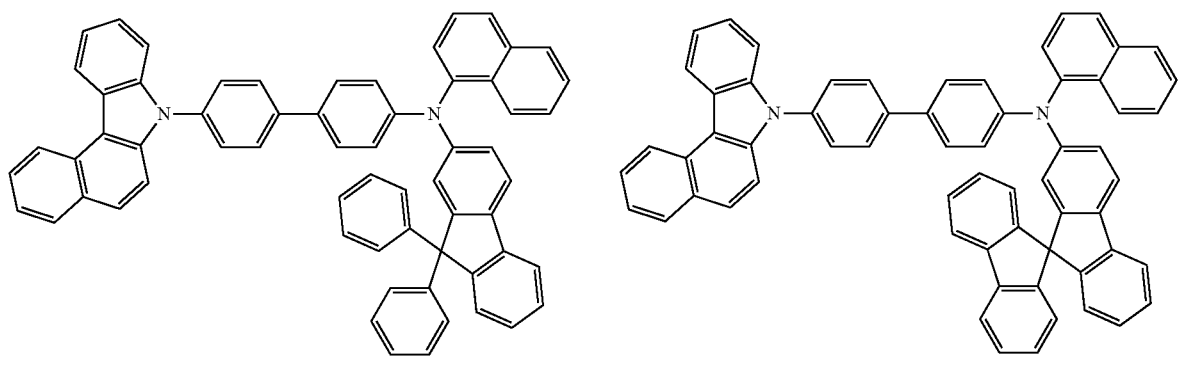
13-54 13-55
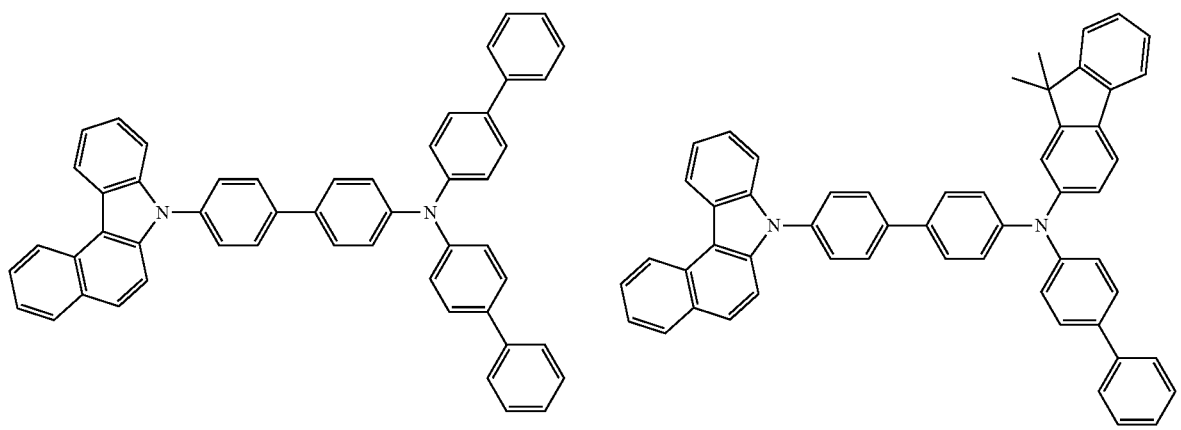

-continued
13-56
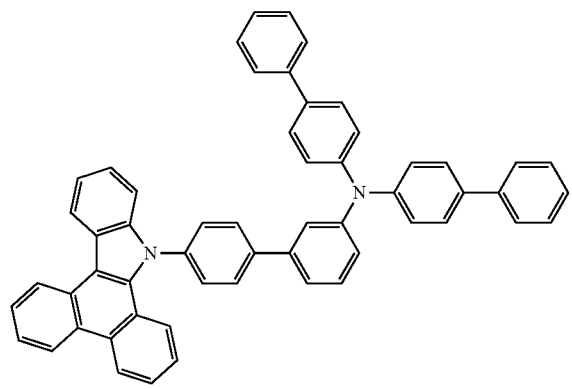
13-57
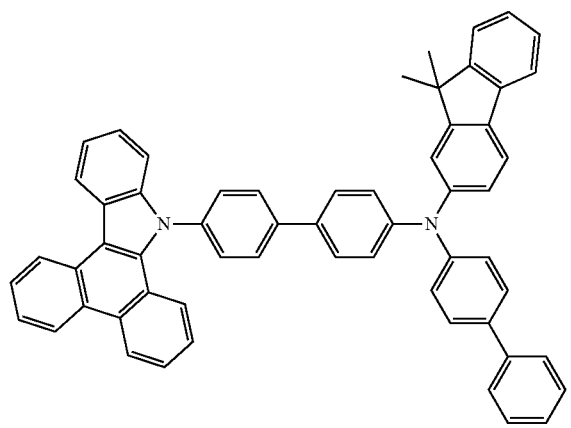
13-58
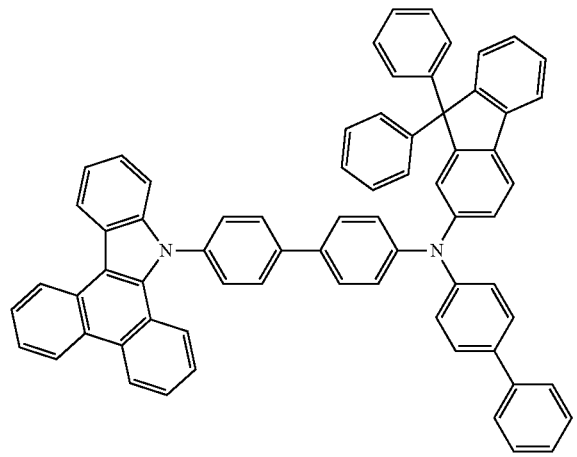
13-59
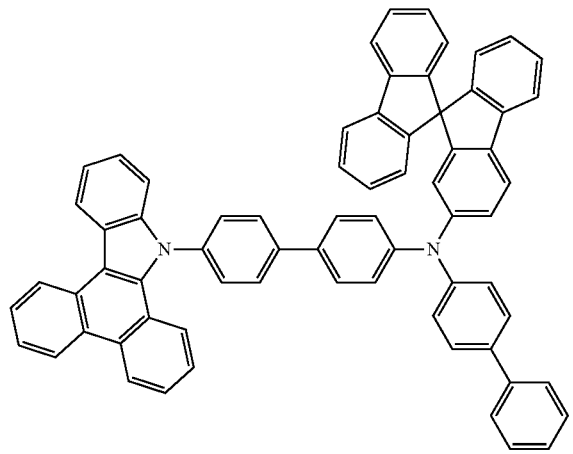
13-60
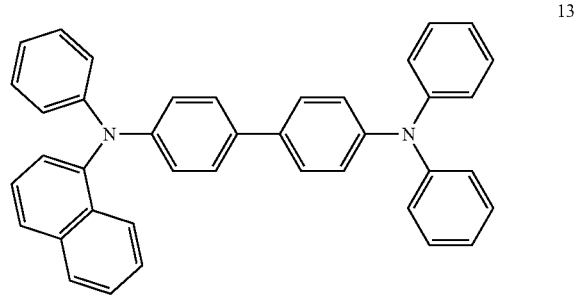
13-61
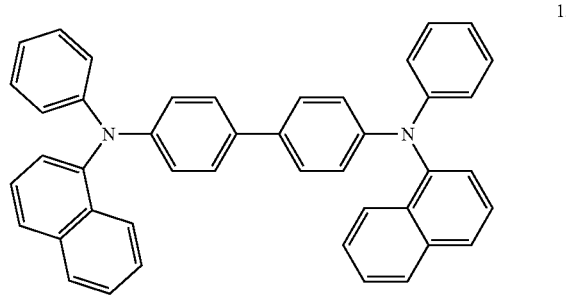
13-62
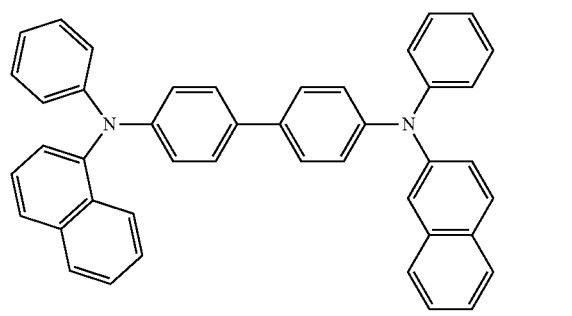
13-63
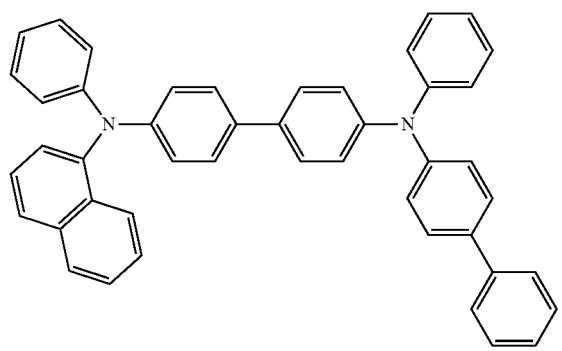

13-64
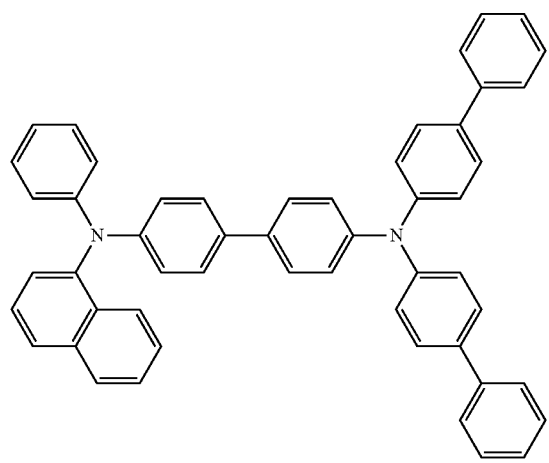
13-65
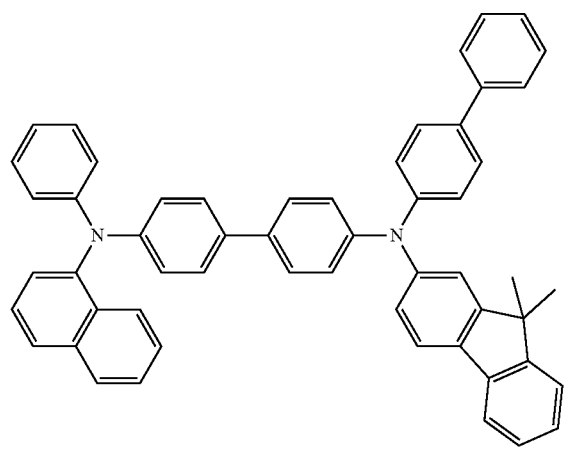
13-66
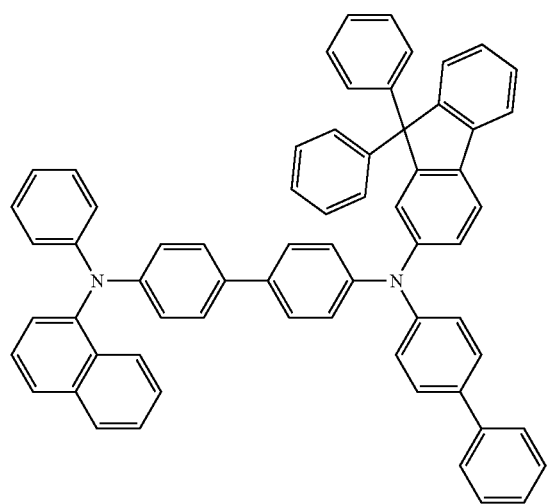
13-67
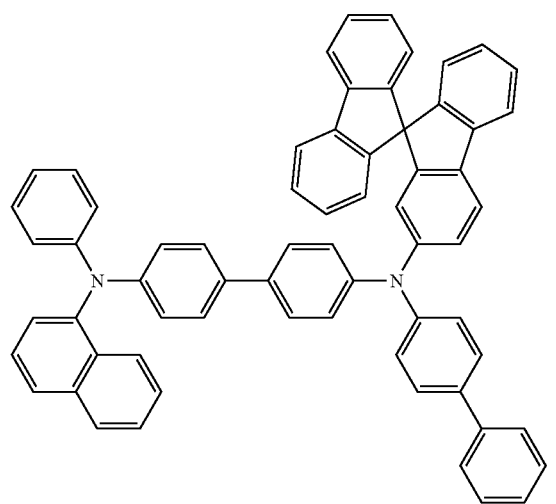
13-68
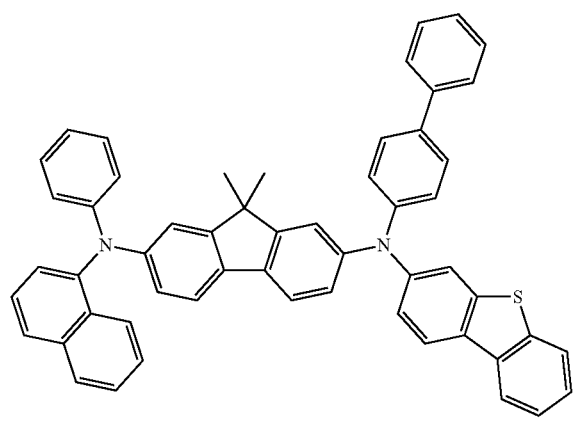
13-69
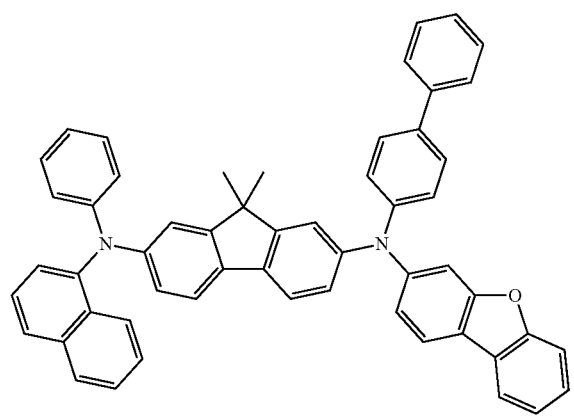

13-70
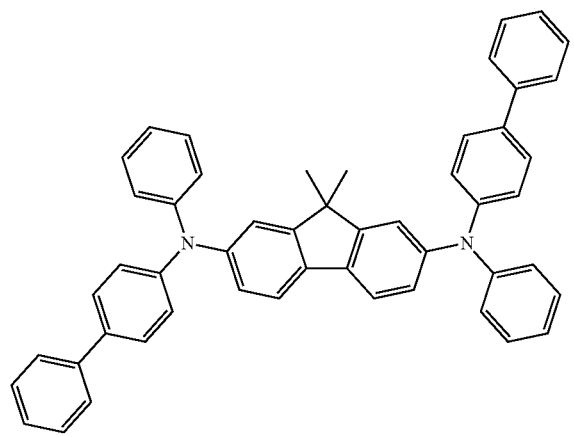
13-71
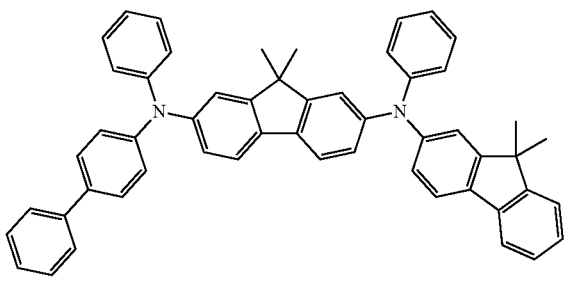
13-72
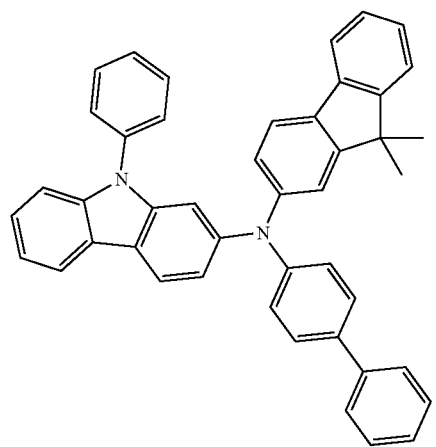
13-73
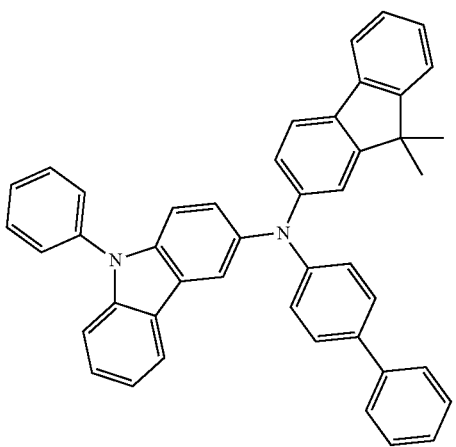
13-74
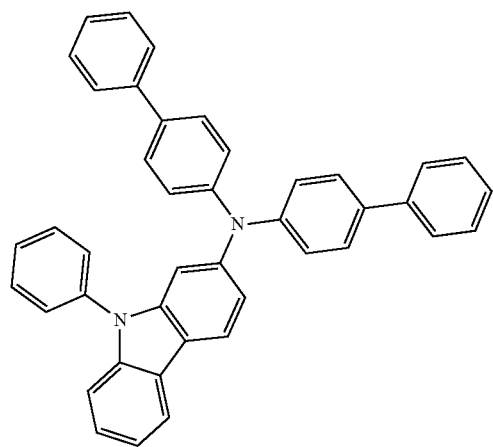
13-75
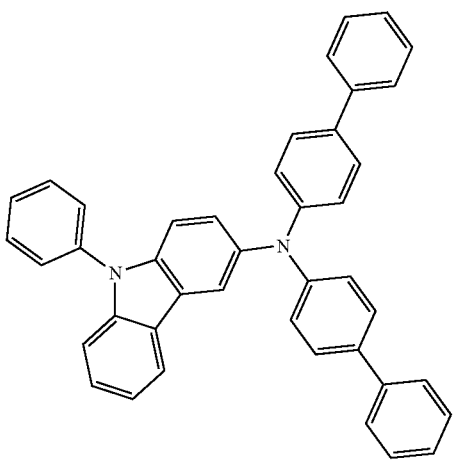

13-76
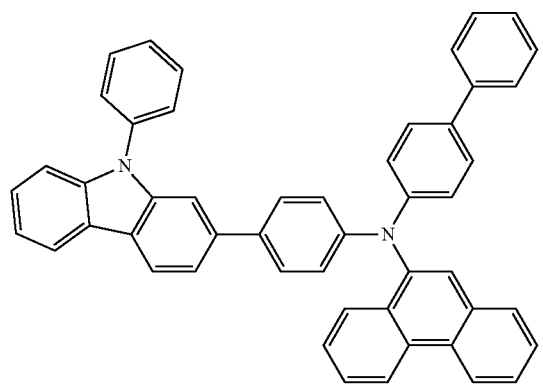
13-77
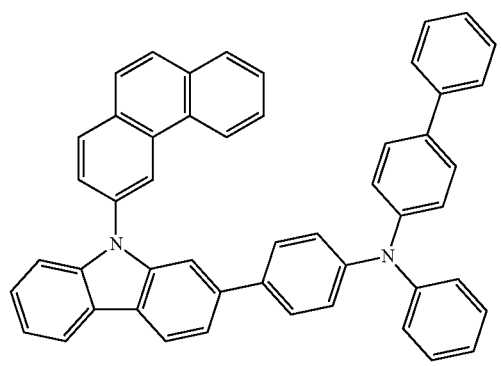
13-78
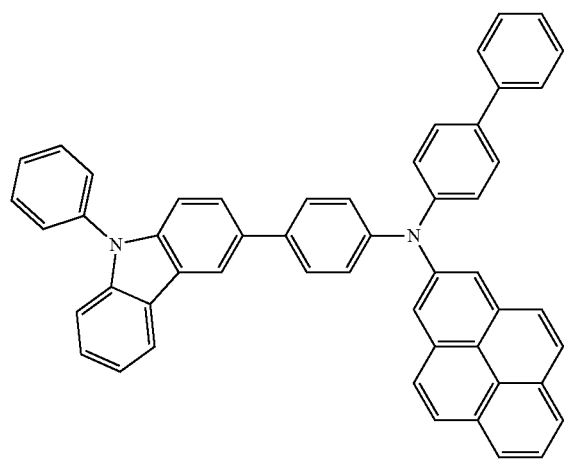
13-79
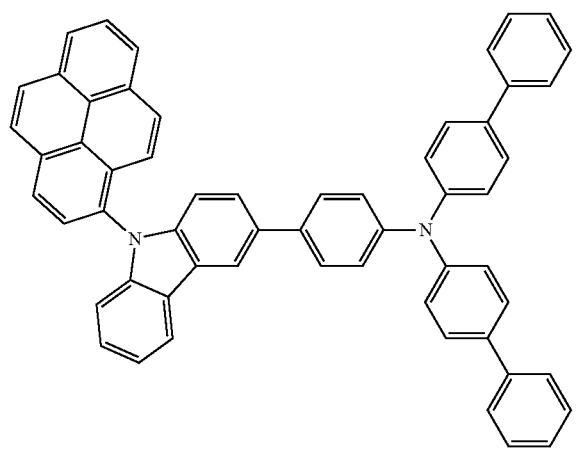
2-1
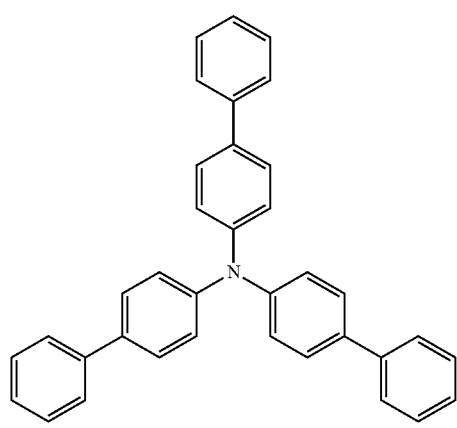
2-2
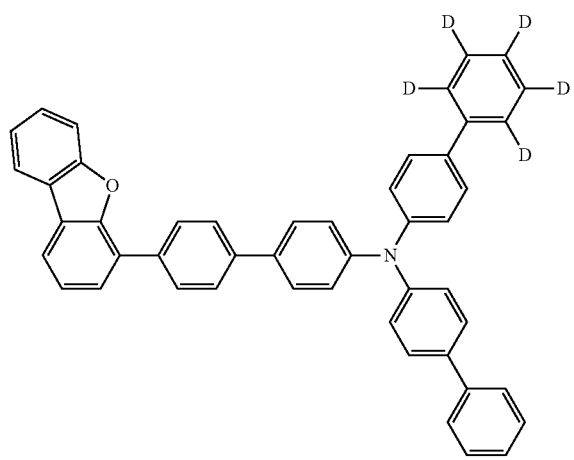

-continued
2-3
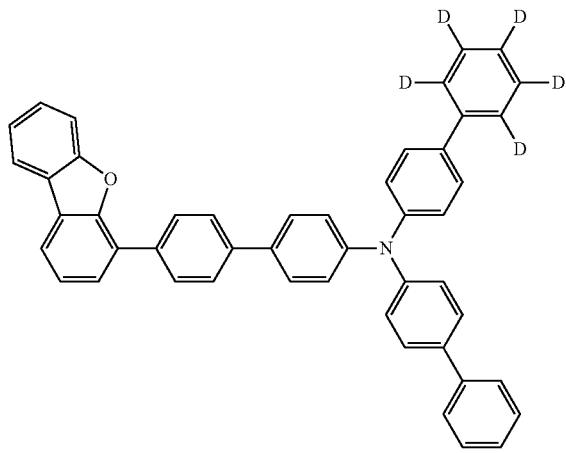
2-4
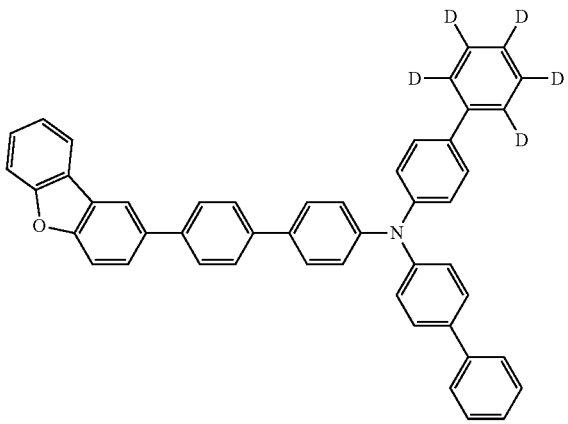
2-5
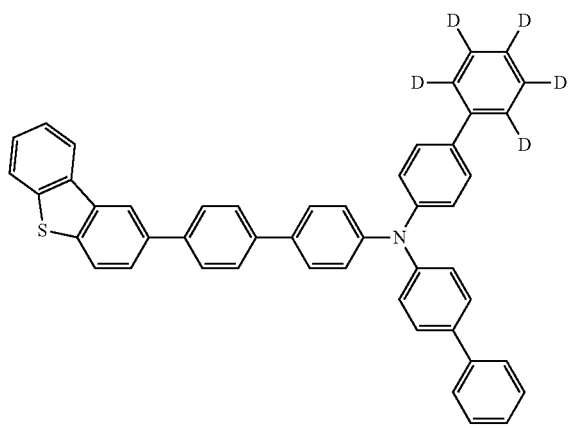
2-6
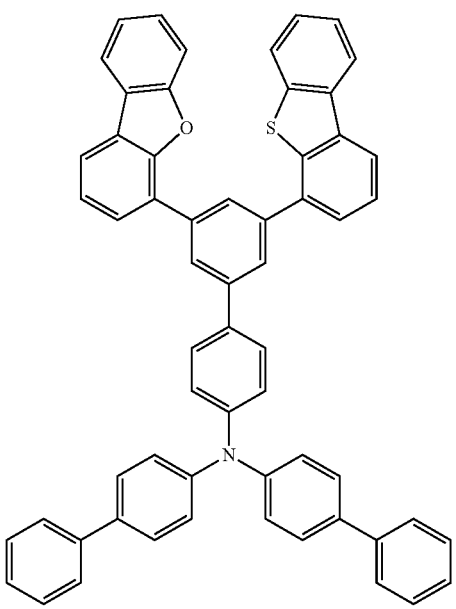
2-7
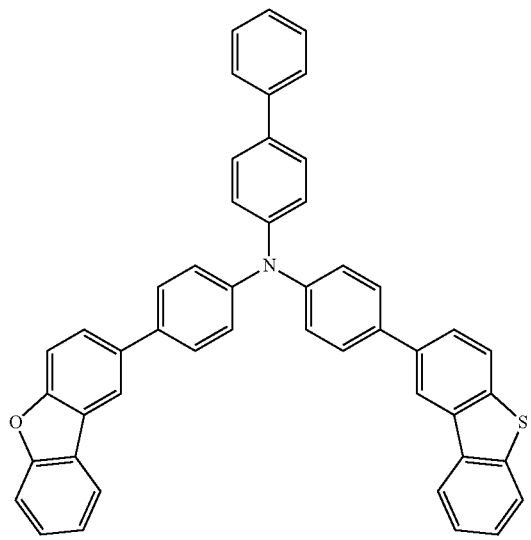
2-8
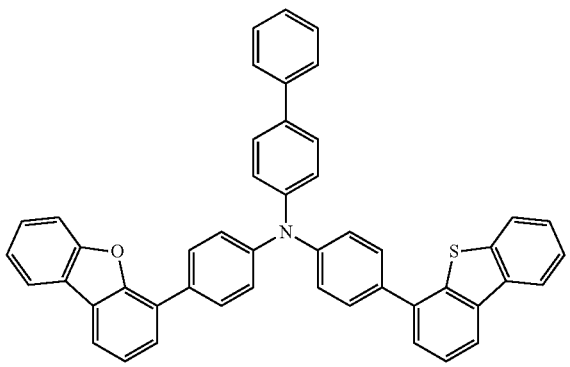

2-9
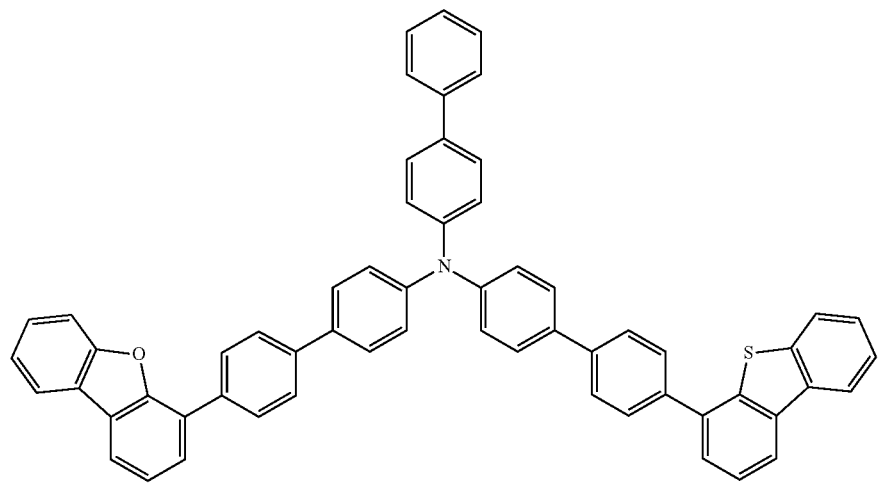
2-10
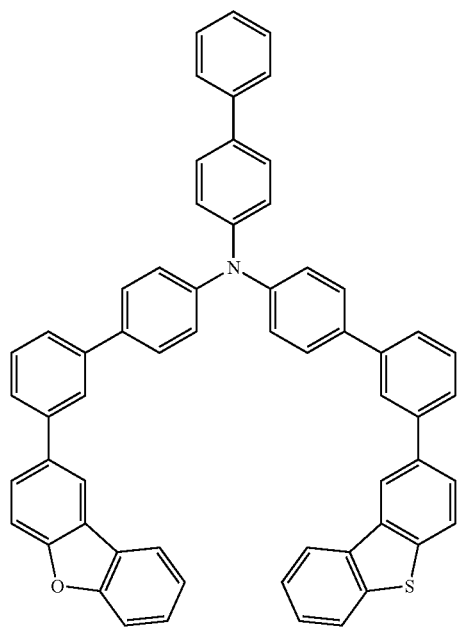
2-11
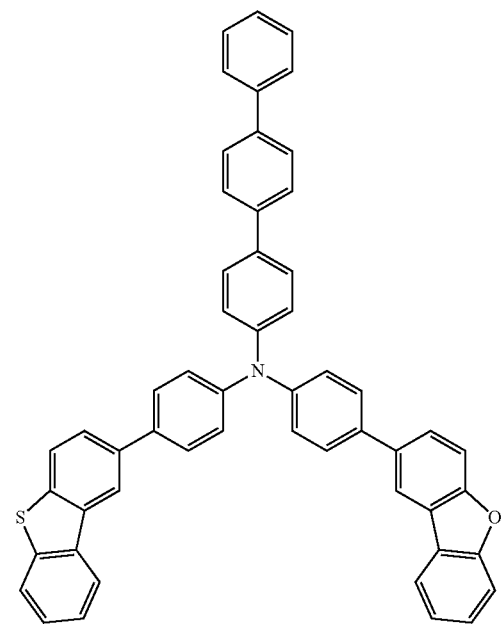
2-12
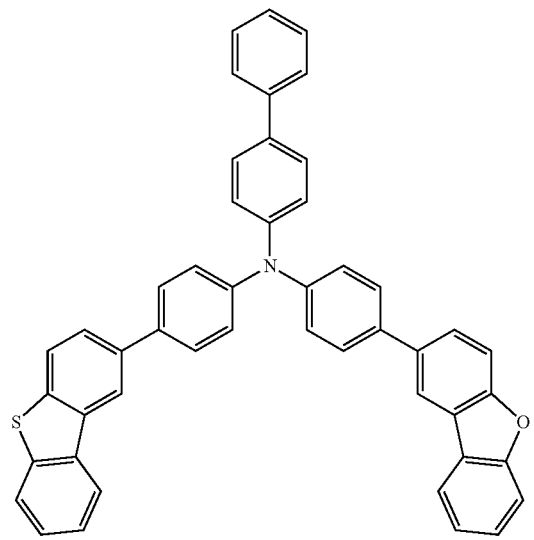
2-13
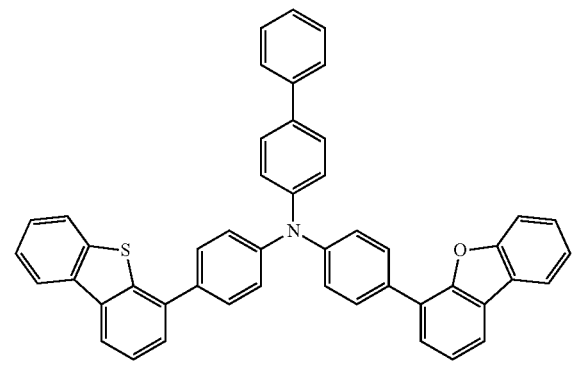

2-14
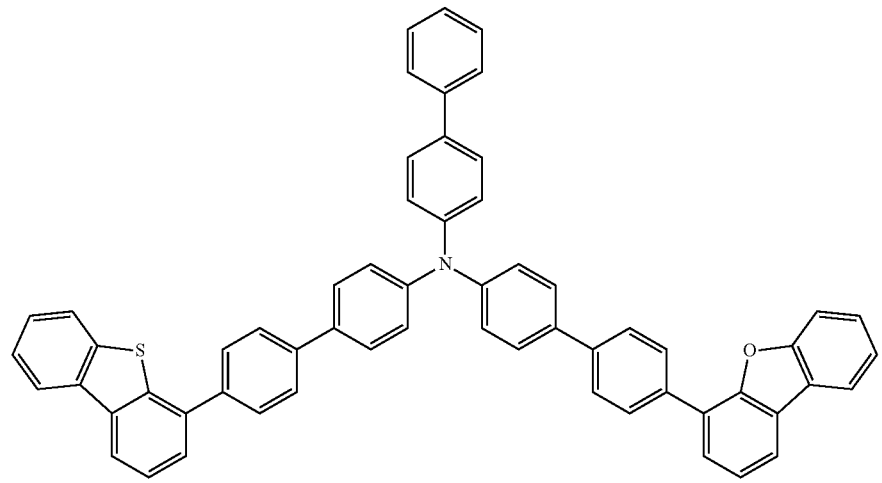
2-15
2-16
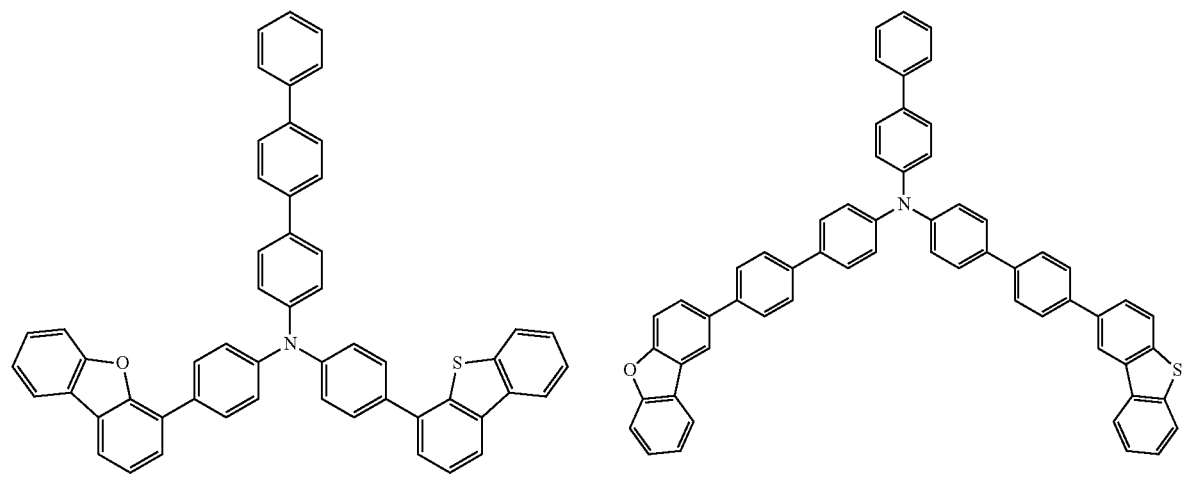
2-17
2-18
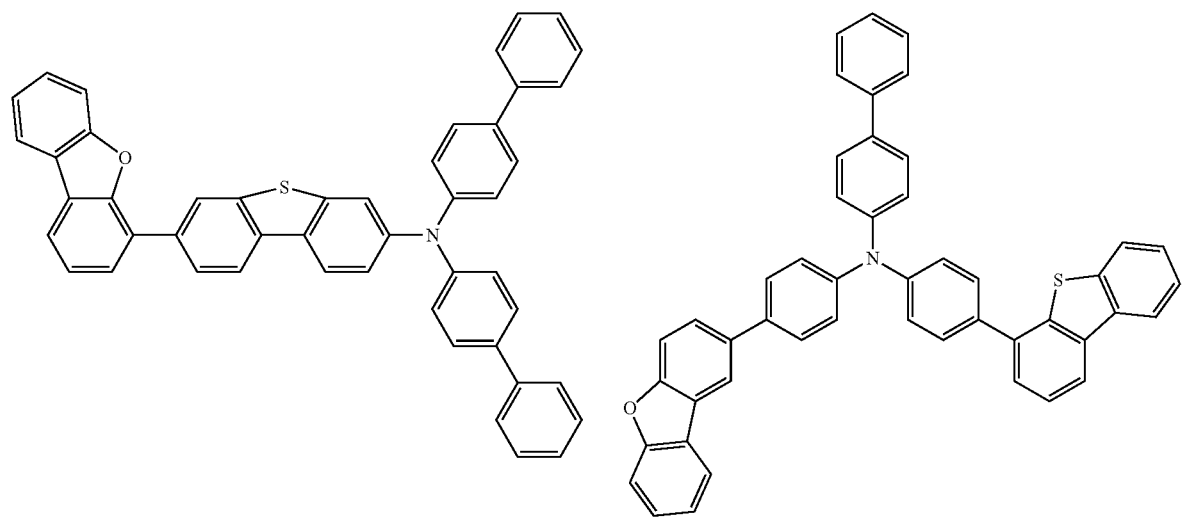

-continued
2-19
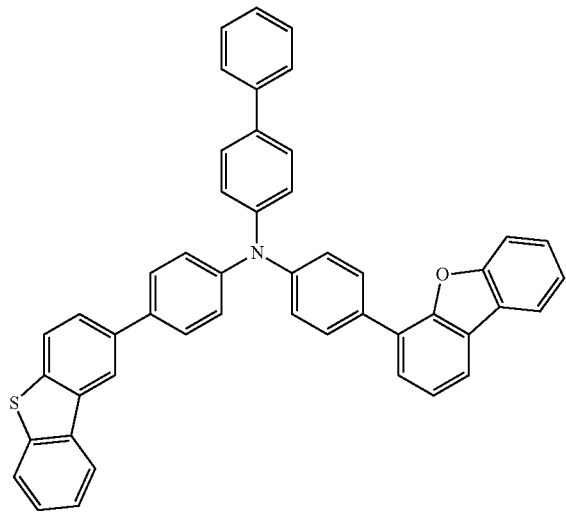
2-20
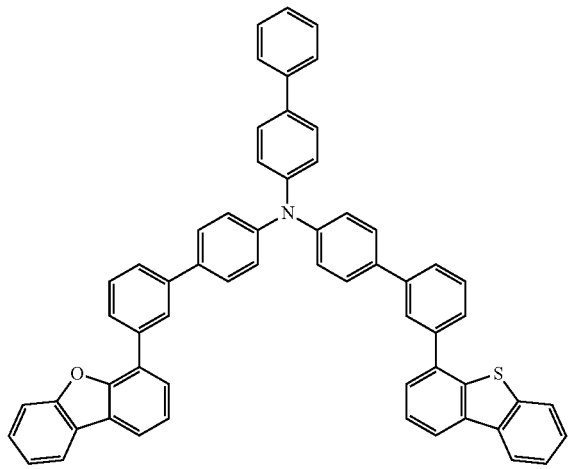
2-21
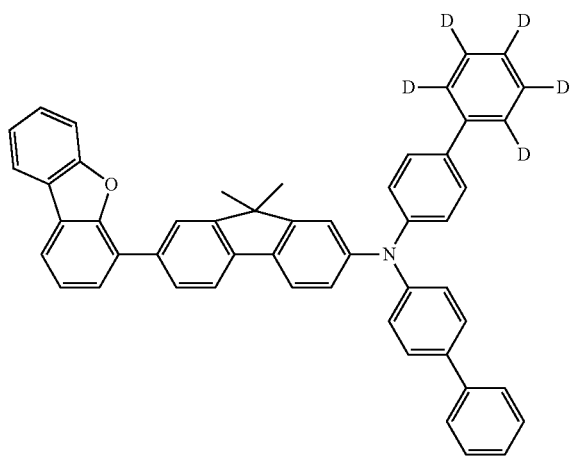
2-22
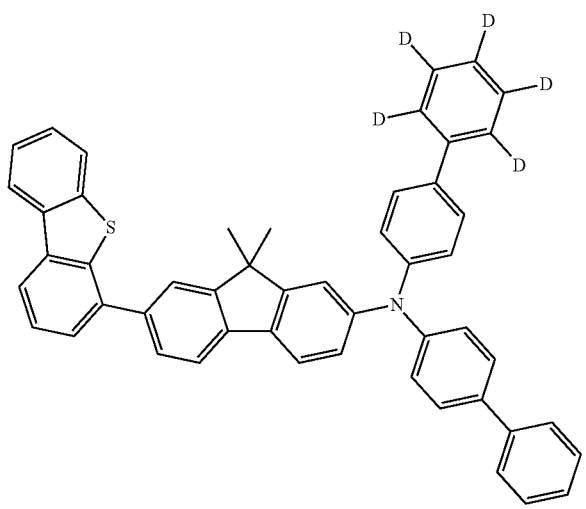
2-23
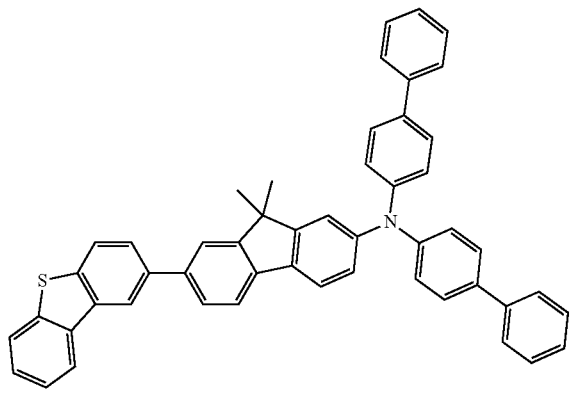
2-24
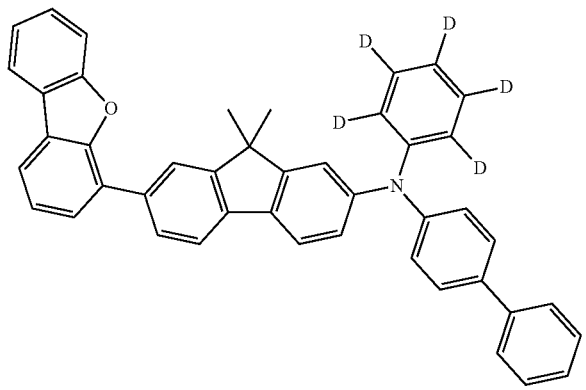

-continued
2-25
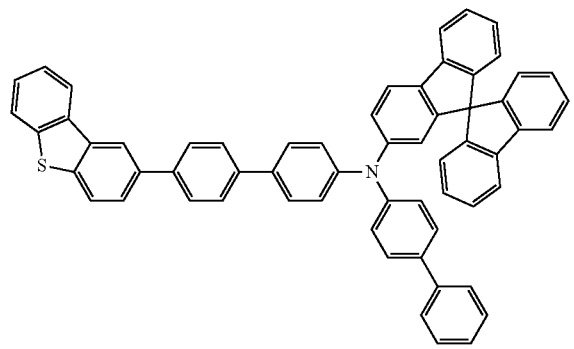
2-26
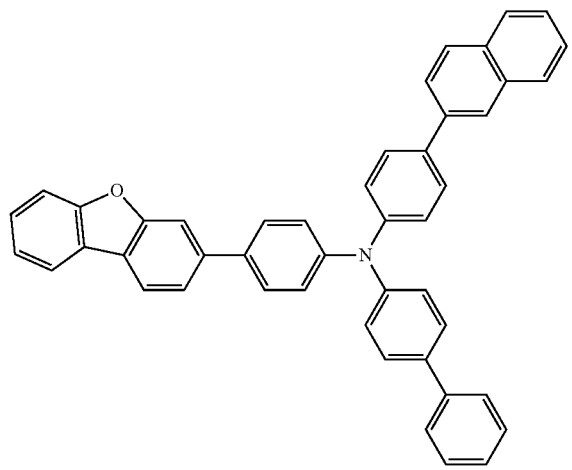
2-27
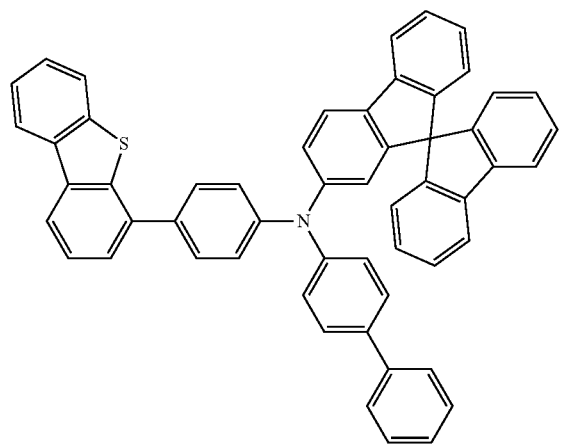
2-28
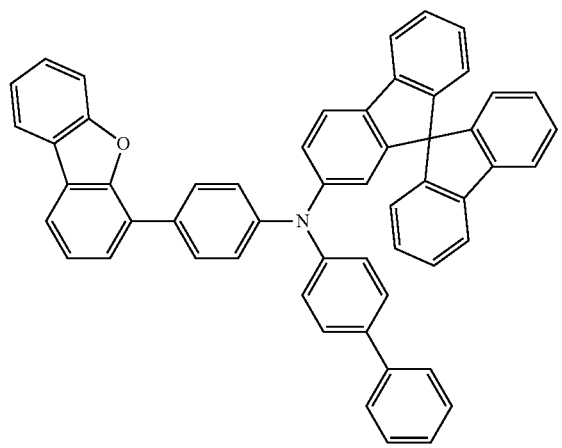
2-29
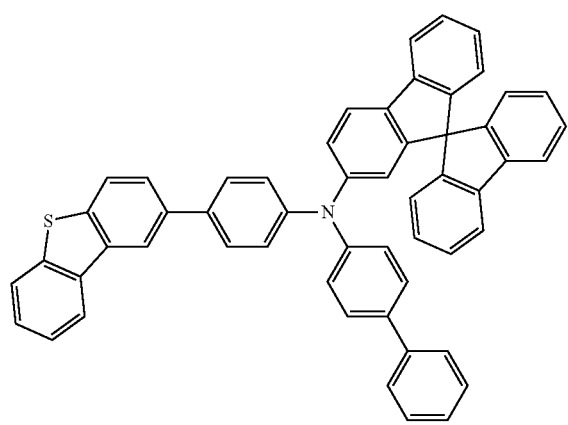
2-30
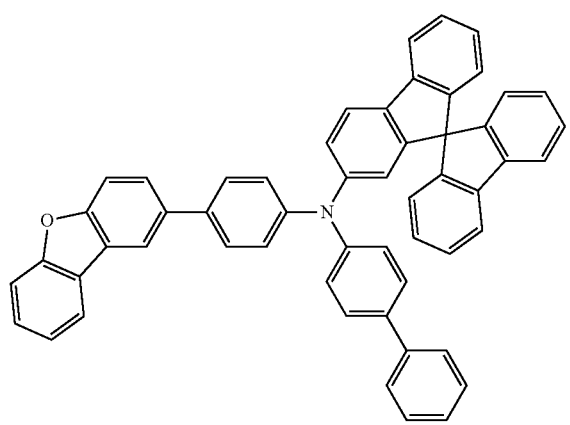

-continued
2-31
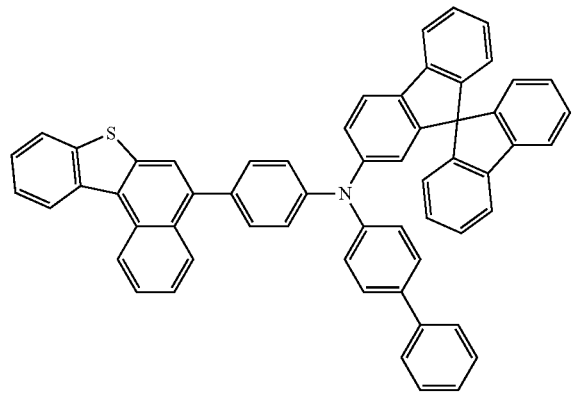
2-32
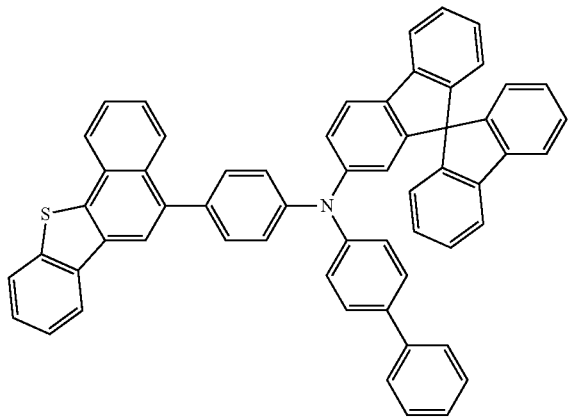
2-33
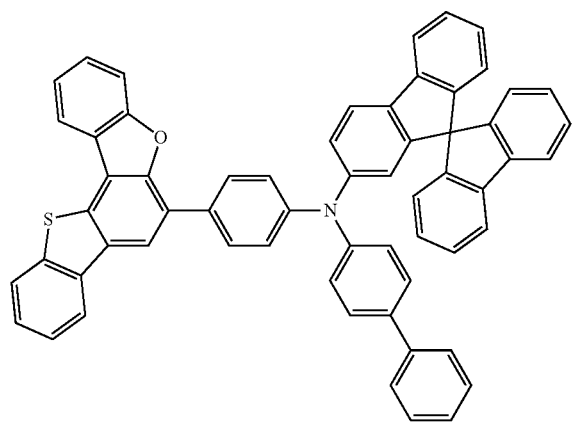
2-34
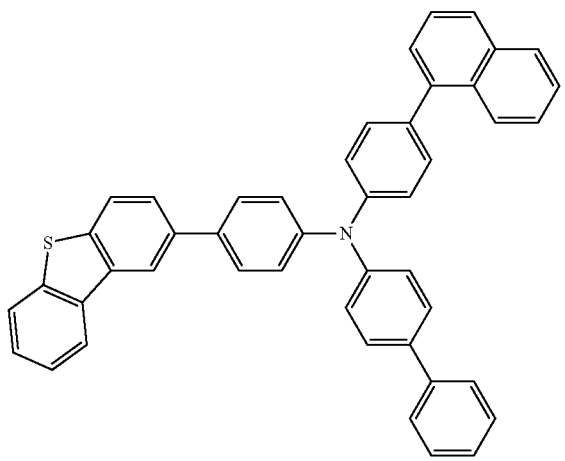
2-35
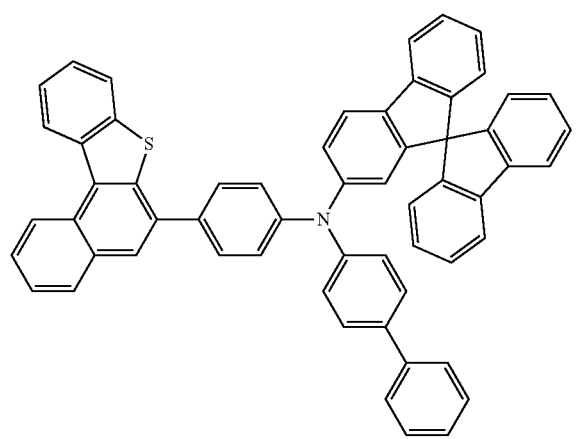
2-36
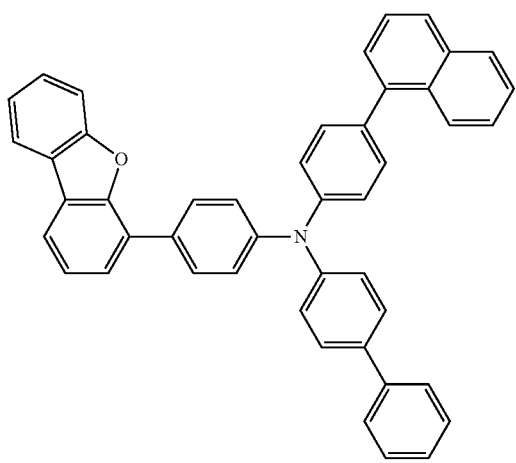

-continued
2-37
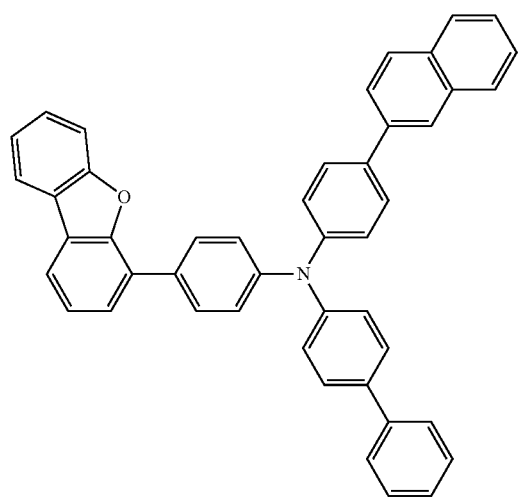
2-38
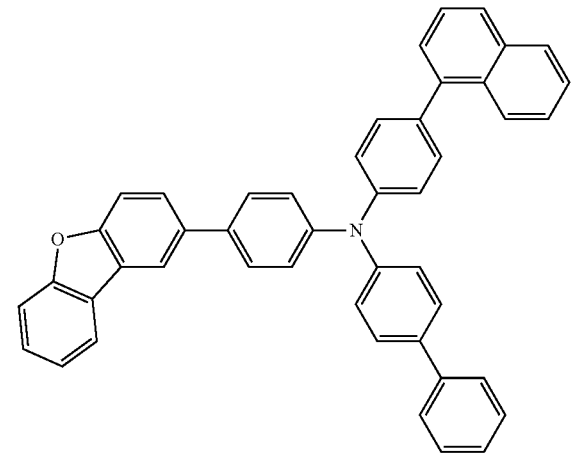
2-39
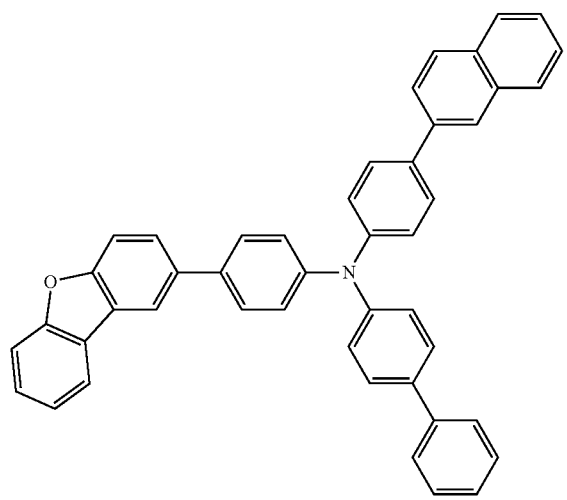
2-40
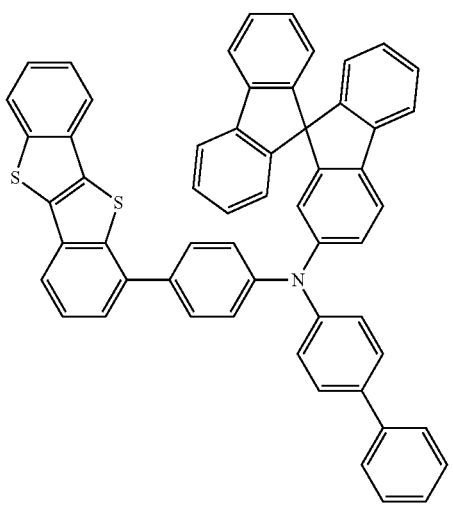
2-41
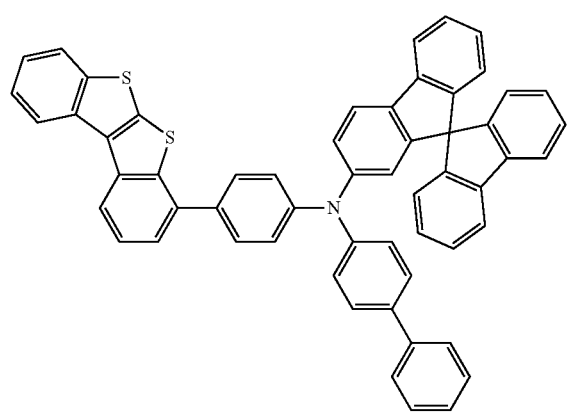
2-42
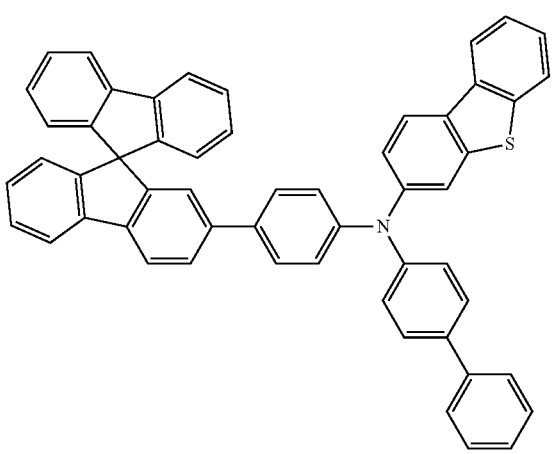

-continued
2-43
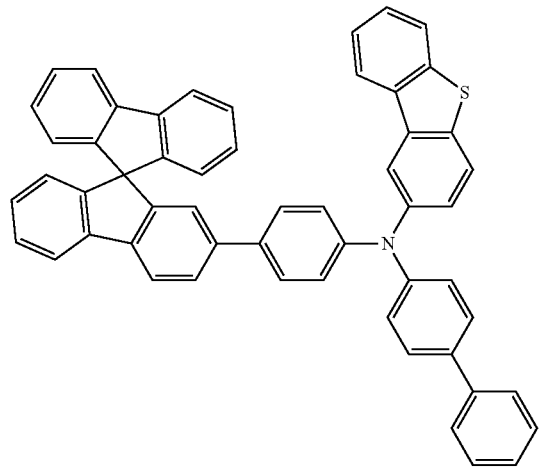
2-44
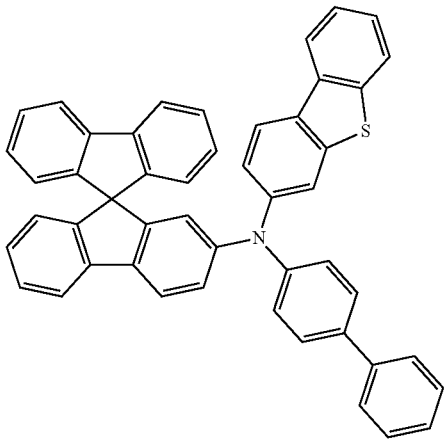
2-45
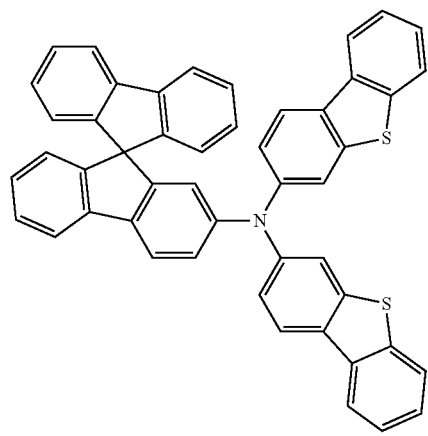
2-46
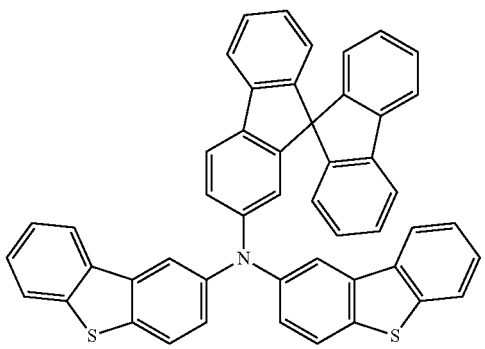
2-47
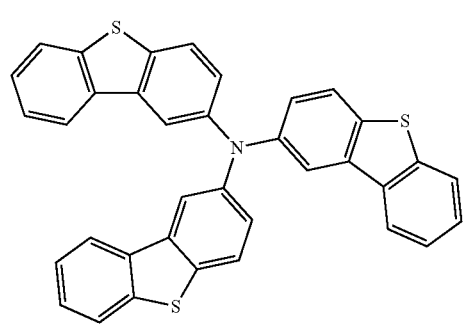
2-48
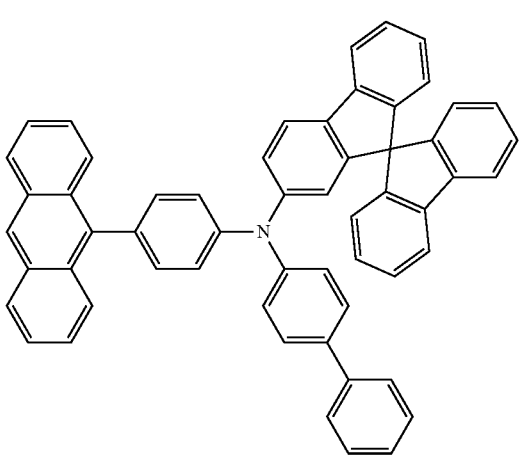

-continued
2-49
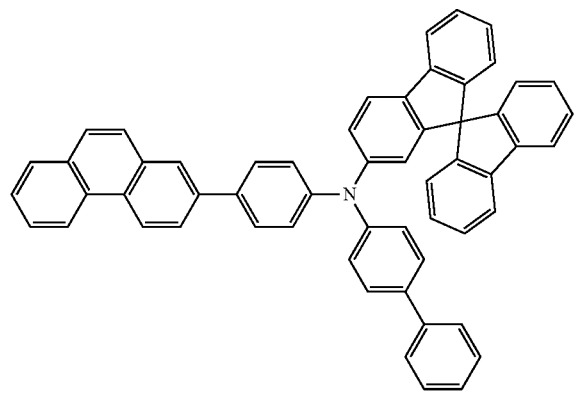
2-50
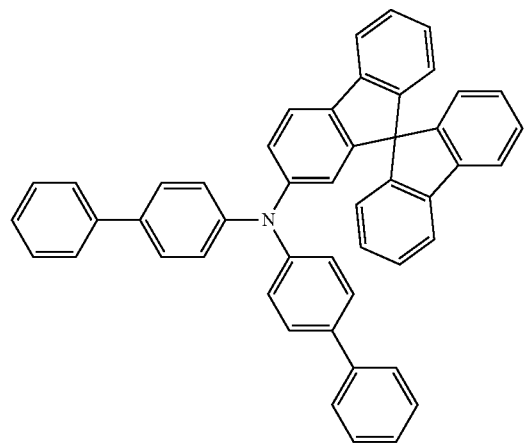
2-51
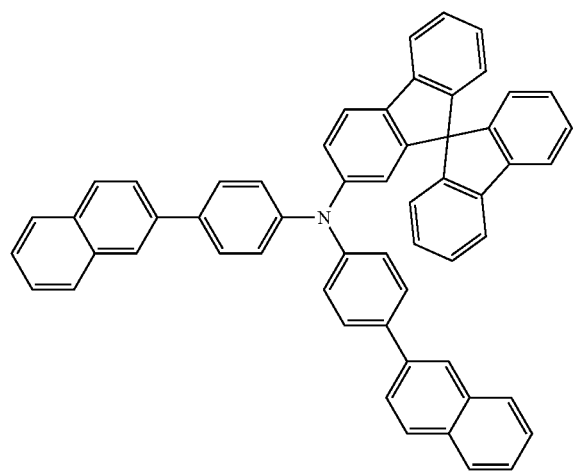
2-52
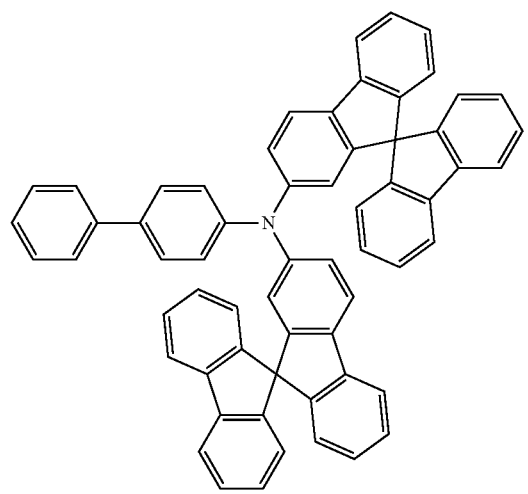
2-53
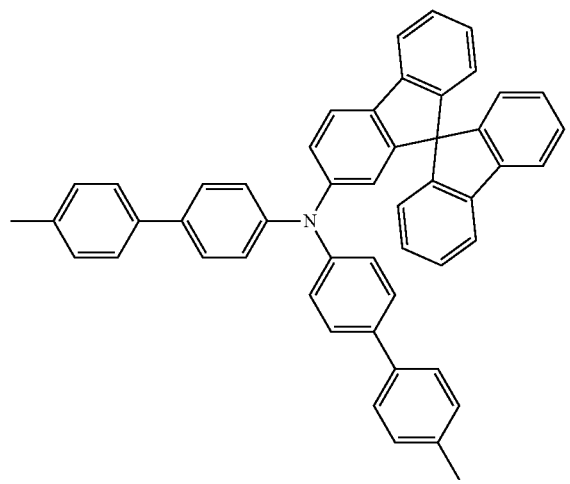
2-54
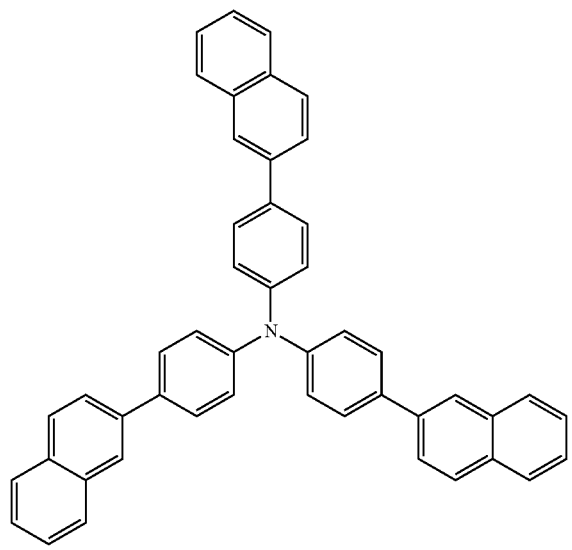

-continued
2-55
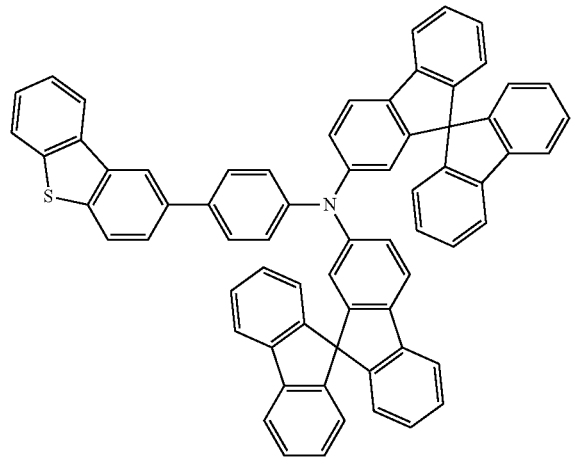
2-56
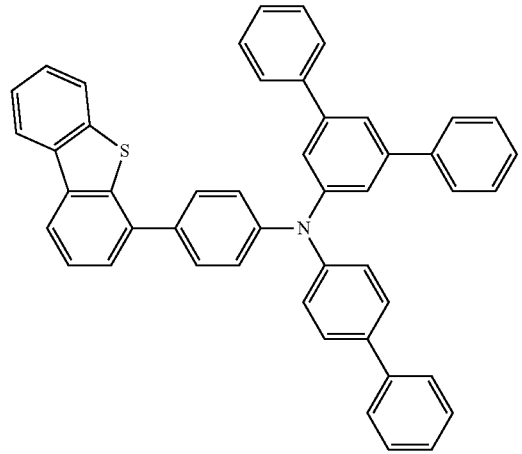
2-57
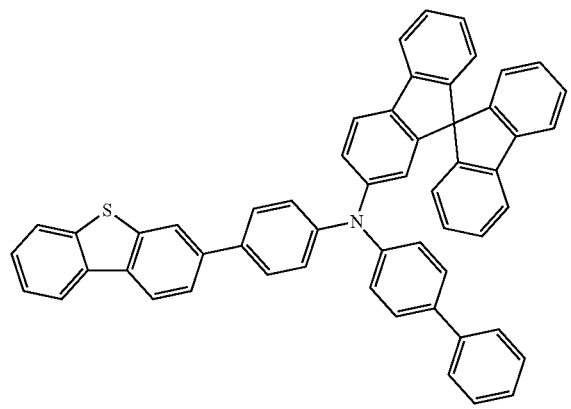
2-58
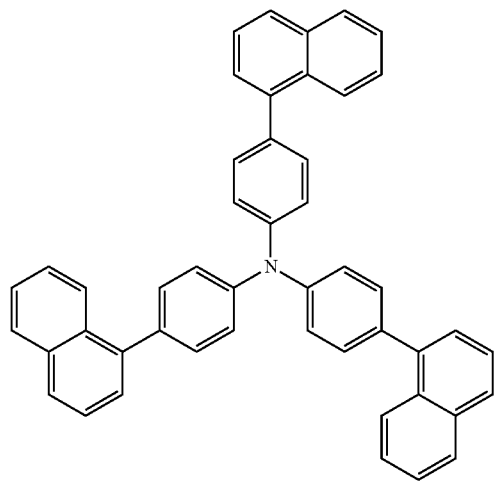
2-59
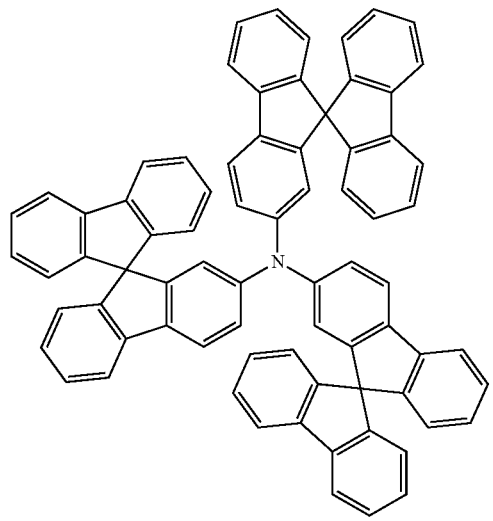
2-60
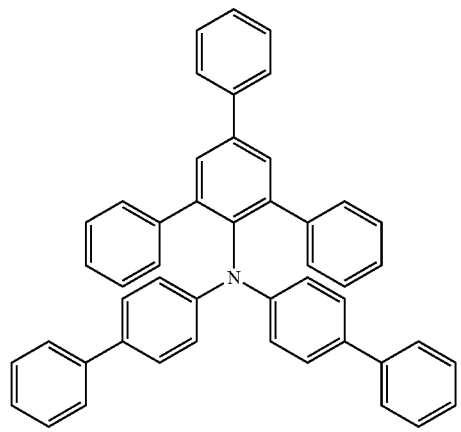

-continued
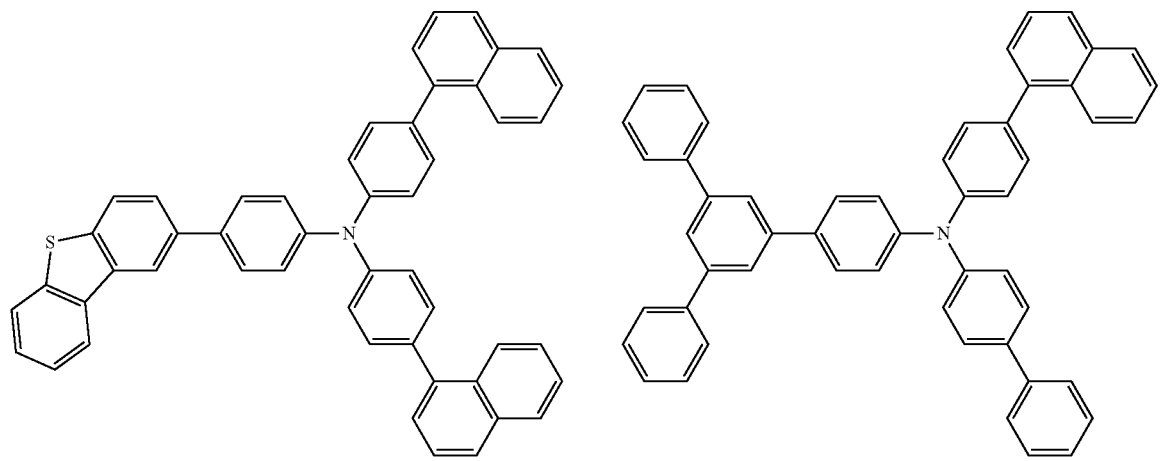
2-61　　2-62
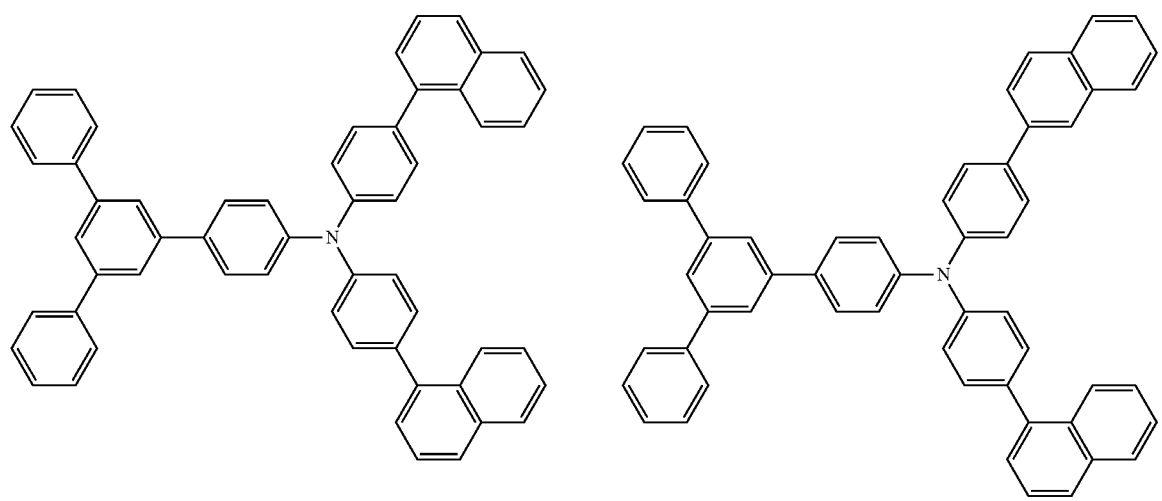
2-63　　2-64
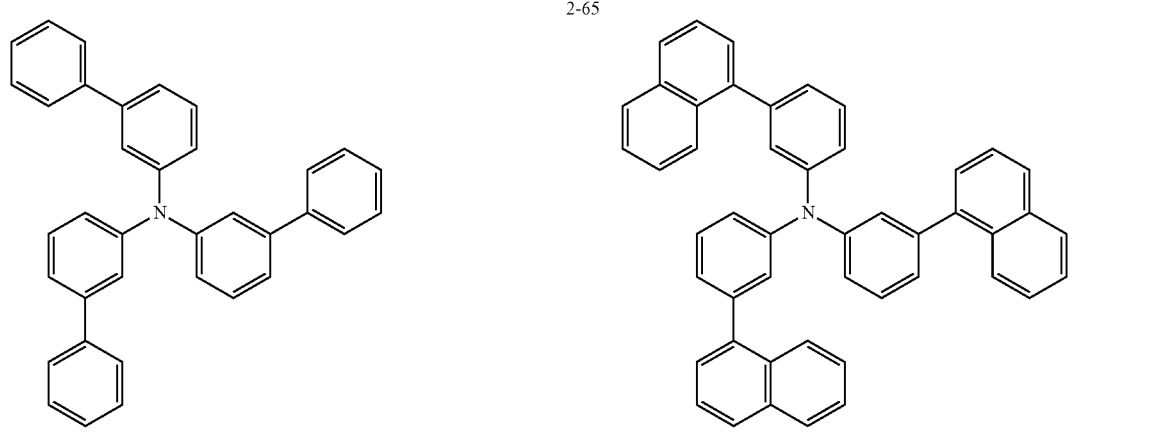
2-65　　2-66

-continued
2-67
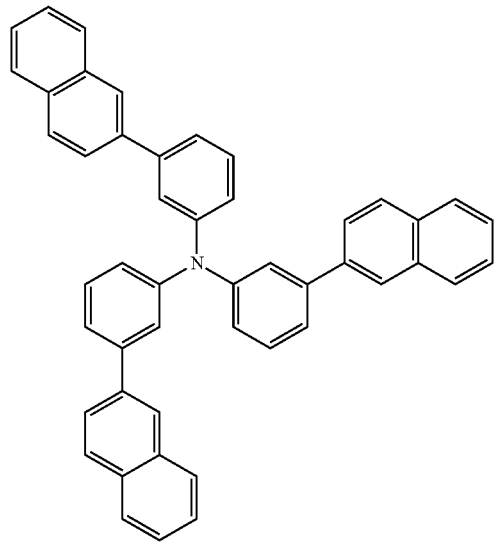
2-68
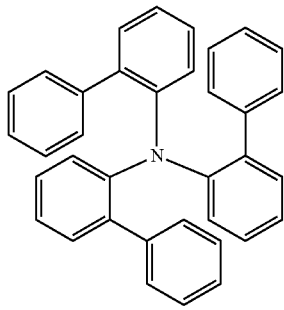
2-69
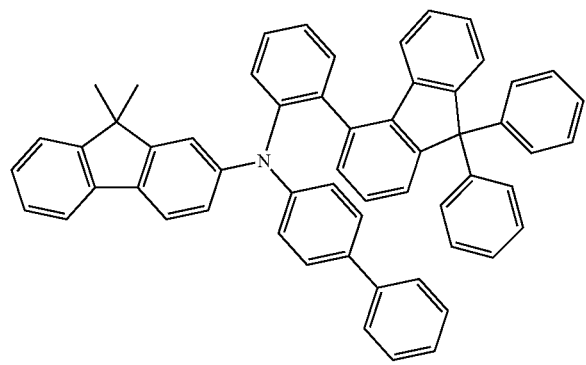
2-70
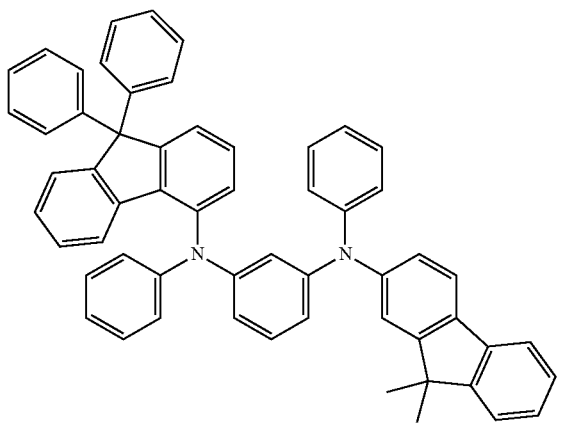
2-71
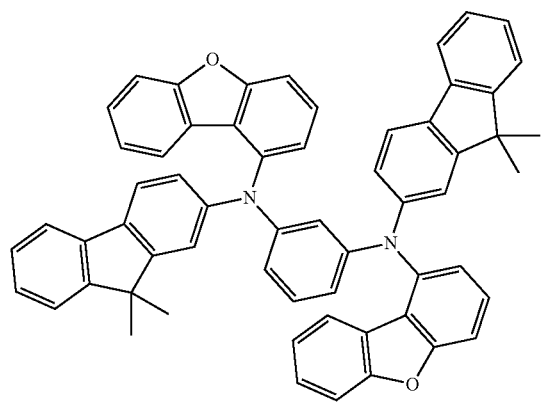
2-72
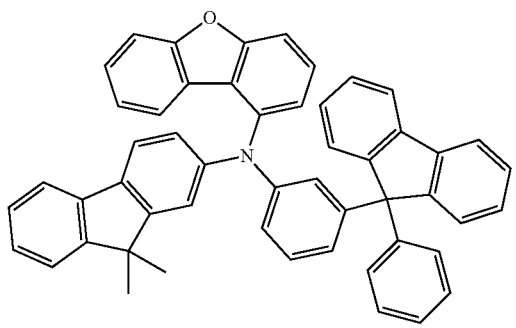

-continued
2-73
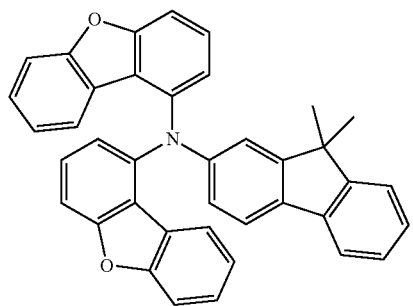
2-74
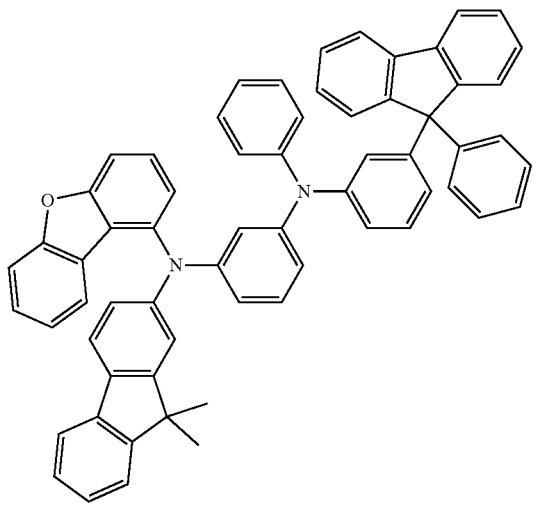
2-75
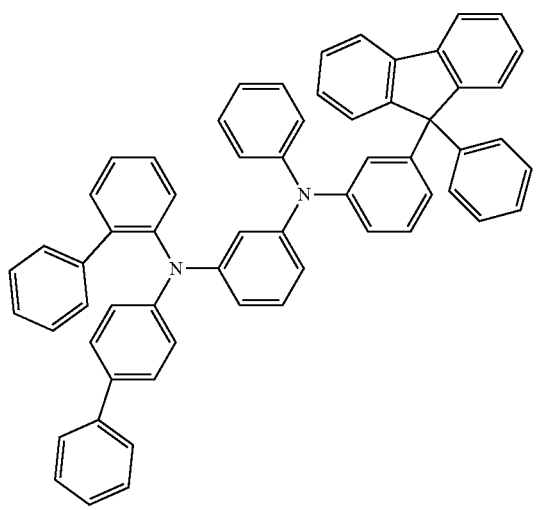
2-76
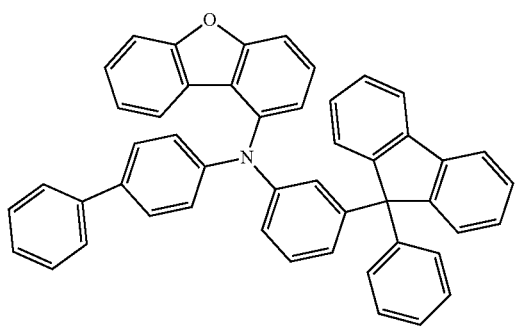
2-77
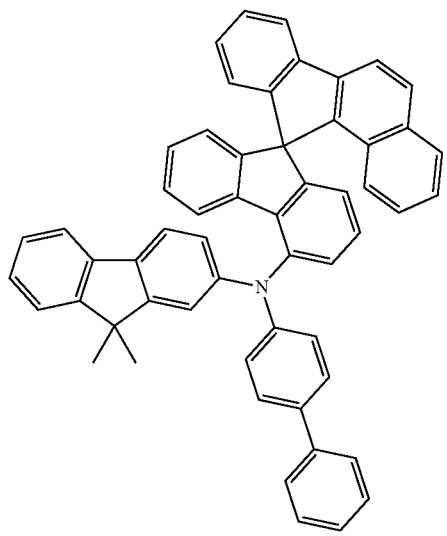
2-78
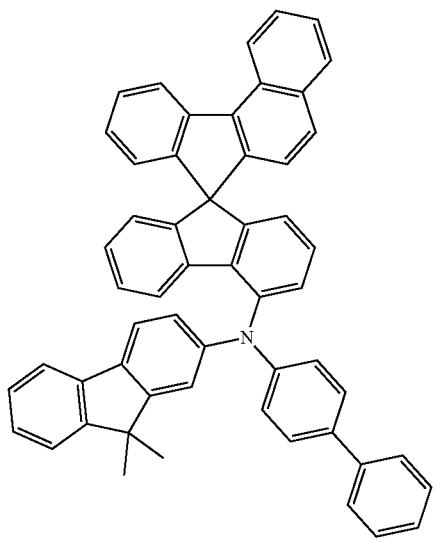

-continued
2-79
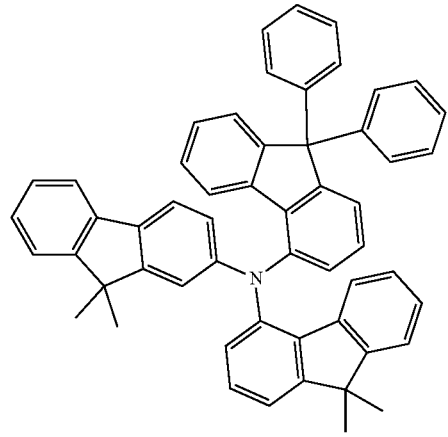
2-80
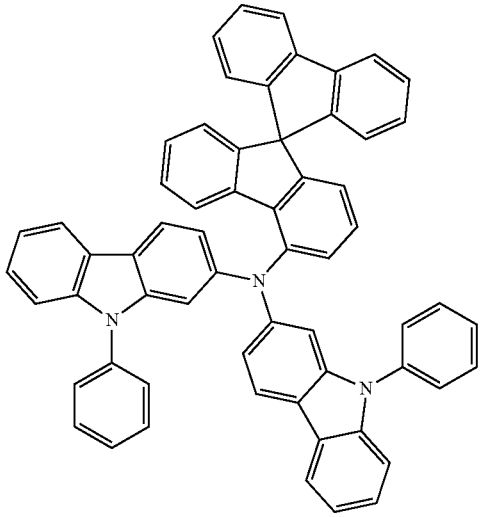
2-81
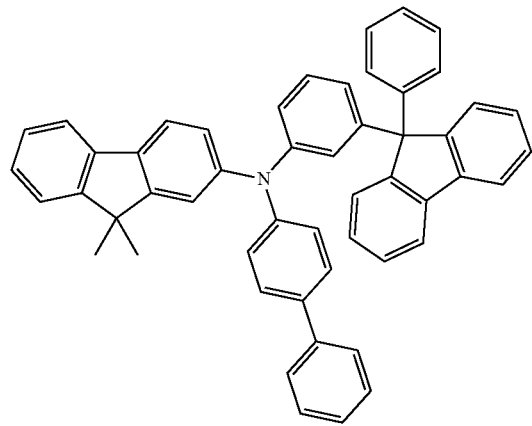
2-82
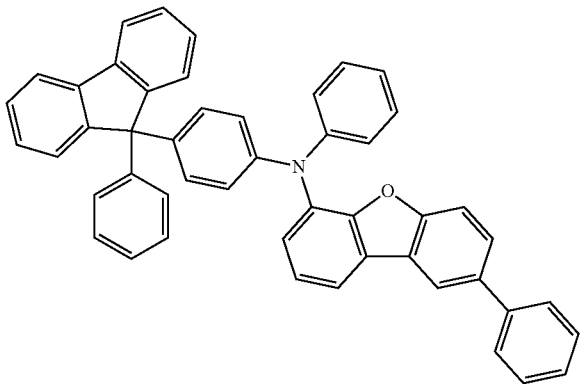
2-83
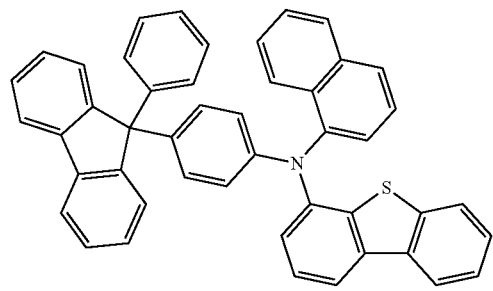
2-84
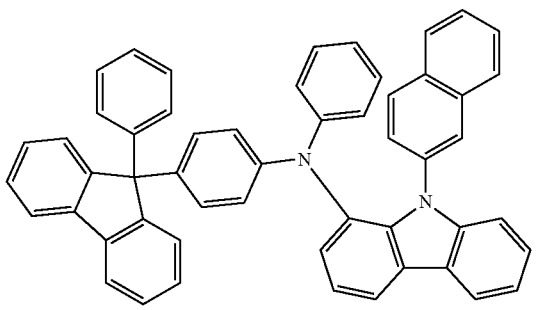

2-85
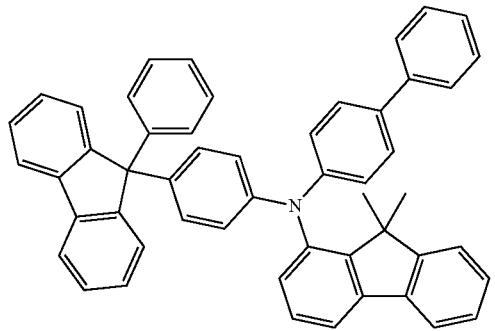
2-86
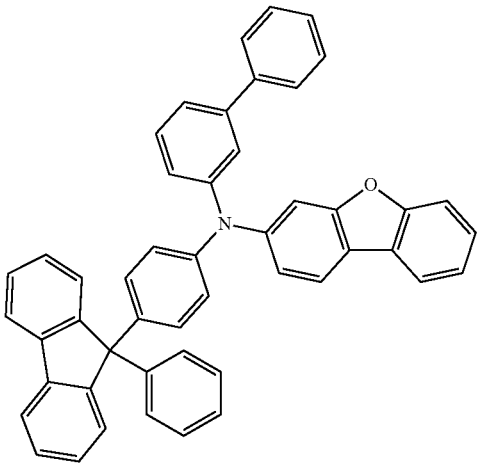
2-87
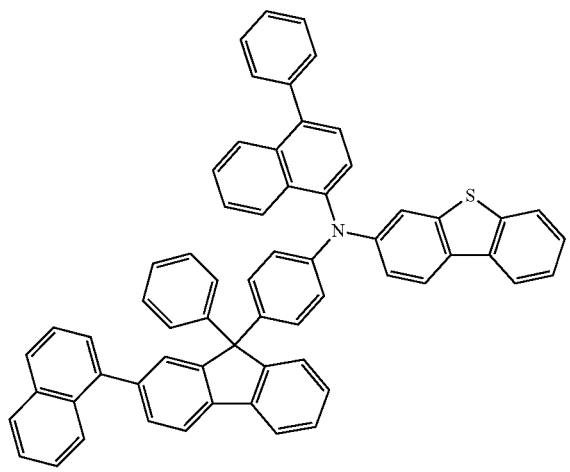
2-88
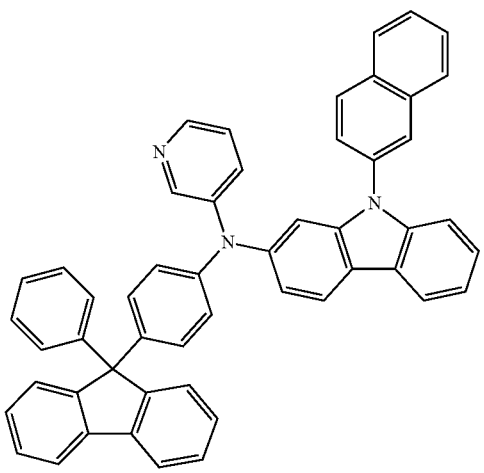
2-89
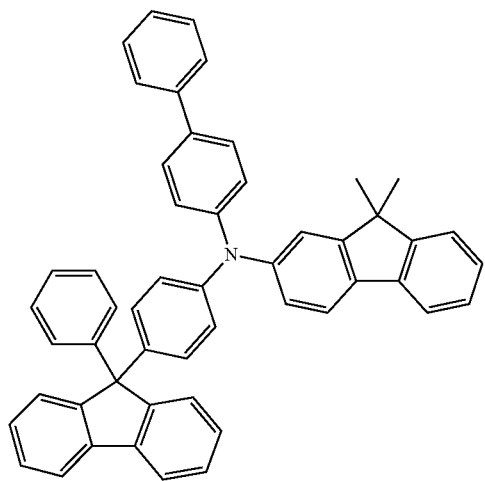
2-90
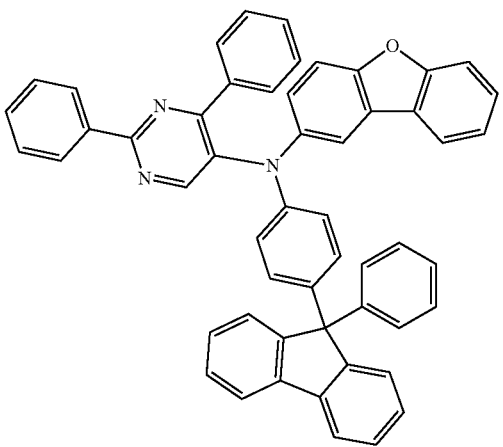

2-91
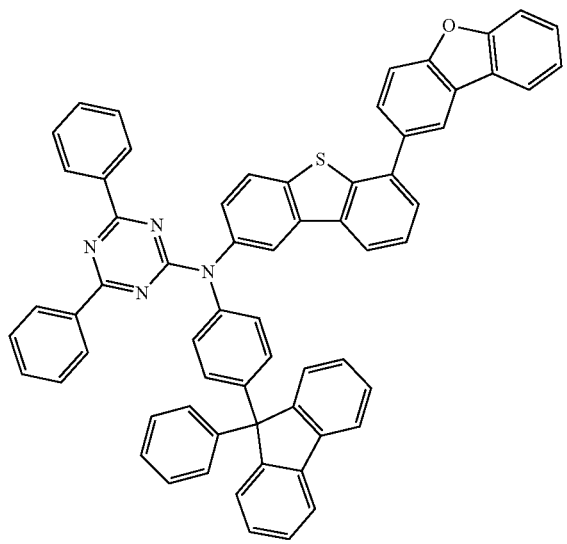
2-92
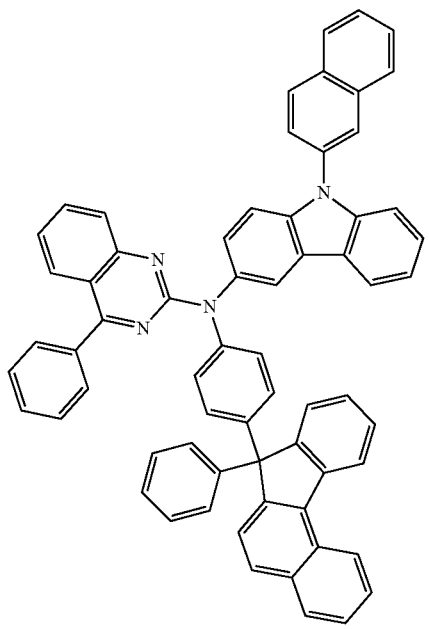
2-93
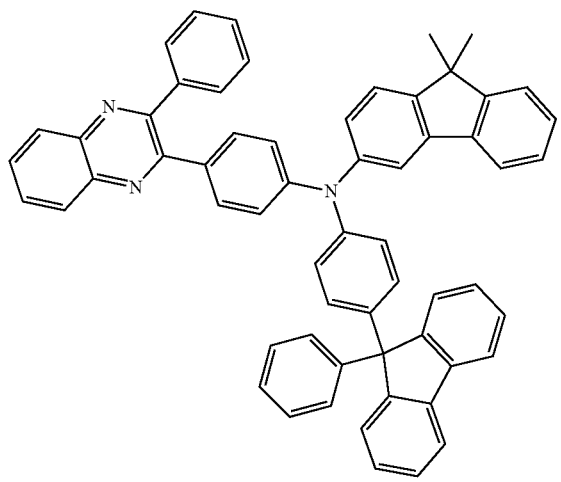
2-94
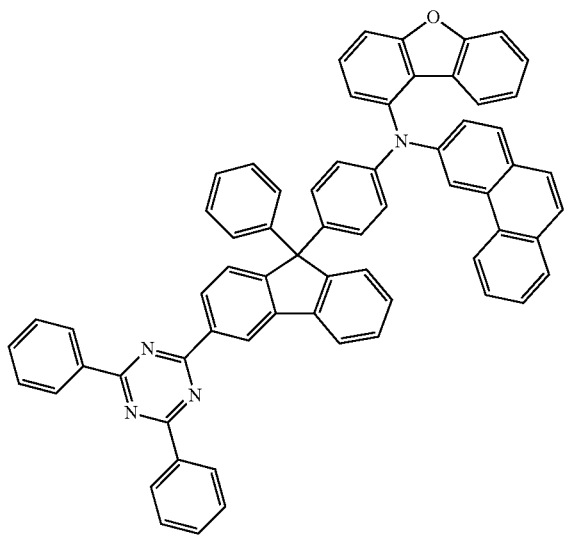
2-95
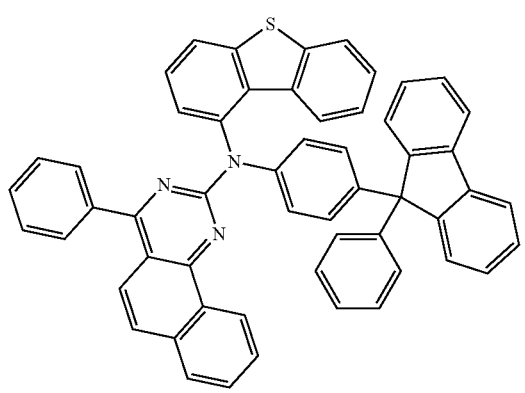
2-96
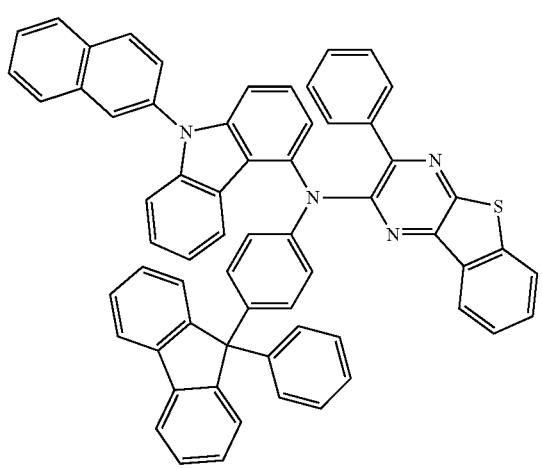

-continued
2-97
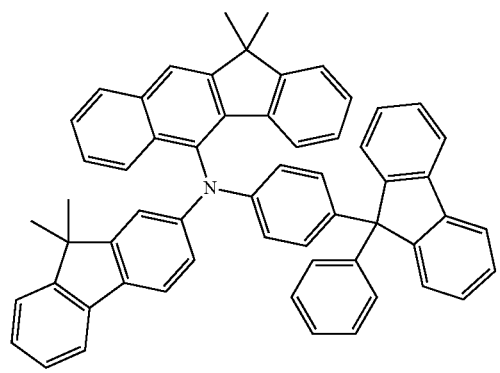
2-98
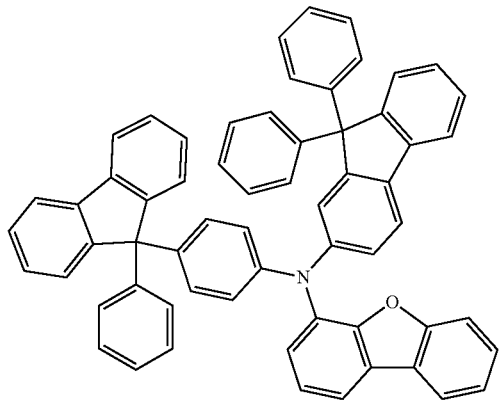
2-99
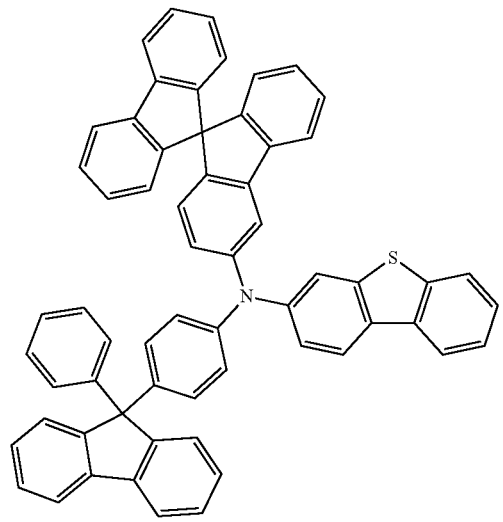
2-100
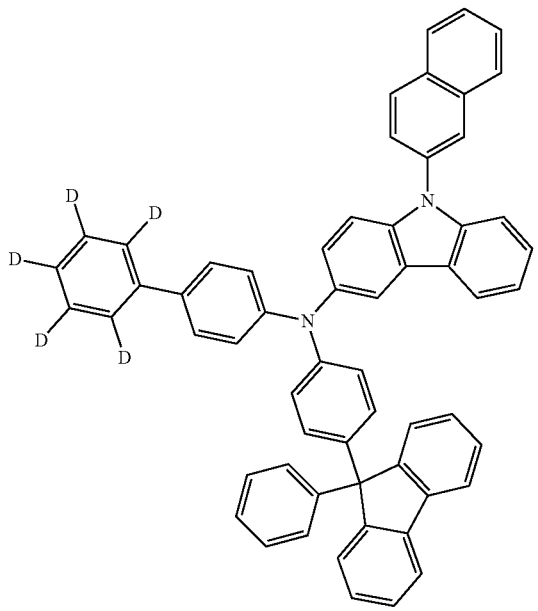
2-101
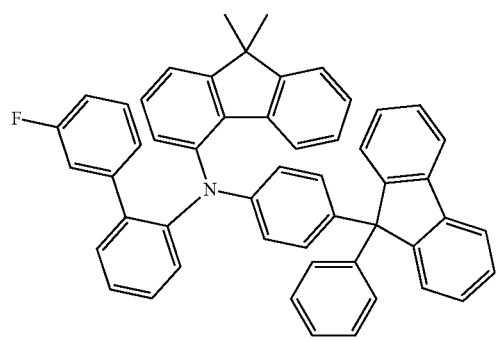
2-102
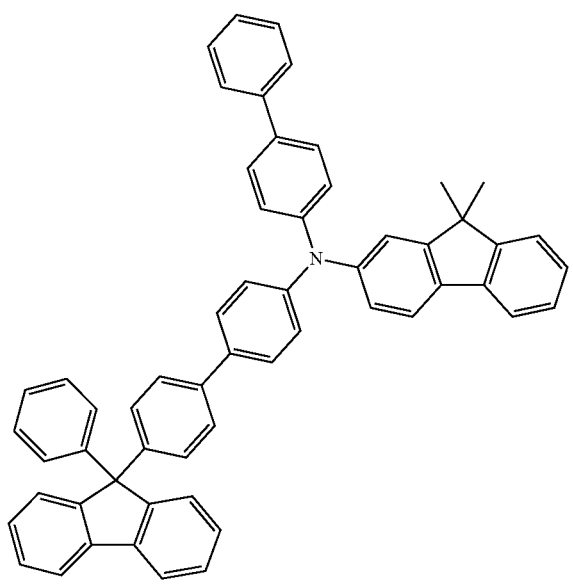

-continued
2-103
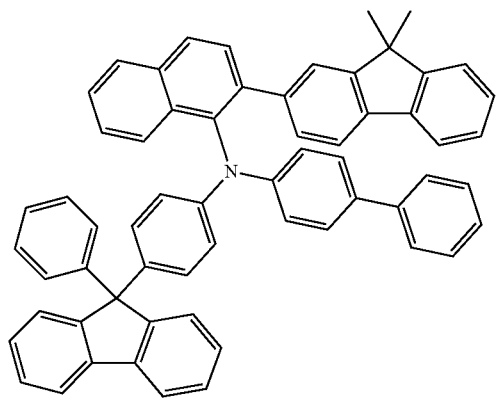
2-104
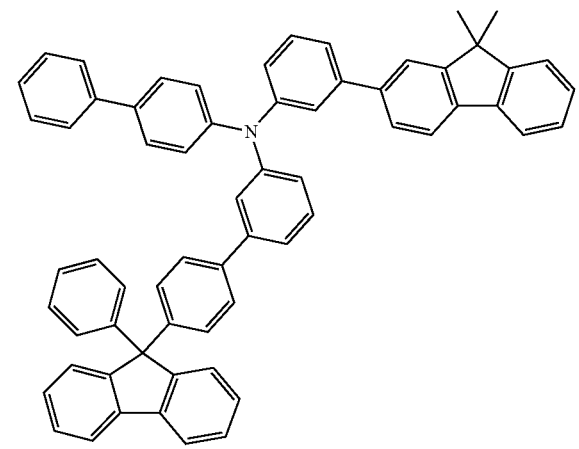
2-105
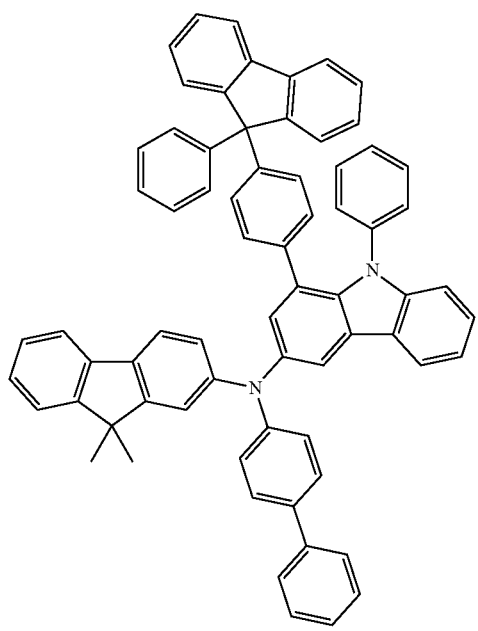
2-106
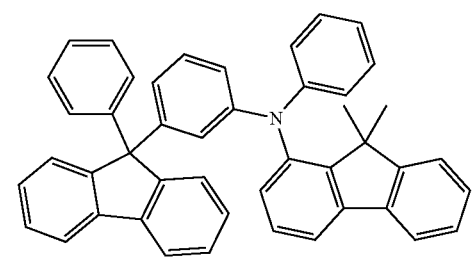
2-107
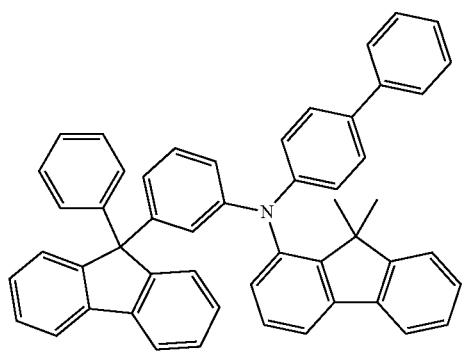
2-108
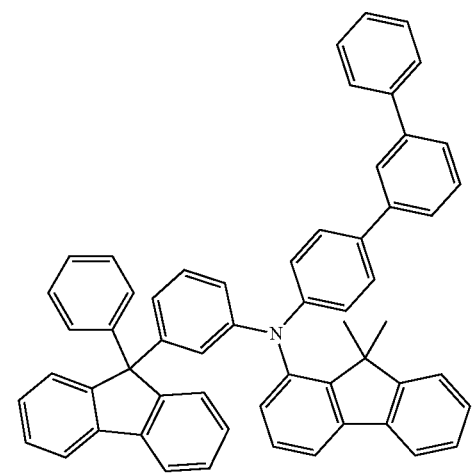

-continued
2-109
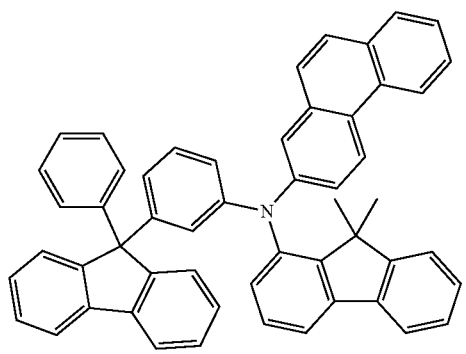
2-110
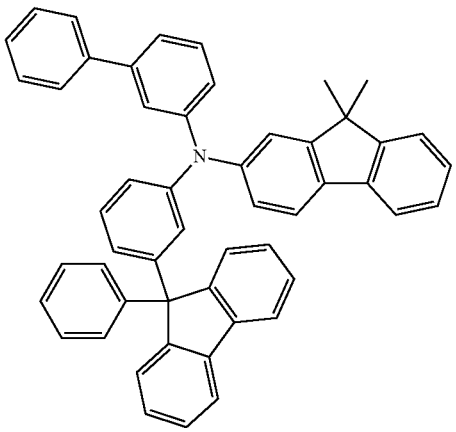
2-111
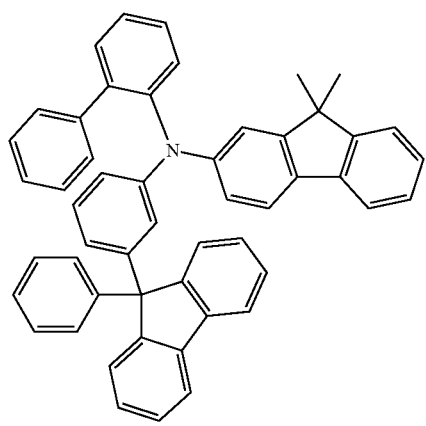
2-112
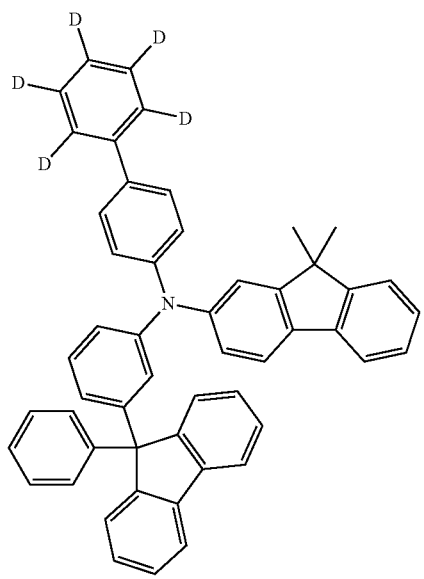
2-113
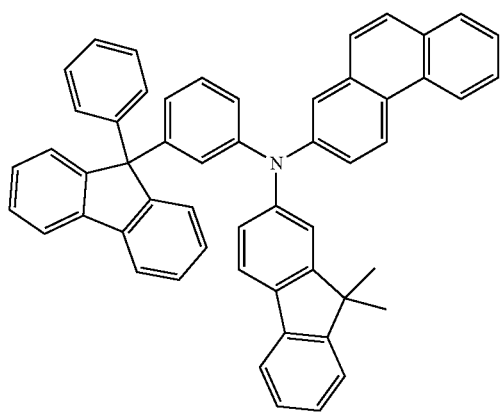
2-114
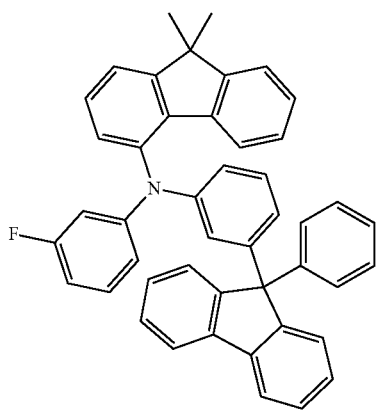

-continued
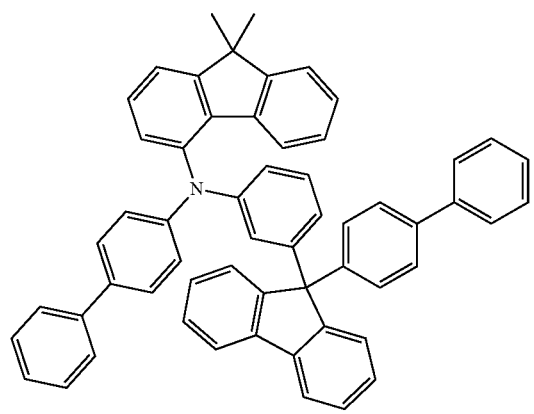
2-115
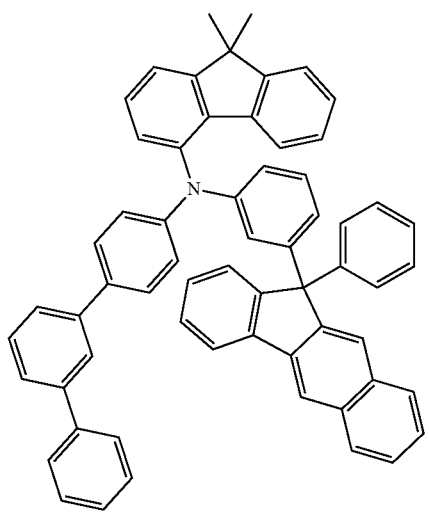
2-116
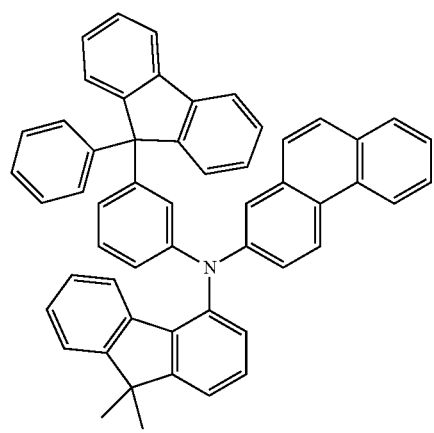
2-117
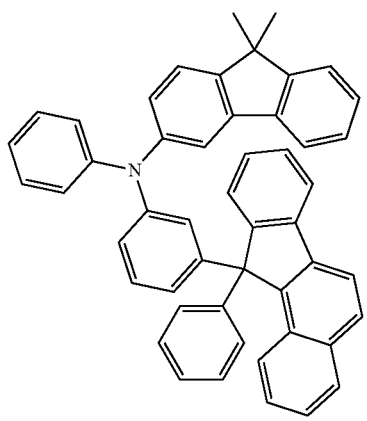
2-118
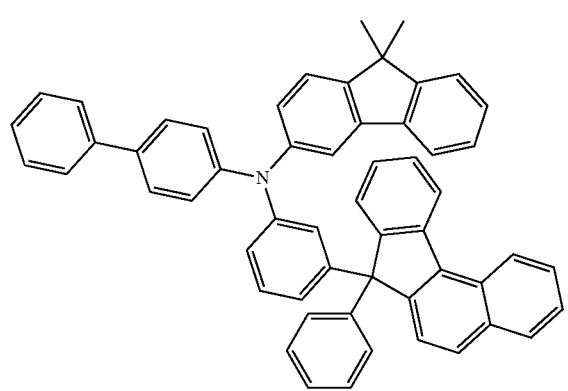
2-119
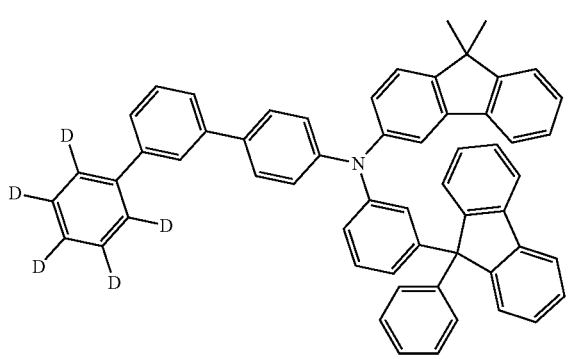
2-120

-continued
2-121
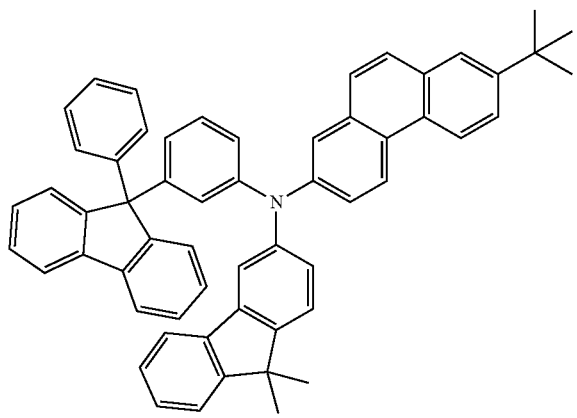
2-122
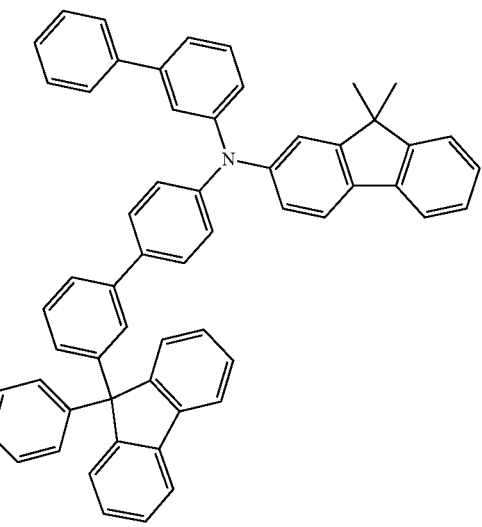
2-123
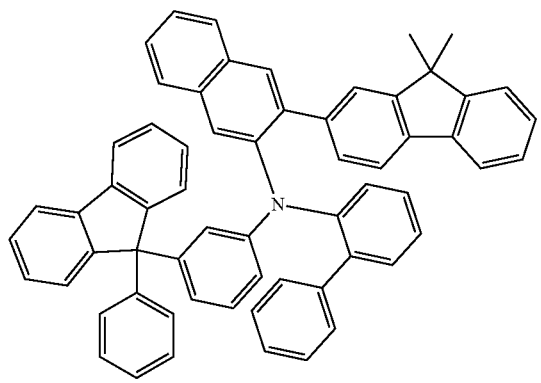
2-124
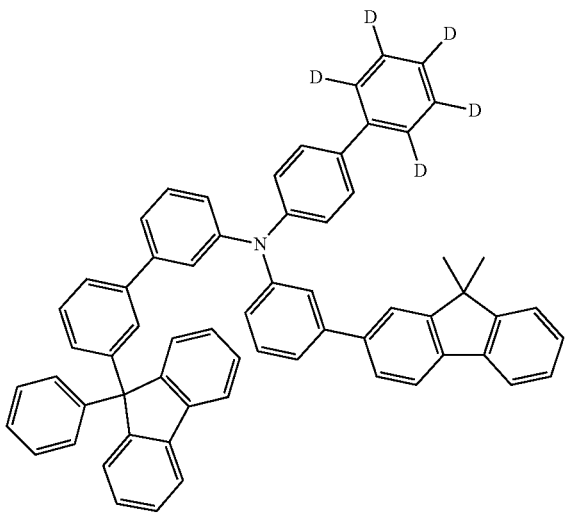
2-125
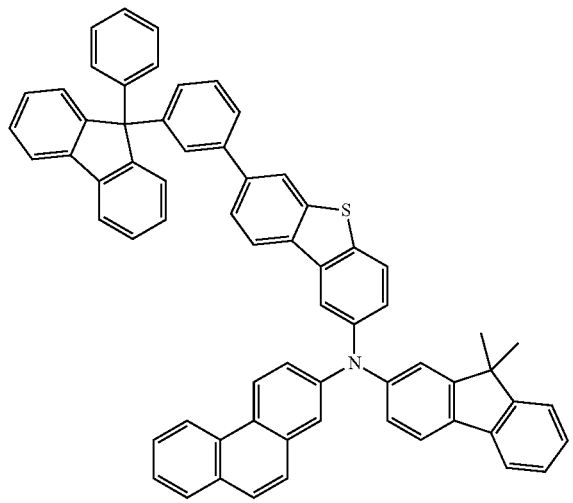
2-126
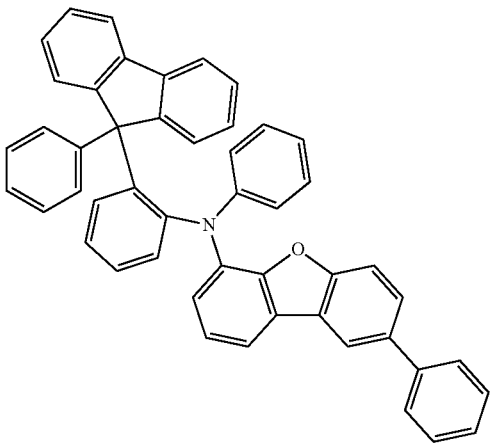

2-127
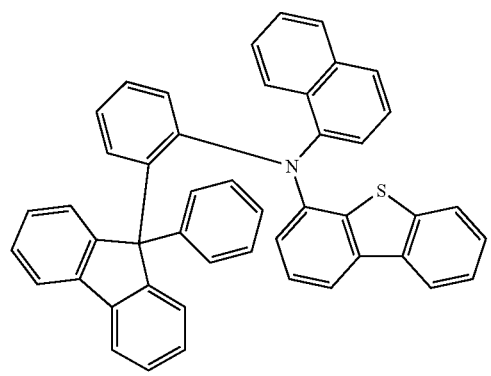
2-128
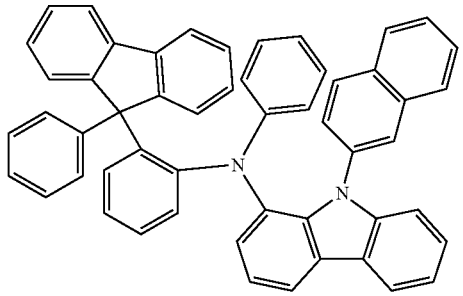
2-129
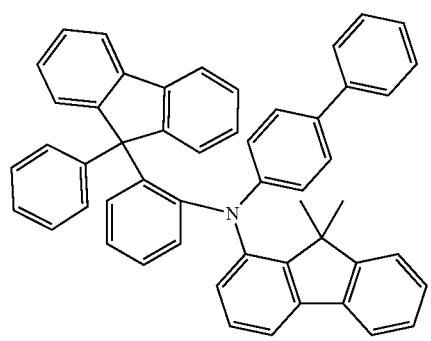
2-130
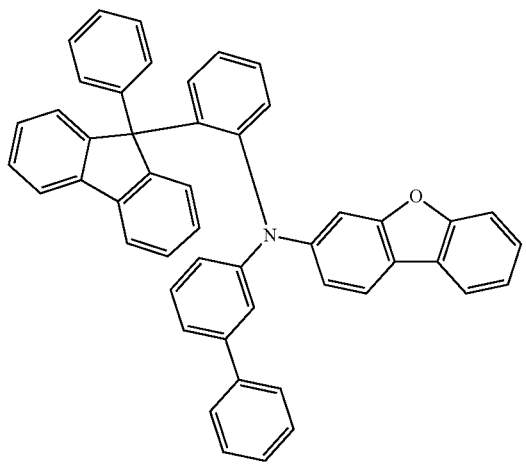
2-131
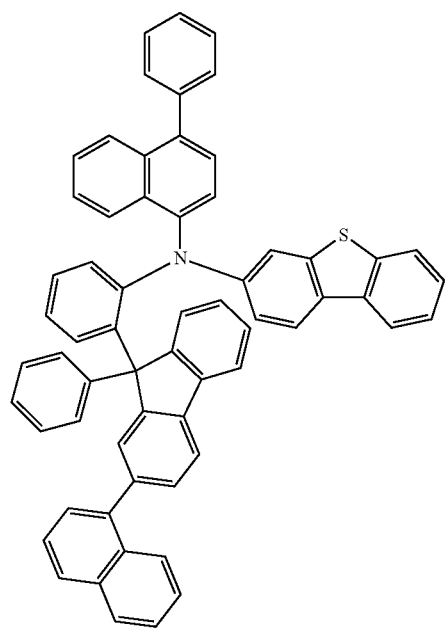
2-132
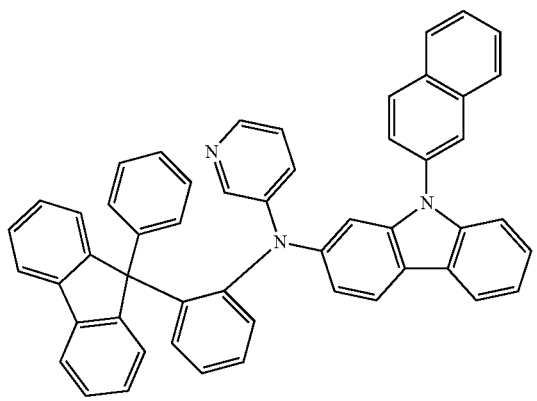

-continued
2-133
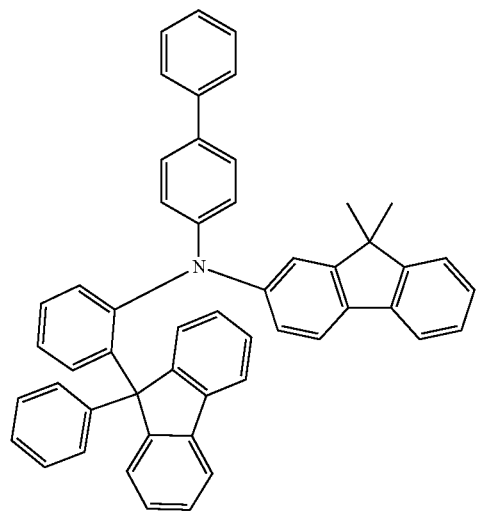
2-134
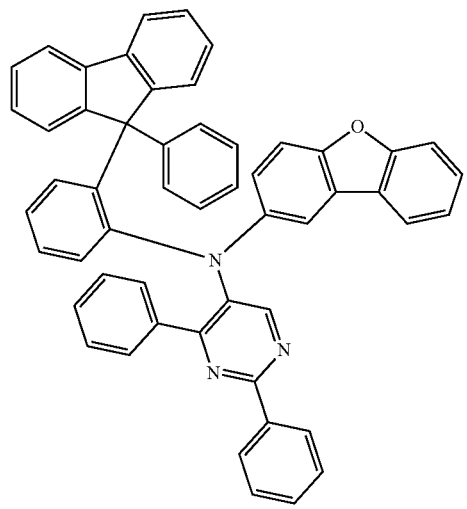
2-135
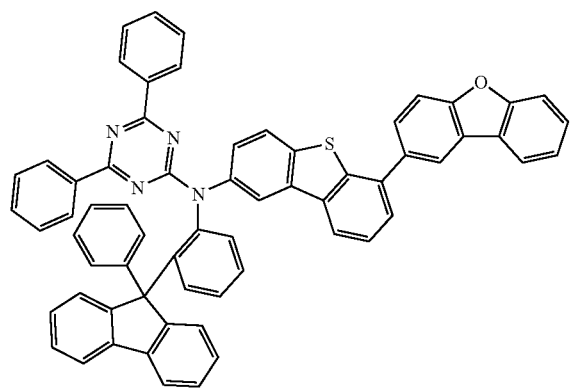
2-136
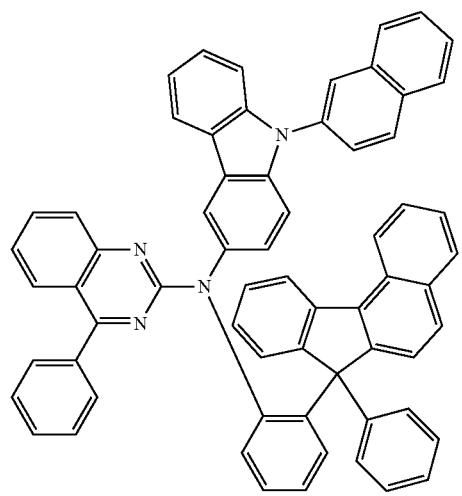
2-137
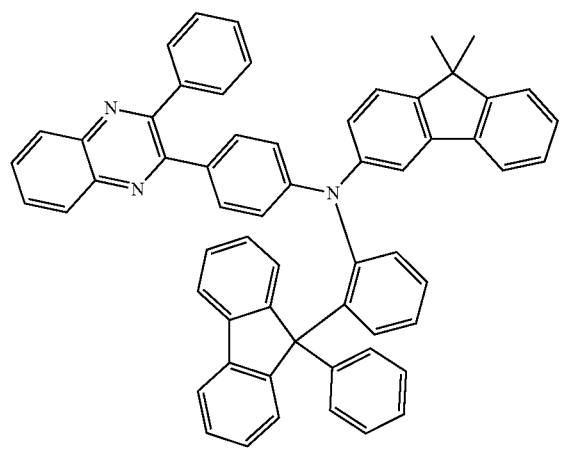
2-138
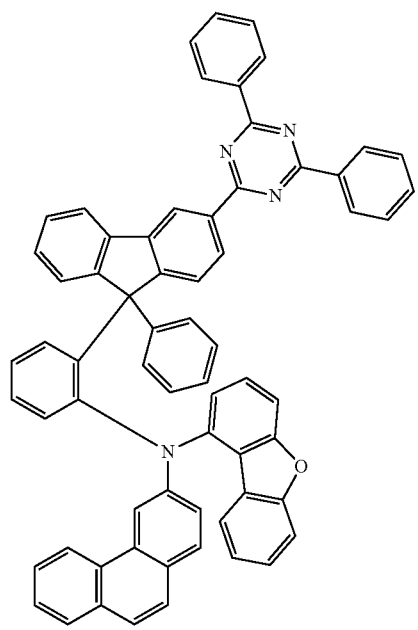

-continued
2-139
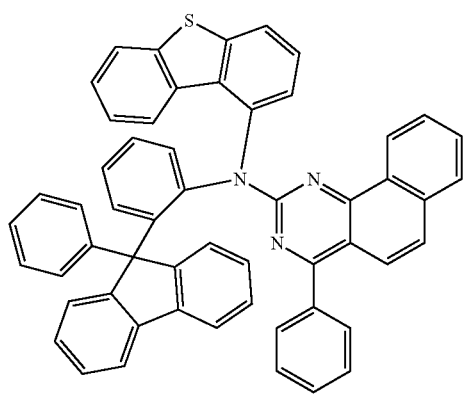
2-140
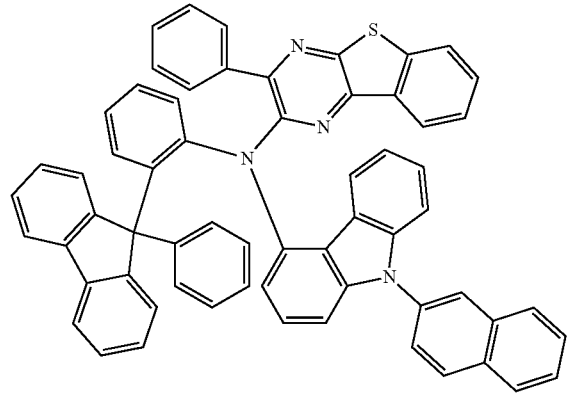
2-141
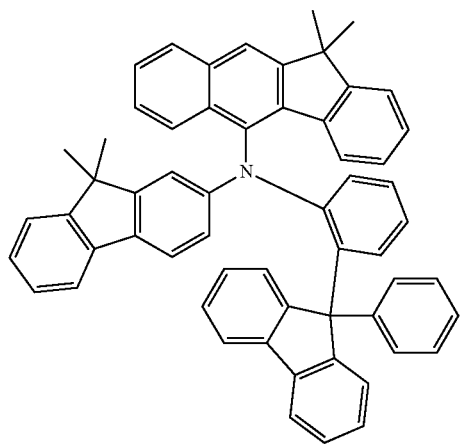
2-142
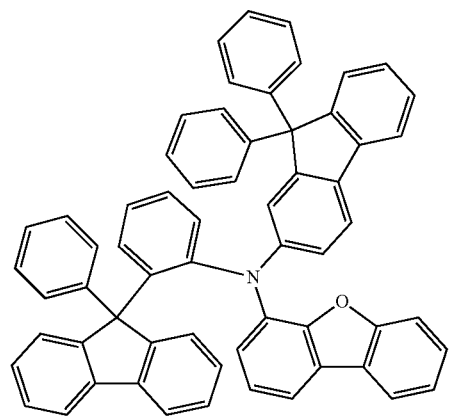
2-143
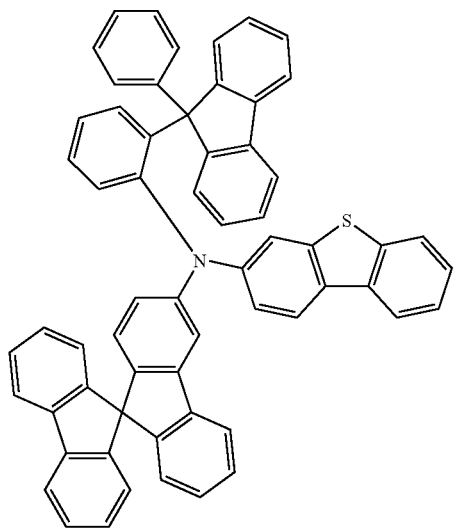
2-144
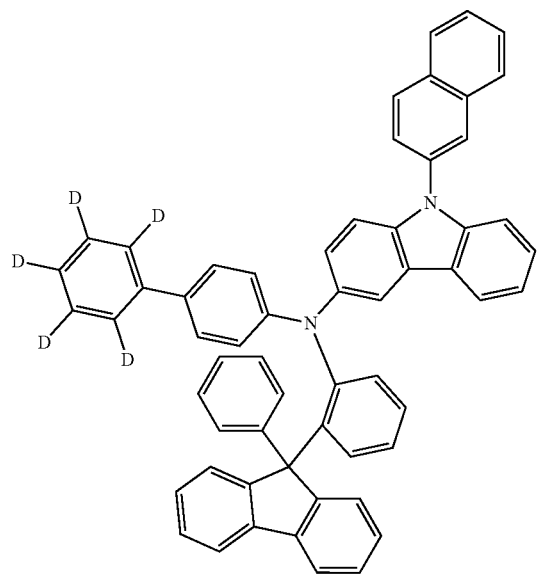

-continued
2-145
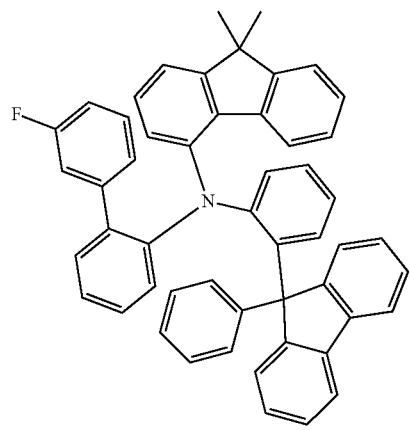
2-146
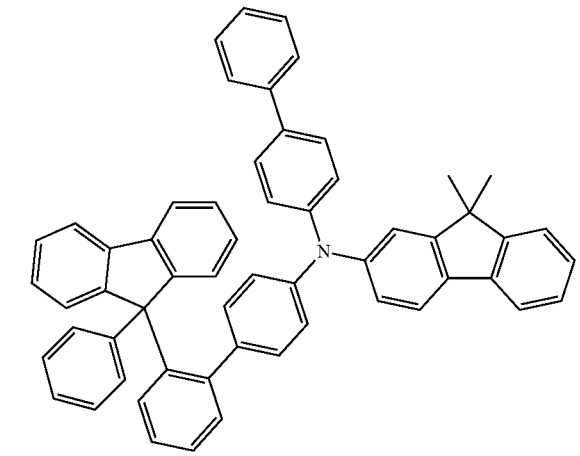
2-147
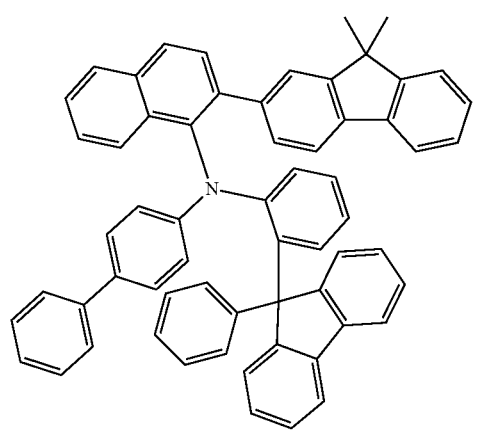
2-148
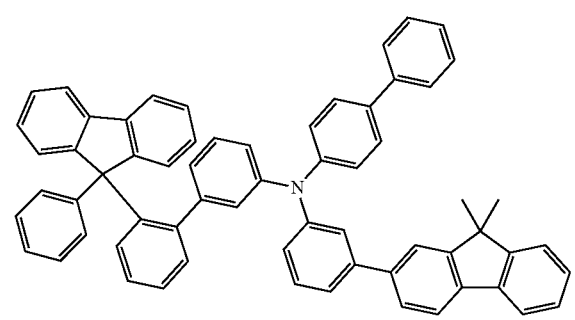
2-149
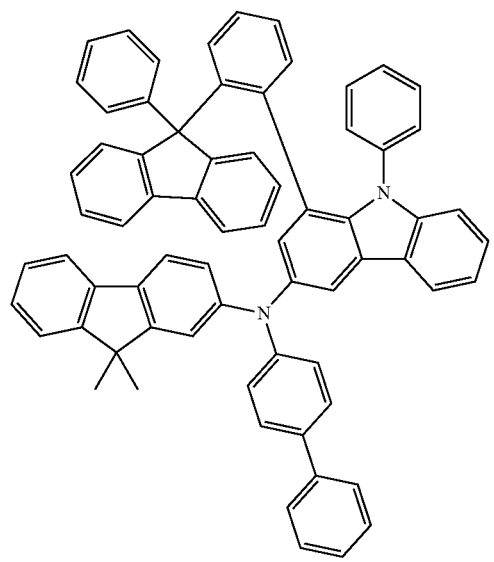
2-150
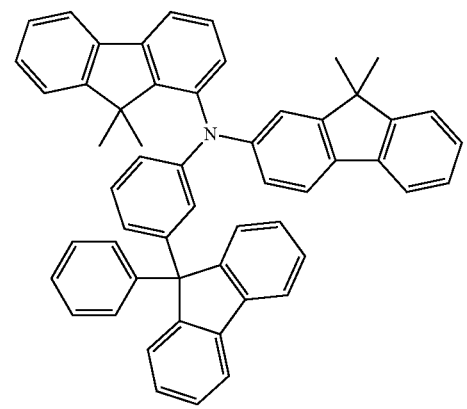

-continued 2-151
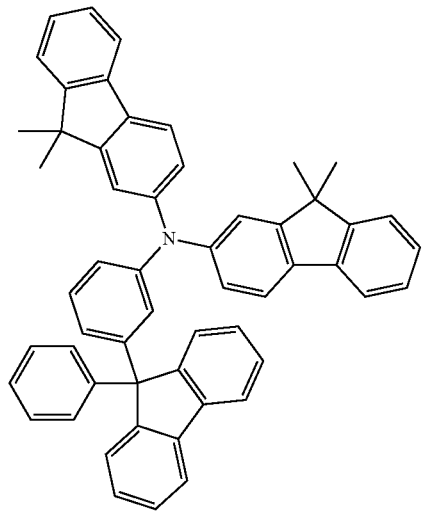

2-152
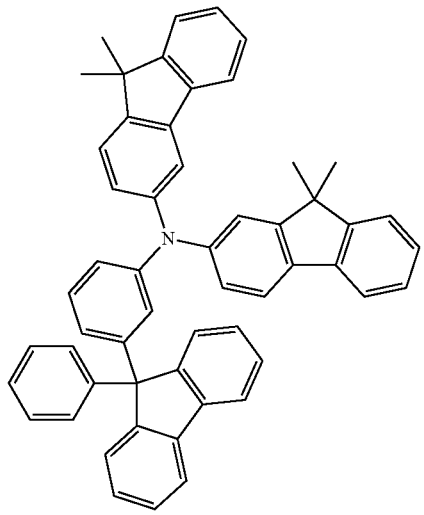

2-153
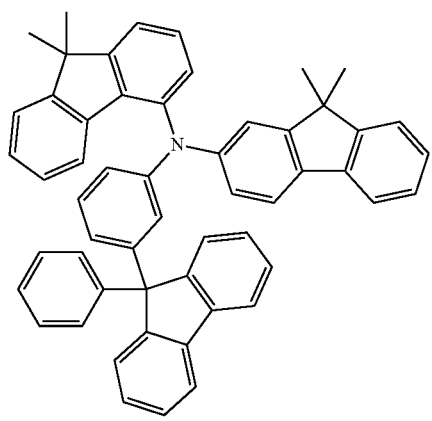

As another example, the present invention provides an organic electronic element comprising an anode; a cathode; an organic material layer formed between the anode and the cathode; wherein the organic material layer includes an emitting layer, an hole transport layer formed between the anode and the emitting layer; an emitting auxiliary layer or an electron blocking layer(EBL) formed between the emitting layer and the hole transport layer; wherein the emitting auxiliary layer or the electron blocking layer comprises a compound represented by Formula(30).

Formula (30)

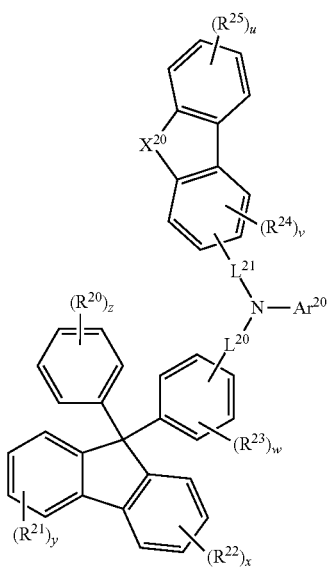

In present invention, the compound represented by Formula (30) is represented by any of the Formulas (31) to (38)

Formula (31)

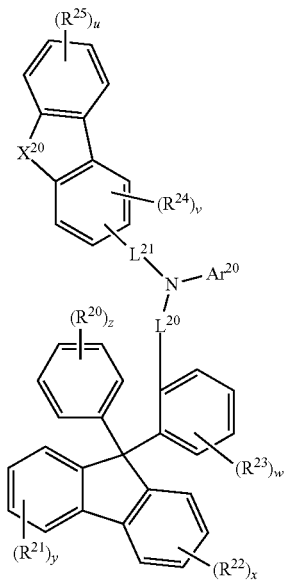

{In Formula (30), $R^{20}$, $R^{21}$, $R^{22}$, $R^{23}$, $R^{24}$, and $R^{25}$ are each independently selected from the group consisting of hydrogen; deuterium; halogen; a $C_6$-$C_{30}$ aryl group; a fluorenyl group; a $C_2$-$C_{30}$ heterocyclic group including at least one heteroatom of O, N, S, Si or P; a fused ring group of a $C_3$-$C_{30}$ aliphatic ring and a $C_6$-$C_{30}$ aromatic ring; a $C_1$-$C_{30}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; or a plurality of $R^{20}$, a plurality of $R^{22}$, a plurality of $R^{23}$, a plurality of $R^{24}$, and a plurality of $R^{25}$ may be bonded to each other to form an aromatic ring or and heteroaromatic ring, v is an integer of 0 to 3, u, w, x and y are each independently an integer of 0 to 4, Z is an integer of 0 to 5, $L^{20}$ and $L^{21}$ are each independently a single bond; a $C_6$-$C_{30}$ arylene group; a $C_3$-$C_{30}$ heteroarylene group;

$Ar^{20}$ is a $C_6$-$C_{30}$ aryl group; or a $C_3$-$C_{30}$ heteroarylene group;

$X^{20}$ is O, S, NR' or CR'R"

R' and R" are each independently selected from the group of a $C_1$-$C_{30}$ alkyl group; a $C_6$-$C_{30}$ aryl group; a $C_3$-$C_{30}$ heterocyclic group including at least one heteroatom of O, N, S, Si, or P; and R' and R" may be bonded to each other to form a spiro.}

Formula (32)

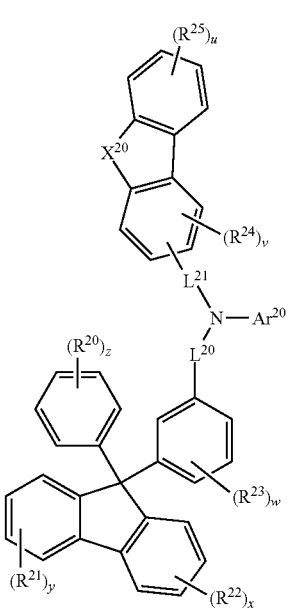

Formula (33)
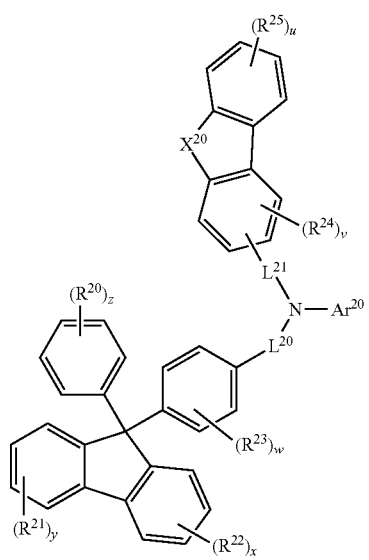
Formula (34)
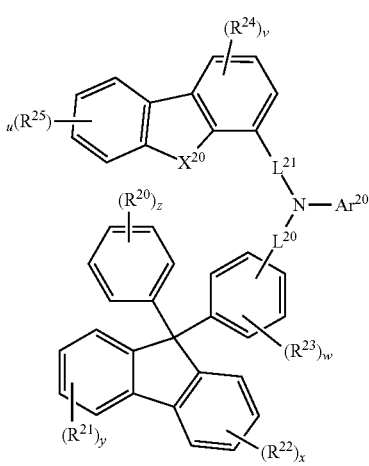
Formula (35)
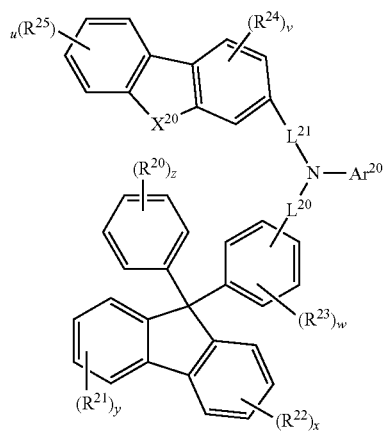
Formula (36)
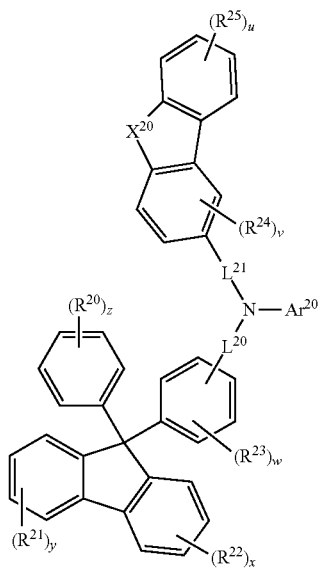
Formula (37)
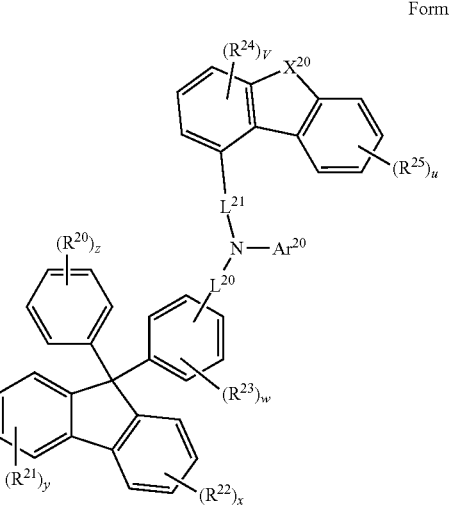
Formula (38)
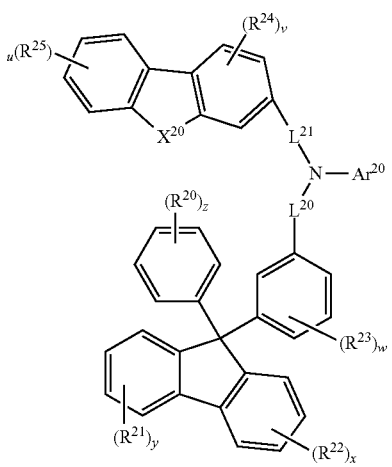

Formula (39)
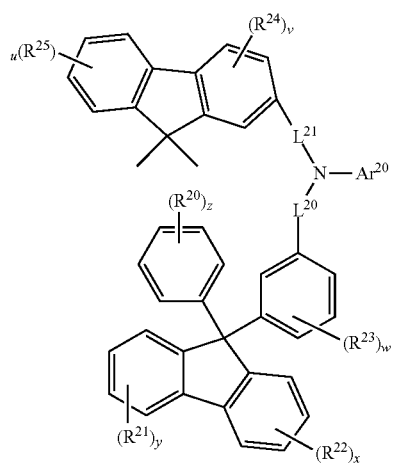
Formula (40)
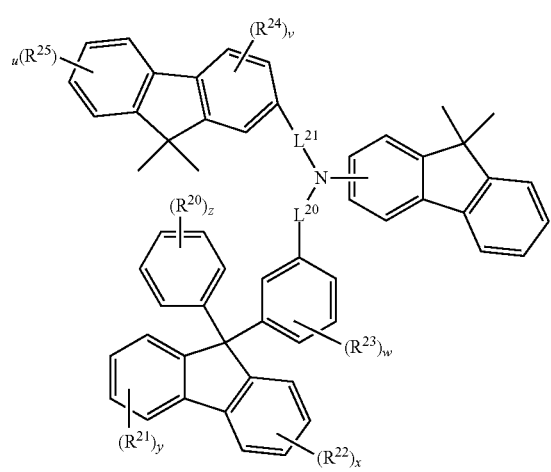
{In Formulas (31) to (40),
R$^{20}$, R$^{21}$, R$^{22}$, R$^{23}$, R$^{24}$, R$^{25}$, L$^{20}$, L$^{21}$, Ar$^{20}$ and X$^{20}$, u, v, w, x, y and z are the same as defined above.}
In the present invention, the compound represented by Formula (30) comprises the following compounds.
2-72
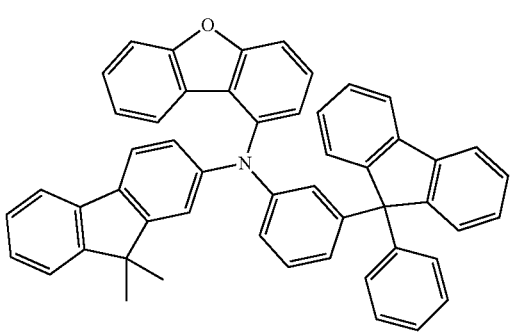
2-76
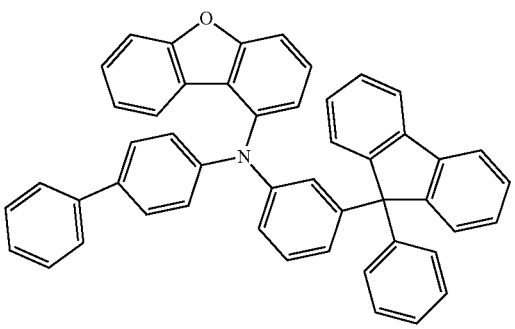
2-81
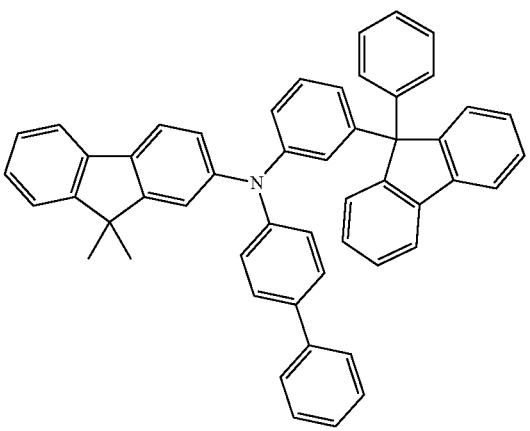
2-82
2-83
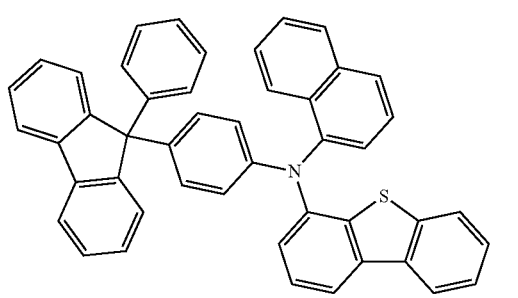

2-84
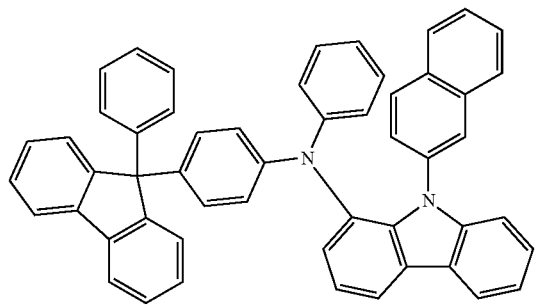
2-85
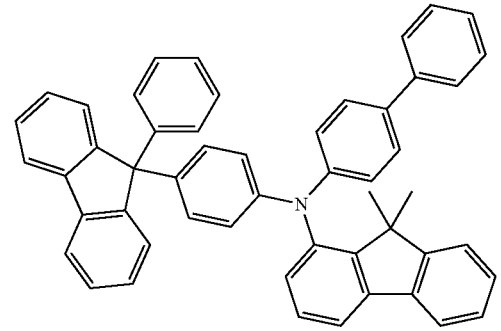
2-86
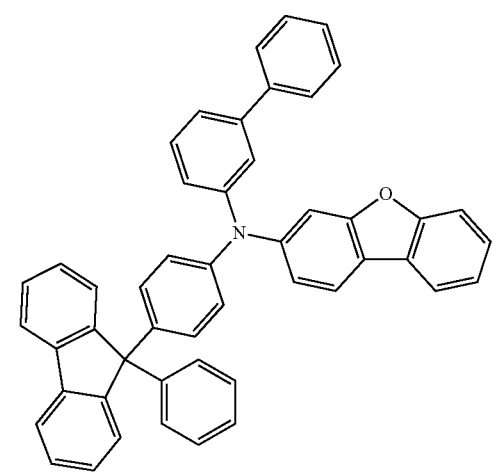
2-87
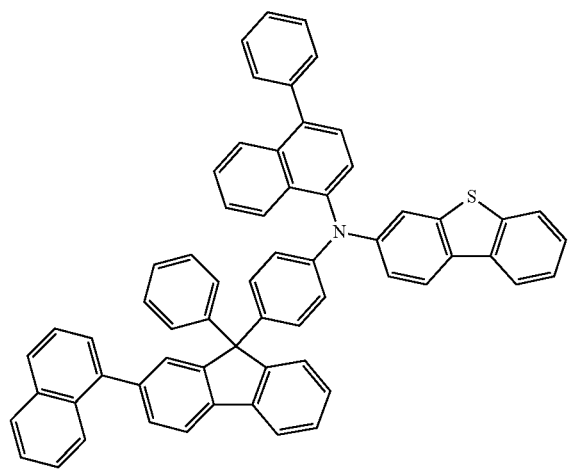
2-88
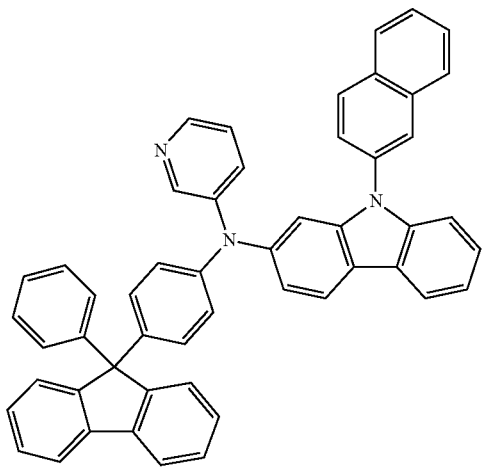
2-89
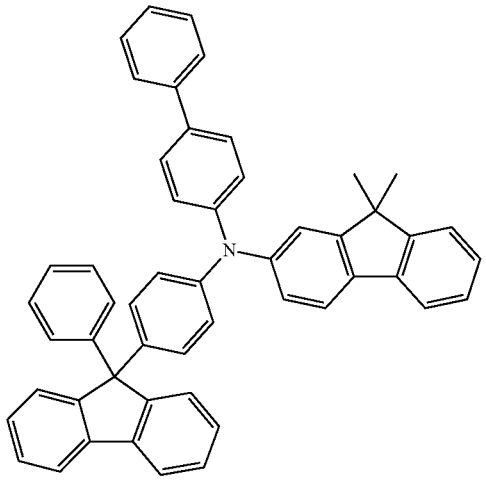
2-90
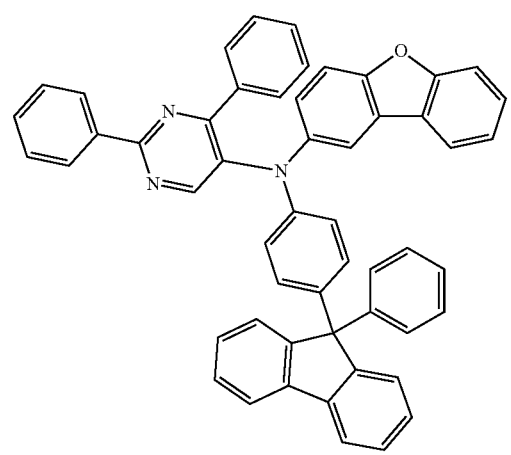

2-91
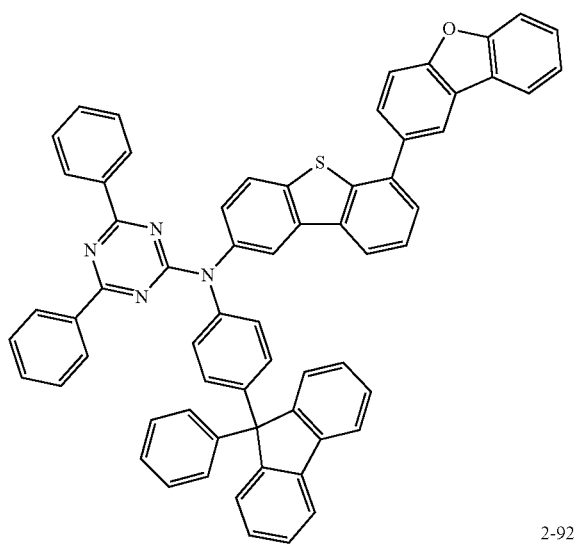
2-92
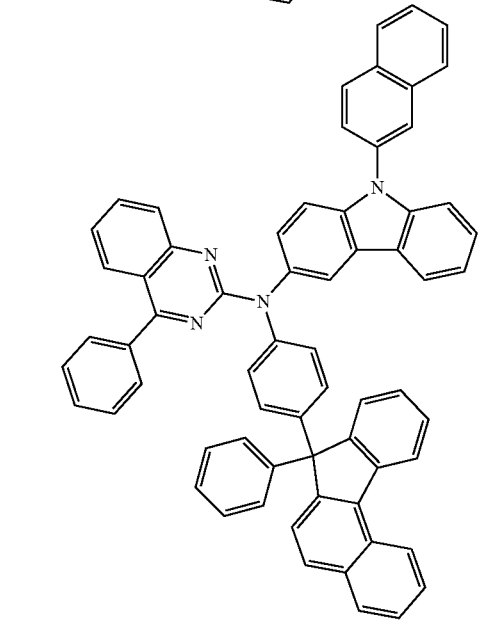
2-93
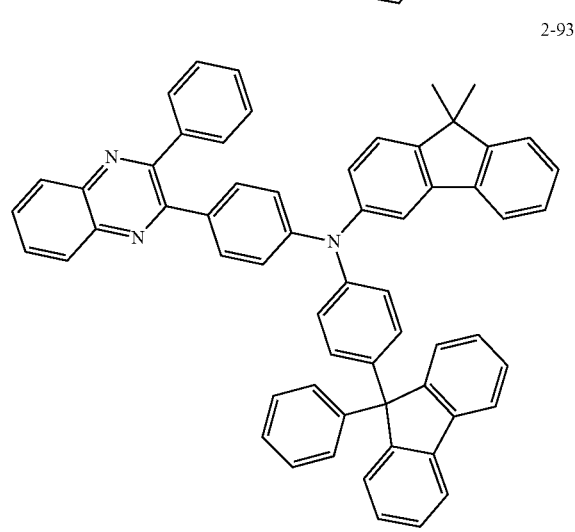
2-94
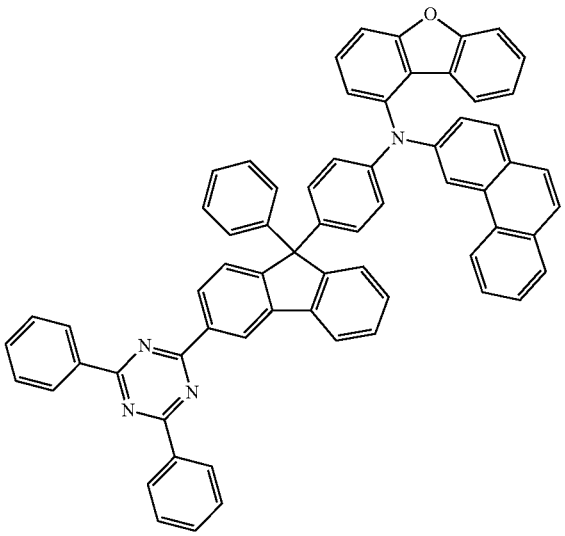
2-95
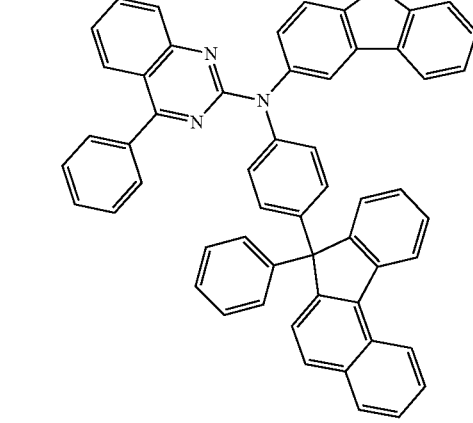
2-96
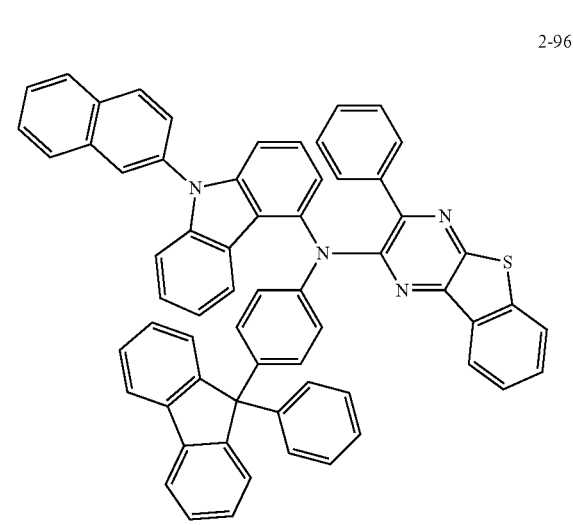

2-97
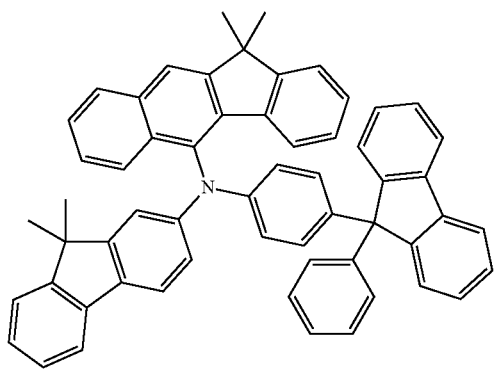
2-98
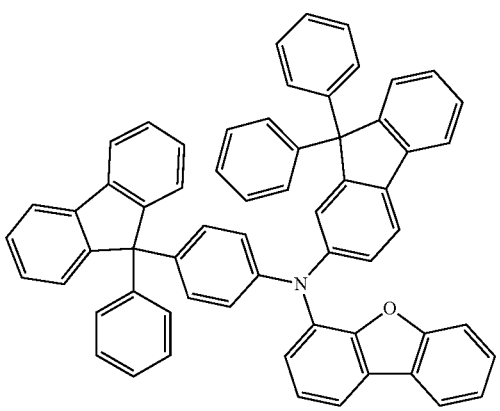
2-99
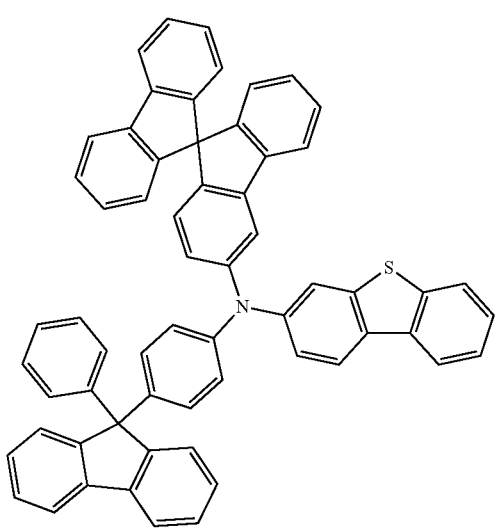
2-100
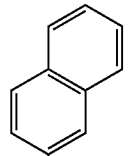
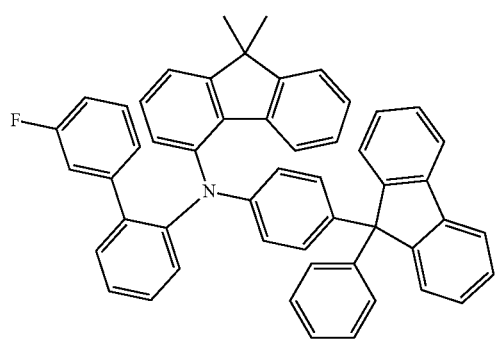
2-101
2-102
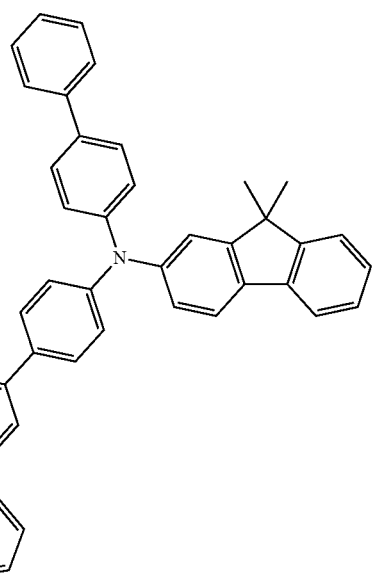

2-103
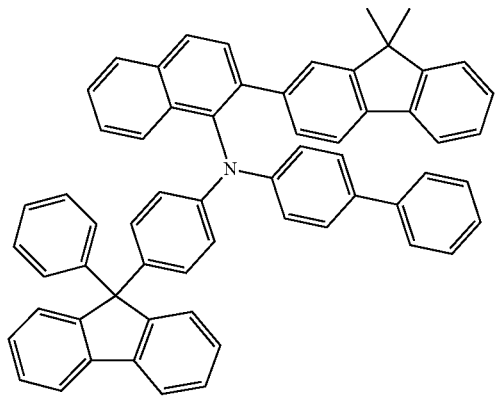
2-104
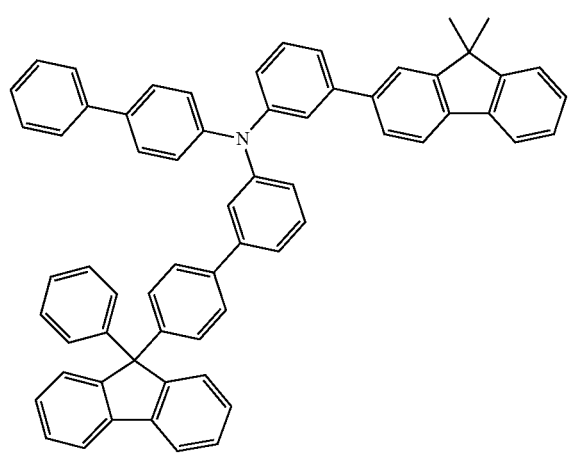
2-105
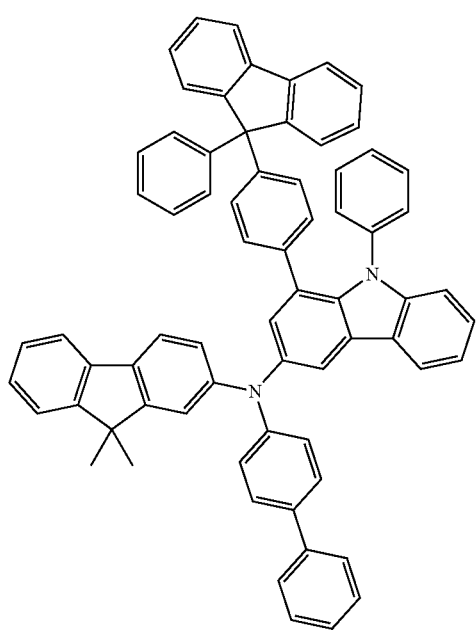
2-106
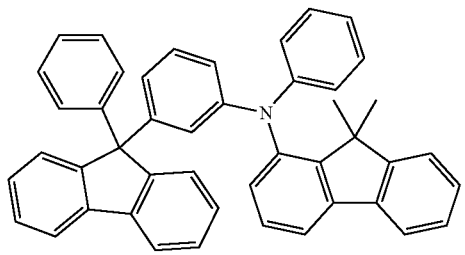
2-107
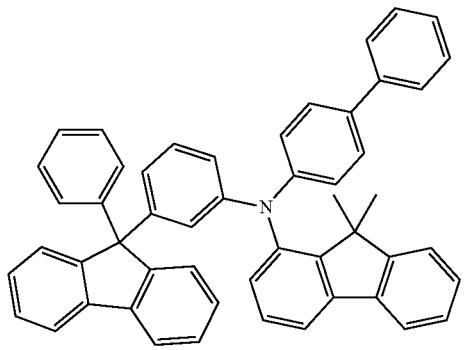
2-108
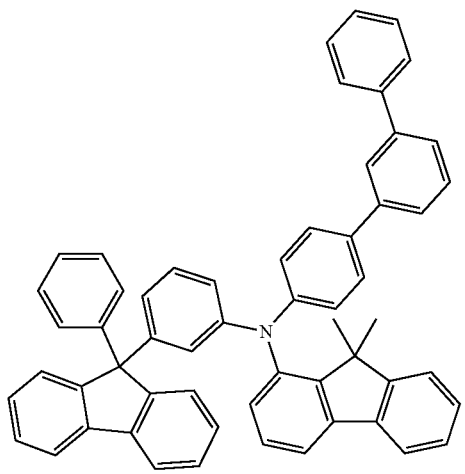
2-109
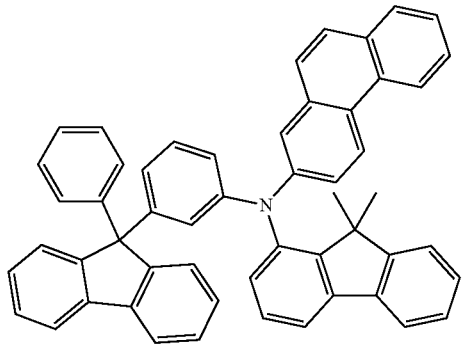

2-110
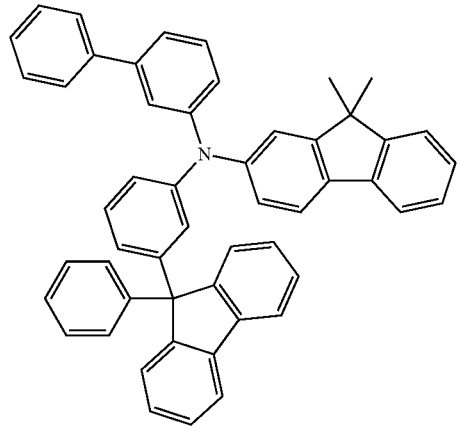
2-113
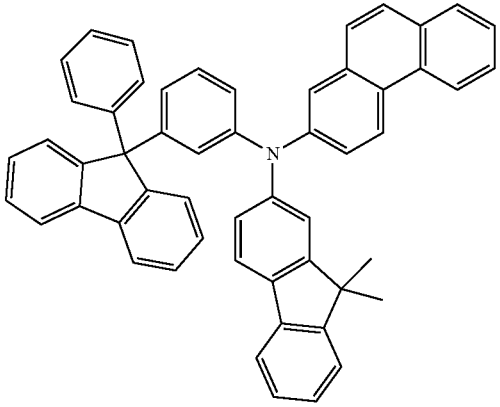
2-111
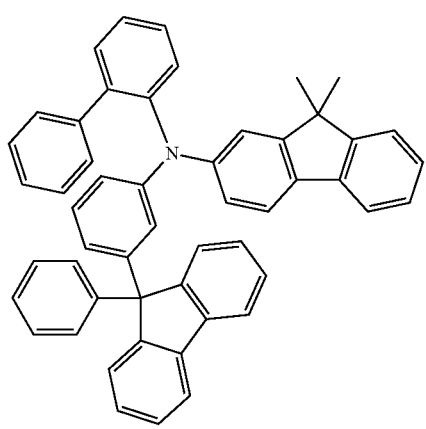
2-114
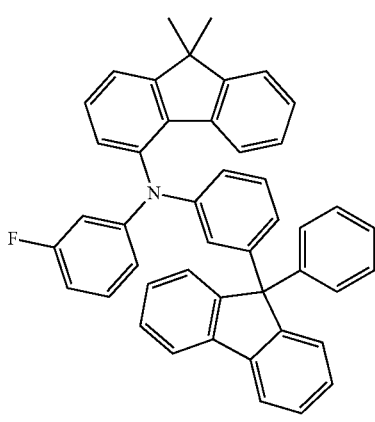
2-112
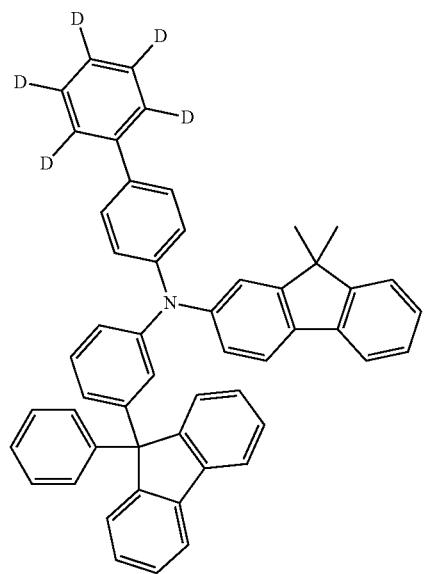
2-115
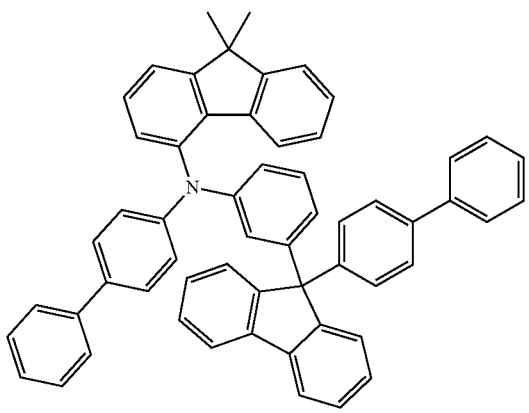

2-116
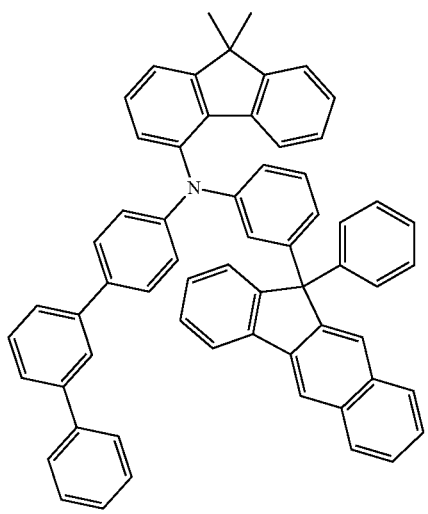
2-119
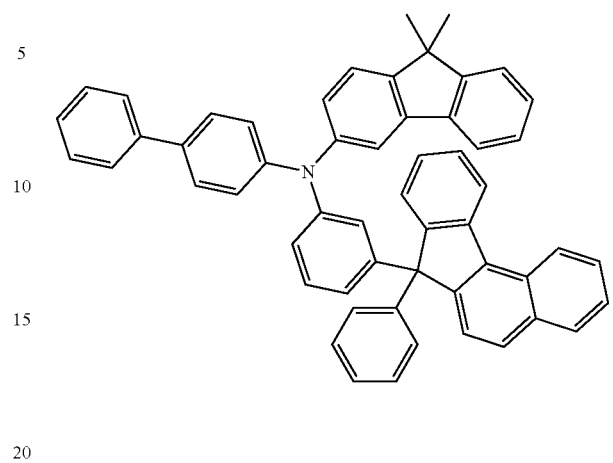
2-117
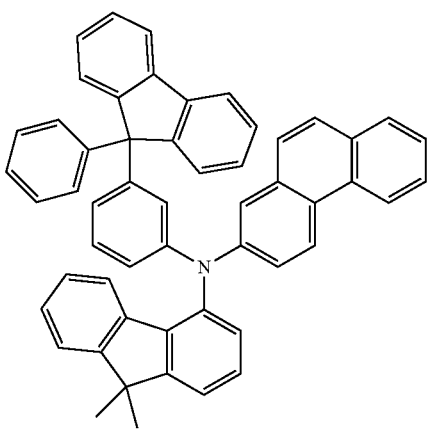
2-120
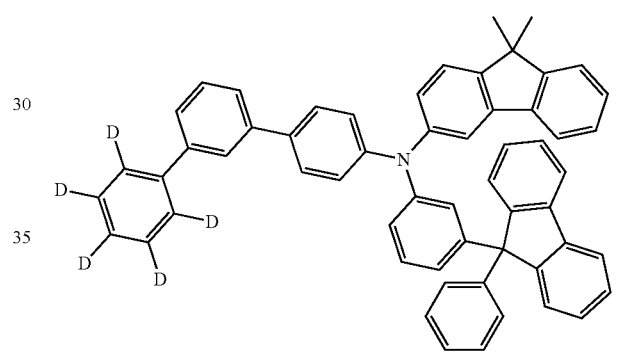
2-118
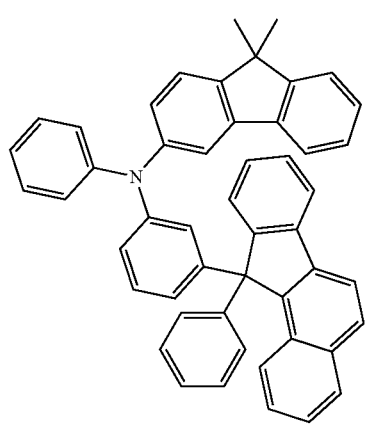
2-121
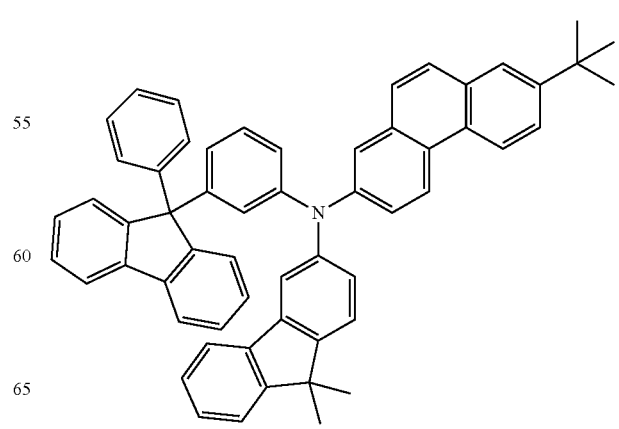

-continued
2-122
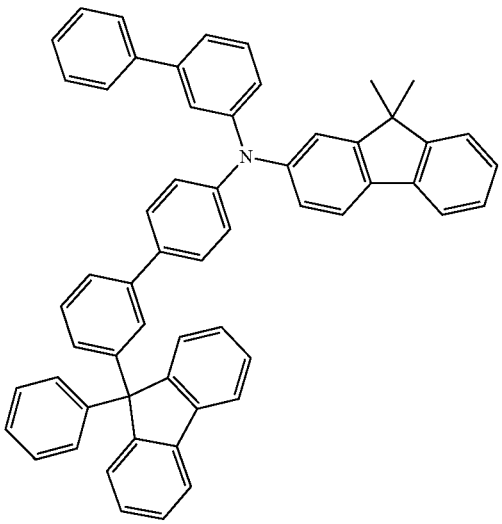
2-123
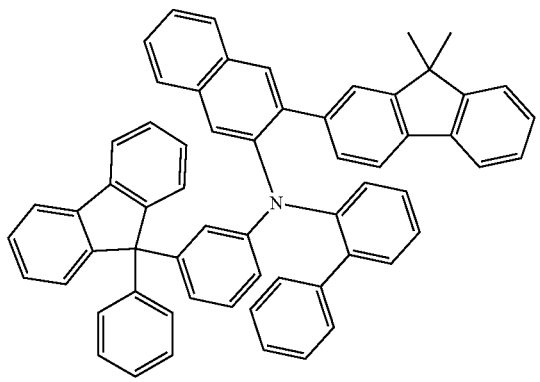
2-124
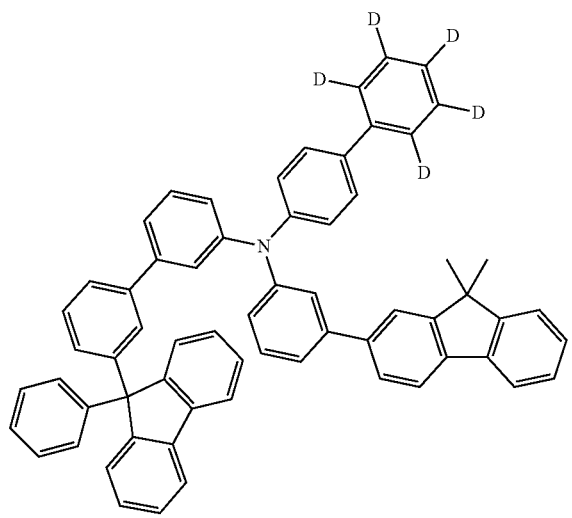
-continued
2-125
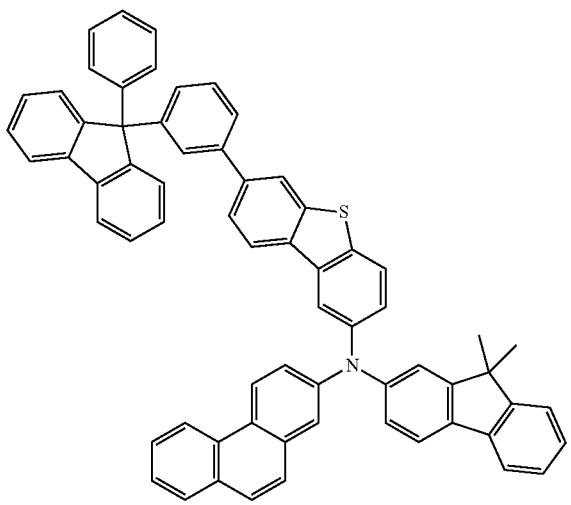
2-126
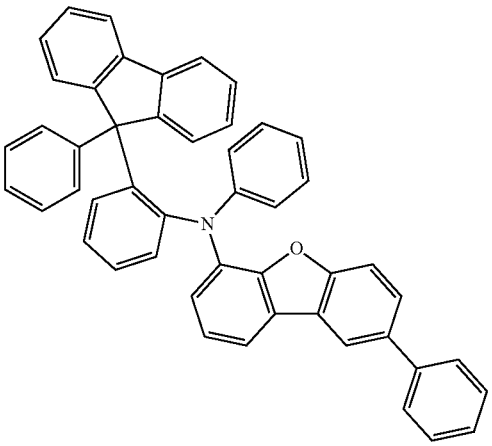
2-127
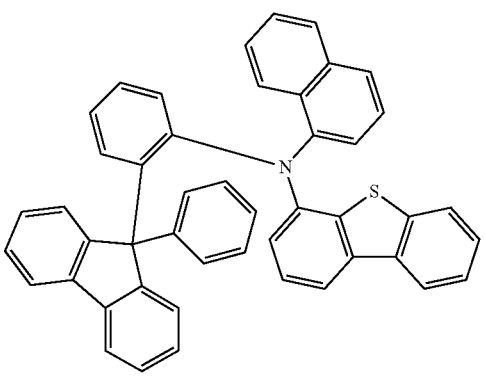
2-128
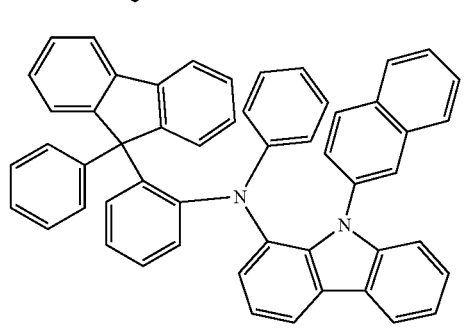

-continued
2-129
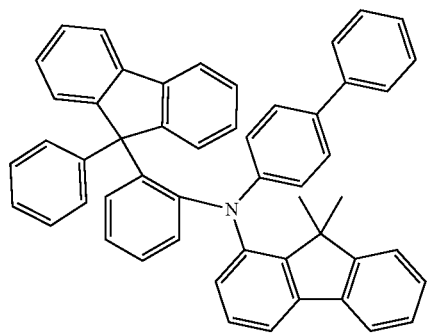
2-130
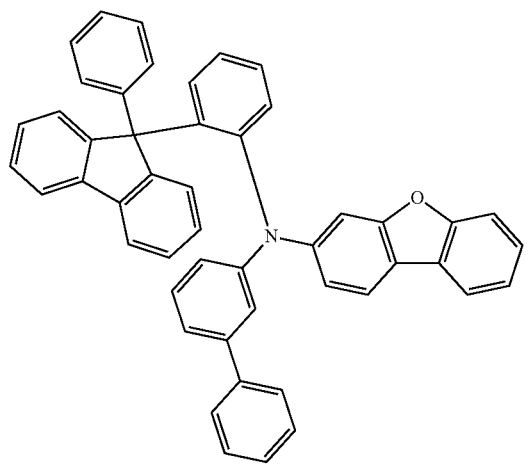
2-131
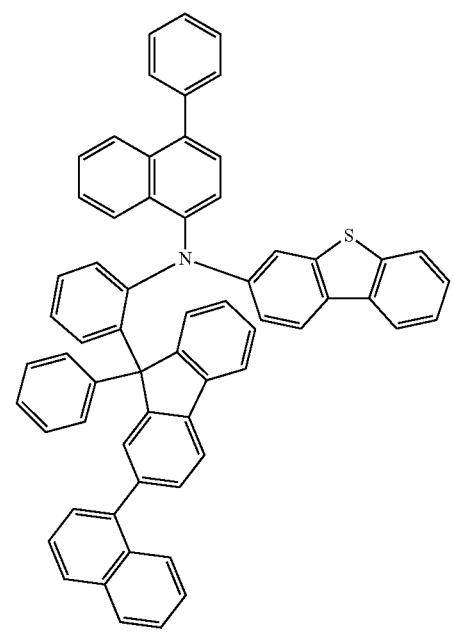
-continued
2-132
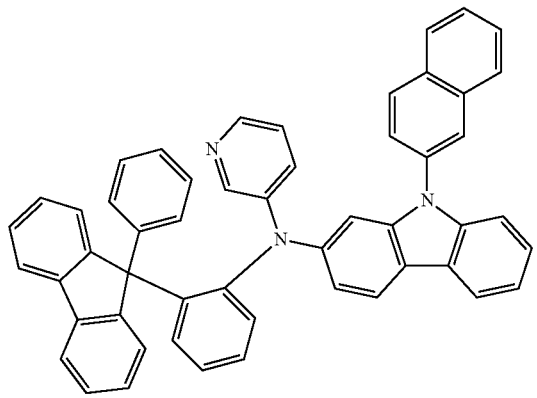
2-133
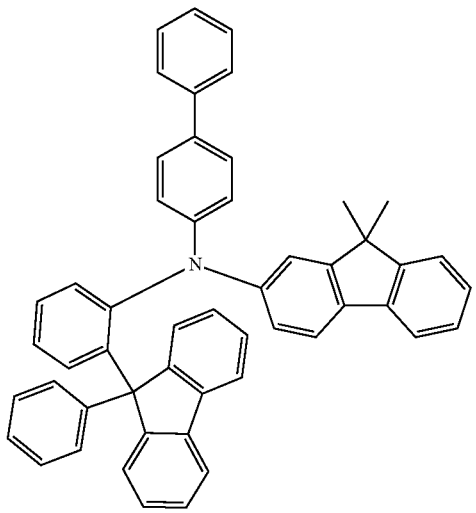
2-134
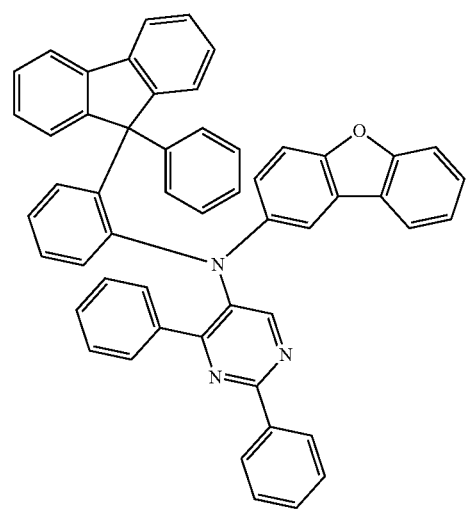

2-135
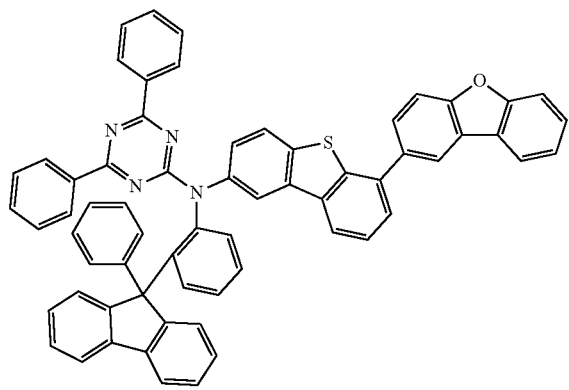
2-136
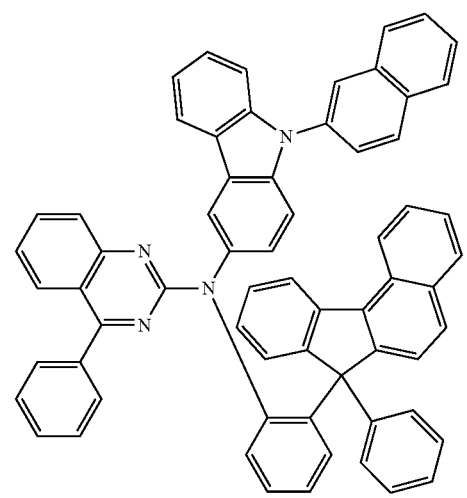
2-137
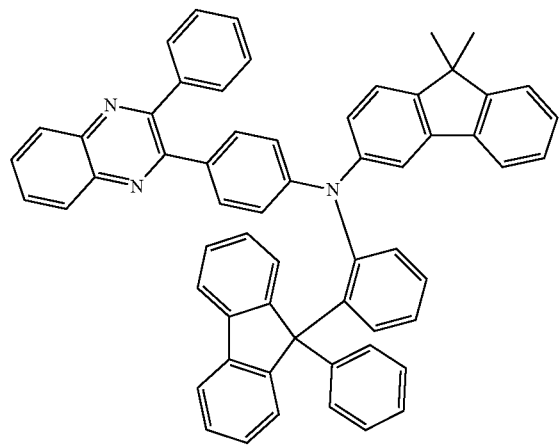
2-138
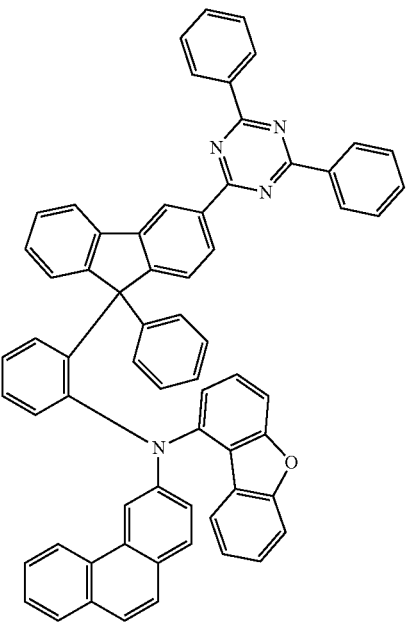
2-139
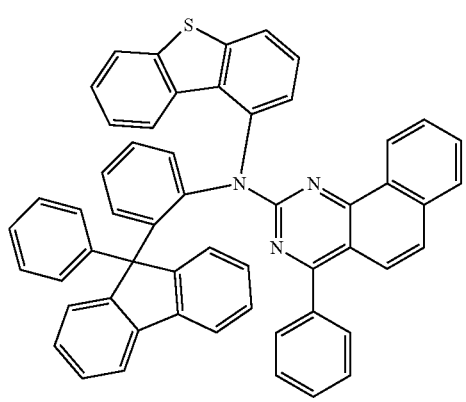
2-140
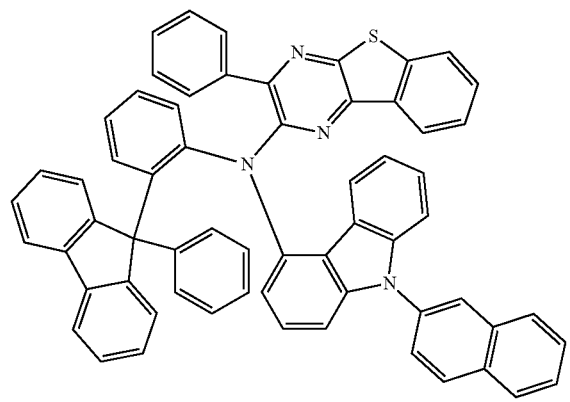

2-141
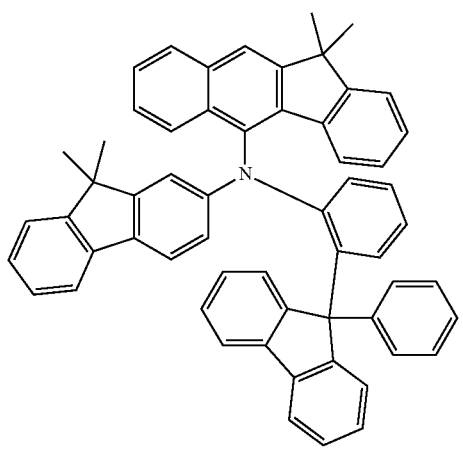
2-142
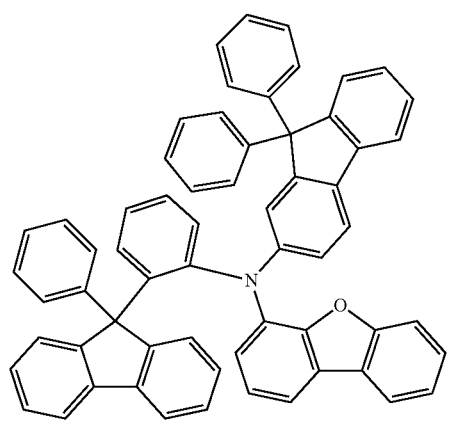
2-143
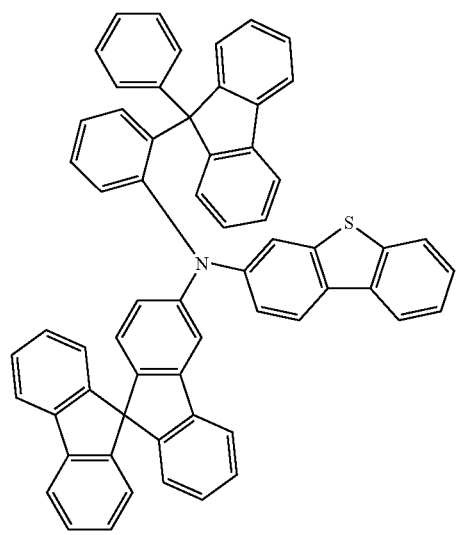
2-144
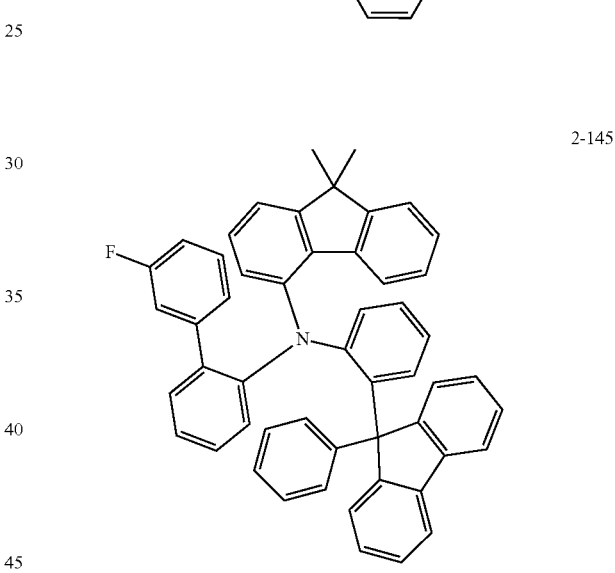
2-145
2-146
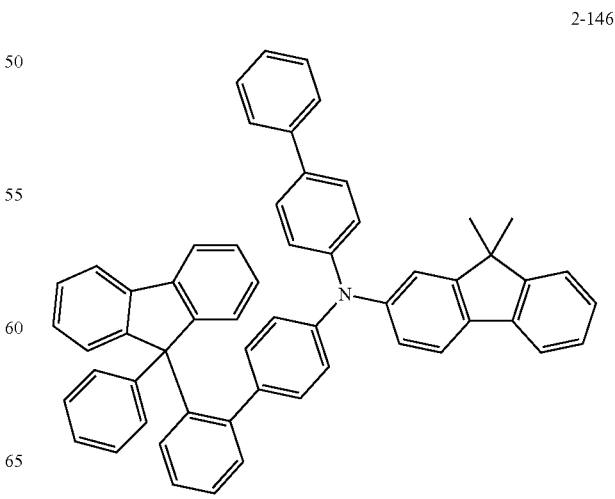

2-147

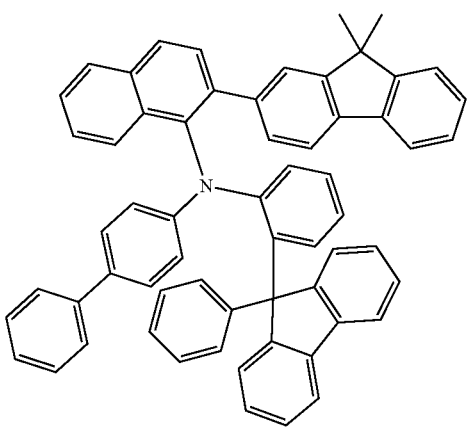

2-148

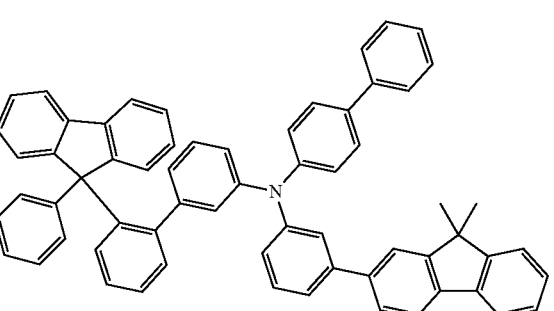

2-149

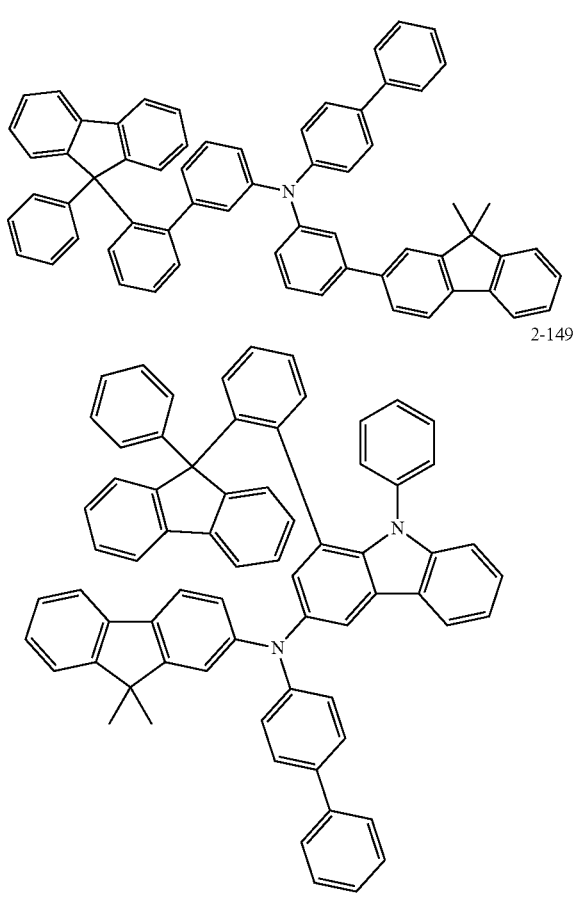

Referring to the FIGURE, the organic electric element (100) according to the present invention includes a first electrode(120) formed on a substrate(110), a second electrode(180), and an organic material layer including the compound represented by Formula (1) between the first electrode(120) and the second electrode(180). Here, the first electrode(120) may be an anode (positive electrode), and the second electrode(180) may be a cathode (negative electrode). In the case of an inverted organic electric element, the first electrode may be a cathode, and the second electrode may be an anode.

The organic material layer may include a hole injection layer(130), a hole transport layer(140), an emitting layer (150), an emitting auxiliary layer(151), an electron transport layer(160), and an electron injection layer(170) formed in sequence on the first electrode(120). Here, the remaining layers except the emitting layer(150) may not be formed. The organic material layer may further include a hole blocking layer, an electron blocking layer, an emitting-auxiliary layer(151), an electron transport auxiliary layer, a buffer layer(141), etc., and the electron transport layer(160) and the like may serve as a hole blocking layer.

Although not shown, the organic electric element according to the present invention may further include a protective layer formed on at least one side of the first and second electrodes, which is a side opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials(mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer(130), the hole transport layer(140), the emitting layer (150), the electron transport layer(160), and the electron injection layer(170) is formed thereon, and then depositing a material usable as a cathode thereon can manufacture an organic electroluminescent device according to an embodiment of the present invention. In addition, an emission auxiliary layer(151) may be further formed between the hole transport layer(140) and the emitting layer(150), and an electron transport auxiliary layer may be further formed between the emitting layer(150) and the electron transport layer (160).

As another specific example, the present invention provides an organic electric element wherein the emitting layer in the organic material layer is a phosphorescent light emitting layer.

The compounds represented by Formula (1) and (18) are mixed in a ratio of any one of 1:9 to 9:1 to be included in the emitting layer of the organic material layer, wherein the compound represented by Formula (12) is further mixed to be included in the emitting layer.

The present invention may further include a light efficiency enhancing layer formed on at least one of the opposite side to the organic material layer among one side of the first electrode, or one of the opposite side to the organic material layer among one side of the second electrode.

As another example, the present invention provides an organic electronic device wherein the compound represented by Formula (30) is used in an emitting auxiliary layer or an electron blocking layer and is preferably included in a green emitting auxiliary layer. More specifically, the compound represented by Formula (39) or Formula (40) is included in the green emitting auxiliary layer.

Also, the present invention provides the organic electric element wherein the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

The organic electric element according to an embodiment of the present invention may be a front emission type, a back emission type, or a both-sided emission type, depending on the material used.

WOLED (White Organic Light Emitting Device) has advantages of high resolution realization and excellent fairness, and can be manufactured using conventional LCD color filter technology. Various structures for a white organic light emitting device mainly used as a backlight device have been proposed and patented. Representatively, there are side-by-side arrangement of the radiation part of the R(red), G(green) and B(blue), a stacking method in which R, G, and B emitting layers are laminated on top and bottom, electroluminescence by the blue (B) organic emitting layer and, by using the light from this, a color conversion material (CCM) method using a photo-luminescence of an inorganic phosphor, etc., and the present invention may be applied to such WOLED.

The present invention also provides an electronic device comprising a display device including the organic electric element; and a control unit for driving the display device.

According to another aspect, the present invention provides an display device wherein the organic electric element is at least one of an OLED, an organic solar cell, an organic photo conductor, an organic transistor(organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant(PDA), an electronic dictionary, a point-to-multipoint(PMP), a remote controller, a navigation unit, a game player, various kinds of TVs, and various kinds of computers.

Hereinafter, Synthesis Examples of the compound represented by Formula (1) and (2) of the present invention and preparation examples of the organic electric element of the present invention will be described in detail by way of example, but are not limited to the following examples.

Synthesis Example 1

Final product1 represented by Formula(1) according to the present invention is prepared by reacting Core and Sub as shown in Reaction Scheme 1 below, but is not limited thereto.

<Reaction Scheme 1>

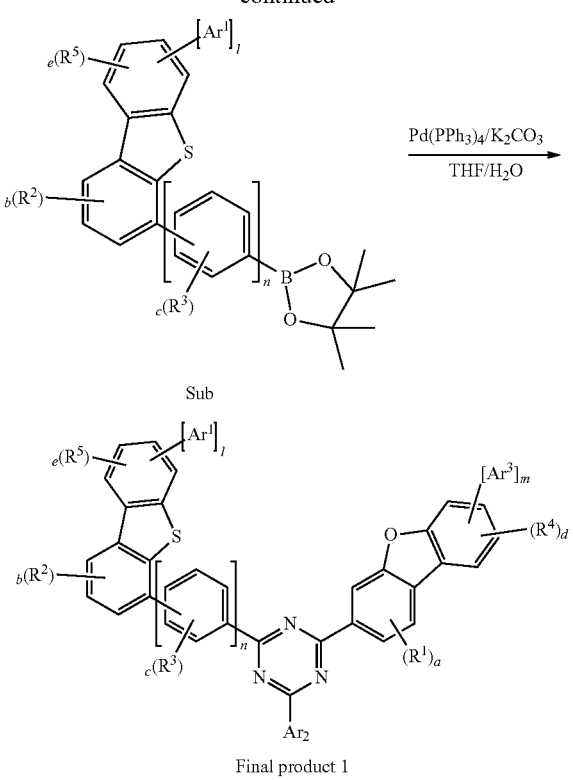

Synthesis Example of Core

The Core of the Reaction Scheme 1 can be synthesized by the reaction path of the following Reaction Schemes 2, but is not limited thereto.

<Reaction Scheme 2>

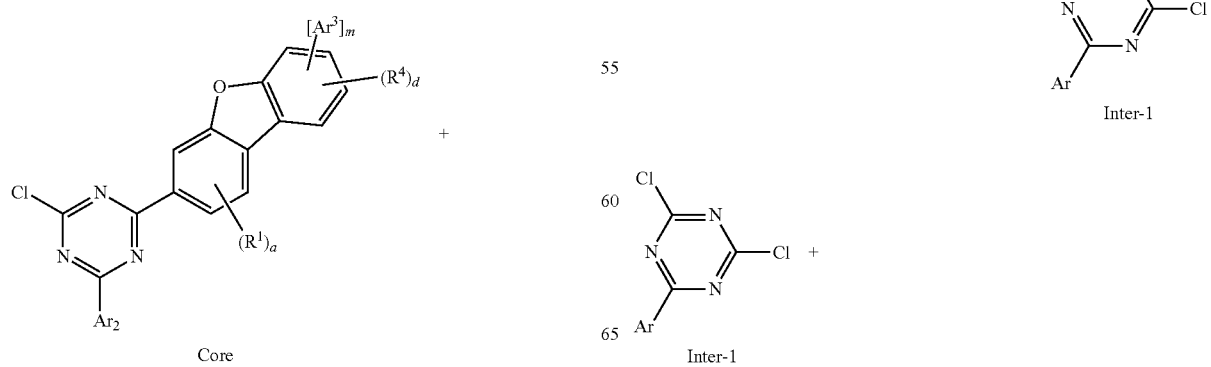

-continued

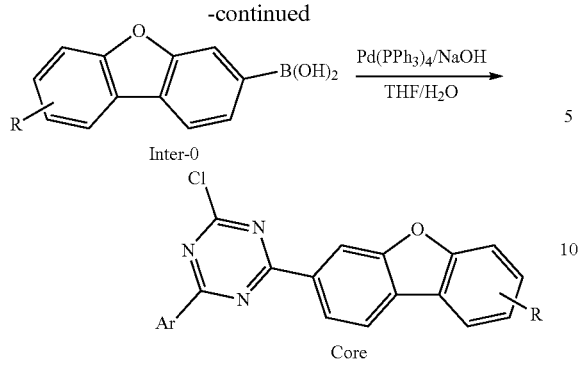

Synthesis of Inter-1

In a round bottom flask, 2,4,6-trichloro-1,3,5-triazine (50 g, 410.1 mmol), phenylboronic acid (83.2 g, 451.1 mmol), Pd(PPh$_3$)$_4$ (14.2 g, 12.3 mmol), K$_2$CO$_3$ (170 g, 1.2 mol), THF (1.3 L) and water(700 ml) were added and stirred at 90° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain 55 g (yield: 60%) of Inter 1.

Synthesis of Core

In a round bottom flask, Inter-1 (10 g, 47 mmol), dibenzo[b,d]furan-3-ylboronic acid(12 g, 51.9 mmol), Pd(PPh$_3$)$_4$ (1.6 g, 1.4 mmol), K$_2$CO$_3$ (20 g, 141 mmol), THF (160 ml), and water(80 ml) were added and stirred at 90° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain 5.7 g (yield: 53%) of Core 1.

Examples of the Core are as follows, but are not limited thereto. In addition, [Table 1] shows FD-MS (Field Desorption-Mass Spectrometry) values of some compounds belonging to Core.

Core 1

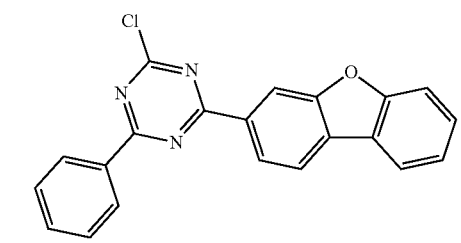

Core 2

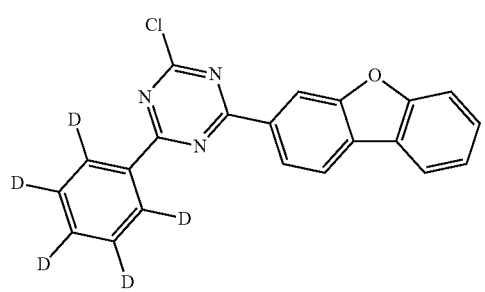

Core 3

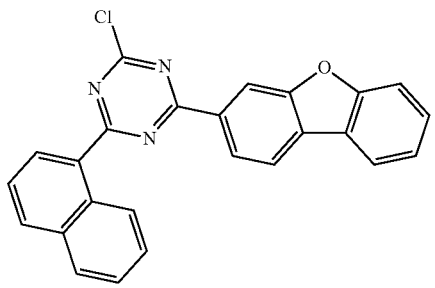

Core 3

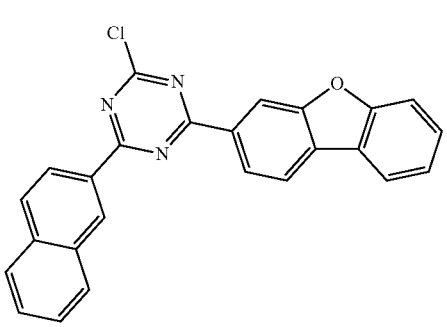

Core 4

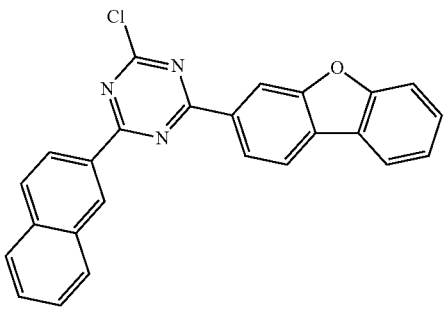

Core 5

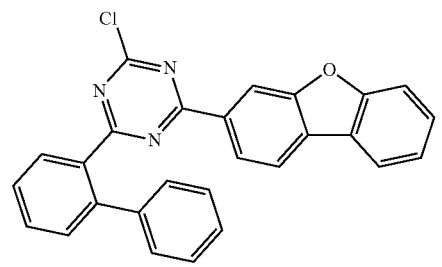

Core 6

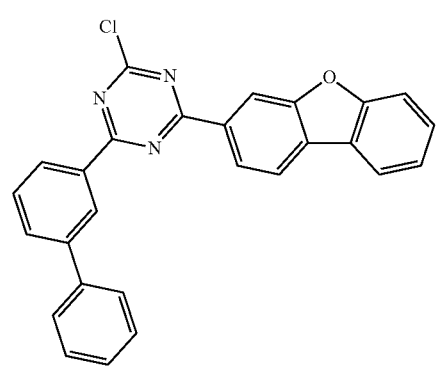

Core 7
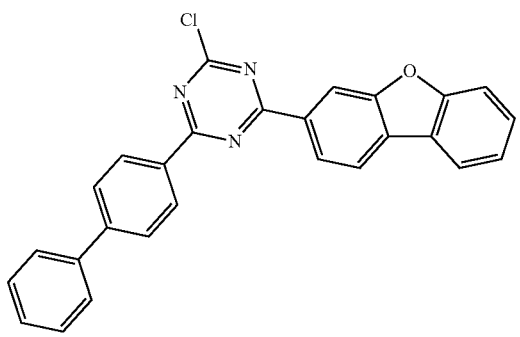
Core 8
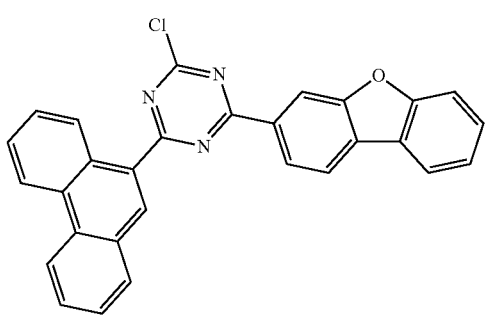
Core 9
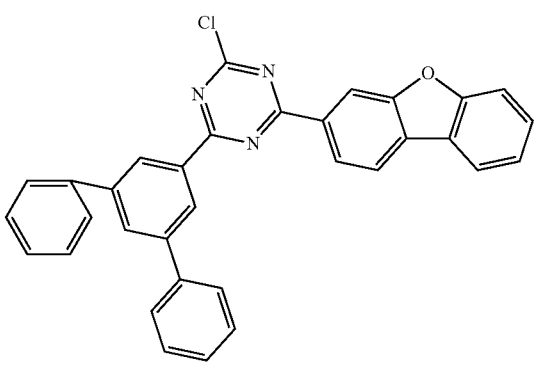
Core 10
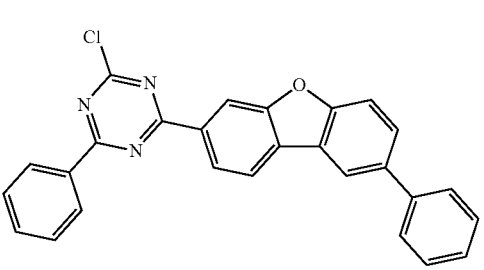
Core 11
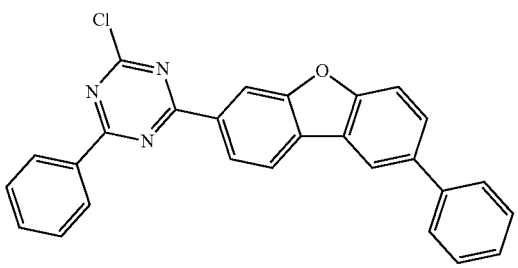
Core 12
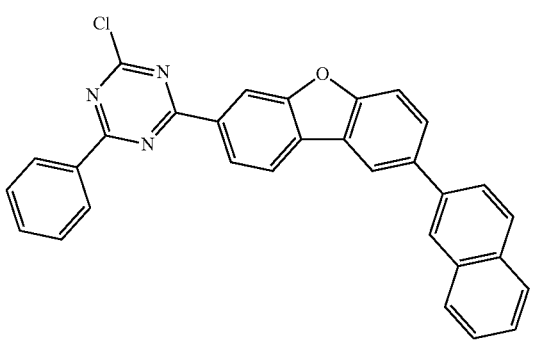
Core 13
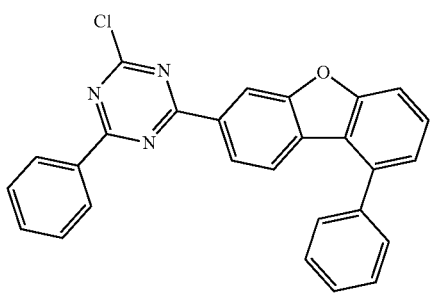
Core 14
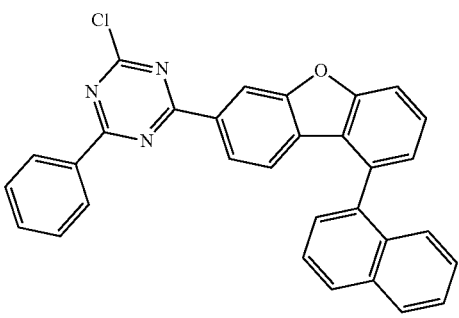

Core 15
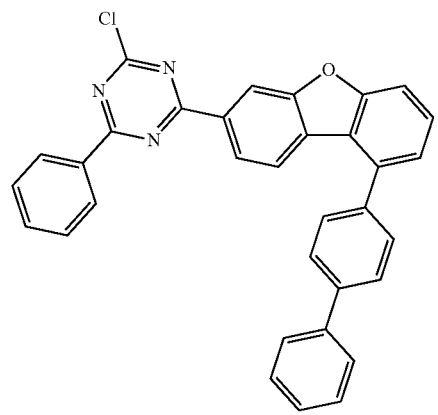

Core 18
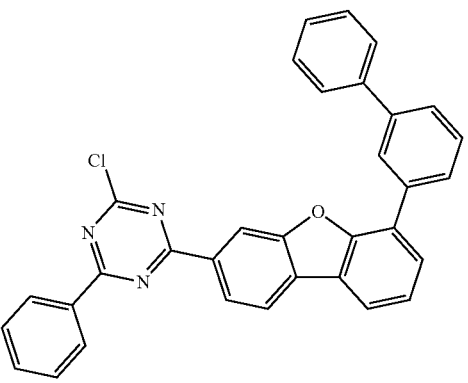

Core 16
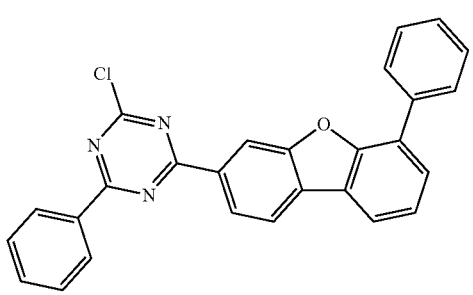

Core 19
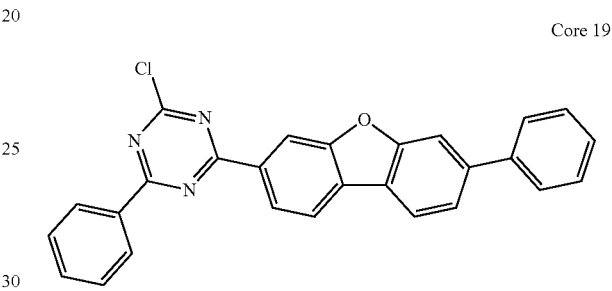

Core 17
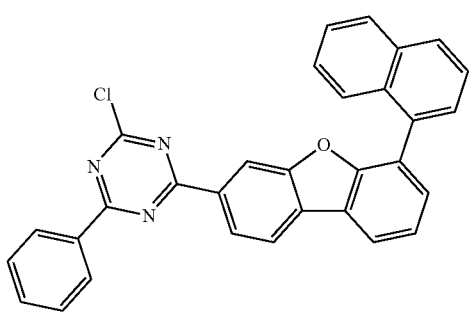

Core 20
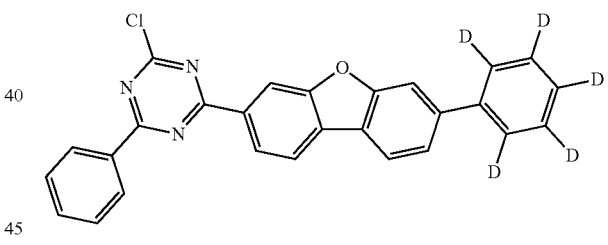

TABLE 1

| Compound | FD-MS | Compound | FD-MS |
|---|---|---|---|
| Core 1 | m/z = 357.07($C_{21}H_{12}ClN_3O$ = 357.80) | Core 2 | m/z = 362.10($C_{21}H_7D_5ClN_3O$ = 362.83) |
| Core 3 | m/z = 407.08($C_{25}H_{14}ClN_3O$ = 407.86) | Core 4 | m/z = 407.08($C_{25}H_{14}ClN_3O$ = 407.86) |
| Core 5 | m/z = 433.10($C_{27}H_{16}ClN_3O$ = 433.90) | Core 6 | m/z = 433.10($C_{27}H_{16}ClN_3O$ = 433.90) |
| Core 7 | m/z = 433.10($C_{27}H_{16}ClN_3O$ = 433.90) | Core 8 | m/z = 457.10($C_{29}H_{16}ClN_3O$ = 457.92) |
| Core 9 | m/z = 509.13 $C_{33}H_{20}ClN_3O$ = 509.99) | Core 10 | m/z = 433.10($C_{27}H_{16}ClN_3O$ = 433.90) |
| Core 11 | m/z = 433.10($C_{27}H_{16}ClN_3O$ = 433.90) | Core 12 | m/z = 483.11($C_{31}H_{18}ClN_3O$ = 483.96) |
| Core 13 | m/z = 433.10($C_{27}H_{16}ClN_3O$ = 433.90) | Core 14 | m/z = 483.11($C_{31}H_{18}ClN_3O$ = 483.96) |
| Core 15 | m/z = 509.13($C_{33}H_{20}ClN_3O$ = 509.99) | Core 16 | m/z = 433.10($C_{27}H_{16}ClN_3O$ = 433.90) |
| Core 17 | m/z = 483.11($C_{31}H_{18}ClN_3O$ = 483.96) | Core 18 | m/z = 509.13($C_{33}H_{20}ClN_3O$ = 509.99) |
| Core 19 | m/z = 433.10($C_{27}H_{16}ClN_3O$ = 433.90) | Core 20 | m/z = 438.13($C_{27}H_{11}D_5ClN_3O$ = 438.93) |

Example of Sub
Examples of Sub are as follows, but are not limited thereto. In addition, [Table 2] shows FD-MS (Field Desorption-Mass Spectrometry) values of some compounds belonging to Sub.
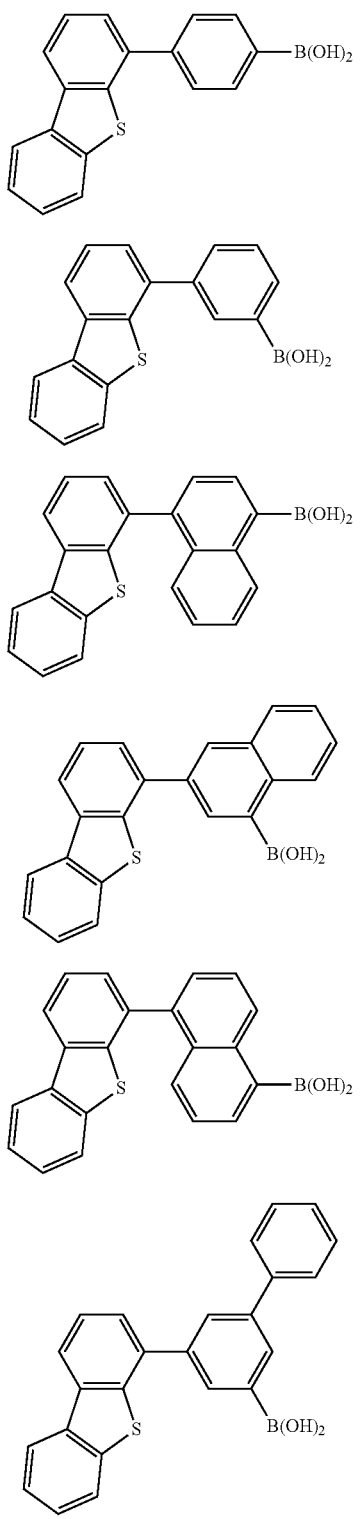
Sub 1
Sub 2
Sub 3
Sub 4
Sub 5
Sub 6
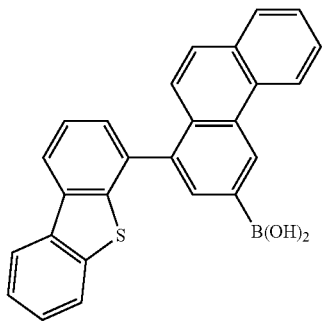
Sub 7
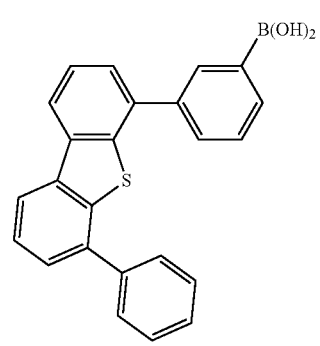
Sub 8
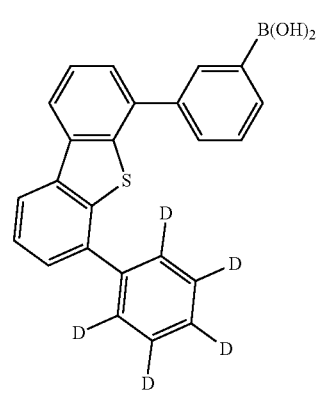
Sub 9
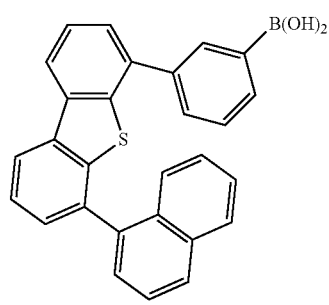
Sub 10
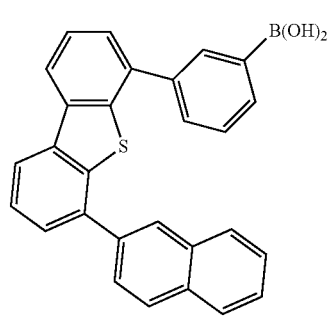
Sub 11

Sub 12
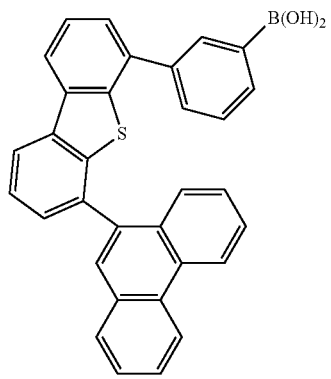
Sub 13
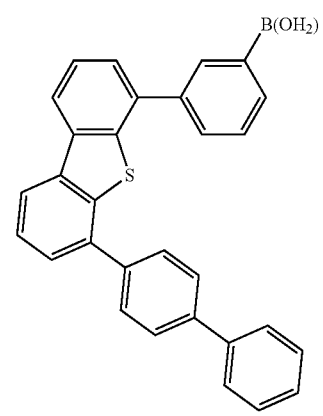
Sub 14
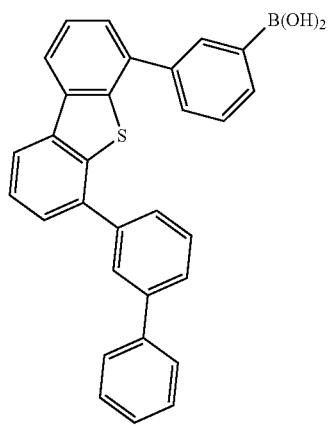
Sub 15
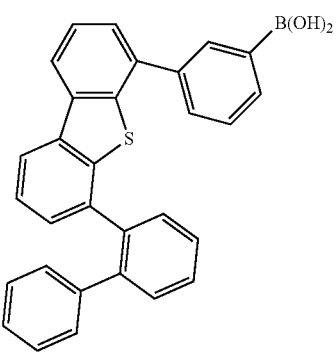
Sub 16
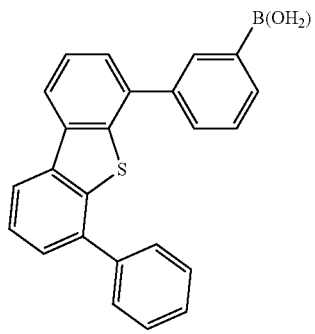
Sub 17
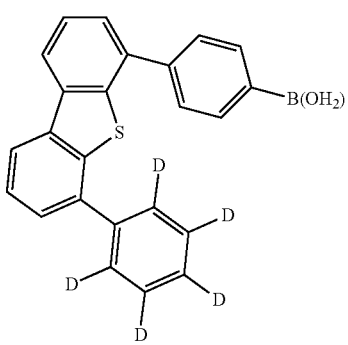
Sub 18
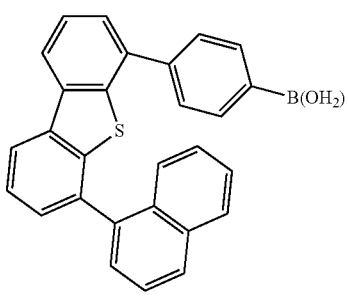
Sub 19
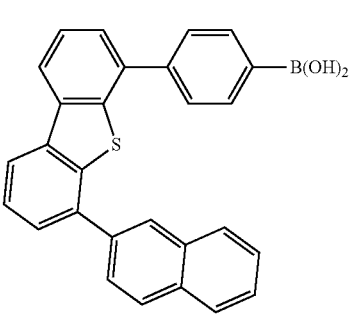
Sub 20
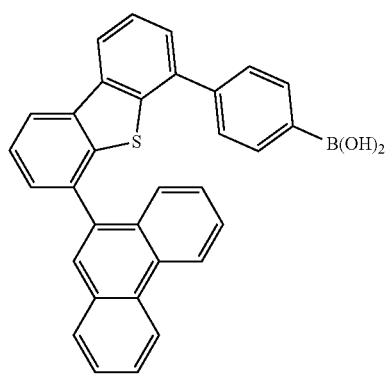

-continued

Sub 21

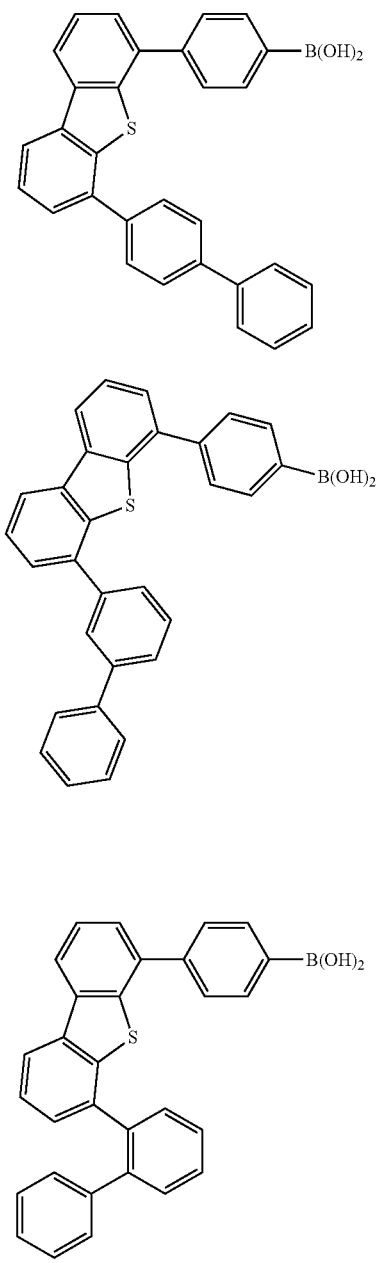

Sub 22

Sub 23

Synthesis Example of Product

Synthesis Example of P-41

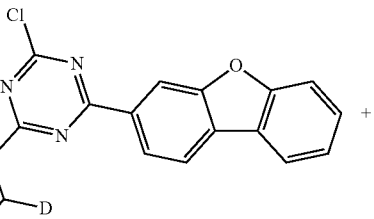

In a round bottom flask, Core 2 (5 g, 14 mmol), Sub 1 (4.6 g, 15.2 mmol), Pd(PPh$_3$)$_4$(0.5 g, 0.4 mmol), K$_2$CO$_3$ (5.7 g, 41.3 mmol), THF and water were added and stirred at 90° C. When the reaction was complete, the reaction mixture was

TABLE 2

| Compound | FD-MS | Compound | FD-MS |
|---|---|---|---|
| Sub 1 | m/z = 304.07(C$_{18}$H$_{13}$BO$_2$S = 304.17) | Sub 2 | m/z = 304.07(C$_{18}$H$_{13}$BO$_2$S = 304.17) |
| Sub 3 | m/z = 354.09(C$_{22}$H$_{15}$BO$_2$S = 354.23) | Sub 4 | m/z = 354.09(C$_{22}$H$_{15}$BO$_2$S = 354.23) |
| Sub 5 | m/z = 354.09(C$_{22}$H$_{15}$BO$_2$S = 354.23) | Sub 6 | m/z = 380.10(C$_{24}$H$_{17}$BO$_2$S = 380.27) |
| Sub 7 | m/z = 404.10(C$_{26}$H$_{17}$BO$_2$S = 404.29) | Sub 8 | m/z = 380.10(C$_{24}$H$_{17}$BO$_2$S = 380.27) |
| Sub 9 | m/z = 385.14(C$_{24}$H$_{12}$D$_5$BO$_2$S = 385.30) | Sub 10 | m/z = 430.12(C$_{28}$H$_{19}$BO$_2$S = 430.33) |
| Sub 11 | m/z = 430.12(C$_{28}$H$_{19}$BO$_2$S = 430.33) | Sub 12 | m/z = 480.14(C$_{32}$H$_{21}$BO$_2$S = 480.39) |
| Sub 13 | m/z = 456.14(C$_{30}$H$_{21}$BO$_2$S = 456.37) | Sub 14 | m/z = 456.14(C$_{30}$H$_{21}$BO$_2$S = 456.37) |
| Sub 15 | m/z = 456.14(C$_{30}$H$_{21}$BO$_2$S = 456.37) | Sub 16 | m/z = 380.10(C$_{24}$H$_{17}$BO$_2$S = 380.27) |
| Sub 17 | m/z = 385.14(C$_{24}$H$_{12}$D$_5$BO$_2$S = 385.30) | Sub 18 | m/z = 430.12(C$_{28}$H$_{19}$BO$_2$S = 430.33) |
| Sub 19 | m/z = 430.12(C$_{28}$H$_{19}$BO$_2$S = 430.33) | Sub 20 | m/z = 480.14(C$_{32}$H$_{21}$BO$_2$S = 480.39) |
| Sub 21 | m/z = 456.14(C$_{30}$H$_{21}$BO$_2$S = 456.37) | Sub 22 | m/z = 456.14(C$_{30}$H$_{21}$BO$_2$S = 456.37) |
| Sub 23 | m/z = 456.14(C$_{30}$H$_{21}$BO$_2$S = 456.37) | | | extracted with CH$_2$Cl$_2$ and water. The organic layer was dried over MgSO$_4$ and concentrated. The resulting compound was separated by silicagel column chromatography and recrystallization to obtain 4.6 g (yield: 57%) of P-41.

Synthesis Example of P-91

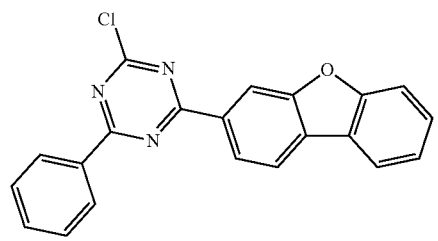

Core 1

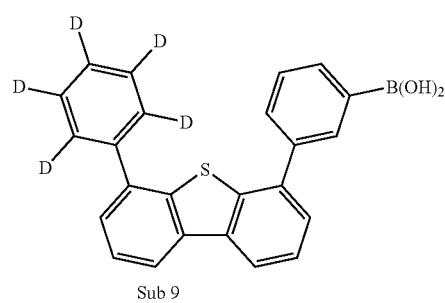

Sub 9

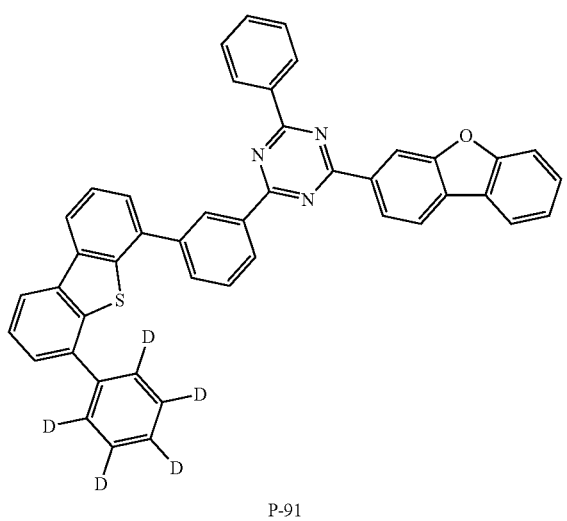

P-91

In a round bottom flask, Core 1 (5 g, 14 mmol), Sub 9 (5.8 g, 15.4 mmol), Pd(PPh$_3$)$_4$(0.5 g, 0.4 mmol), K$_2$CO$_3$ (5.8 g, 41.9 mmol), THF and water were added and stirred at 90° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain 4.7 g (yield: 51%) of P-91.

Synthesis Example of P-106

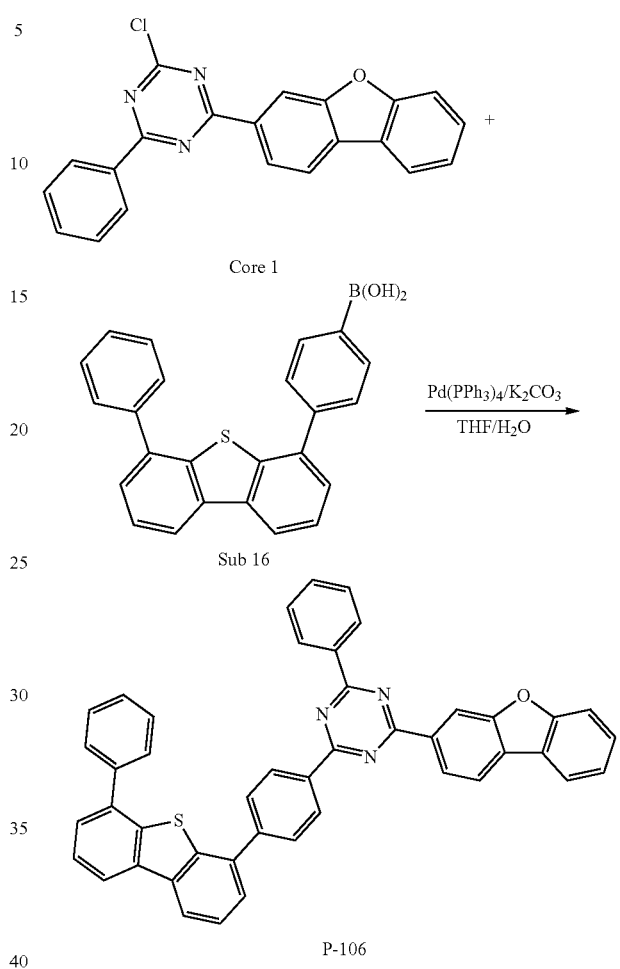

In a round bottom flask, Core 1 (5 g, 14 mmol), Sub 16 (5.8 g, 15.4 mmol), Pd(PPh$_3$)$_4$(0.5 g, 0.4 mmol), K$_2$CO$_3$ (5.8 g, 41.9 mmol), THF and water were added and stirred at 90° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain 5.8 g (yield: 63%) of P-106.

Synthesis Example of P-146

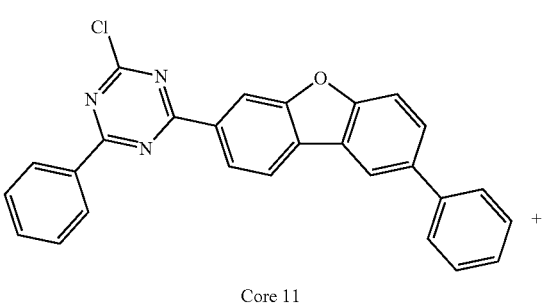

Core 11

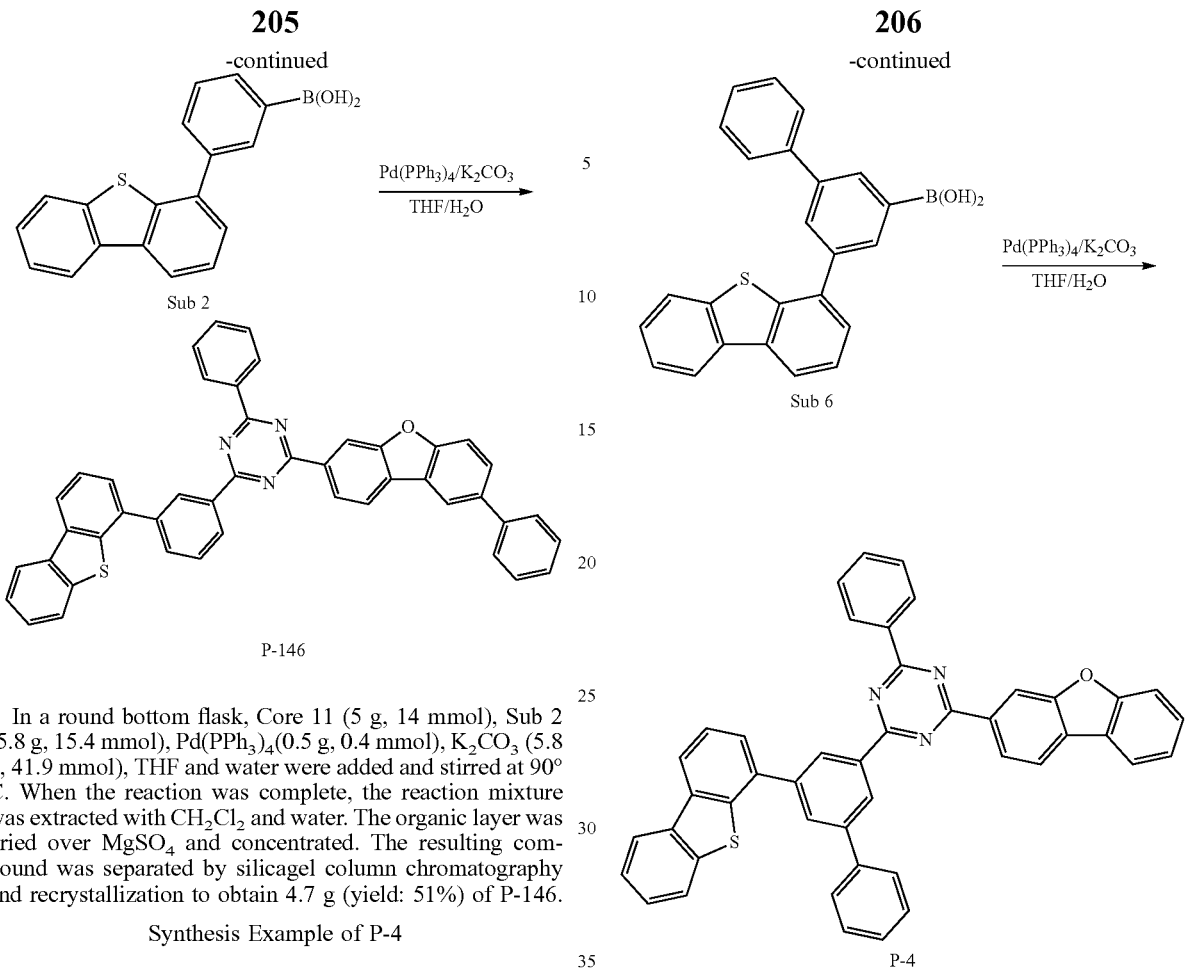

In a round bottom flask, Core 11 (5 g, 14 mmol), Sub 2 (5.8 g, 15.4 mmol), Pd(PPh₃)₄(0.5 g, 0.4 mmol), K₂CO₃ (5.8 g, 41.9 mmol), THF and water were added and stirred at 90° C. When the reaction was complete, the reaction mixture was extracted with CH₂Cl₂ and water. The organic layer was dried over MgSO₄ and concentrated. The resulting compound was separated by silicagel column chromatography and recrystallization to obtain 4.7 g (yield: 51%) of P-146.

Synthesis Example of P-4

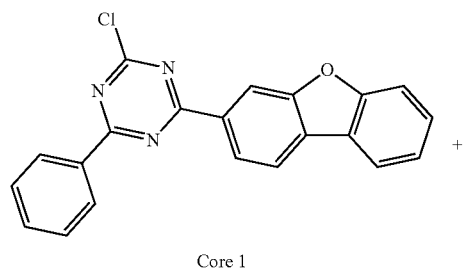

In a round bottom flask, Core 1 (5 g, 14 mmol), Sub 6 (5.9 g, 15.4 mmol), Pd(PPh₃)₄(0.5 g, 0.4 mmol), K₂CO₃ (5.8 g, 41.9 mmol), THF and water were added and stirred at 90° C. When the reaction was complete, the reaction mixture was extracted with CH₂Cl₂ and water. The organic layer was dried over MgSO₄ and concentrated. The resulting compound was separated by silicagel column chromatography and recrystallization to obtain 6.1 g (yield: 66%) of P-4. [Table 3] shows FD-MS (Field Desorption-Mass Spectrometry) values of some compounds belonging to Product.

TABLE 3

| compound | FD-MS | compound | FD-MS |
|---|---|---|---|
| P-1 | m/z = 581.16($C_{39}H_{23}N_3OS$ = 581.69) | P-2 | m/z = 631.17($C_{43}H_{25}N_3OS$ = 631.75) |
| P-3 | m/z = 631.17($C_{43}H_{25}N_3OS$ = 631.75) | P-4 | m/z = 657.19($C_{45}H_{27}N_3OS$ = 657.79) |
| P-5 | m/z = 681.19($C_{47}H_{27}N_3OS$ = 681.81) | P-6 | m/z = 631.17($C_{43}H_{25}N_3OS$ = 631.75) |
| P-7 | m/z = 631.17($C_{43}H_{25}N_3OS$ = 631.75) | P-8 | m/z = 657.19($C_{45}H_{27}N_3OS$ = 657.79) |
| P-9 | m/z = 657.19($C_{45}H_{27}N_3OS$ = 657.79) | P-10 | m/z = 657.19($C_{45}H_{27}N_3OS$ = 657.79) |
| P-11 | m/z = 586.19($C_{39}H_{18}D_5N_3OS$ = 586.72) | P-12 | m/z = 681.19($C_{47}H_{27}N_3OS$ = 681.81) |
| P-13 | m/z = 681.19($C_{47}H_{27}N_3OS$ = 681.81) | P-14 | m/z = 707.20($C_{49}H_{29}N_3OS$ = 707.85) |
| P-15 | m/z = 707.20($C_{49}H_{29}N_3OS$ = 707.85) | P-16 | m/z = 707.20($C_{49}H_{29}N_3OS$ = 707.85) |
| P-17 | m/z = 636.20($C_{43}H_{20}D_5N_3OS$ = 636.78) | P-18 | m/z = 681.19($C_{47}H_{27}N_3OS$ = 681.81) |
| P-19 | m/z = 681.19($C_{47}H_{27}N_3OS$ = 681.81) | P-20 | m/z = 707.20($C_{49}H_{29}N_3OS$ = 707.85) |
| P-21 | m/z = 707.20($C_{49}H_{29}N_3OS$ = 707.85) | P-22 | m/z = 707.20($C_{49}H_{29}N_3OS$ = 707.85) |
| P-23 | m/z = 636.20($C_{43}H_{20}D_5N_3OS$ = 636.78) | P-24 | m/z = 707.20($C_{49}H_{29}N_3OS$ = 707.85) |
| P-25 | m/z = 707.20($C_{49}H_{29}N_3OS$ = 707.85) | P-26 | m/z = 733.22($C_{51}H_{31}N_3OS$ = 733.89) |
| P-27 | m/z = 733.22($C_{51}H_{31}N_3OS$ = 733.89) | P-28 | m/z = 733.22($C_{51}H_{31}N_3OS$ = 733.89) |
| P-29 | m/z = 662.22($C_{45}H_{22}D_5N_3OS$ = 662.82) | P-30 | m/z = 662.22($C_{45}H_{22}D_5N_3OS$ = 662.82) |
| P-31 | m/z = 581.16($C_{39}H_{23}N_3OS$ = 581.69) | P-32 | m/z = 631.17($C_{43}H_{25}N_3OS$ = 631.75) |
| P-33 | m/z = 631.17($C_{43}H_{25}N_3OS$ = 631.75) | P-34 | m/z = 657.19($C_{45}H_{27}N_3OS$ = 657.79) |

TABLE 3-continued

| compound | FD-MS | compound | FD-MS |
|---|---|---|---|
| P-35 | m/z = 681.19($C_{47}H_{27}N_3OS$ = 681.81) | P-36 | m/z = 631.17($C_{43}H_{25}N_3OS$ = 631.75) |
| P-37 | m/z = 631.17($C_{43}H_{25}N_3OS$ = 631.75) | P-38 | m/z = 657.19($C_{45}H_{27}N_3OS$ = 657.79) |
| P-39 | m/z = 657.19($C_{45}H_{27}N_3OS$ = 657.79) | P-40 | m/z = 657.19($C_{45}H_{27}N_3OS$ = 657.79) |
| P-41 | m/z = 586.19($C_{39}H_{18}D_5N_3OS$ = 586.72) | P-42 | m/z = 681.19($C_{47}H_{27}N_3OS$ = 681.81) |
| P-43 | m/z = 681.19($C_{47}H_{27}N_3OS$ = 681.81) | P-44 | m/z = 707.20($C_{49}H_{29}N_3OS$ = 707.85) |
| P-45 | m/z = 707.20($C_{49}H_{29}N_3OS$ = 707.85) | P-46 | m/z = 707.20($C_{49}H_{29}N_3OS$ = 707.85) |
| P-47 | m/z = 636.20($C_{43}H_{20}D_5N_3OS$ = 636.78) | P-48 | m/z = 681.19($C_{47}H_{27}N_3OS$ = 681.81) |
| P-49 | m/z = 681.19($C_{47}H_{27}N_3OS$ = 681.81) | P-50 | m/z = 707.20($C_{49}H_{29}N_3OS$ = 707.85) |
| P-51 | m/z = 707.20($C_{49}H_{29}N_3OS$ = 707.85) | P-52 | m/z = 707.20($C_{49}H_{29}N_3OS$ = 707.85) |
| P-53 | m/z = 733.22($C_{51}H_{31}N_3OS$ = 733.89) | P-54 | m/z = 707.20($C_{49}H_{29}N_3OS$ = 707.85) |
| P-55 | m/z = 707.20($C_{49}H_{29}N_3OS$ = 707.85) | P-56 | m/z = 733.22($C_{51}H_{31}N_3OS$ = 733.89) |
| P-57 | m/z = 733.22($C_{51}H_{31}N_3OS$ = 733.89) | P-58 | m/z = 733.22($C_{51}H_{31}N_3OS$ = 733.89) |
| P-59 | m/z = 662.22($C_{45}H_{22}DN_3OS$ = 662.82) | P-60 | m/z = 662.22($C_{45}H_{22}DN_3OS$ = 662.82) |
| P-61 | m/z = 657.19($C_{45}H_{27}N_3OS$ = 657.79) | P-62 | m/z = 707.20($C_{49}H_{29}N_3OS$ = 707.85) |
| P-63 | m/z = 707.20($C_{49}H_{29}N_3OS$ = 707.85) | P-64 | m/z = 733.22($C_{51}H_{31}N_3OS$ = 733.89) |
| P-65 | m/z = 757.22($C_{53}H_{31}N_3OS$ = 757.91) | P-66 | m/z = 707.20($C_{49}H_{29}N_3OS$ = 707.85) |
| P-67 | m/z = 707.20($C_{49}H_{29}N_3OS$ = 707.85) | P-68 | m/z = 733.22($C_{51}H_{31}N_3OS$ = 733.89) |
| P-69 | m/z = 733.22($C_{51}H_{31}N_3OS$ = 733.89) | P-70 | m/z = 733.22($C_{51}H_{31}N_3OS$ = 733.89) |
| P-71 | m/z = 662.22($C_{45}H_{22}D_5N_3OS$ = 662.82) | P-72 | m/z = 757.22($C_{53}H_{31}N_3OS$ = 757.91) |
| P-73 | m/z = 757.22($C_{53}H_{31}N_3OS$ = 757.91) | P-74 | m/z = 783.23($C_{55}H_{33}N_3OS$ = 783.95) |
| P-75 | m/z = 783.23($C_{55}H_{33}N_3OS$ = 783.95) | P-76 | m/z = 783.23($C_{55}H_{33}N_3OS$ = 783.95) |
| P-77 | m/z = 712.23($C_{49}H_{24}D_5N_3OS$ = 712.88) | P-78 | m/z = 757.22($C_{53}H_{31}N_3OS$ = 757.91) |
| P-79 | m/z = 757.22($C_{53}H_{31}N_3OS$ = 757.91) | P-80 | m/z = 783.23($C_{55}H_{33}N_3OS$ = 783.95) |
| P-81 | m/z = 783.23($C_{55}H_{33}N_3OS$ = 783.95) | P-82 | m/z = 783.23($C_{55}H_{33}N_3OS$ = 783.95) |
| P-83 | m/z = 712.23($C_{49}H_{24}D_5N_3OS$ = 712.88) | P-84 | m/z = 783.23($C_{55}H_{33}N_3OS$ = 783.95) |
| P-85 | m/z = 783.23($C_{55}H_3N_3OS$ = 783.95) | P-86 | m/z = 809.25($C_{57}H_{35}N_3OS$ = 809.99) |
| P-87 | m/z = 809.25($C_{57}H_{35}N_3OS$ = 809.99) | P-88 | m/z = 809.25($C_{57}H_{35}N_3OS$ = 809.99) |
| P-89 | m/z = 738.25($C_{51}H_{26}D_5N_3OS$ = 738.92) | P-90 | m/z = 738.25($C_{51}H_{26}D_5N_3OS$ = 738.92) |
| P-91 | m/z = 662.22($C_{45}H_{22}DN_3OS$ = 662.82) | P-92 | m/z = 712.23($C_{49}H_{24}D_5N_3OS$ = 712.88) |
| P-93 | m/z = 712.23($C_{49}H_{24}D_5N_3OS$ = 712.88) | P-94 | m/z = 738.25($C_{51}H_{26}D_5N_3OS$ = 738.92) |
| P-95 | m/z = 762.25($C_{53}H_{26}D_5N_3OS$ = 762.94) | P-96 | m/z = 712.23($C_{49}H_{24}D_5N_3OS$ = 712.88) |
| P-97 | m/z = 712.23($C_{49}H_{24}D_5N_3OS$ = 712.88) | P-98 | m/z = 738.25($C_{51}H_{26}D_5N_3OS$ = 738.92) |
| P-99 | m/z = 738.25($C_{51}H_{26}D_5N_3OS$ = 738.92) | P-100 | m/z = 738.25($C_{51}H_{26}D_5N_3OS$ = 738.92) |
| P-101 | m/z = 667.25($C_{45}H_{17}D_{10}N_3OS$ = 667.85) | P-102 | m/z = 707.20($C_{49}H_{29}N_3OS$ = 707.85) |
| P-103 | m/z = 707.20($C_{49}H_{29}N_3OS$ = 707.85) | P-104 | m/z = 733.22($C_{51}H_{31}N_3OS$ = 733.89) |
| P-105 | m/z = 733.22($C_{51}H_{31}N_3OS$ = 733.89) | P-106 | m/z = 657.19($C_{45}H_{27}N_3OS$ = 657.79) |
| P-107 | m/z = 707.20($C_{49}H_{29}N_3OS$ = 707.85) | P-108 | m/z = 707.20($C_{49}H_{29}N_3OS$ = 707.85) |
| P-109 | m/z = 733.22($C_{51}H_{31}N_3OS$ = 733.89) | P-110 | m/z = 757.22($C_{53}H_{31}N_3OS$ = 757.91) |
| P-111 | m/z = 707.20($C_{49}H_{29}N_3OS$ = 707.85) | P-112 | m/z = 707.20($C_{49}H_{29}N_3OS$ = 707.85) |
| P-113 | m/z = 733.22($C_{51}H_{31}N_3OS$ = 733.89) | P-114 | m/z = 733.22($C_{51}H_{31}N_3OS$ = 733.89) |
| P-115 | m/z = 733.22($C_{51}H_{31}N_3OS$ = 733.89) | P-116 | m/z = 662.22($C_{45}H_{22}D_5N_3OS$ = 662.82) |
| P-117 | m/z = 757.22($C_{53}H_{31}N_3OS$ = 757.91) | P-118 | m/z = 757.22($C_{53}H_{31}N_3OS$ = 757.91) |
| P-119 | m/z = 783.23($C_{55}H_{33}N_3OS$ = 783.95) | P-120 | m/z = 783.23($C_{55}H_{33}N_3OS$ = 783.95) |
| P-121 | m/z = 783.23($C_{55}H_{33}N_3OS$ = 783.95) | P-122 | m/z = 712.23($C_{49}H_{24}D_5N_3OS$ = 712.88) |
| P-123 | m/z = 757.22($C_{53}H_{31}N_3OS$ = 757.91) | P-124 | m/z = 757.22($C_{53}H_{31}N_3OS$ = 757.91) |
| P-125 | m/z = 783.23($C_{55}H_{33}N_3OS$ = 783.95) | P-126 | m/z = 783.23($C_{55}H_{33}N_3OS$ = 783.95) |
| P-127 | m/z = 783.23($C_{55}H_{33}N_3OS$ = 783.95) | P-128 | m/z = 712.23($C_{49}H_{24}D_5N_3OS$ = 712.88) |
| P-129 | m/z = 783.23($C_{55}H_{33}N_3OS$ = 783.95) | P-130 | m/z = 783.23($C_{55}H_{33}N_3OS$ = 783.95) |
| P-131 | m/z = 809.25($C_{57}H_{35}N_3OS$ = 809.99) | P-132 | m/z = 809.25($C_{57}H_{35}N_3OS$ = 809.99) |
| P-133 | m/z = 809.25($C_{57}H_{35}N_3OS$ = 809.99) | P-134 | m/z = 738.25($C_{51}H_{26}D_5N_3OS$ = 738.92) |
| P-135 | m/z = 738.25($C_{51}H_{26}D_5N_3OS$ = 738.92) | P-136 | m/z = 662.22($C_{45}H_{22}D_5N_3OS$ = 662.82) |
| P-137 | m/z = 712.23($C_{49}H_{24}D_5N_3OS$ = 712.88) | P-138 | m/z = 712.23($C_{49}H_{24}D_5N_3OS$ = 712.88) |
| P-139 | m/z = 738.25($C_{51}H_{26}D_5N_3OS$ = 738.92) | P-140 | m/z = 762.25($C_{53}H_{26}D_5N_3OS$ = 762.94) |
| P-141 | m/z = 712.23($C_{49}H_{24}D_5N_3OS$ = 712.88) | P-142 | m/z = 712.23($C_{49}H_{24}D_5N_3OS$ = 712.88) |
| P-143 | m/z = 738.25($C_{51}H_{26}D_5N_3OS$ = 738.92) | P-144 | m/z = 738.25($C_{51}H_{26}D_5N_3OS$ = 738.92) |
| P-145 | m/z = 738.25($C_{51}H_{26}D_5N_3OS$ = 738.92) | P-146 | m/z = 657.19($C_{45}H_{27}N_3OS$ = 657.79) |
| P-147 | m/z = 733.22($C_{51}H_{31}N_3OS$ = 733.89) | P-148 | m/z = 662.22($C_{45}H_{22}D_5N_3OS$ = 662.82) |
| P-149 | m/z = 657.19($C_{45}H_{27}N_3OS$ = 657.79) | P-150 | m/z = 662.22($C_{45}H_{22}D_5N_3OS$ = 662.82) |
| P-151 | m/z = 657.19($C_{45}H_{27}N_3OS$ = 657.79) | P-152 | m/z = 733.22($C_{51}H_{31}N_3OS$ = 733.89) |
| P-153 | m/z = 662.22($C_{45}H_{22}D_5N_3OS$ = 662.82) | p-154 | m/z = 657.19($C_{45}H_{27}N_3OS$ = 657.79) |
| p-155 | m/z = 657.19($C_{45}H_{27}N_3OS$ = 657.79) | P-156 | m/z = 631.17($C_{43}H_{25}N_3OS$ = 631.75) |
| P-157 | m/z = 681.19($C_{45}H_{27}N_3OS$ = 681.81) | p-158 | m/z = 681.19($C_{47}H_{27}N_3OS$ = 681.81) |
| P-159 | m/z = 707.20($C_{49}H_{29}N_3OS$ = 707.85) | p-160 | m/z = 781.22($C_{55}H_{31}N_3OS$ = 781.93) |

Synthesis Example 2

The compounds (final products 2) represented by Formula (12) according to the present invention can be prepared by reacting Sub 3-1 and Sub 3-2 as shown in the following Reaction Scheme 4, but are not limited thereto.

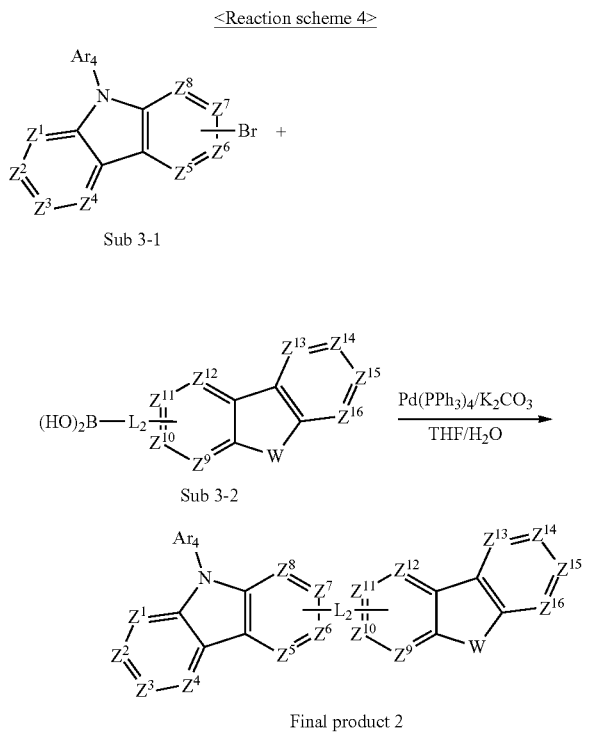

Synthesis Example of 4-1

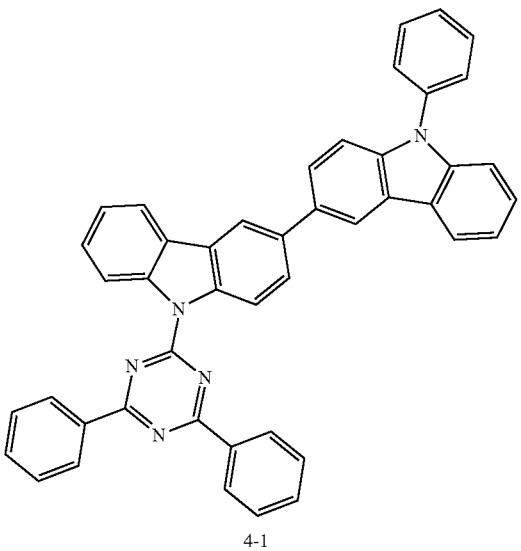

4-1

3-bromo-9-phenyl-9H-carbazole (6.4 g, 20 mmol) was dissolved in THF, and (9-(4,6-diphenyl-1,3,5-triazin-2-yl)-9H-carbazol-3-yl)boronic acid (8.8 g, 20 mmol), Pd(PPh$_3$)$_4$ (0.03 eq.), K2CO3(3 eq.) and water were added and refluxed with stirring. After the reaction was completed, the reaction mixture was extracted with ether and water. The organic layer was dried over MgSO$_4$ and concentrated. The resulting organic material was separated by silicagel column chromatography and recrystallization to obtain 9.2 g (yield: 72%) of the product.

Synthesis Example of 4-21

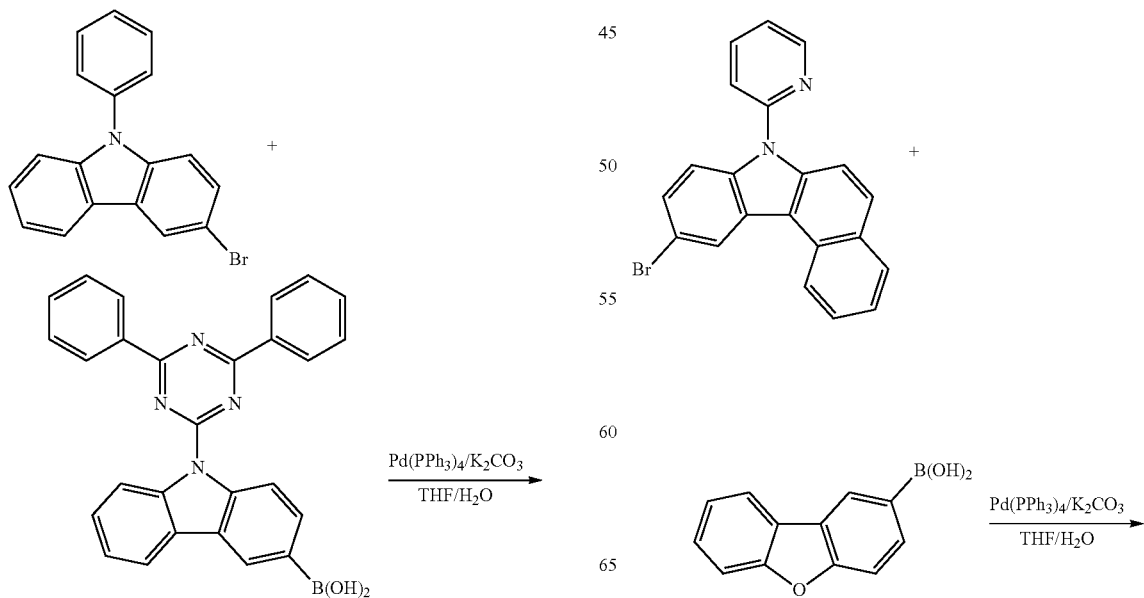

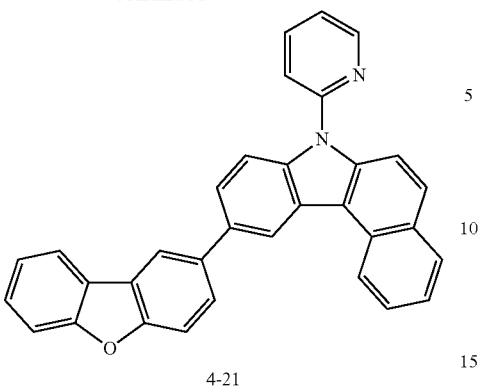
4-21
10-bromo-7-(pyridin-2-yl)-7H-benzo[c]carbazole (7.5 g, 2 mmol), dibenzo[b,d]furan-2-ylboronic acid (4.2 g, 20 mmol) were carried out in the same manner as 4-1 to obtain 6.5 g of the product (yield: 71%)
Synthesis Example of 4-25
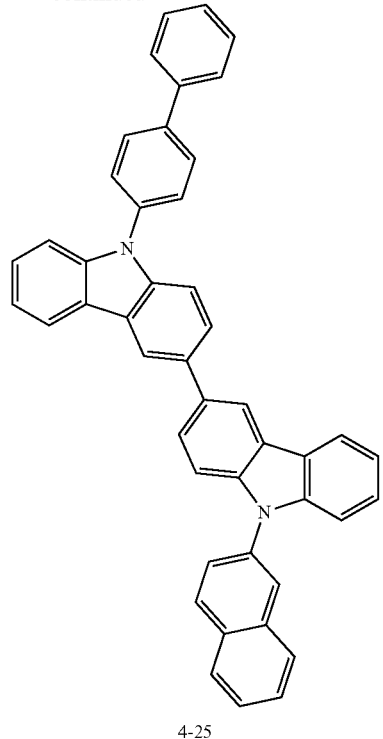
4-25
9-([1,1'-biphenyl]-4-yl)-3-bromo-9H-carbazole (8.0 g, 20 mmol), (9-(naphthalen-2-yl)-9H-carbazol-3-yl)boronic acid (6.7 g, 20 mmol) were carried out in the same manner as 4-1 to obtain 9.2 g of the product (yield: 75%)
Synthesis Example of 4-31
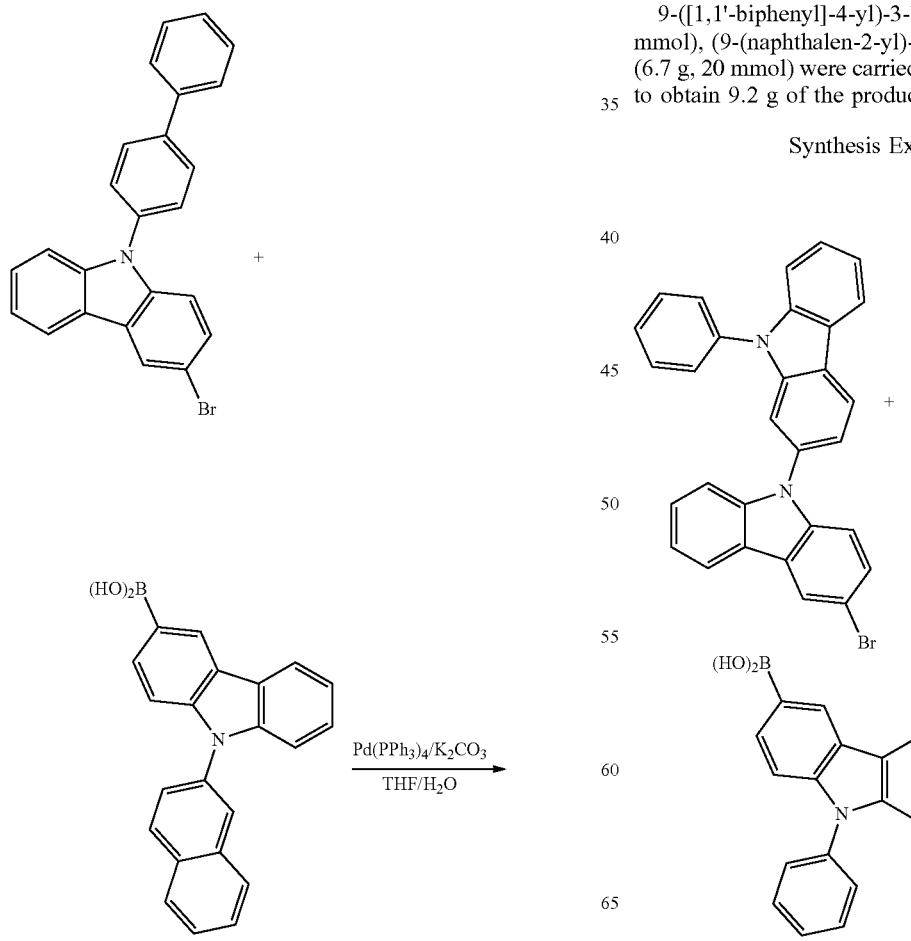

213
-continued

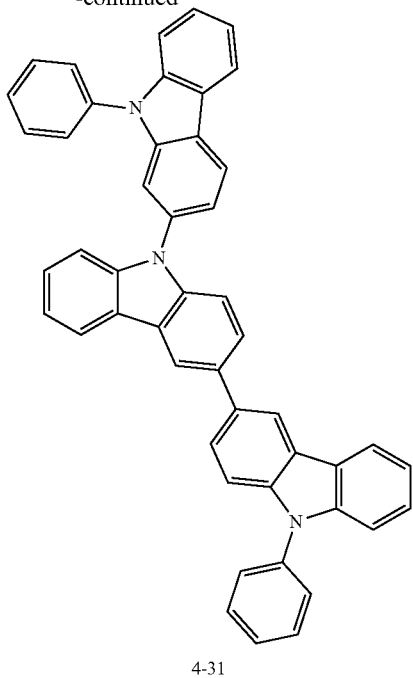

4-31

3'-bromo-9-phenyl-9H-2,9'-bicarbazole (9.7 g, 20 mmol), (9-phenyl-9H-carbazol-3-yl)boronic acid (5.7 g, 20 mmol) were carried out in the same manner as 4-1 to obtain 9.5 g of the product (yield: 73%)

Synthesis Example of 4-32

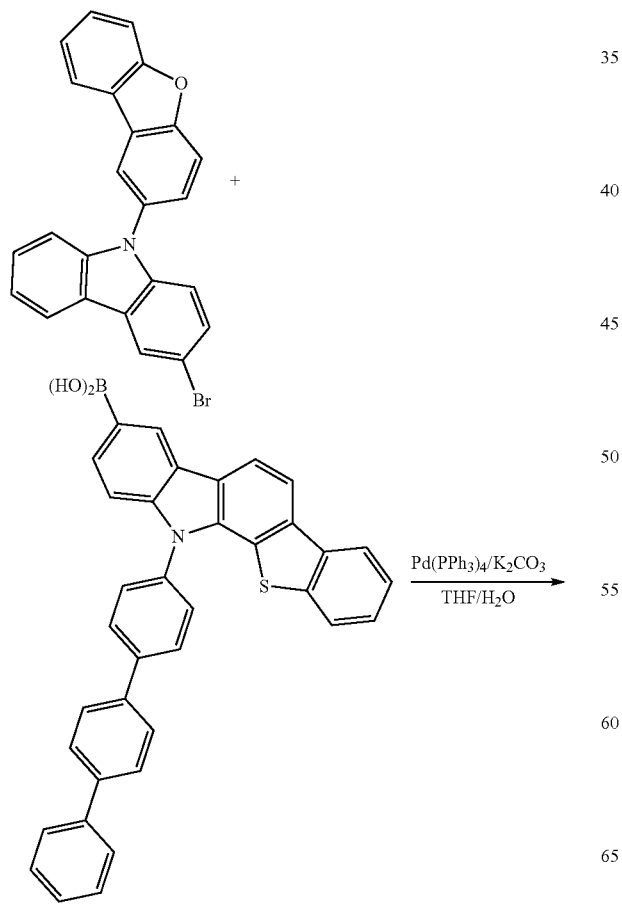

214
-continued

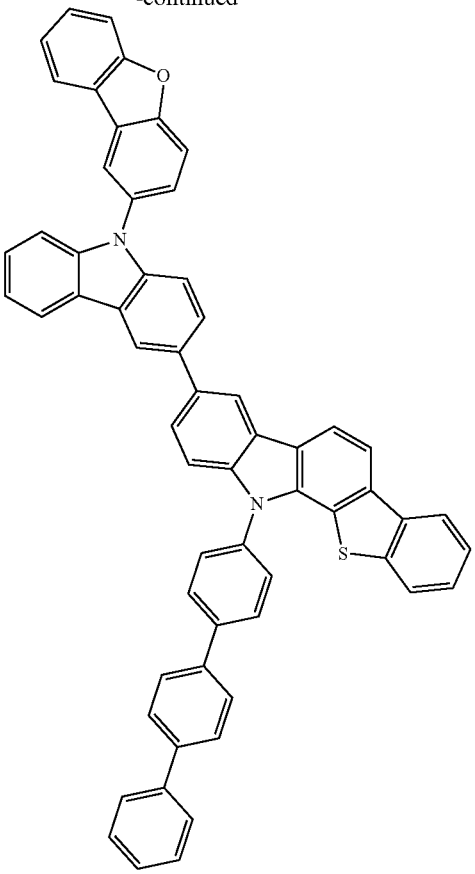

4-32

3-bromo-9-(dibenzo[b,d]furan-2-yl)-9H-carbazole (8.2 g, 20 mmol), (12-([1, 1':4', 1"-terphenyl]-4-yl)-12H-benzo[4,5]thieno[2,3-a]carbazol-3-yl)boronic acid (10.9 g, 20 mmol) were carried out in the same manner as 4-1 to obtain 11.5 g of the product (yield: 69%)

Synthesis Example of 4-34

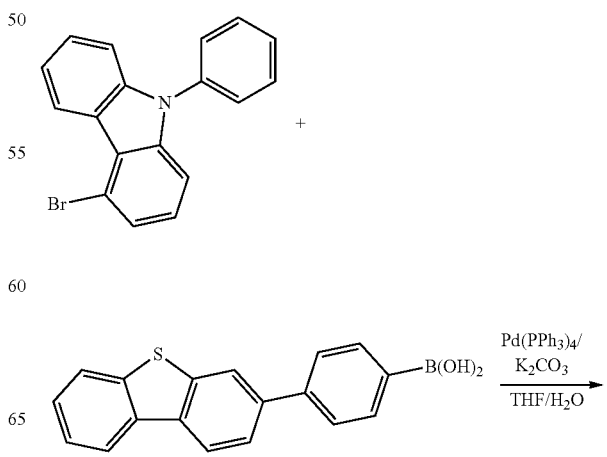

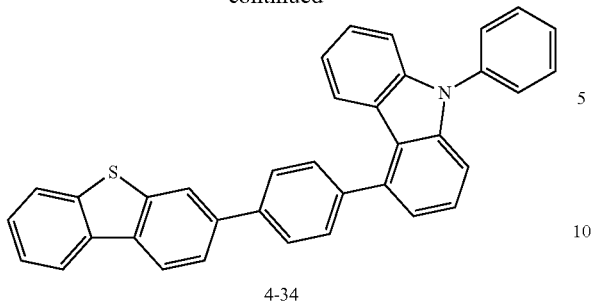

4-34

4-bromo-9-phenyl-9H-carbazole (6.4 g, 20 mmol), (4-(dibenzo[b,d]thiophen-3-yl)phenyl)boronic acid (6.1 g, 20 mmol) were carried out in the same manner as 4-1 to obtain 6.7 g of the product (yield: 67%)

Synthesis Example of 4-35

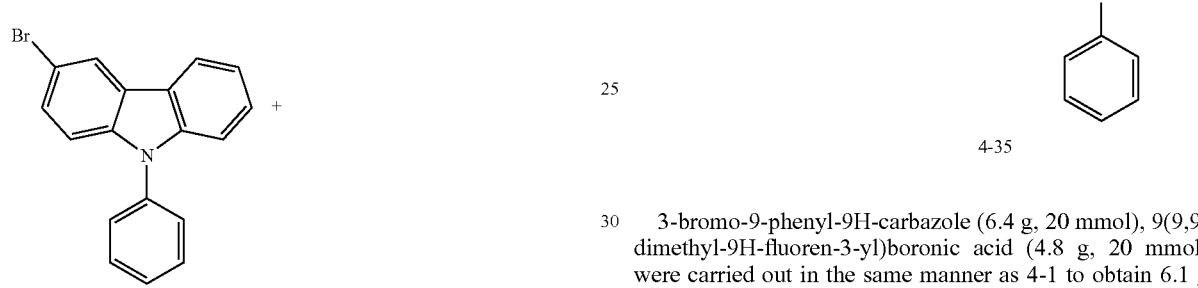

4-35

3-bromo-9-phenyl-9H-carbazole (6.4 g, 20 mmol), 9(9,9-dimethyl-9H-fluoren-3-yl)boronic acid (4.8 g, 20 mmol) were carried out in the same manner as 4-1 to obtain 6.1 g of the product (yield: 70%)

TABLE 4

| compound | FD-MS | compound | FD-MS |
|---|---|---|---|
| 4-1 | m/z = 639.24($C_{45}H_{29}N_5$ = 639.75) | 4-2 | m/z = 715.27($C_{51}H_{33}N_5$ = 715.84) |
| 4-3 | m/z = 780.33($C_{57}H_{40}N_4$ = 780.95) | 4-4 | m/z = 639.24($C_{45}H_{29}N_5$ = 639.75) |
| 4-5 | m/z = 715.27($C_{51}H_{33}N_5$ = 715.84) | 4-6 | m/z = 780.33($C_{57}H_{40}N_4$ = 780.95) |
| 4-7 | m/z = 612.23($C_{44}H_{28}N_4$ = 612.72) | 4-8 | m/z = 612.23($C_{44}H_{28}N_4$ = 612.72) |
| 4-9 | m/z = 662.25($C_{48}H_{30}N_4$ = 662.78) | 4-10 | m/z = 484.19($C_{36}H_{24}N_2$ = 484.59) |
| 4-11 | m/z = 639.24($C_{45}H_{29}N_5$ = 639.75) | 4-12 | m/z = 715.27($C_{51}H_{33}N_5$ = 715.84) |
| 4-13 | m/z = 715.27($C_{51}H_{33}N_5$ = 715.84) | 4-14 | m/z = 638.25($C_{46}H_{30}N_4$ = 638.76) |
| 4-15 | m/z = 579.18($C_{40}H_{25}N_3S$ = 579.71) | 4-16 | m/z = 410.14($C_{29}H_{18}N_2S$ = 410.47) |
| 4-17 | m/z = 486.17($C_{35}H_{22}N_2O$ = 486.56) | 4-18 | m/z = 486.17($C_{35}H_{22}N_2O$ = 486.56) |
| 4-19 | m/z = 486.17($C_{35}H_{22}N_2O$ = 486.56) | 4-20 | m/z = 563.20($C_{40}H_{25}N_3O$ = 563.65) |
| 4-21 | m/z = 460.16($C_{33}H_{20}N_2O$ = 460.52) | 4-22 | m/z = 536.19($C_{39}H_{24}N_2O$ = 536.62) |
| 4-23 | m/z = 689.26($C_{49}H_{31}N_5$ = 689.80) | 4-24 | m/z = 585.22($C_{43}H_{27}N_3$ = 585.69) |
| 4-25 | m/z = 610.24($C_{46}H_{30}N_2$ = 610.76) | 4-26 | m/z = 610.24($C_{46}H_{30}N_2$ = 610.76) |
| 4-27 | m/z = 636.26($C_{48}H_{32}N_2$ = 636.80) | 4-28 | m/z = 636.26($C_{48}H_{32}N_2$ = 636.80) |
| 4-29 | m/z = 610.24($C_{46}H_{30}N_2$ = 610.76) | 4-30 | m/z = 610.24($C_{46}H_{30}N_2$ = 610.76) |
| 4-31 | m/z = 649.25($C_{48}H_{31}N_3$ = 649.80) | 4-32 | m/z = 832.25($C_{60}H_{36}N_2OS$ = 833.02) |
| 4-33 | m/z = 560.23($C_{42}H_{28}N_2$ = 560.70) | 4-34 | m/z = 501.16($C_{36}H_{23}NS$ = 501.65) |
| 4-35 | m/z = 435.20($C_{33}H_{25}N$ = 435.57) | 4-36 | m/z = 725.28($C_{54}H_{35}N_3$ = 725.90) |
| 4-37 | m/z = 650.24($C_{48}H_{30}N_2O$ = 650.78) | 4-38 | m/z = 650.24($C_{48}H_{30}N_2O$ = 650.78) |
| 4-39 | m/z = 650.24($C_{48}H_{30}N_2O$ = 650.78) | 4-40 | m/z = 650.24($C_{48}H_{30}N_2O$ = 650.78) |
| 4-41 | m/z = 666.21($C_{48}H_{30}N_2S$ = 666.84) | 4-42 | m/z = 666.21($C_{48}H_{30}N_2S$ = 666.84) |
| 4-43 | m/z = 666.21($C_{48}H_{30}N_2S$ = 666.84) | 4-44 | m/z = 666.21($C_{48}H_{30}N_2S$ = 666.84) |
| 4-45 | m/z = 650.24($C_{48}H_{30}N_2O$ = 650.78) | 4-46 | m/z = 650.24($C_{48}H_{30}N_2O$ = 650.78) |
| 4-47 | m/z = 650.24($C_{48}H_{30}N_2O$ = 650.78) | 4-48 | m/z = 650.24($C_{48}H_{30}N_2O$ = 650.78) |
| 4-49 | m/z = 666.21($C_{48}H_{30}N_2S$ = 666.84) | 4-50 | m/z = 666.21($C_{48}H_{30}N_2S$ = 666.84) |
| 4-51 | m/z = 666.21($C_{48}H_{30}N_2S$ = 666.84) | 4-52 | m/z = 666.21($C_{48}H_{30}N_2S$ = 666.84) |

217

Synthesis Example 3

Final products represented by Formula (18) according to the present invention can be prepared by reacting as follows, but are not limited thereto.

Synthesis Example of 13-17

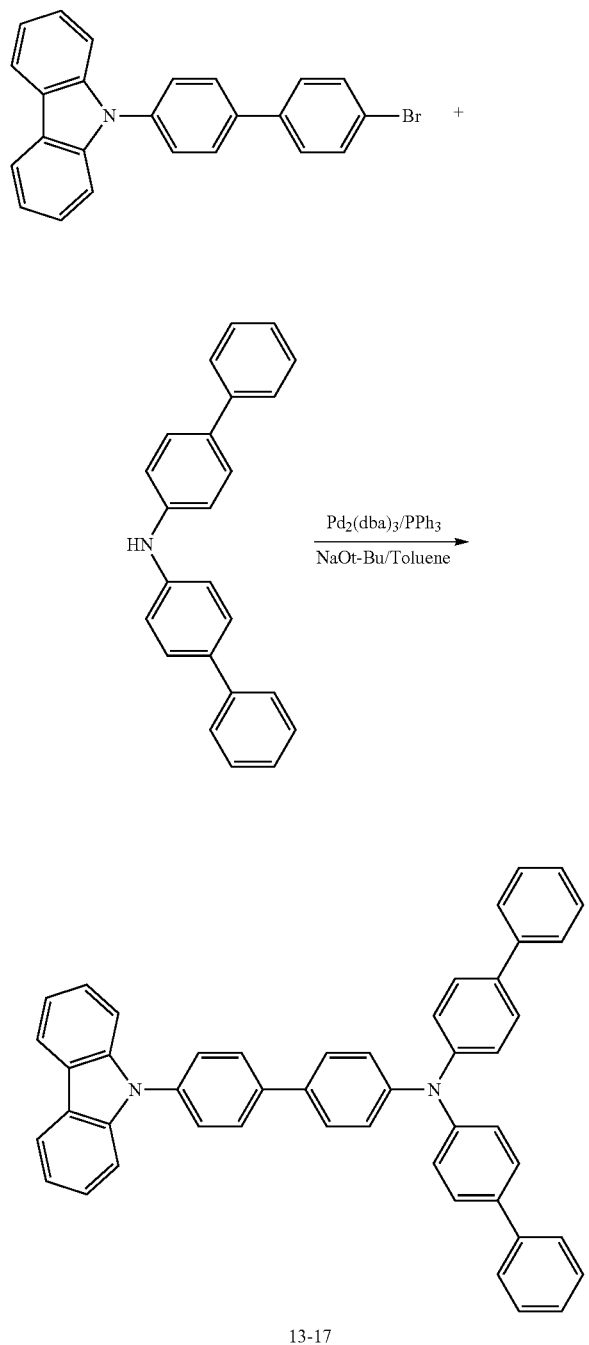

13-17

9-(4'-bromo-[1,1'-biphenyl]-4-yl)-9H-carbazole(9.6 g, 24 mmol) was dissolved in toluene, and di([1,1'-biphenyl]-4-yl)amine(6.4 g, 20 mmol), Pd$_2$(dba)$_3$ (0.05 eq.), PPh$_3$(0.1 eq.), NaOt-Bu (3 eq.) were added and refluxed with stirring at 100° C. at 24 hours. After the reaction was completed, the reaction mixture was extracted with ether and water. The organic layer was dried over MgSO$_4$ and concentrated. The resulting organic material was separated by silicagel column chromatography and recrystallization to obtain 12.9 g (yield: 84%) of the product.

Synthesis Example of 13-32

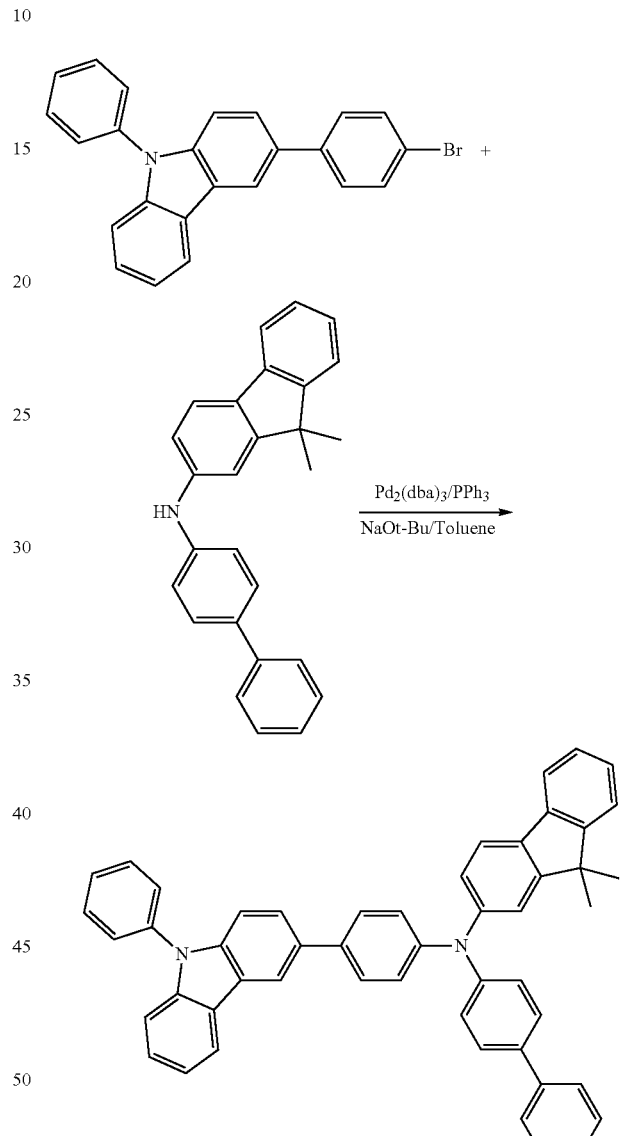

13-32

3-(4-bromophenyl)-9-phenyl-9H-carbazole (9.6 g, 24 mmol) was dissolved in toluene, and N-([1,1'-biphenyl]-4-yl)-9,9-dimethyl-9H-fluoren-2-amine(7.2 g, 20 mmol), Pd$_2$(dba)$_3$ (0.05 eq.), PPh$_3$(0.1 eq.), NaOt-Bu (3 eq.) were added and refluxed with stirring at 100° C. at 24 hours. After the reaction was completed, the reaction mixture was extracted with ether and water. The organic layer was dried over MgSO$_4$ and concentrated. The resulting organic material was separated by silicagel column chromatography and recrystallization to obtain 13.8 g (yield: 85%) of the product.

Synthesis Example of 2-34

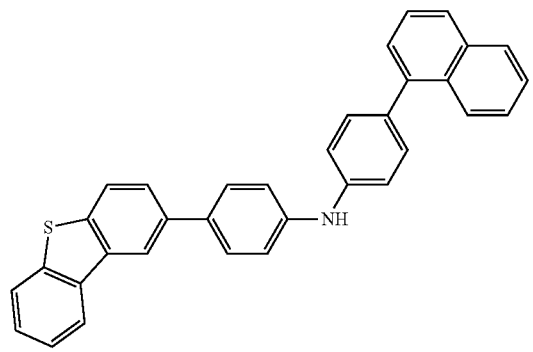

Sub 4(19)

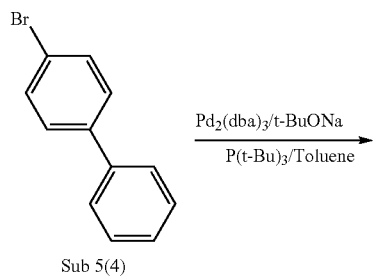

Sub 5(4)

Pd₂(dba)₃/t-BuONa
———————————→
P(t-Bu)₃/Toluene

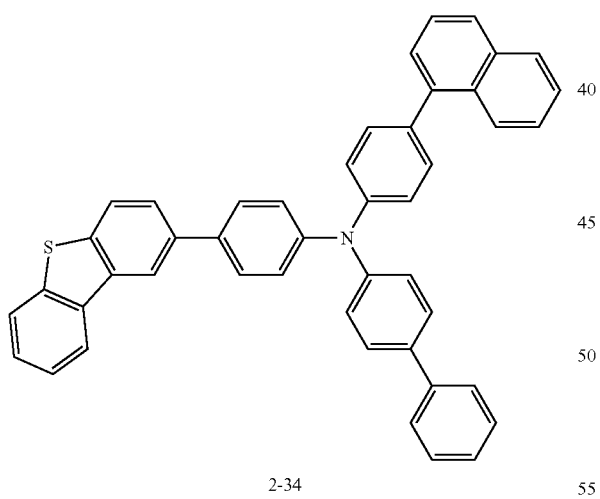

2-34

In a round bottom flask, Sub 4(19) (9.5 g, 20 mmol), Sub 5(4) (4.7 g, 20 mmol), Pd₂(dba)₃ (0.5 g, 0.6 mmol), P(t-Bu)₃ (0.2 g, 2 mmol), t-BuONa (5.8 g, 60 mmol), toluene (300 mL) were added and were carried out at 100° C. When the reaction was complete, the reaction mixture was extracted with CH₂Cl₂ and water. The organic layer was dried over MgSO₄ and concentrated. The resulting compound was separated by silicagel column chromatography and recrystallization to obtain 9.8 g (yield: 78%) of 2-34.

Synthesis Example of 2-58

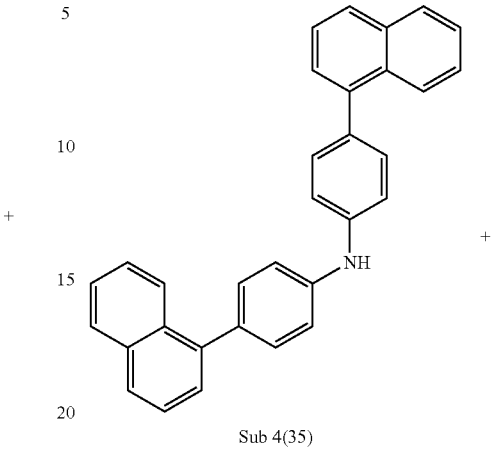

Sub 4(35)

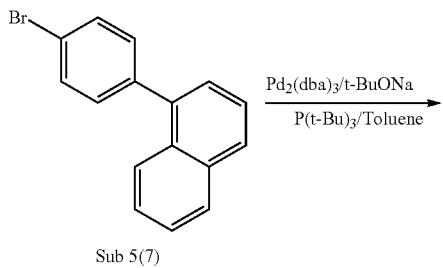

Sub 5(7)

Pd₂(dba)₃/t-BuONa
———————————→
P(t-Bu)₃/Toluene

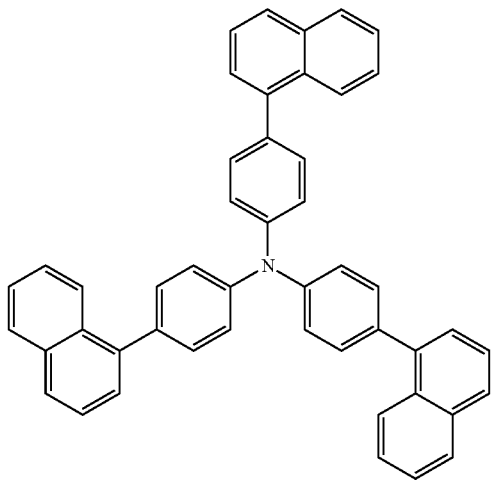

2-58

In a round bottom flask, Sub 4(35) (8.4 g, 20 mmol), Sub 5(7) (5.7 g, 20 mmol), Pd₂(dba)₃ (0.5 g, 0.6 mmol), P(t-Bu)₃ (0.2 g, 2 mmol), t-BuONa (5.8 g, 60 mmol) and toluene(300 mL) were carried out in the same manner as in 2-34 to give 2-58(10.4 g, 83%).

Synthesis Example of 2-59

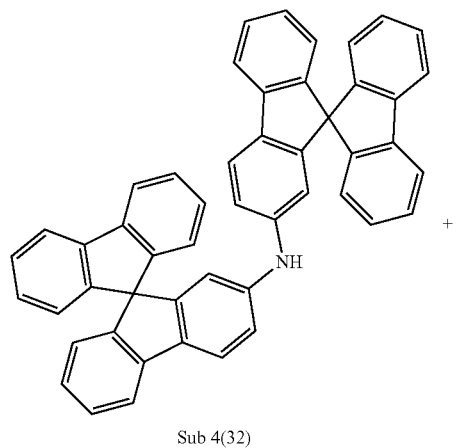

Sub 4(32)

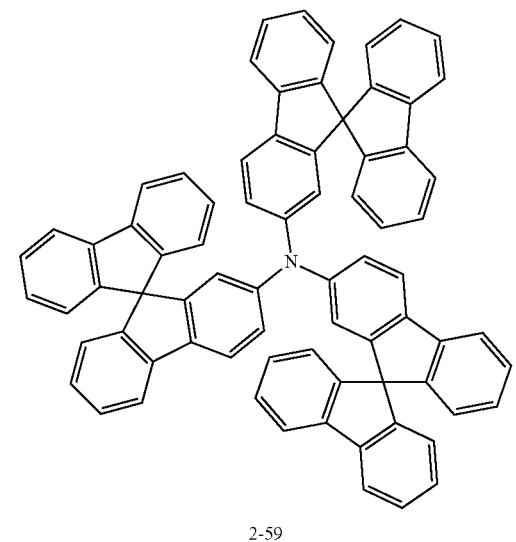

Sub 5(11) → 2-59

In a round bottom flask, Sub 4(32) (12.9 g, 20 mmol), Sub 5(11) (7.9 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene(300 mL) were carried out in the same manner as in 2-34 to give 2-59. (5.2 g, 79%).

Synthesis Example of 2-69

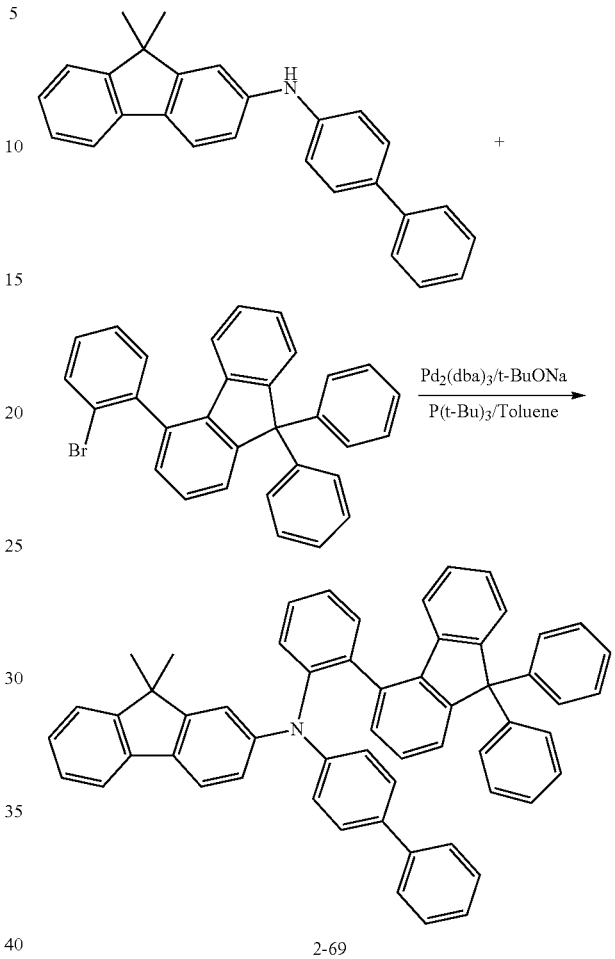

2-69

In a round bottom flask, N-([1,1'-biphenyl]-4-yl)-9,9-dimethyl-9H-fluoren-2-amine(7.2 g, 20 mmol), 4-(2-bromophenyl)-9,9-diphenyl-9H-fluorene (9.5 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene(300 mL) were carried out in the same manner as in 2-34 to give 2-69. (12.2 g, 81%).

Synthesis Example of 2-71

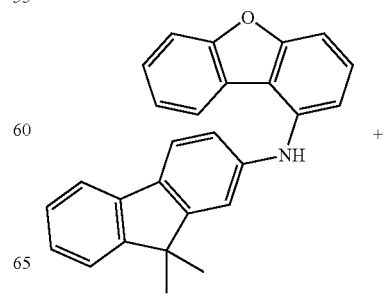

-continued

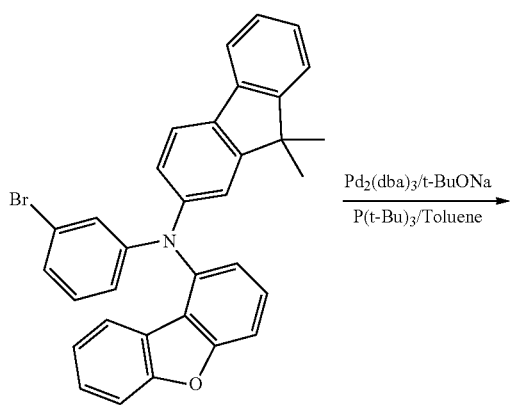

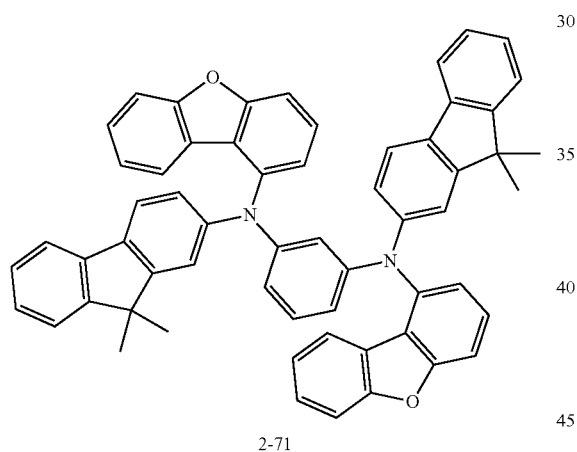

2-71

In a round bottom flask, N-(9,9-dimethyl-9H-fluoren-2-yl)dibenzo[b,d]furan-1-amine(7.5 g, 20 mmol), N-(3-bromophenyl)-N-(9,9-dimethyl-9H-fluoren-2-yl)dibenzo[b,d]furan-1-amine(10.6 g, 20 mmol), $Pd_2(dba)_3$ (0.5 g, 0.6 mmol), $P(t-Bu)_3$ (0.2 g, 2 mmol), t-BuONa (5.8 g, 60 mmol) and toluene(300 mL) were carried out in the same manner as in 2-34 to give 2-71. (12.9 g, 78%).

Synthesis Example 4

Final products represented by Formula (30) according to the present invention can be prepared by reacting Sub 30 and Sub 31 as shown in Reaction Scheme 5 below, but are not limited thereto.

<Reaction Scheme 5>

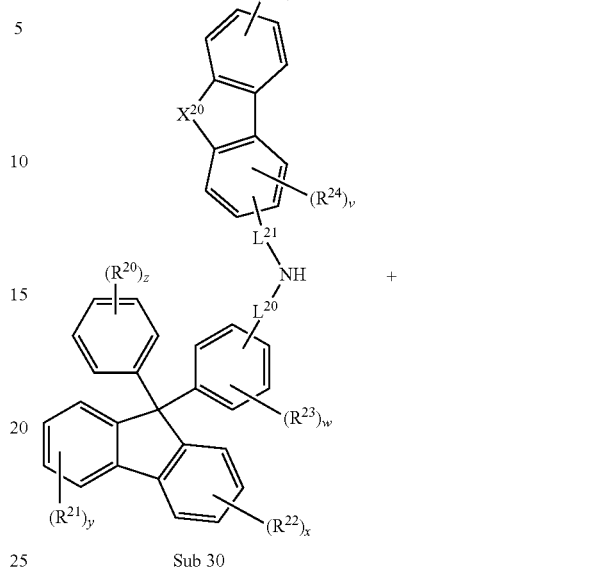

Sub 30

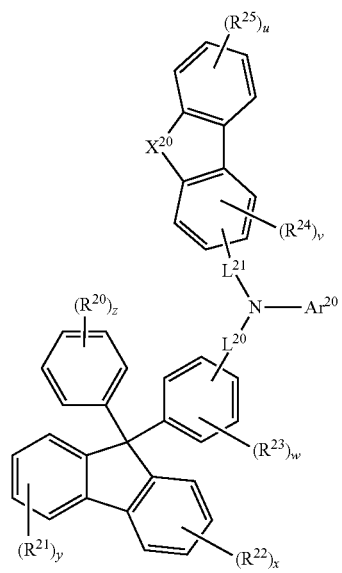

Final products 4

Synthesis Example of Sub 30

<Reaction Scheme 6>

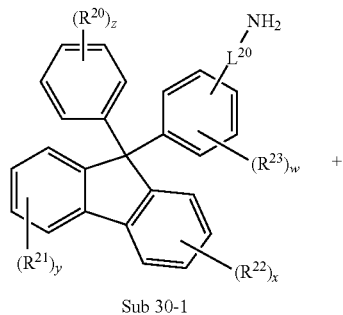

Sub 30-1

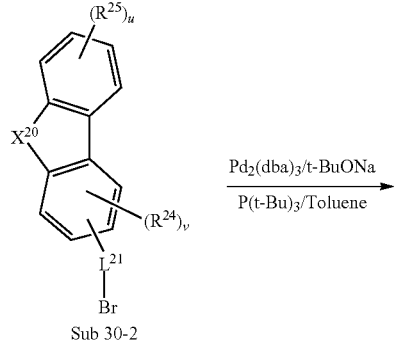

Sub 30-2

Synthesis Example of Sub 30(81)

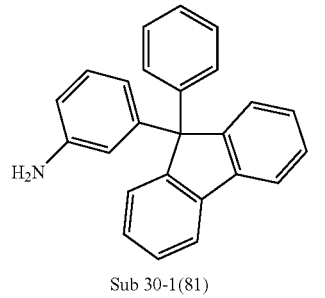

Sub 30-1(81)

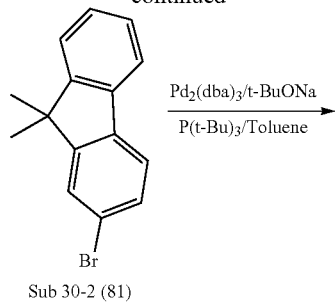

Sub 30-2 (81)

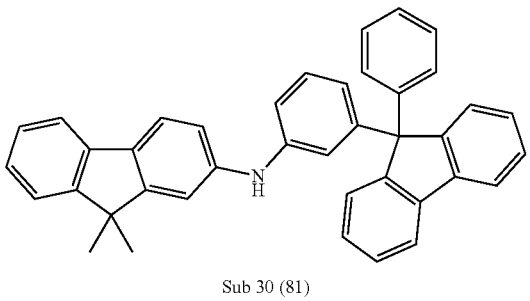

Sub 30 (81)

In a round bottom flask, 3-(9-phenyl-9H-fluoren-9-yl) aniline (6.7 g, 20 mmol), 2-bromo-9,9-dimethyl-9H-fluorene (5.5 g, 20 mmol), Pd$_2$(dba): (0.5 g, 0.6 mmol), P(t-Bu)$_3$ (0.2 g, 2 mmol), t-BuONa (5.8 g, 60 mmol) and toluene(300 mL) were carried out in the same manner as in 2-34 to give Sub 30(81). (8.83 g, 84%).

Examples of Sub 31

Examples of Sub 31 are as follows, but are not limited thereto.

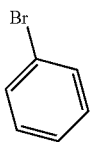

Sub 31-1

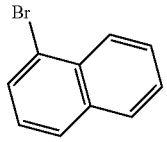

Sub 31-2

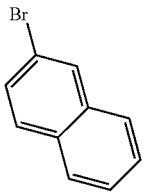

Sub 31-3

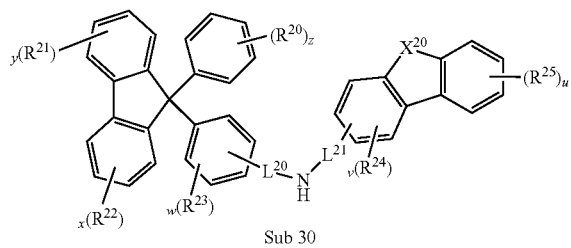

Sub 30

Sub 31-4
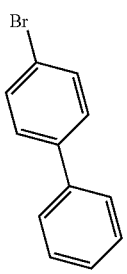
Sub 31-5
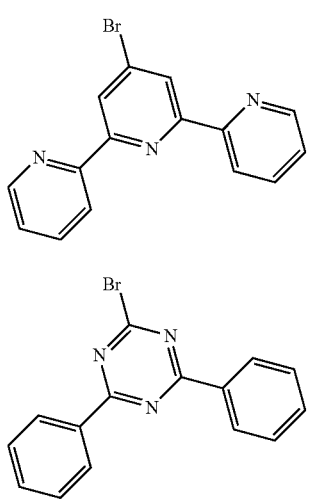
Sub 31-6
Sub 31-7
Sub 31-8
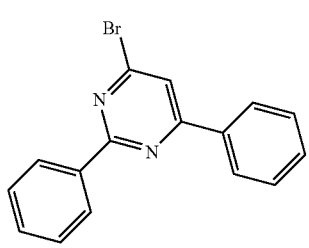
Sub 31-9
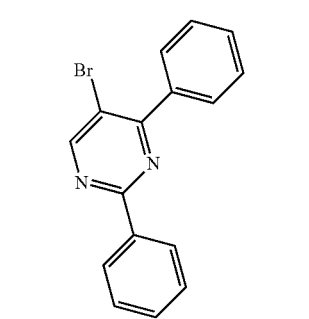
Sub 31-10
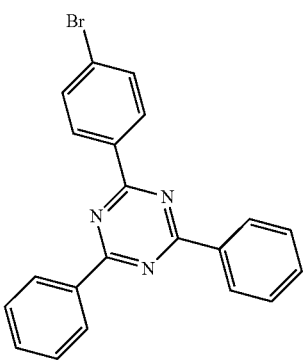
Sub 31-11
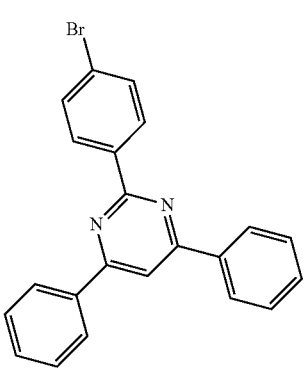
Sub 31-12
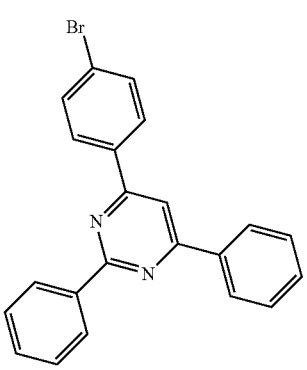
Sub 31-13
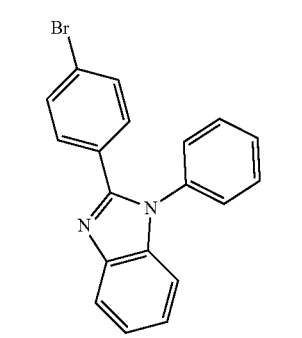

-continued

Sub 31-14

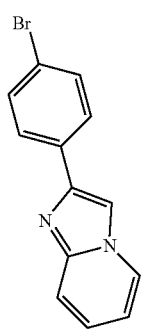

Sub 31-15

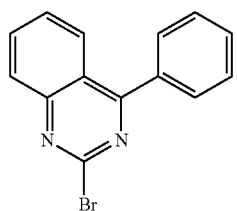

Sub 31-16

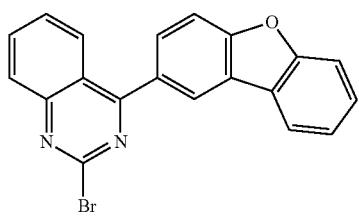

Sub 31-17

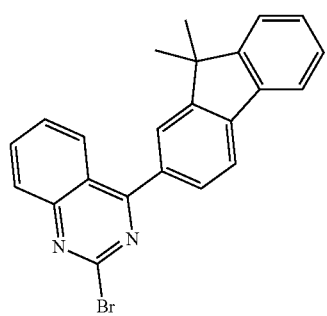

-continued

Sub 31-18

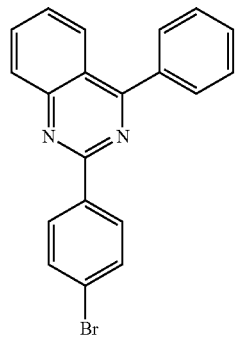

Sub 31-19

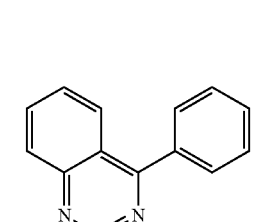

TABLE 5

| compound | FD-MS | compound | FD-MS |
|---|---|---|---|
| Sub 31-1 | m/z = 155.96($C_6H_5Br$ = 157.01) | Sub 31-2 | m/z = 205.97($C_{10}H_7Br$ = 207.07) |
| Sub 31-3 | m/z = 205.97($C_{10}H_7Br$ = 207.07) | Sub 31-4 | m/z = 231.99($C_{12}H_9Br$ = 233.10) |
| Sub 31-5 | m/z = 309.02($C_{17}H_{12}BrN$ = 310.19) | Sub 31-6 | m/z = 311.01($C_{15}H_{10}BrN_3$ = 312.16) |
| Sub 31-7 | m/z = 310.01($C_{16}H_{11}BrN_2$ = 311.18) | Sub 31-8 | m/z = 310.01($C_{16}H_{11}BrN_2$ = 311.18) |
| Sub 31-9 | m/z = 310.01($C_{16}H_{11}BrN_2$ = 311.18) | Sub 31-10 | m/z = 387.04($C_{21}H_{14}BrN_3$ = 388.26) |
| Sub 31-11 | m/z = 386.04($C_{22}H_{15}BrN_2$ = 387.27) | Sub 31-12 | m/z = 386.04($C_{22}H_{15}BrN_2$ = 387.27) |
| Sub 31-13 | m/z = 348.03($C_{19}H_{13}BrN_2$ = 349.22) | Sub 31-14 | m/z = 271.99($C_{13}H_9BrN_2$ = 273.13) |
| Sub 31-15 | m/z = 283.99($C_{14}H_9BrN_2$ = 285.14) | Sub 31-16 | m/z = 374.01($C_{20}H_{11}BrN_2O$ = 375.22) |
| Sub 31-17 | m/z = 400.06($C_{23}H_{17}BrN_2$ = 401.30) | Sub 31-18 | m/z = 360.03($C_{20}H_{13}BrN_2$ = 361.23) |
| Sub 31-19 | m/z = 476.09($C_{29}H_{21}BrN_2$ = 477.39) | | |

Synthesis Example of 2-72

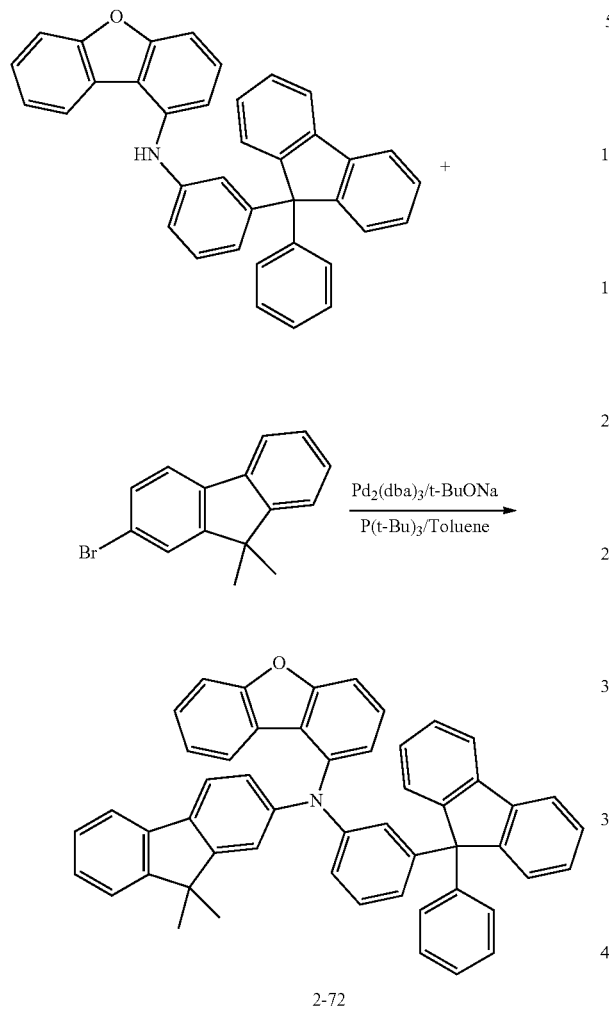

2-72

In a round bottom flask, N-(3-(9-phenyl-9H-fluoren-9-yl)phenyl)dibenzo[b,d]furan-1-amine (10.0 g, 20 mmol), 2-bromo-9,9-dimethyl-9H-fluorene (5.5 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were carried out in the same manner as in 2-34 to give 2-72. (11.1 g, 80%).

Synthesis Example of 2-81

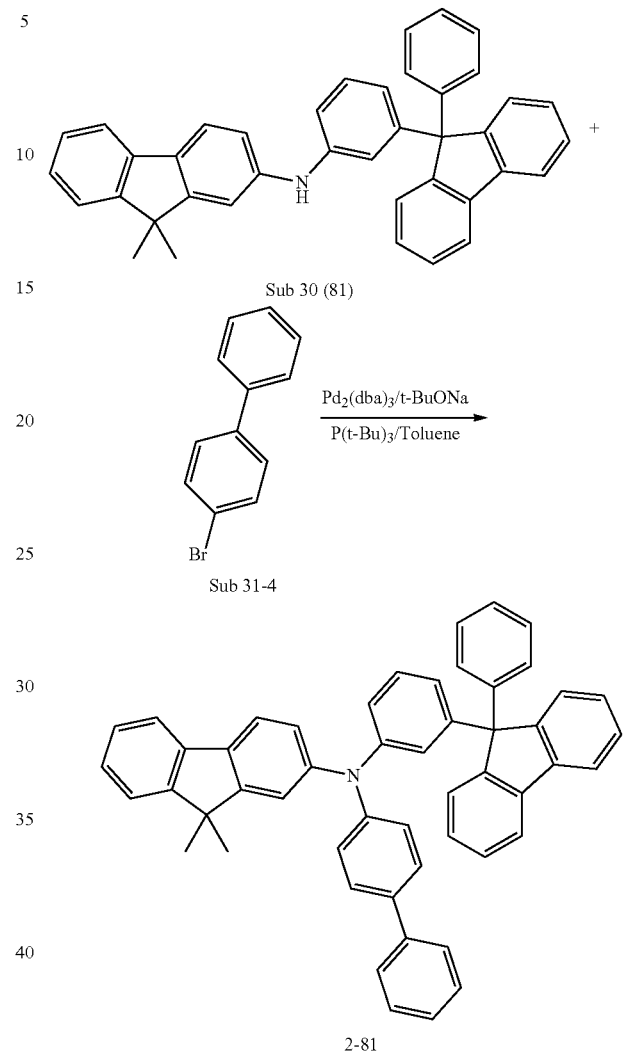

2-81

In a round bottom flask, Sub 30(81) (10.3 g, 20 mmol), Sub 31-4 (4.66 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene(300 mL) were carried out in the same manner as in 2-34 to give 2-81. (10.3 g, 76%).

TABLE 6

| Compound | FD-MS | compound | FD-MS |
|---|---|---|---|
| 2-81 | m/z = 677.31($C_{52}H_{39}N$ = 677.89) | 2-82 | m/z = 651.26($C_{49}H_{33}NO$ = 651.81) |
| 2-83 | m/z = 641.22($C_{47}H_{31}NS$ = 641.83) | 2-84 | m/z = 700.29($C_{53}H_{36}N_2$ = 700.89) |
| 2-85 | m/z = 677.31($C_{52}H_{39}N$ = 677.89) | 2-86 | m/z = 651.26($C_{49}H_{33}NO$ = 651.81) |
| 2-87 | m/z = 843.30($C_{63}H_{41}NS$ = 844.09) | 2-88 | m/z = 701.28($C_{52}H_{35}N_3$ = 701.87) |
| 2-89 | m/z = 677.31($C_{52}H_{39}N$ = 677.89) | 2-90 | m/z = 729.28($C_{53}H_{35}N_3O$ = 729.88) |
| 2-91 | m/z = 912.29($C_{64}H_{40}N_4OS$ = 913.11) | 2-92 | m/z = 878.34($C_{65}H_{42}N_4$ = 879.08) |
| 2-93 | m/z = 805.35($C_{60}H_{43}N_3$ = 806.03) | 2-94 | m/z = 906.34($C_{66}H_{42}N_4O$ = 907.09) |
| 2-95 | m/z = 769.26($C_{55}H_{35}N_3S$ = 769.97) | 2-96 | m/z = 884.30($C_{63}H_{40}N_4S$ = 885.10) |
| 2-97 | m/z = 767.36($C_{59}H_{45}N$ = 768.02) | 2-98 | m/z = 815.32($C_{62}H_{41}NO$ = 816.02) |
| 2-99 | m/z = 829.28($C_{62}H_{39}NS$ = 830.06) | 2-100 | m/z = 781.35($C_{59}H_{35}D_5N_2$ = 782.01) |
| 2-101 | m/z = 695.30($C_{52}H_{38}FN$ = 695.88) | 2-102 | m/z = 753.34($C_{58}H_{43}N$ = 753.99) |
| 2-103 | m/z = 803.36($C_{62}H_{45}N$ = 804.05) | 2-104 | m/z = 6829.37($C_{64}H_{47}N$ = 830.09) |
| 2-105 | m/z = 918.40($C_{70}H_{50}N_2$ = 919.18) | 2-106 | m/z = 601.28($C_{46}H_{35}N$ = 601.79) |
| 2-107 | m/z = 677.31($C_{52}H_{39}N$ = 677.89) | 2-108 | m/z = 753.34($C_{58}H_{43}N$ = 753.99) |
| 2-109 | m/z = 701.31($C_{54}H_{39}N$ = 701.91) | 2-110 | m/z = 677.31($C_{52}H_{39}N$ = 677.89) |

TABLE 6-continued

| Compound | FD-MS | compound | FD-MS |
|---|---|---|---|
| 2-111 | m/z = 677.31($C_{52}H_{39}N$ = 677.89) | 2-112 | m/z = 682.34($C_{52}H_{34}D_5N$ = 682.92) |
| 2-113 | m/z = 701.31($C_{54}H_{39}N$ = 701.91) | 2-114 | m/z = 619.27($C_{46}H_{34}FN$ = 619.78) |
| 2-115 | m/z = 753.34($C_{58}H_{43}N$ = 753.99) | 2-116 | m/z = 803.36($C_{62}H_{45}N$ = 804.05) |
| 2-117 | m/z = 701.31($C_{54}H_{39}N$ = 701.91) | 2-118 | m/z = 651.29($C_{50}H_{37}N$ = 651.85) |
| 2-119 | m/z = 727.32($C_{56}H_{41}N$ = 727.95) | 2-120 | m/z = 758.37($C_{58}H_{38}D_5N$ = 759.02) |
| 2-121 | m/z = 757.37($C_{58}H_{47}N$ = 758.02) | 2-122 | m/z = 753.34($C_{58}H_{43}N$ = 753.99) |
| 2-123 | m/z = 803.36($C_{62}H_{45}N$ = 804.05) | 2-124 | m/z = 834.40($C_{64}H_{42}D_5N$ = 835.12) |
| 2-125 | m/z = 883.33($C_{66}H_{45}NS$ = 884.15) | 2-126 | m/z = 651.26($C_{49}H_{33}NO$ = 651.81) |
| 2-127 | m/z = 641.22($C_{47}H_{31}NS$ = 641.83) | 2-128 | m/z = 700.29($C_{53}H_{36}N_2$ = 700.89) |
| 2-129 | m/z = 677.31($C_{52}H_{39}N$ = 677.89) | 2-130 | m/z = 651.26($C_{49}H_{33}NO$ = 651.81) |
| 2-131 | m/z = 843.30($C_{63}H_{41}NS$ = 844.09) | 2-132 | m/z = 701.28($C_{52}H_{35}N_3$ = 701.87) |
| 2-133 | m/z = 677.31($C_{52}H_{39}N$ = 677.89) | 2-134 | m/z = 729.28($C_{53}H_{35}N_3O$ = 729.88) |
| 2-135 | m/z = 912.29($C_{64}H_{40}N_4OS$ = 913.11) | 2-136 | m/z = 878.34($C_{65}H_{42}N_4$ = 879.08) |
| 2-137 | m/z = 805.35($C_{60}H_{43}N_3$ = 806.03) | 2-138 | m/z = 906.34($C_{66}H_{42}N_4O$ = 907.09) |
| 2-139 | m/z = 769.26($C_{55}H_{35}N_3S$ = 769.97) | 2-140 | m/z = 884.30($C_{63}H_{40}N_4S$ = 885.10) |
| 2-141 | m/z = 767.36($C_{59}H_{45}N$ = 768.02) | 2-142 | m/z = 815.32($C_{62}H_{41}NO$ = 816.02) |
| 2-143 | m/z = 829.28($C_{62}H_{39}NS$ = 830.06) | 2-144 | m/z = 781.35($C_{59}H_{35}D_5N_2$ = 782.01) |
| 2-145 | m/z = 695.30($C_{52}H_{38}FN$ = 695.88) | 2-146 | m/z = 753.34($C_{58}H_{43}N$ = 753.99) |
| 2-147 | m/z = 803.36($C_{62}H_{45}N$ = 804.05) | 2-148 | m/z = 6829.37($C_{64}H_{47}N$ = 830.09) |
| 2-149 | m/z = 918.40($C_{70}H_{50}N_2$ = 919.18) | 2-150 | m/z = 717.34($C_{55}H_{43}N$ = 717.96) |
| 2-151 | m/z = 717.34($C_{55}H_{43}N$ = 717.96) | 2-152 | m/z = 717.34($C_{55}H_{43}N$ = 717.96) |
| 2-153 | m/z = 717.34($C_{55}H_{43}N$ = 717.96) | | |

Evaluation of Manufacture of Organic Electronic Element

Example 1) Manufacture and Evaluation of Green Organic Light Emitting Diode (Host)

First, on an ITO layer(anode) formed on a glass substrate, $N^1$-(naphthalen-2-yl)-$N^4$, $N^4$-bis(4-(naphthalen-2-yl(phenyl)amino)phenyl)-$N^1$-phenyl benzene-1,4-diamine(hereinafter will be abbreviated as 2-TNATA) was vacuum-deposited to form a hole injection layer with a thickness of 60 nm, and on the layer, 4,4-bis [N-(1-naphthyl)-N-phenylamino] biphenyl(hereinafter will be abbreviated as NPD) was vacuum-deposited as hole transport compounds to form a hole transport layer with a thickness of 60 nm. Subsequently, the inventive compound represented by Formula (1) was used as a host, and an emitting layer with a thickness of 30 nm was deposited as a dopant on the hole transport layer by doping Ir(ppy)$_3$[tris(2-phenylpyridine)-iridium] with a weight of 95:5. (1, 1'-bisphenyl)-4-olato)bis(2-methyl-8-quinolinolato)aluminum (hereinafter abbreviated as BAlq) was vacuum deposited as a hole blocking layer to a thickness of 10 nm, and Tris(8-quinolinol) aluminum (hereinafter abbreviated as Alq3) was deposited as an electron transport layer to a thickness of 40 nm. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 5000 cd/m². In the following table, the manufacture of a device and the results of evaluation are shown.

Comparative Examples 1~4

An OLED was prepared in the same manner as in Example 1, except that Comparative Compound A, Comparative Compound B, Comparative Compound C and Comparative Compound D were used as a host.

Comparative Compounds:

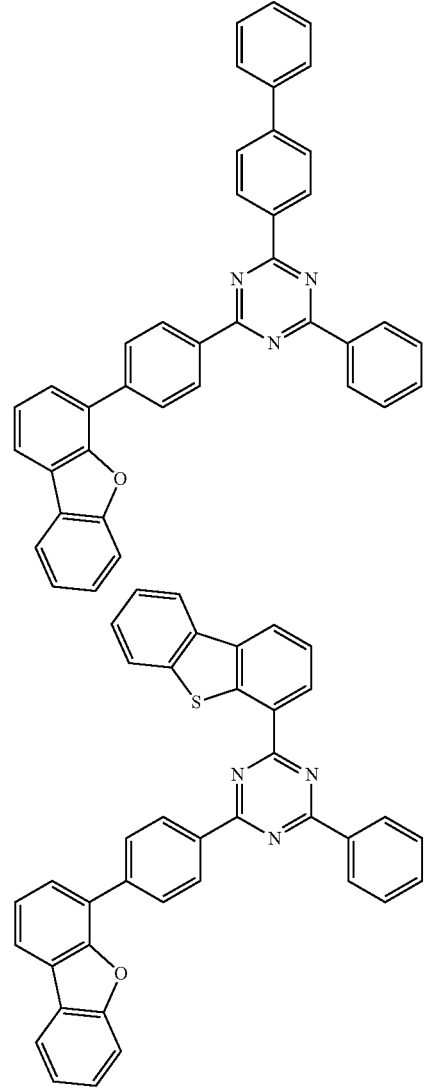

A

B

-continued

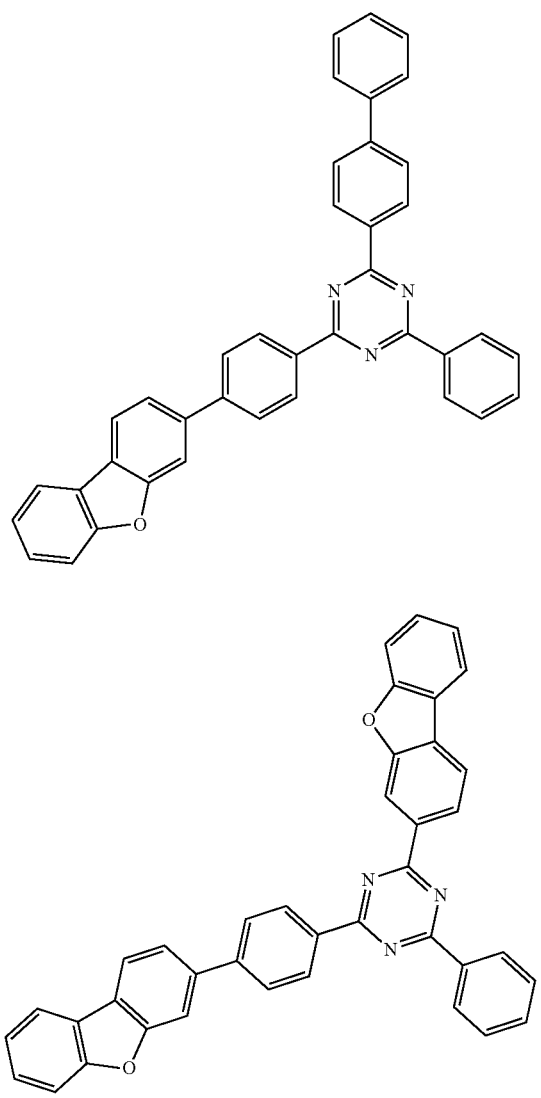

C

D

Example 2) Manufacture and Evaluation of Green Organic Light Emitting Diode (Mixed Host)

First, on an ITO layer(anode) formed on a glass substrate, $N^1$-(naphthalen-2-yl)-$N^4$, $N^4$-bis(4-(naphthalen-2-yl(phenyl)amino)phenyl)-$N^1$-phenyl benzene-1,4-diamine(hereinafter will be abbreviated as 2-TNATA) was vacuum-deposited to form a hole injection layer with a thickness of 60 nm, and on the layer, 4,4-bis [N-(1-naphthyl)-N-phenylamino] biphenyl(hereinafter will be abbreviated as NPD) was vacuum-deposited as hole transport compounds to form a hole transport layer with a thickness of 60 nm. Subsequently, a mixture of the inventive compound represented by Formula (1) and the compound represented by Formula (12) in a ratio of 6:4 was used as a host, and as a dopant, an emitting layer with a thickness of 30 nm was deposited on the hole transport layer by doping Ir(ppy)$_3$[tris(2-phenylpyridine)-iridium] with a weight of 95:5. (1, 1'-bisphenyl)-4-olato)bis (2-methyl-8-quinolinolato)aluminum (hereinafter abbreviated as BAlq) was vacuum deposited as a hole blocking layer to a thickness of 10 nm, and Tris(8-quinolinol) aluminum (hereinafter abbreviated as Alq3) was deposited as an electron transport layer to a thickness of 40 nm. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 5000 cd/m$^2$. In the following table, the manufacture of a device and the results of evaluation are shown.

Comparative Examples 5~8, 10~13

An OLED was prepared in the same manner as in Example 2, except that Comparative Compound A, Comparative Compound B, Comparative Compound C, and Comparative Compound D were used as a host instead of the inventive compound represented by Formula (1).

TABLE 7

| | compound | Voltage | Current Density (mA/cm$^2$) | Brightness (cd/m$^2$) | Efficiency (cd/A) | T(95) | CIE x | y |
|---|---|---|---|---|---|---|---|---|
| comparative example(1) | comparative compound A | 5.9 | 24.9 | 5000.0 | 20.1 | 66.1 | 0.33 | 0.61 |
| comparative example(2) | comparative compound B | 5.6 | 19.4 | 5000.0 | 25.8 | 71.3 | 0.32 | 0.63 |
| comparative example(3) | comparative compound C | 5.7 | 23.1 | 5000.0 | 21.6 | 75.7 | 0.31 | 0.64 |
| comparative example(4) | comparative compound D | 5.5 | 16.8 | 5000.0 | 29.7 | 80.1 | 0.30 | 0.61 |
| example(1) | P-8 | 5.3 | 13.8 | 5000.0 | 36.1 | 91.5 | 0.34 | 0.62 |
| example(2) | P-29 | 5.0 | 13.5 | 5000.0 | 37.1 | 98.5 | 0.34 | 0.61 |
| example(3) | P-32 | 5.4 | 13.8 | 5000.0 | 36.3 | 87.6 | 0.30 | 0.64 |
| example(4) | P-61 | 5.1 | 12.7 | 5000.0 | 39.4 | 94.6 | 0.31 | 0.61 |
| example(5) | P-91 | 5.0 | 12.6 | 5000.0 | 39.6 | 93.3 | 0.33 | 0.63 |
| example(6) | P-146 | 5.1 | 12.5 | 5000.0 | 39.9 | 94.3 | 0.35 | 0.60 |
| example(7) | P-154 | 5.1 | 12.6 | 5000.0 | 39.6 | 94.2 | 0.33 | 0.64 |
| example(8) | P-156 | 5.2 | 13.6 | 5000.0 | 36.7 | 93.0 | 0.31 | 0.60 |

Comparative Example 9 and 14

An OLED was prepared in the same manner as in Example 2, except for using the comparative compound E instead of the inventive compound represented by Formula (12) as a host, Comparative Compound E

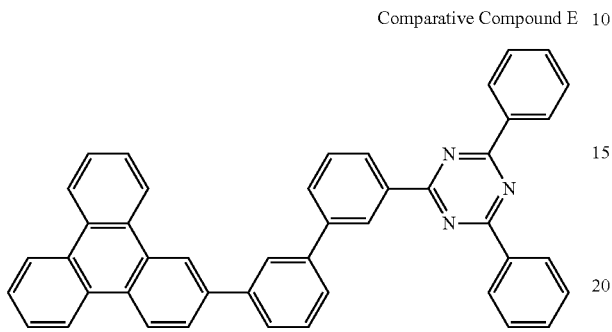

Comparative Compound E ited to form a hole injection layer with a thickness of 60 nm. Subsequently, on the layer, 4,4-bis[N-(1-naphthyl)-N-phenylamino]biphenyl(hereinafter will be abbreviated as NPD) was vacuum-deposited as an hole transport compound to a thickness of 60 nm to form a hole transport layer. Subsequently, the inventive compound represented by Formula (18) was vacuum-deposited as an emitting auxiliary layer material to a thickness of 20 nm to form an emitting auxiliary layer. After forming the emitting auxiliary layer, a mixture of the inventive compound represented by Formula (1) and the compound represented by Formula (12) in a ratio of 6:4 was used on the emitting auxiliary layer, and as a dopant, an emitting layer with a thickness of 30 nm was deposited by doping Ir(ppy)$_3$[tris(2-phenylpyridine)-iridium] with a weight of 95:5. (1,1'-bisphenyl)-4-olato)bis (2-methyl-8-quinolinolato)aluminum (hereinafter abbreviated as BAlq) was vacuum deposited as a hole blocking layer to a thickness of 10 nm, and Tris(8-quinolinol) aluminum (hereinafter abbreviated as Alq3) was deposited as an electron transport layer to a thickness of 40 nm. After that, an alkali metal halide, LiF was vacuum deposited as an electron injection layer to a thickness of 0.2 nm, and Al was deposited to a thickness of 150 nm to form a cathode to manufacture an OLED.

TABLE 8

| | First host | Second host | Voltage | Current Density | Brightness (cd/m$^2$) | Efficiency | Lifetime T(95) |
|---|---|---|---|---|---|---|---|
| comparative example(5) | comparative compound A | 4-27 | 5.3 | 21.4 | 5000.0 | 23.4 | 120.4 |
| comparative example(6) | comparative compound B | | 5.2 | 17.3 | 5000.0 | 28.9 | 124.8 |
| comparative example(7) | comparative compound C | | 5.1 | 19.9 | 5000.0 | 25.1 | 129.6 |
| comparative example(8) | comparative compound D | | 5.0 | 15.0 | 5000.0 | 33.3 | 133.2 |
| comparative example(9) | comparative compound E | | 5.0 | 12.9 | 5000.0 | 38.8 | 110.1 |
| comparative example(10) | comparative compound A | 4-31 | 5.2 | 22.0 | 5000.0 | 22.7 | 109.8 |
| comparative example(11) | comparative compound B | | 5.0 | 17.7 | 5000.0 | 28.2 | 115.4 |
| comparative example(12) | comparative compound C | | 4.8 | 20.2 | 5000.0 | 24.8 | 119.1 |
| comparative example(13) | comparative compound D | | 4.7 | 16.2 | 5000.0 | 30.9 | 123.3 |
| comparative example(14) | comparative compound E | | 5.3 | 13.2 | 5000.0 | 37.9 | 101.7 |
| example(9) | P-8 | 4-27 | 4.7 | 12.2 | 5000.0 | 41.0 | 133.7 |
| example(10) | P-29 | | 4.4 | 11.1 | 5000.0 | 45.2 | 142.8 |
| example(11) | P-32 | | 4.8 | 12.3 | 5000.0 | 40.6 | 130.1 |
| example(12) | P-61 | | 4.5 | 11.8 | 5000.0 | 42.5 | 135.7 |
| example(13) | P-91 | | 4.5 | 11.7 | 5000.0 | 42.8 | 135.3 |
| example(14) | P-146 | | 4.5 | 11.9 | 5000.0 | 42.0 | 135.9 |
| example(15) | P-154 | | 4.5 | 11.9 | 5000.0 | 42.1 | 135.3 |
| example(16) | P-156 | | 4.7 | 12.2 | 5000.0 | 40.9 | 131.4 |
| example(17) | P-8 | 4-31 | 4.2 | 12.2 | 5000.0 | 40.9 | 130.9 |
| example(18) | P-29 | | 4.1 | 11.1 | 5000.0 | 45.0 | 140.4 |
| example(19) | P-32 | | 4.6 | 12.4 | 5000.0 | 40.4 | 128.2 |
| example(20) | P-61 | | 4.3 | 11.8 | 5000.0 | 42.5 | 133.5 |
| example(21) | P-91 | | 4.4 | 11.8 | 5000.0 | 42.4 | 130.1 |
| example(22) | P-146 | | 4.2 | 11.8 | 5000.0 | 42.3 | 132.4 |
| example(23) | P-154 | | 4.4 | 11.9 | 5000.0 | 42.2 | 133.9 |
| example(24) | P-156 | | 4.6 | 12.3 | 5000.0 | 40.6 | 129.7 |

Example 3) Manufacture and Evaluation of Green Organic Light Emitting Diode (Emitting Auxiliary Layer+Mixed Host)

First, on an ITO layer(anode) formed on a glass substrate, N$^1$-(naphthalen-2-yl)-N$^4$, N$^4$-bis(4-(naphthalen-2-yl(phenyl)amino)phenyl)-N$^1$-phenylbenzene-1,4-diamine(hereinafter will be abbreviated as 2-TNATA) was vacuum-depos- To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 5000 cd/m$^2$. In the following table, the manufacture of a device and the results of evaluation are shown.

Comparative Examples 15~29

An OLED was prepared in the same manner as in Example 3, except that the comparative compound A to E are each used instead of the inventive compound represented by Formula (1) as a host,

TABLE 9

| | Emitting auxiliary layer | First host | Second host | Voltage | Current Density | Brightness (cd/m$^2$) | Efficiency | Lifetime T(95) |
|---|---|---|---|---|---|---|---|---|
| comparative example(15) | 2-69 | comparative compound A | 4-27 | 5.2 | 16.6 | 5000.0 | 30.1 | 125.1 |
| comparative example(16) | | comparative compound B | | 5.2 | 13.8 | 5000.0 | 36.2 | 130.1 |
| comparative example(17) | | comparative compound C | | 5.0 | 16.2 | 5000.0 | 30.8 | 135.3 |
| comparative example(18) | | comparative compound D | | 5.0 | 12.6 | 5000.0 | 39.7 | 138.4 |
| comparative example(19) | | comparative compound E | | 5.4 | 11.0 | 5000.0 | 45.4 | 115.6 |
| example(25) | | P-8 | | 4.6 | 9.8 | 5000.0 | 51.1 | 140.4 |
| example(26) | | P-29 | | 4.3 | 9.0 | 5000.0 | 55.7 | 150.9 |
| example(27) | | P-61 | | 4.4 | 9.6 | 5000.0 | 52.2 | 144.5 |
| example(28) | | P-146 | | 4.4 | 9.7 | 5000.0 | 51.6 | 143.8 |
| comparative example(20) | 2-72 | comparative compound A | | 5.1 | 14.1 | 5000.0 | 35.4 | 130.4 |
| comparative example(21) | | comparative compound B | | 5.0 | 12.1 | 5000.0 | 41.3 | 135.9 |
| comparative example(22) | | comparative compound C | | 4.9 | 13.9 | 5000.0 | 35.9 | 140.7 |
| comparative example(23) | | comparative compound D | | 5.0 | 11.4 | 5000.0 | 43.7 | 143.1 |
| comparative example(24) | | comparative compound E | | 5.3 | 10.6 | 5000.0 | 47.1 | 120.3 |
| example(29) | | P-8 | | 4.4 | 8.3 | 5000.0 | 59.9 | 145.9 |
| example(30) | | P-29 | | 4.0 | 7.7 | 5000.0 | 65.1 | 157.4 |
| example(31) | | P-61 | | 4.2 | 8.2 | 5000.0 | 60.7 | 150.1 |
| example(32) | | P-146 | | 4.3 | 8.2 | 5000.0 | 61.1 | 149.4 |
| comparative example(25) | 2-74 | comparative compound A | | 5.0 | 13.9 | 5000.0 | 36.1 | 130.8 |
| comparative example(26) | | comparative compound B | | 5.1 | 12.0 | 5000.0 | 41.7 | 136.1 |
| comparative example(27) | | comparative compound C | | 4.8 | 14.2 | 5000.0 | 35.3 | 141.2 |
| comparative example(28) | | comparative compound D | | 4.9 | 11.5 | 5000.0 | 43.4 | 143.7 |
| comparative example(29) | | comparative compound E | | 5.1 | 9.8 | 5000.0 | 50.8 | 120.9 |
| example(33) | | P-8 | | 4.3 | 8.5 | 5000.0 | 59.1 | 146.2 |
| example(34) | | P-29 | | 3.9 | 7.7 | 5000.0 | 64.8 | 157.8 |
| example(35) | | P-61 | | 4.0 | 8.3 | 5000.0 | 60.3 | 150.6 |
| example(36) | | P-146 | | 4.1 | 8.2 | 5000.0 | 60.9 | 150.4 |
| comparative example(30) | 2-82 | comparative compound A | | 4.9 | 10.4 | 5000.0 | 48.2 | 141.8 |
| comparative example(31) | | comparative compound B | | 4.9 | 10.2 | 5000.0 | 48.8 | 142.4 |
| comparative example(32) | | comparative compound C | | 4.8 | 10.3 | 5000.0 | 48.5 | 143.7 |
| comparative example(33) | | comparative compound D | | 4.9 | 10.0 | 5000.0 | 50.1 | 145.3 |
| comparative example(34) | | comparative compound E | | 4.9 | 9.9 | 5000.0 | 50.5 | 140.9 |
| example(37) | | P-8 | | 3.7 | 8.0 | 5000.0 | 62.5 | 160.8 |
| example(38) | | P-29 | | 3.7 | 7.6 | 5000.0 | 65.4 | 163.8 |
| example(39) | | P-61 | | 3.6 | 7.7 | 5000.0 | 64.8 | 163.2 |
| example(40) | | P-146 | | 3.6 | 8.0 | 5000.0 | 62.8 | 161.5 |

Example 4) Manufacture and Evaluation of Green Organic Light Emitting Diode (Hole Transport Layer+Emitting Auxiliary Layer+Mixed Host)

First, on an ITO layer(anode) formed on a glass substrate, $N^1$-(naphthalen-2-yl)-$N^4$, $N^4$-bis(4-(naphthalen-2-yl(phenyl)amino)phenyl)-$N^1$-phenylbenzene-1,4-diamine(hereinafter will be abbreviated as 2-TNATA) was vacuum-deposited to form a hole injection layer with a thickness of 60 nm. Subsequently, on the layer, the compound represented by Formula(18) was vacuum-deposited to a thickness of 60 nm to form a hole transport layer. Subsequently, the compound represented by Formula(18) was vacuum-deposited as an emitting auxiliary material to a thickness of 20 nm to form an emitting auxiliary layer. After forming the emitting auxiliary layer, a mixture of the inventive compound represented by Formula (1) and the compound represented by Formula (12) in a ratio of 6:4 was used as a host, and as a dopant, an emitting layer with a thickness of 30 nm was deposited by doping Ir(ppy)$_3$[tris(2-phenylpyridine)-iridium] with a weight of 95:5. (1,1'-bisphenyl)-4-olato)bis (2-methyl-8-quinolinolato)aluminum (hereinafter abbreviated as BAlq) was vacuum deposited as a hole blocking layer to a thickness of 10 nm, and Tris(8-quinolinol) aluminum (hereinafter abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 5000 cd/m$^2$. In the following table, the manufacture of a device and the results of evaluation are shown.

a linker with 4-dibenzothiophen to the other side, exhibits an improved result which is significantly different from the comparative compounds A to D. It is suggested that the energy level (HOMO, LUMO, T1, etc.) of the compound may vary significantly depending on the kind of the substituent or the substitution position, and the differences in the physical properties of compounds may act as key factors(ex. energy balance) in improving device performance during device deposition, resulting in different device results.

Table 8 shows that when the compound represented by Formula (12) and the compound of Formula (1) are mixed, they are significantly better than other comparison combinations. This result is also supported the explanations in the case of a single host, and when bonded to Formula (12), the driving and efficiency can be improved by about 24% and the lifetime can be improved by about 63% compared with a single host. When two hosts are premixed, the aging rate is very important to deposit at a certain rate, and the compound of the present invention was superior in the aging rate compared with other materials, and particularly, the

TABLE 10

|  | Hole transport layer | Emitting auxiliary layer | First host | Second host | Voltage | Current Density | Brightness (cd/m$^2$) | Efficiency | Lifetime T(95) |
|---|---|---|---|---|---|---|---|---|---|
| example(37) | 13-32 | 2-72 | P-8 | 4-27 | 4.2 | 7.8 | 5000.0 | 64.2 | 149.1 |
| example(38) |  |  | P-29 |  | 3.9 | 7.1 | 5000.0 | 70.1 | 160.6 |
| example(39) |  |  | P-61 |  | 4.1 | 7.6 | 5000.0 | 65.9 | 155.8 |
| example(40) |  |  | P-146 |  | 4.2 | 7.6 | 5000.0 | 66.2 | 154.3 |
| example(41) |  | 2-74 | P-8 |  | 4.0 | 7.8 | 5000.0 | 63.8 | 151.4 |
| example(42) |  |  | P-29 |  | 3.8 | 7.2 | 5000.0 | 69.7 | 162.1 |
| example(43) |  |  | P-61 |  | 3.9 | 7.6 | 5000.0 | 65.4 | 155.8 |
| example(44) |  |  | P-146 |  | 3.8 | 7.6 | 5000.0 | 66.0 | 155.7 |
| example(45) |  | 2-72 | P-8 |  | 4.2 | 7.8 | 5000.0 | 64.2 | 149.1 |
| example(46) |  |  | P-29 |  | 3.9 | 7.1 | 5000.0 | 70.1 | 160.6 |
| example(47) |  |  | P-61 |  | 4.1 | 7.6 | 5000.0 | 65.9 | 155.8 |
| example(48) |  |  | P-146 |  | 4.2 | 7.6 | 5000.0 | 66.2 | 154.3 |
| example(49) |  | 2-74 | P-8 |  | 4.0 | 7.8 | 5000.0 | 63.8 | 151.4 |
| example(50) |  |  | P-29 |  | 3.8 | 7.2 | 5000.0 | 69.7 | 162.1 |
| example(51) |  |  | P-61 |  | 3.9 | 7.6 | 5000.0 | 65.4 | 155.8 |
| example(52) |  |  | P-146 |  | 3.8 | 7.6 | 5000.0 | 66.0 | 155.7 |
| example(53) |  | 2-82 | P-8 |  | 3.4 | 7.3 | 5000.0 | 68.9 | 163.6 |
| example(54) |  |  | P-29 |  | 3.2 | 6.8 | 5000.0 | 73.4 | 168.7 |
| example(55) |  |  | P-61 |  | 3.3 | 7.1 | 5000.0 | 70.2 | 166.7 |
| example(56) |  |  | P-146 |  | 3.3 | 7.2 | 5000.0 | 69.3 | 165.4 |

As can be seen from the results of Table 7 to 10, the organic electronic element using the organic electronic device material of the present invention as a phosphorescent host can remarkably improve the high luminous efficiency, the low driving voltage and the lifetime.

Table 7 shows the superiority of the compounds of the invention compared to the comparative compounds when the inventive compound represented by Formula (1) was used as a single host. In the results of Comparative Compound A and Comparative Compound C, when the 3-dibenzofuran was substituted, the performance was improved in all aspects of driving voltage, efficiency and lifetime, compared with 4-dibenzofuran. In the results of Comparative Compound A and Comparative Compound B, or Comparative Compound C and Comparative Compound D, it can be confirmed that the performance of the triazine substituted with two dibenzothiophen or dibenzofuran moiety is improved compared with the triazine substituted with one dibenzothiophen or dibenzofuran moiety. Thus, it can be finally confirmed that the inventive compound, in which triazine is substituted with 3-dibenzofuran and is linked by compound that at least one of Ar$^1$, Ar$^3$ and R$^3$ is a C$_6$-C$_{24}$ aryl group has the best results in the aging test.

Table 9 is the examples using the mixed compound of Formula (1) and Formula (12) as the emitting layer host and using the compound represented by Formula (18) in the emitting auxiliary layer, and shows that the efficiency is improved by about 60% and the lifetime is improved by about 20% compared with Table 8.

Here, using the compound represented by Formula (18) as the hole transport compound also yielded slightly improved results in terms of driving voltage, efficiency, and lifetime in comparison with the results in Table 7.

That is, the compound of the present invention exhibits improved results compared with the known compounds even when used as a single host, but when used in combination with the compound represented by Formula (12), or when the compound represented by Formula (18) was used for the emitting auxiliary layer or the hole transport layer, remarkable results were obtained.

Example 5) Manufacture and Evaluation of Blue Organic Light Emitting Diode

First, on an ITO layer(anode) formed on a glass substrate, $N^1$-(naphthalen-2-yl)-$N^4$, $N^4$-bis(4-(naphthalen-2-yl(phenyl)amino)phenyl)-$N^1$-phenylbenzene-1,4-diamine(hereinafter will be abbreviated as 2-TNATA) was vacuum-deposited to form a hole injection layer with a thickness of 60 nm. Subsequently, and on the layer, 4,4-bis[N-(1-naphthyl)-N-phenylamino]biphenyl(hereinafter will be abbreviated as NPD) was vacuum-deposited to a thickness of 60 nm to form a hole transport layer. Subsequently, the inventive compound was vacuum-deposited as an emitting auxiliary layer material to a thickness of 20 nm to form an emitting auxiliary layer. After forming the emitting auxiliary layer, on the emitting auxiliary layer, 9,10-di(naphthalen-2-yl)anthracene is used as a host, and BD-052X(Idemitsu kosan) is used as dopant in a ratio of 96:4, therefore an emitting layer with a thickness of 30 nm was deposited on the emitting auxiliary layer. (1,1'-bisphenyl)-4-olato)bis(2-methyl-8-quinolinolato)aluminum (hereinafter abbreviated as BAlq) was vacuum deposited as a hole blocking layer to a thickness of 10 nm, and Tris(8-quinolinol) aluminum (hereinafter abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 5000 cd/m². In the following table, the manufacture of a device and the results of evaluation are shown.

Comparative Examples 35~37

An OLED was prepared in the same manner as in Comparative Example 5 except that the emitting auxiliary layer was not used and Comparative Compound F, Comparative Compound G and Invention Compound 2-81 were used as the hole transport layer material.

Comparative Example 38

An OLED was prepared in the same manner as in Comparative Example 5 except that the emitting auxiliary layer was not used.

Comparative Examples 39~40

An OLED was prepared in the same manner as in Comparative Example 5 except that the Comparative Compound F or Comparative Compound G were used as the emitting auxiliary layer material.

Comparative Compound F Comparative Compound G

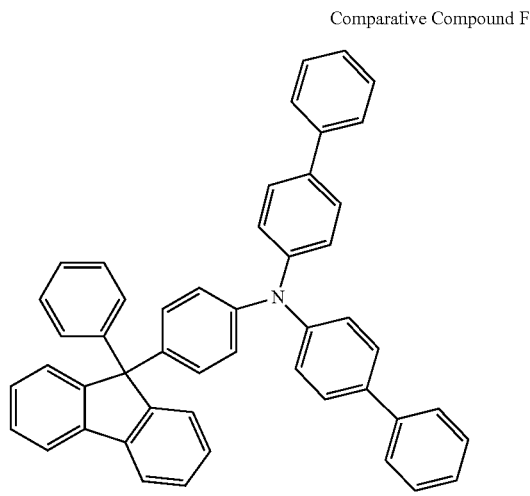

Comparative Compound F

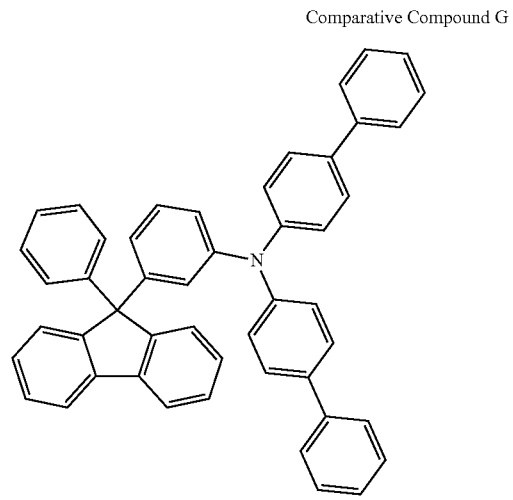

Comparative Compound G

TABLE 11

| | Hole transport compound | Emitting auxiliary layer compound | voltage | Current density (mA/cm²) | brightness (cd/m²) | Efficiency (cd/A) | T(95) |
|---|---|---|---|---|---|---|---|
| comparative example (35) | comparative compound F | — | 6.8 | 14.3 | 500.0 | 3.5 | 70.4 |
| comparative example (36) | comparative compound G | | 7.0 | 15.2 | 500.0 | 3.3 | 69.6 |
| comparative example (37) | 2-81 | | 6.9 | 13.5 | 500.0 | 3.7 | 71.2 |
| comparative example (38) | NPB | — | 7.3 | 17.9 | 500.0 | 2.8 | 65.3 |
| comparative example (39) | | comparative compound F | 6.8 | 11.1 | 500.0 | 4.5 | 80.4 |
| comparative example (40) | | comparative compound G | 6.5 | 10.2 | 500.0 | 4.9 | 81.7 |

TABLE 11-continued

|  | Hole transport compound | Emitting auxiliary layer compound | voltage | Current density (mA/cm$^2$) | brightness (cd/m$^2$) | Efficiency (cd/A) | T(95) |
|---|---|---|---|---|---|---|---|
| example(57) |  | 2-81 | 6.3 | 9.1 | 500.0 | 5.5 | 94.9 |
| example(58) |  | 2-83 | 6.2 | 8.6 | 500.0 | 5.8 | 97.0 |
| example(59) |  | 2-85 | 6.1 | 9.2 | 500.0 | 5.4 | 93.2 |
| example(60) |  | 2-86 | 6.2 | 8.9 | 500.0 | 5.6 | 96.9 |
| example(61) |  | 2-89 | 6.1 | 9.3 | 500.0 | 5.4 | 94.1 |
| example(62) |  | 2-107 | 6.1 | 9.3 | 500.0 | 5.4 | 94.8 |
| example(63) |  | 2-122 | 6.0 | 9.1 | 500.0 | 5.5 | 94.7 |
| example(64) |  | 2-127 | 6.2 | 8.8 | 500.0 | 5.7 | 96.0 |
| example(65) |  | 2-128 | 6.1 | 8.7 | 500.0 | 5.7 | 95.6 |
| example(66) |  | 2-133 | 6.1 | 9.4 | 500.0 | 5.3 | 94.3 |
| example(67) |  | 2-150 | 6.2 | 9.2 | 500.0 | 5.4 | 93.6 |
| example(68) |  | 2-151 | 6.0 | 9.4 | 500.0 | 5.3 | 94.1 |
| example(69) |  | 2-152 | 6.0 | 9.1 | 500.0 | 5.5 | 93.7 |
| example(70) |  | 2-153 | 6.1 | 9.4 | 500.0 | 5.3 | 93.2 |

Example 6) Manufacture and Evaluation of Green Organic Light Emitting Diode

First, on an ITO layer(anode) formed on a glass substrate, N$^1$-(naphthalen-2-yl)-N$^4$, N$^4$-bis(4-(naphthalen-2-yl(phenyl)amino)phenyl)-N$^1$-phenylbenzene-1,4-diamine(hereinafter will be abbreviated as 2-TNATA) was vacuum-deposited to form a hole injection layer with a thickness of 60 nm. Subsequently, and on the layer, 4,4-bis[N-(1-naphthyl)-N-phenylamino]biphenyl(hereinafter will be abbreviated as NPD) was vacuum-deposited as a hole transport compound to a thickness of 60 nm to form a hole transport layer. Subsequently, the inventive compound represented by Formula(30) was vacuum-deposited as an emitting auxiliary layer material to a thickness of 20 nm to form an emitting auxiliary layer. After forming the emitting auxiliary layer, on the emitting auxiliary layer, 4,4'-di(9H-carbazol-9-yl)-1, 1'-biphenyl is used as a host, and Ir(ppy)$_3$[tris(2-phenylpyridine)-iridium] is used as dopant in a ratio of 95:5, and an emitting layer with a thickness of 30 nm was deposited. (1,1'-bisphenyl)-4-olato)bis(2-methyl-8-quinolinolato)aluminum(hereinafter abbreviated as BAlq) was vacuum deposited as a hole blocking layer to a thickness of 10 nm, and Tris(8-quinolinol) aluminum (hereinafter abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 5000 cd/m$^2$. In the following table, the manufacture of a device and the results of evaluation are shown.

Comparative Examples 41~42

An OLED was prepared in the same manner as in Comparative Example 5 except that Comparative Compound F or Comparative Compound G were used as the emitting auxiliary layer material.

TABLE 12

|  | compound | voltage | Current density (mA/cm$^2$) | brightness (cd/m$^2$) | Efficiency (cd/A) | T(95) | CIE x | CIE y |
|---|---|---|---|---|---|---|---|---|
| comparative example(41) | comparative compound F | 7.3 | 17.4 | 5000.0 | 28.7 | 80.4 | 0.30 | 0.61 |
| comparative example(42) | comparative compound G | 7.4 | 19.9 | 5000.0 | 25.1 | 80.9 | 0.33 | 0.64 |
| example(71) | 2-81 | 5.6 | 11.0 | 5000.0 | 45.4 | 120.3 | 0.31 | 0.64 |
| example(72) | 2-83 | 6.3 | 14.2 | 5000.0 | 35.1 | 104.3 | 0.31 | 0.64 |
| example(73) | 2-85 | 5.8 | 13.8 | 5000.0 | 36.2 | 110.1 | 0.34 | 0.61 |
| example(74) | 2-86 | 6.4 | 14.3 | 5000.0 | 35.0 | 103.6 | 0.33 | 0.63 |
| example(75) | 2-89 | 6.0 | 14.1 | 5000.0 | 35.5 | 113.0 | 0.33 | 0.65 |
| example(76) | 2-107 | 5.8 | 11.3 | 5000.0 | 44.3 | 112.6 | 0.32 | 0.65 |
| example(77) | 2-122 | 5.9 | 11.4 | 5000.0 | 43.8 | 112.3 | 0.34 | 0.63 |
| example(78) | 2-127 | 6.4 | 12.6 | 5000.0 | 39.8 | 104.2 | 0.33 | 0.65 |
| example(79) | 2-128 | 6.3 | 12.8 | 5000.0 | 39.2 | 102.5 | 0.32 | 0.65 |
| example(80) | 2-133 | 5.9 | 12.5 | 5000.0 | 39.9 | 111.2 | 0.32 | 0.65 |
| example(81) | 2-150 | 5.4 | 11.4 | 5000.0 | 43.8 | 114.8 | 0.31 | 0.64 |
| example(82) | 2-151 | 5.2 | 11.2 | 5000.0 | 44.8 | 111.5 | 0.30 | 0.63 |
| example(83) | 2-152 | 5.2 | 11.6 | 5000.0 | 43.1 | 112.1 | 0.31 | 0.63 |
| example(84) | 2-153 | 5.3 | 11.2 | 5000.0 | 44.8 | 114.4 | 0.30 | 0.62 |

As can be seen from the results of Table 11 to 12, when OLED was manufactured by using the material for an organic electroluminescence device of the present invention as an emitting auxiliary layer material, the driving voltage of the organic electroluminescent device can be lowered and the luminous efficiency and lifetime can be remarkably improved as compared with the comparative example not using the material for the emitting auxiliary layer or using the comparative compound F or the comparative compound G.

Table 11 shows the results of the production of a blue organic light emitting device. It can be confirmed that excellent results are obtained when the compound of the present invention is used as an emitting auxiliary layer. The results of Comparative Example 39 or Comparative Example 40 and Examples 57 to 70 show that compounds of the present invention substituted with specific substituents such as DBT, DBF, Cz, and Fluorene are remarkably superior to the comparative compounds substituted with the general aryl group even though the mother compound is similar. That is, when specific substituents such as DBT, DBF, Cz, and Fluorene are introduced, the refractive index, the Tg, and the energy level of the compound (HOMO, LUMO, T1, etc.) become significantly different, and this difference in physical properties is a major factor in improving the device performance during device deposition(for example, such as an energy balance), such that different device results can be derived.

Table 12 shows the results of the production of a green organic light emitting device. When the compound of the present invention was used as an emitting auxiliary layer, the results were significantly superior to the comparative compounds. This is also the effect of certain substituents such as DBT, DBF, Cz, and Fluorene, and a specific feature is that the superiority of the green auxiliary layer is significantly improved than the blue auxiliary layer. Further, in the case of the blue auxiliary layer, DBT and DBF substituted compounds showed the most excellent properties, but the results of the green auxiliary layer showed the best results with the Fluorene substituted compounds. This suggests that even if the emitting auxiliary layer compound is the same, the properties required depending on the color of the emitting layer are different, so that a result which can not be deduced by those skilled in the art can be obtained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. An organic electronic element comprising an anode; a cathode; an organic material layer formed between the anode and the cathode,
wherein the organic material layer includes an emitting layer, an hole transport layer formed between the anode and the emitting layer, and an emitting auxiliary layer or an electron blocking layer (EBL) formed between the emitting layer and the hole transport layer, and
wherein the emitting auxiliary layer or the electron blocking layer comprises a compound selected from the group consisting of the following compounds:

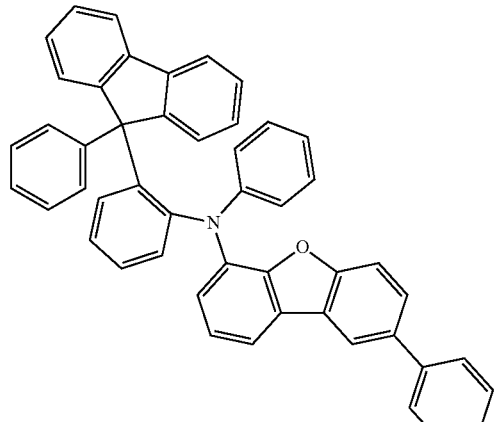

2-126

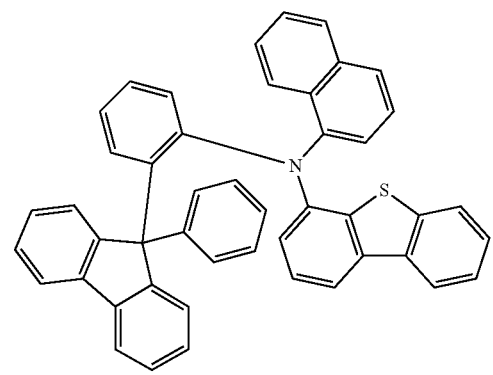

2-127

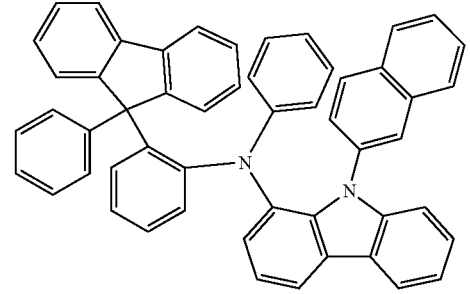

2-128

-continued
2-130
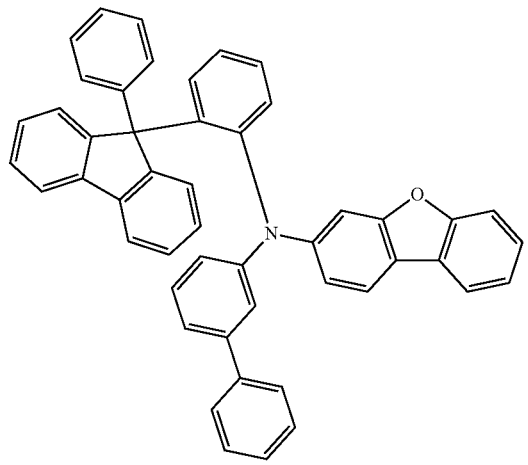
2-131
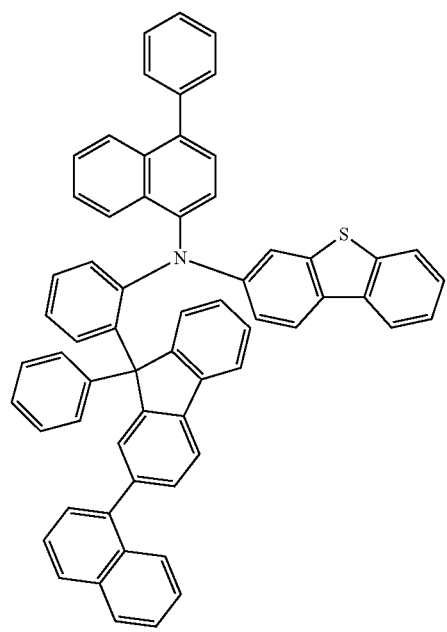
2-132
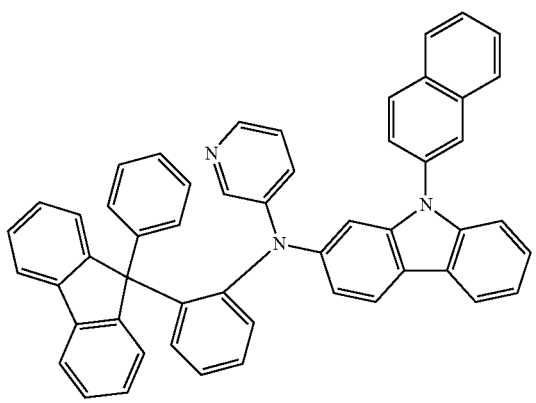
-continued
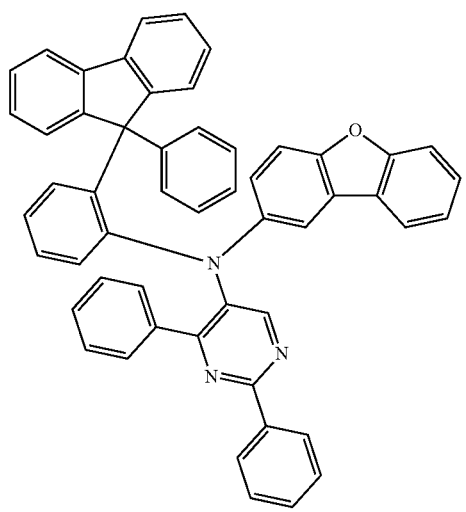
2-134
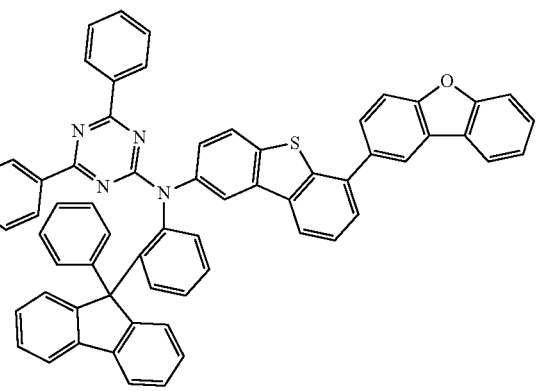
2-135
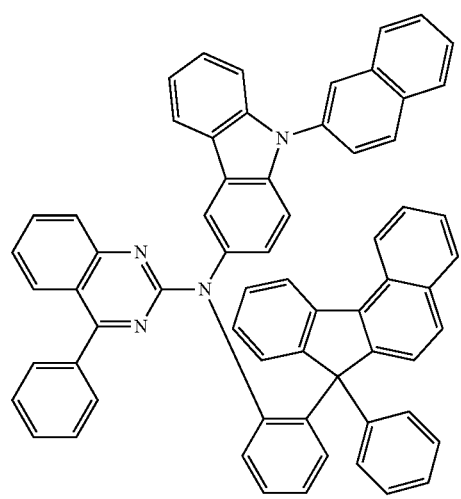
2-136

251
-continued
2-137
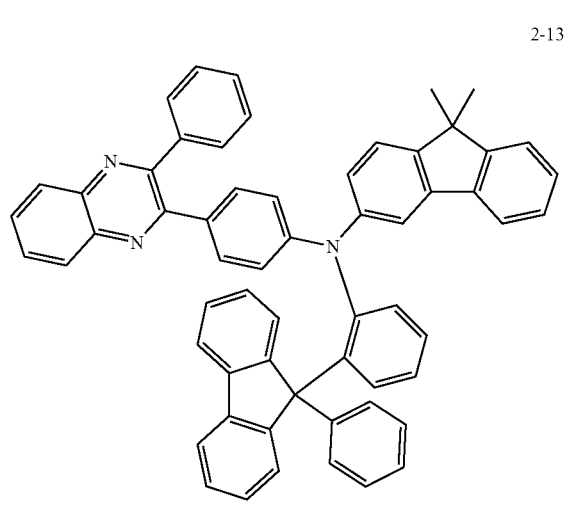
2-138
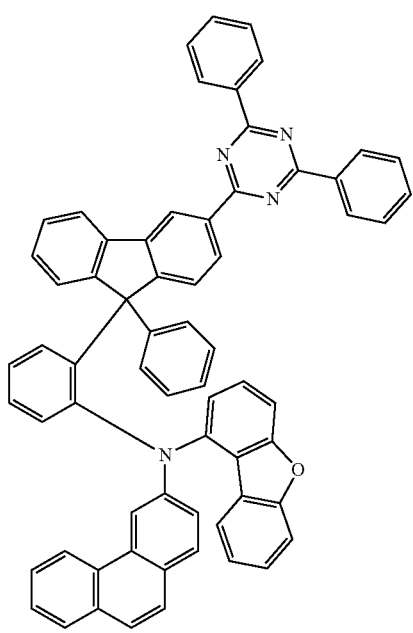
252
-continued
2-139
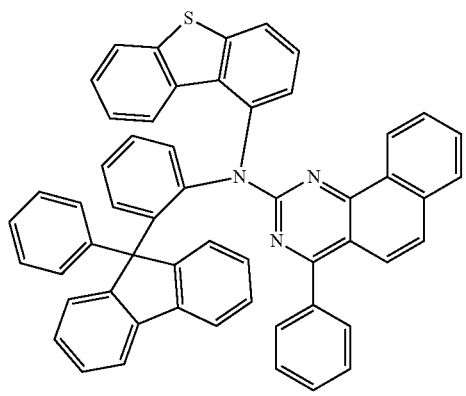
2-140
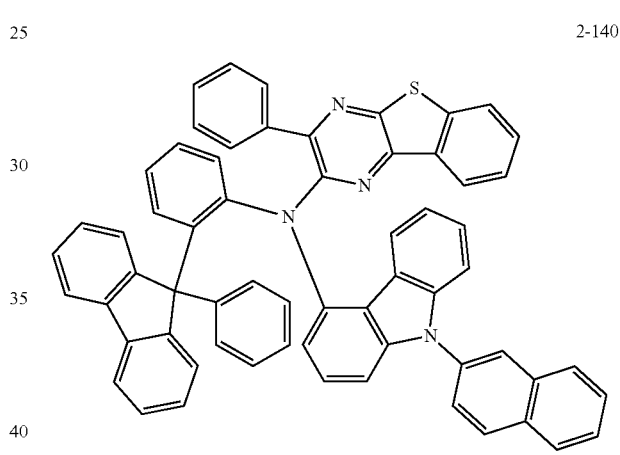
2-141
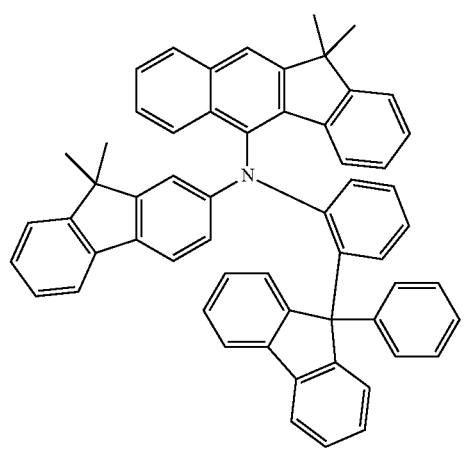

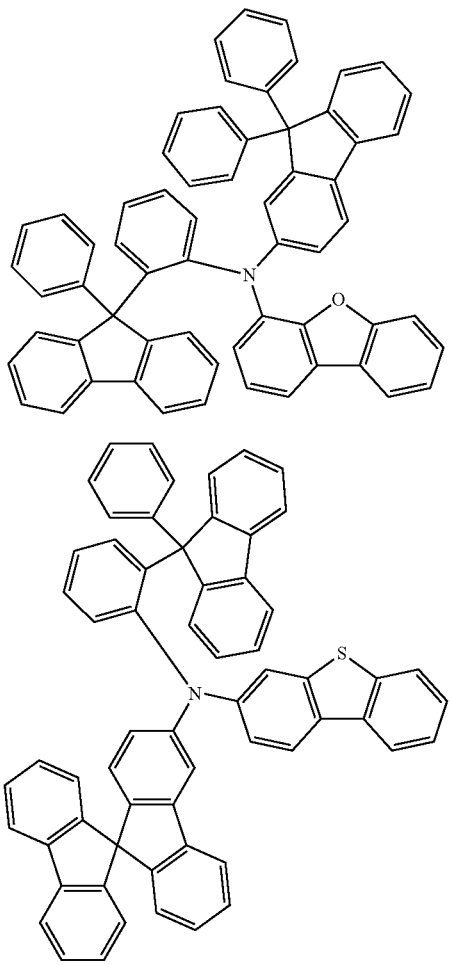

2. The organic electronic element according to claim 1, wherein the compound is used as a green emitting auxiliary layer material.

3. A display device comprising the organic electronic element of claim 1; and a control part driving the display device.

4. The display device according to claim 3, wherein the organic electronic element is an OLED, an organic solar cell, an organic photo conductor (OPC), organic transistor (organic TFT), or an element for monochromic or white illumination.

* * * * *